(12) United States Patent
Kung et al.

(10) Patent No.: US 10,688,200 B2
(45) Date of Patent: Jun. 23, 2020

(54) UREA-BASED PROSTATE SPECIFIC MEMBRANE ANTIGEN (PSMA) INHIBITORS FOR IMAGING AND THERAPY

(71) Applicant: Five Eleven Pharma Inc., Philadelphia, PA (US)

(72) Inventors: Hank F. Kung, Springfield, PA (US); Karl Ploessl, Wilmington, DE (US); Seok Rye Choi, Aston, PA (US); Zhihao Zha, Philadelphia, PA (US); Zehui Wu, Philadelphia, PA (US)

(73) Assignee: FIVE ELEVEN PHARMA INC., Philadelphia, PA (US)

( * ) Notice: Subject to any disclaimer, the term of this patent is extended or adjusted under 35 U.S.C. 154(b) by 628 days.

(21) Appl. No.: 15/385,490

(22) Filed: Dec. 20, 2016

(65) Prior Publication Data

US 2017/0189568 A1 Jul. 6, 2017

Related U.S. Application Data

(60) Provisional application No. 62/273,786, filed on Dec. 31, 2015.

(51) Int. Cl.
*A61K 51/04* (2006.01)
*C07K 5/02* (2006.01)

(52) U.S. Cl.
CPC ...... *A61K 51/0482* (2013.01); *A61K 51/0478* (2013.01); *A61K 51/0491* (2013.01); *A61K 51/0497* (2013.01); *C07K 5/0202* (2013.01)

(58) Field of Classification Search
CPC ............ A61K 51/0491; A61K 51/0497; A61K 51/0482; A61K 51/0478; C07K 5/0202
See application file for complete search history.

(56) References Cited

U.S. PATENT DOCUMENTS

| | | |
|---|---|---|
| 2004/0054190 A1 | 3/2004 | Pomper et al. |
| 2013/0034494 A1* | 2/2013 | Babich ................. C07D 255/02 424/1.65 |
| 2015/0078998 A1 | 3/2015 | Babich et al. |
| 2015/0110715 A1 | 4/2015 | Eder et al. |
| 2016/0228587 A1 | 8/2016 | Eder et al. |

FOREIGN PATENT DOCUMENTS

| | | |
|---|---|---|
| WO | WO-2010022249 A2 | 2/2010 |
| WO | WO-2017116994 A1 | 7/2017 |

OTHER PUBLICATIONS

Afshar-Oromieh, A., et al., "Comparison of PET/CT and PET/MRI Hybrid Systems using a $^{68}$Ga-Labelled PSMA Ligand for the Diagnosis of Recurrent Prostate Cancer: Initial Experience," European Journal of Nuclear Medicine and Molecular Imaging 41(5):887-897, Springer-Verlag, Germany (2014).

Afshar-Oromieh, A., et al., "The Diagnostic Value of PET/CT Imaging with the $^{68}$Ga-Labelled PSMA ligand HBED-CC in the Diagnosis of Recurrent Prostate Cancer," European Journal of Nuclear Medicine and Molecular Imaging 42(2):197-209, Springer-Verlag, Germany (Feb. 2015).

Afshar-Oromieh, A., et al., "The Theranostic PSMA Ligand PSMA-617 in the Diagnosis of Prostate Cancer by PET/CT: Biodistribution in Humans, Radiation Dosimetry, and First Evaluation of Tumor Lesions," Journal of Nuclear Medicine 56(11):1697-1705, Society of Nuclear Medicine, United States (Nov. 2015).

Ahmadzadehfar, H., et al., "Early Side Effects and First Results of Radioligand Therapy With $^{177}$Lu-DKFZ-617 PSMA of Castrate-Resistant Metastatic Prostate Cancer: A Two-Centre Study," European Journal of Nuclear Medicine and Molecular Imaging 5(1):36, Springer Berlin, Germany, 8 pages (Dec. 2015).

Akhtar, N. H., et al., "Prostate-specific Membrane Antigen-based Therapeutics," Advances in Urology Article ID 973820, 9 pages, Hindawi Publishing Corporation, Egypt (2012).

Banerjee, S.R. and Pomper, M.G., "Clinical Applications of Gallium-68," Applied Radiation and Isotopes 76:2-13, Elsevier Ltd., England (2013).

Banerjee, S.R., et al., "$^{68}$Ga-labeled Inhibitors of Prostate-Specific Membrane Antigen (PSMA) for Imaging Prostate Cancer," Journal of Medicinal Chemistry 53(14):5333-5341, American Chemical Society, United States (2010).

Banerjee, S.R., et al., "$^{64}$Cu-Labeled Inhibitors of Prostate-Specific Membrane Antigen for PET Imaging of Prostate Cancer," Journal of Medicinal Chemistry 57(6):2657-2669, American Chemical Society, United States (2014).

Barinka, C., et al., "Glutamate Carboxypeptidase II in Diagnosis and Treatment of Neurologic Disorders and Prostate Cancer," Current Medicinal Chemistry 19(6):856-870, Bentham Science Publishers, Netherlands (2012).

Barrett, J.A., et al., "First-In-Man Evaluation of 2 High-Affinity PSMA-Avid Small Molecules for Imaging Prostate Cancer," Journal of Nuclear Medicine 54(3):380-387, Society of Nuclear Medicine, United States (Mar. 2013).

Baum, R.P., et al., "First-In-Human Study Demonstrating Tumor-Angiogenesis by PET/CT Imaging with $^{68}$Ga-NODAGA-THERANOST, a High-Affinity Peptidomimetic for $\alpha_v\beta_3$ Integrin Receptor Targeting," Cancer Biotherapy and Radiopharmaceuticals 30(4):152-159, Mary Ann Liebert Inc., United States (May 2015).

(Continued)

*Primary Examiner* — Michael G. Hartley
*Assistant Examiner* — Leah H Schlientz
(74) *Attorney, Agent, or Firm* — Sterne, Kessler, Goldstein & Fox P.L.L.C.

(57) ABSTRACT

The present invention relates to compounds according to Formula I and Formula IV. These compounds display very good binding affinities to the PSMA binding sites. They can be labeled with [$^{68}$Ga]GaCl$_3$ with high yields and excellent radiochemical purity. The present invention also relates to pharmaceutical compositions comprising a pharmaceutical acceptable carrier and a compound of Formula I or Formula IV, or a pharmaceutically acceptable salt thereof.

22 Claims, 5 Drawing Sheets

(56) References Cited

OTHER PUBLICATIONS

Baur, B., et al., "Synthesis, Radiolabelling and In Vitro Characterization of the Gallium-68-, Yttrium-90- and Lutetium-177-Labelled PSMA Ligand, CHX-A-DTPA-DUPA-Pep," Pharmaceuticals 7(5):517-529, MDPI, Switzerland (2014).
Bechara, G., et al., "Polyazamacrocycles Based on a Tetraaminoacetate Moiety and a (Poly)Pyridine Intracyclic Unit: Direct Synthesis and Application to the Photosensitization of Eu(III) and Tb(III) Ions in Aqueous Solutions," Tetrahedron 66:8594-8604, Elsevier Ltd., England (2010).
Beiderwellen, K.J., et al., "Simultaneous $^{68}$Ga-DOTATOC PET/MRI in Patients with Gastroenteropancreatic Neuroendocrine Tumors: Initial Results," Investigative Radiology 48(5):273-279, Lippincott Williams & Wilkins, United States (2013).
Benesova, M., et al., "Preclinical Evaluation of a Tailor-Made DOTA-Conjugated PSMA Inhibitor with Optimized Linker Moiety for Imaging and Endoradiotherapy of Prostate Cancer," Journal of Nuclear Medicine 56(6):914-920, Society of Nuclear Medicine, United States (Jun. 2015).
Boros, E., et al., "RGD Conjugates of the H$_2$dedpa Scaffold: Synthesis, Labeling and Imaging with $^{68}$Ga," Nuclear Medicine and Biology 39(6):785-794, Elsevier Inc., United States (2012).
Breeman, W.A.P., et al., "$^{68}$Ga-Labeled DOTA-Peptides and $68$Ga-Labeled Radiopharmaceuticals for Positron Emission Tomography: Current Status of Research, Clinical Applications, and Future Perspectives," Seminars in Nuclear Medicine 41(4):314-321, Elsevier Inc., United States (2011).
Burke, B.P., et al., "Recent Advances in Chelator Design and Labelling Methodology for $^{68}$Ga Radiopharmaceuticals," Journal of Labelled Compounds and Radiopharmaceuticals 57(4):239-243, John Wiley & Sons, Ltd., England (2014).
Castanares, M.A., et al., "Evaluation of Prostate-specific Membrane Antigen as an Imaging Reporter," Journal of Nuclear Medicine 55(5):805-811, Society of Nuclear Medicine, United States (2014).
Chakraborty, P.S., et al., "Metastatic Poorly Differentiated Prostatic Carcinoma with Neuroendocrine Differentiation: Negative on $^{68}$Ga-PSMA PET/CT," Clinical Nuclear Medicine 40(2):e163-e166, Wolters Kluwer Health, Inc., United States (Feb. 2015).
Chen, Y., et al., "2-(3-{1-Carboxy-5-[(6-[$^{18}$F]Fluoro-Pyridine-3-Carbonyl)-Amino]-Pentyl}-Ureido)-Pentanedioic Acid, [$^{18}$F]DCFPyL, a PSMA-based PET Imaging Agent for Prostate Cancer," Clinical Cancer Research 17(24):7645-7653, American Association of Cancer Research, United States (2011).
Cho, S.Y., et al., "Biodistribution, Tumor Detection, and Radiation Dosimetry of $^{18}$F-DCFBC, a Low-molecular-weight Inhibitor of Prostate-specific Membrane Antigen, in Patients with Metastatic Prostate Cancer," Journal of Nuclear Medicine 53(12):1883-1891, Society of Nuclear Medicine, United States (2012).
Davis, M.I., et al., "Crystal Structure of Prostate-specific Membrane Antigen, a Tumor Marker and Peptidase," Proceedings of the National Academy of Sciences 102(17):5981-5986, National Academy of Sciences, United States (Apr. 2005).
Delker, A., et al., "Dosimetry for $^{177}$Lu-DKFZ-PSMA-617: a New Radiopharmaceutical for the Treatment of Metastatic Prostate Cancer," European Journal of Nuclear Medicine and Molecular Imaging 43(1):42-51, Springer-Verlag Berlin, Germany (2016).
Dietlein, M., et al., "Comparison of [$^{18}$F]DCFPyL and [$^{68}$Ga]Ga-PSMA-HBED-CC for PSMA-PET Imaging in Patients with Relapsed Prostate Cancer," Molecular Imaging and Biology 17(4):575-584, Springer, United States (Aug. 2015).
Eder, M., et al., "PSMA as a Target for Radiolabelled Small Molecules," European Journal of Nuclear Medicine and Molecular Imaging 40(6):819-823, Springer-Verlag Berlin, Germany (2013).
Eder, M., et al., "$^{68}$Ga-Complex Lipophilicity and the Targeting Property of a Urea-based PSMA Inhibitor for PET Imaging," Bioconjugate Chemistry 23(4):688-697, American Chemical Society, United States (2012).
Eder, M., et al., "Novel Preclinical and Radiopharmaceutical Aspects of [$^{68}$Ga]Ga-PSMA-HBED-CC: A New PET Tracer for Imaging of Prostate Cancer," Pharmaceuticals 7(7):779-796, MDPI, Switzerland (2014).
Eder, M., et al., "Tetrafluorophenolate of HBED-CC: a Versatile Conjugation Agent for $^{68}$Ga-labeled Small Recombinant Antibodies," European Journal of Nuclear Medicine and Molecular Imaging 35(10):1878-1886, Springer-Verlag Berlin, Germany (2008).
Eiber, M., et al., "$^{68}$Ga-PSMA PET/MR with Multimodality Image Analysis for Primary Prostate Cancer," Abdominal Imaging 40(6):1769-1771, Springer International, United States (Aug. 2015).
Eiber, M., et al., "Evaluation of Hybrid $^{68}$Ga-PSMA Ligand PET/CT in 248 Patients with Biochemical Recurrence After Radical Prostatectomy," Journal of Nuclear Medicine 56(5):668-674, Society of Nuclear Medicine, United States (May 2015).
Eisenwiener, K.P., et al., "NODAGATOC, a New Chelator-Coupled Somatostatin Analogue Labeled with [$^{67/68}$Ga] and [$^{111}$In] for SPECT, PET, and Targeted Therapeutic Applications of Somatostatin Receptor (hsst2) Expressing Tumors," Bioconjugate Chemistry 13(3):530-541, American Chemical Society, United States (2002).
Franc, B.L., et al., "Detection and localization of Carcinoma within the Prostate Using High Resolution Transrectal Gamma Imaging (TRGI) of Monoclonal Antibody Directed at Prostate Specific Membrane Antigen (PSMA)-Proof of Concept and Initial Imaging Results," European Journal of Radiology 82(11):1877-1884, Elsevier Science Ireland Ltd, Ireland (2013).
Hao, G., et al., "A Multivalent Approach of Imaging Probe Design to Overcome an Endogenous Anion Binding Competition for Noninvasive Assessment of Prostate Specific Membrane Antigen," Molecular Pharmaceutics 10(8):2975-2985, American Chemical Society, United States (2013).
Herrmann, K., et al., "Biodistribution and Radiation Dosimetry for a Probe Targeting Prostate-specific Membrane Antigen for Imaging and Therapy," Journal of Nuclear Medicine 56(6):855-861, Society of Nuclear Medicine, United States (Jun. 2015).
Holland, J.P., et al., "$^{89}$Zr-DFO-J591 for ImmunoPET of Prostate-Specific Membrane Antigen Expression In Vivo," Journal of Nuclear Medicine 51(8):1293-1300, Society of Nuclear Medicine, United States (2010).
Huang, S.S., et al., "Improving the Biodistribution of PSMA-targeting Tracers with a Highly Negatively Charged Linker," Prostate 74(7):702-713, Wiley-Liss, United States (2014).
Humblet, V., et al., "Multivalent Scaffolds for Affinity Maturation of Small Molecule Cell Surface-binders and Their Application to Prostate Tumor Targeting," Journal of Medicinal Chemistry 52(2):544-550, American Chemical Society, United States (2009).
International Search Report and Written Opinion for International Application No. PCT/US2016/68327, ISA/US Alexandria, Virginia, dated May 4, 2017, 10 pages.
Kabasakal, L., et al., "Pre-Therapeutic Dosimetry of Normal Organs and Tissues of $^{177}$Lu-PSMA-617 Prostate-Specific Membrane Antigen (PSMA) Inhibitor in Patients With Castration-Resistant Prostate Cancer," European Journal of Nuclear Medicine and Molecular Imaging 42(13):1976-1983, Springer-Verlag Berlin, Germany (Dec. 2015).
Kantchev, E.A.B., et al., "Practical Heck-Mizoroki Coupling Protocol for Challenging Substrates Mediated by an N-Heterocyclic Carbene-Ligated Palladacycle," Organic Letters 10(18):3949-3952, American Chemical Society, United States (2008).
Kozikowski, A.P., et al., "Synthesis of Urea-based Inhibitors as Active Site Probes of Glutamate Carboxypeptidase II: Efficacy as Analgesic Agents," Journal of Medicinal Chemistry 47(7):1729-1738, American Chemical Society, United States (2004).
Lapi, S.E., et al., "Assessment of an $^{18}$F-labeled Phosphoramidate Peptidomimetic as a New Prostate-specific Membrane Antigen-targeted Imaging Agent for Prostate Cancer," Journal of Nuclear Medicine 50(12):2042-2048, Society of Nuclear Medicine, United States (2009).
Li, Y., et al., "In vitro and preclinical targeted alpha therapy of human prostate cancer with Bi-213 labeled J591 antibody against the prostate specific membrane antigen," Prostate Cancer and Prostatic Diseases 5(1):36-46, Nature Publishing Group, England (2002).

(56) References Cited

OTHER PUBLICATIONS

Mandal, P.K., et al., "Pd-C-induced Catalytic Transfer Hydrogenation With Triethylsilane," Journal of Organic Chemistry 72(17):6599-6601, American Chemical Society, United States (2007).

Manzoni, L., et al., "Synthesis of Gd and $^{68}$Ga Complexes in Conjugation with a Conformationally Optimized RGD Sequence as Potential MRI and PET Tumor-imaging Probes," ChemMedChem 7(6):1084-1093, Wiley-VCH, Germany (2012).

Maresca, K.P., et al., "A Series of Halogenated Heterodimeric Inhibitors of Prostate Specific Membrane Antigen (PSMA) as Radiolabeled Probes for Targeting Prostate Cancer," Journal of Medicinal Chemistry 52(2):347-357, American Chemical Society, United States (2009).

Maurer, T., et al., "Positron Emission Tomography/magnetic Resonance Imaging with $^{68}$Gallium-labeled Ligand of Prostate-specific Membrane Antigen: Promising Novel Option in Prostate Cancer Imaging?," International Journal of Urology 21(12):1286-1288, Blackwell Science, Australia (2014).

Mease, R.C., et al., "PET Imaging in Prostate Cancer: Focus on Prostate-Specific Membrane Antigen," Current Topics in Medicinal Chemistry 13(8):951-962, Bentham Science Publishers, Netherlands (2013).

Misra, P., et al., "Production of Multimeric Prostate-specific Membrane Antigen Small-molecule Radiotracers Using a Solid-phase $^{99m}$Tc Preloading Strategy," Journal of Nuclear Medicine 48(8):1379-1389, Society of Nuclear Medicine, United States (2007).

Mjos, K.D. and Orvig, C., "Metallodrugs in Medicinal Inorganic Chemistry," Chemical Reviews 114(8):4540-4563, American Chemical Society, United States (2014).

Motekaitis, R.J., et al., "Stability and Structure of Activated Macrocycles. Ligands with Biological Applications," Inorganic Chemistry 35(13):3821-3827, American Chemical Society, United States (1996).

Nan, F., et al., "Dual Function Glutamate-Related Ligands: Discovery of a Novel, Potent Inhibitor of Glutamate Carboxypeptidase II Possessing mGluR3 Agonist Activity," Journal of Medicinal Chemistry 43(5):772-774, American Chemical Society, United States (2000).

Nedrow-Byers, J.R., et al., "A Phosphoramidate-Based Prostate-Specific Membrane Antigen-Targeted SPECT Agent," Prostate 72(8):904-912, Wiley-Liss, United States (2012).

Nedrow-Byers, J.R., et al., "PSMA-Targeted SPECT Agents: Mode of Binding Effect on In Vitro Performance," Prostate 73(4):355-362, Wiley-Liss, United States (2013).

Notni, J., et al., "Phosphinic Acid Functionalized Polyazacycloalkane Chelators for Radiodiagnostics and Radiotherapeutics: Unique Characteristics and Applications," ChemMedChem 9(6):1107-1115, Wiley-VCH, Germany (2014).

Osborne, J.R., et al., "A Prospective Pilot Study of $^{89}$Zr-J591/Prostate Specific Membrane Antigen Positron Emission Tomography in Men with Localized Prostate Cancer Undergoing Radical Prostatectomy," Journal of Urology 191(5):1439-1445, Elsevier, United States (2014).

Osborne, J.R., et al., "Prostate-specific Membrane Antigen-based Imaging," Urologic Oncology: Seminars and Original Investigations 31(2):144-154, Elsevier, United States (2013).

Pavlicek, J., et al., "Structural Characterization of P1'-Diversified Urea-Based Inhibitors of Glutamate Carboxypeptidase II," Bioorganic & Medicinal Chemistry Letters 24(10):2340-2345, Elsevier Science Ltd, England (2014).

Pomper, M.G., et al., "$^{11}$C-MCG: Synthesis, Uptake Selectivity, and Primate PET of a Probe for Glutamate Carboxypeptidase II (NAALADase)," Molecular Imaging 1(2):96-101, SAGE Publications, United States (2002).

Price, E.W. and Orvig, C., "Matching Chelators to Radiometals for Radiopharmaceuticals," Chemical Society Reviews 43(1):260-290, Chemical Society, England (2014).

Ramogida, C.F., et al., "H$_2$CHXdedpa and H$_4$CHXoctapa-Chiral Acyclic Chelating Ligands for $^{67/68}$Ga and $^{111}$In Radiopharmaceuticals," Inorganic Chemistry 54(4):2017-2031, American Chemical Society, United States (Jan. 2015).

Ristau, B.T., et al., "The Prostate-specific Membrane Antigen: Lessons and Current Clinical Implications From 20 Years of Research," Urologic Oncology: Seminars and Original Investigations 32(3):272-279, Elsevier, United States (2014).

Rong, S.B., et al., "Molecular Modeling of the Interactions of Glutamate Carboxypeptidase II With Its Potent NAAG-based Inhibitors ," Journal of Medicinal Chemistry 45(19):4140-4152, American Chemical Society, United States (Sep. 2002).

Roosenburg, S., et al., "PET and SPECT Imaging of a Radiolabeled Minigastrin Analogue Conjugated with DOTA, NOTA, and NODAGA and Labeled with $^{64}$Cu, $^{68}$Ga, and $^{111}$In," Molecular Pharmaceutics 11(11):3930-3937, American Chemical Society, United States (2014).

Rosch, F., "Past, Present and Future of $^{68}$Ge/$^{68}$Ga Generators," Applied Radiation and Isotopes 76:24-30, Elsevier Ltd., England (2013).

Rowe, S.P., et al., "$^{18}$F-DCFBC PET/CT for PSMA-Based Detection and Characterization of Primary Prostate Cancer," Journal of Nuclear Medicine 56(7):1003-1010, Society of Nuclear Medicine, United States (Jul. 2015).

Rowe, S.P., et al., "Imaging of Metastatic Clear Cell Renal Cell Carcinoma with PSMA-targeted $^{18}$F-DCFPyL PET/CT," Annals of Nuclear Medicine 29(10):877-882, Springer Japanese Society of Nuclear Medicine, Japan (Dec. 2015).

Sanchez-Crespo, A., "Comparison of Gallium-68 and Fluorine-18 Imaging Characteristics in Positron Emission Tomography," Applied Radiation and Isotopes 76:55-62, Elsevier Ltd., England (2013).

Sandstrom, M., et al., "Comparative Biodistribution and Radiation Dosimetry of $^{68}$Ga-DOTATOC and $^{68}$Ga-DOTATATE in Patients with Neuroendocrine Tumors," Journal of Nuclear Medicine 54(10):1755-1759, Society of Nuclear Medicine, United States (2013).

Schafer, M., et al., "A Dimerized Urea-based Inhibitor of the Prostate-specific Membrane Antigen for $^{68}$Ga-PET Imaging of Prostate Cancer," EJNMMI Research 2(1):23, Springer Berlin, Germany, 11 pages (2012).

Simecek, J., et al, "A Cyclen-based Tetraphosphinate Chelator for the Preparation of Radiolabeled Tetrameric Bioconjugates," Chemistry a European Journal 19(24):7748-7757, Wiley-VCH, Germany (2013).

Simecek, J., et al., "Benefits of NOPO as Chelator in Gallium-68 Peptides, Exemplified by Preclinical Characterization of $^{68}$Ga-NOPO-c(RGDfK)," Molecular Pharmaceutics 11(5):1687-1695, American Chemical Society, United States (2014).

Simecek, J., et al, "How is $^{68}$Ga Labeling of Macrocyclic Chelators Influenced by Metal Ion Contaminants in $^{68}$Ge/$^{68}$Ga Generator Eluates?," ChemMedChem 8(1):95-103, Wiley-VCH, Germany (2013).

Simecek, J., et al., "Tailored Gallium(III) Chelator NOPO: Synthesis, Characterization, Bioconjugation, and Application in Preclinical Ga-68-PET Imaging," Molecular Pharmaceutics 11(11):3893-3903, American Chemical Society, United States (2014).

Smith, D.L., et al., "The Untapped Potential of Gallium 68-PET: The Next Wave of $^{68}$Ga-agents," Applied Radiation and Isotopes 76:14-23, Elsevier Ltd., England (2013).

Stasiuk, G.J. and Long, N. J., "The Ubiquitous DOTA and Its Derivatives: The Impact of 1,4,7,10-tetraazacyclododecane-1,4,7,10-tetraacetic Acid on Biomedical Imaging," Chemical Communications 49(27):2732-2746, Royal Society of Chemistry, England (2013).

Sun, Y., et al., "Indium(III) and Gallium(III) Complexes of Bis(aminoethanethiol) Ligands with Different Denticities: Stabilities, Molecular Modeling, and in Vivo Behavior," Journal of Medicinal Chemistry 39(2):458-470, American Chemical Society, United States (1996).

Szabo, Z., et al., "Initial Evaluation of [$^{18}$F]DCFPyL for Prostate-Specific Membrane Antigen (PSMA)-Targeted PET Imaging of Prostate Cancer," Molecular Imaging and Biology 17(4):565-574, Springer, United States (Aug. 2015).

Tagawa, S.T., et al., "Phase II Study of Lutetium-177-Labeled Anti-Prostate-Specific Membrane Antigen Monoclonal Antibody J591 for Metastatic Castration-Resistant Prostate Cancer," Clinical Cancer Research 19(18):5182-5191, The Association, United States (2013).

Vallabhajosula, S., et al., "$^{99m}$Tc-labeled Small-molecule Inhibitors of Prostate-specific Membrane Antigen: Pharmacokinetics and

(56) References Cited

OTHER PUBLICATIONS

Biodistribution Studies in Healthy Subjects and Patients with Metastatic Prostate Cancer," Journal of Nuclear Medicine 55(11):1791-1798, Society of Nuclear Medicine, United States (2014).

Velikyan, I., et al., "Convenient Preparation of $^{68}$Ga-based PET-radiopharmaceuticals at Room Temperature," Bioconjugate Chemistry 19(2):569-573, American Chemical Society, United States (2008).

Velikyan, I., "$^{68}$Ga-Based Radiopharmaceuticals: Production and Application Relationship," Molecules 20(7):12913-12943, Basel, Switzerland (Jul. 2015).

Velikyan, I., "Prospective of $^{68}$Ga-Radiopharmaceutical Development," Theranostics 4(1):47-80, Ivyspring International, Australia (2013).

Velikyan, I., et al., "Quantitative and Qualitative Intrapatient Comparison of $^{68}$Ga-DOTATOC and $^{68}$Ga-DOTATATE: Net Uptake Rate for Accurate Quantification," Journal of Nuclear Medicine 55(2):204-210, Society of Nuclear Medicine, United States (2014).

Verburg, F.A., et al., "First Evidence of PSMA Expression in Differentiated Thyroid Cancer Using [$^{68}$Ga]PSMA-HBED-CC PET/CT," European Journal of Nuclear Medicine and Molecular Imaging 42(10):1622-1623, Springer-Verlag Berlin, Germany (Sep. 2015).

Waldron, B.P., et al., "Structure and Stability of Hexadentate Complexes of Ligands Based on AAZTA for Efficient PET Labelling with Gallium-68," Chemical Communications 49(6):579-581, Royal Society of Chemistry, England (2013).

Weineisen, M., et al., "$^{68}$Ga- and $^{177}$Lu-Labeled PSMA I&T: Optimization of a PSMA-Targeted Theranostic Concept and First Proof-of-Concept Human Studies," Journal of Nuclear Medicine 56(8):1169-1176, Society of Nuclear Medicine, United States (Aug. 2015).

Weineisen, M., et al., "Synthesis and Preclinical Evaluation of DOTAGA-Conjugated PSMA ligands for Functional Imaging and Endoradiotherapy of Prostate Cancer," European Journal of Nuclear Medicine and Molecular Imaging 4(1):63, Springer Berlin, Germany, 15 pages (2014).

Wuts, P.G.M. and Greene, T.W., "Protection for Phenols and Catechols," in Greene's Protective Groups in Organic Synthesis, 4th Ed., Wuts, P.G.M. and Greene, T.W., eds., pp. 367-430, John Wiley & Sons, Inc., United States (2007).

Zechmann, C.M., et al., "Radiation Dosimetry and First Therapy Results with a $^{124}$I/$^{131}$I-Labeled Small Molecule (MIP-1095) Targeting PSMA for Prostate Cancer Therapy," European Journal of Nuclear Medicine and Molecular Imaging 41(7):1280-1292, Springer-Verlag, Germany (2014).

\* cited by examiner

Compound 1a

Compound 1b

Compound 1c

Compound 1d

Compound 1e

Compound 1f

Compound 1g

Compound 2

Compound 3

Compound 4a

Compound 4b

UREA-BASED PROSTATE SPECIFIC MEMBRANE ANTIGEN (PSMA) INHIBITORS FOR IMAGING AND THERAPY

BACKGROUND OF THE INVENTION

This invention is in the field of radiolabeled imaging and radioactive therapy agents. In particular, derivatives of urea based prostate-specific membrane antigen (PSMA) inhibitors are disclosed. Derivatives with a chelating moiety are capable of chelating a radioactive metal. Compounds containing a novel phenoxy linker were also prepared, and the linker attaches a chelating moiety or a radioactive group with an urea based PSMA targeting moiety.

Prostate-specific membrane antigen is a highly specific prostate epithelial cell membrane antigen. It is a type II transmembrane protein consisting of a short NH2-terminal cytoplasmic domain, hydrophobic transmembrane region, and a large extracellular domain. This is a transmembrane enzyme with overlapping carboxypeptidase enzyme activities similar to (a) glutamate carboxypeptidase II (GCPII, E.C.3.17.21), a zinc-dependent metallopeptidase, and (b) folylpolyglutamate synthetase (FPGS). The extracellular portion of the peptide sequence exists as a dimer and shows a strong binding to glutamate and glutamate related structures (brain related PSMA), its natural substrates are N-acetyl-aspartylglutamate and folyl-poly-γ-glutamates (prostate related PSMA) (Scheme 1).

computer tomography) imaging of this agent exhibits prolonged background activity and an unfavorable signal to background ratio even at 4 days post injection.

A specific antibody targeting the extracellular portion of PSMA, J591, has been reported and shown to have improved PSMA targeting properties. This antibody has been radiolabeled with various isotopes, $^{89}$Zr, $^{111}$In, $^{177}$Lu, etc., for imaging and radiotherapy. J591 is an antibody against the extracellular epitope of PSMA, and it is targeting the PSMA binding sites on the membrane of tumor cells. Its in vivo retention and circulation time is relatively long, thus contributing to a prolonged waiting period to reach optimal imaging. An isotope with a longer physical half-life is essential for this purpose, therefore $^{89}$Zr, a positron-emitting isotope with a physical half-life of 78.4 hours, is more appropriate. [$^{89}$Zr]J591 bound strongly to PSMA, and clinical studies in humans suggested that it is useful for defining the tumor location by PET imaging.

A number of small molecule-based PSMA imaging agents have been reported in the literature. Different PSMA-targeting core structures have been employed, including: 2[(3-amino-3-carboxypropyl)(hydroxy)(phosphinyl)-methyl] pentane-1,5-dioic acid (GPI), 2-(3-mercaptopropyl)pentanedioic acid (2-PMPA), phosphoramidates, and urea (Glu-NH—CO—NH-Lys(Ahx)), originally reported in 2000 (Scheme 2). See e.g. US2004054190; Kozikowski A P, et al., *J. Med. Chem.* 47:1729-38 (2004). Based on these binding core structures, many of the PSMA inhibitors were reported

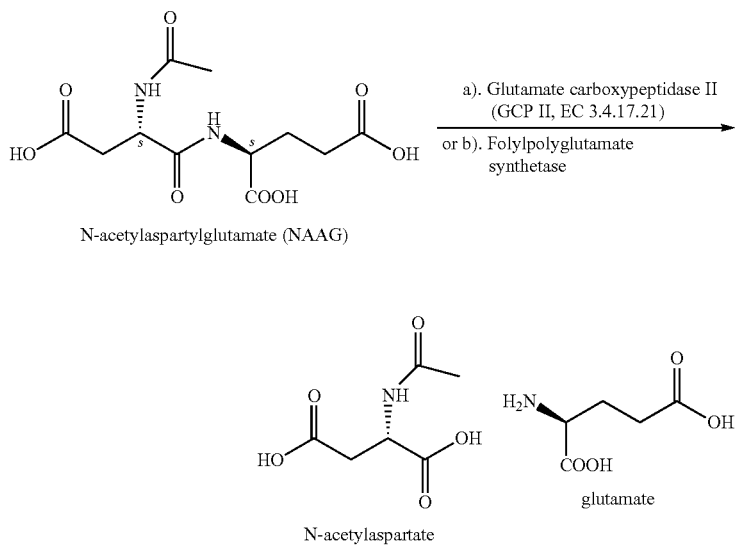

PSMA is highly expressed in various tumors, including prostate cancer. Often, PSMA expression increases in higher-grade cancers and metastatic diseases. In the vast majority of neovasculature in solid tumors, there is high expression of PSMA, but not in normal vasculature. This makes PSMA a suitable target for cancer detection and therapy. Prostascint® (In-111 Capromab pendetide) developed by Cytogen was the first antibody of PSMA approved for clinical use. This antibody only recognizes the intracellular epitope on PSMA, which is associated with dead or necrotic cells commonly found in lymph nodes. Prostascint® is not useful for imaging living tumor cells because of its lack of cell penetration. SPECT (single photon emission to be highly selective and potent. After labeling with different isotopes, they can be employed for in vivo imaging (SPECT or PET).

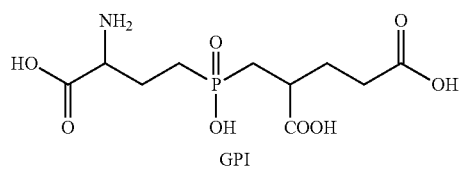

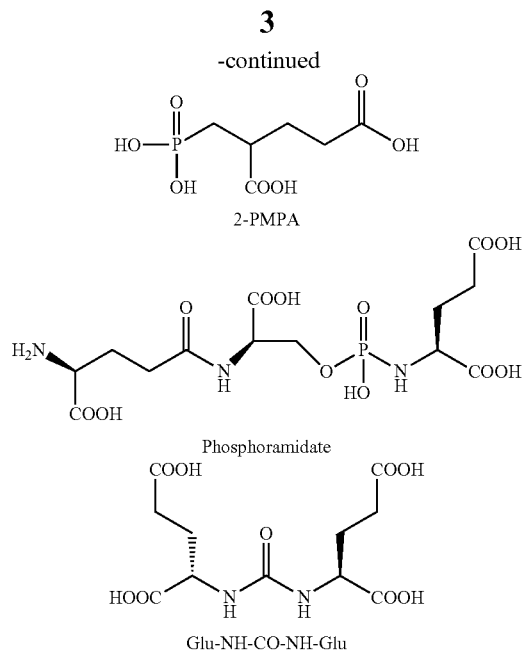

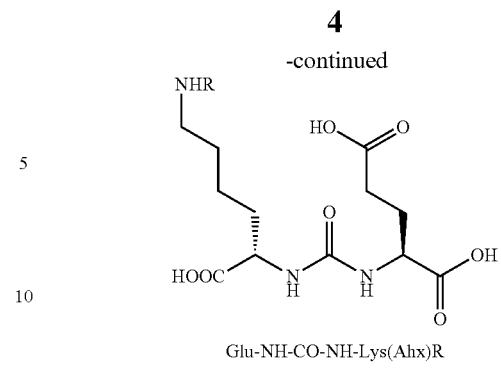

Several potential PSMA-targeted imaging agents using urea based ligand systems (Glu-NH—CO—NH or Glu-NH—CO—NH-Lys(Ahx)), including SPECT imaging agents: [$^{123}$I]MIP-1072, [$^{123}$I]MIP-1095 [49-51], [$^{99m}$Tc]MIP-1404, and [$^{99m}$Tc]Tc-MIP-1405 (Scheme 3), have entered into clinical trials. Results of phase II clinical studies suggest that these SPECT PSMA imaging agents are suitable for the diagnosis of prostate and other related solid tumors.

Scheme 3

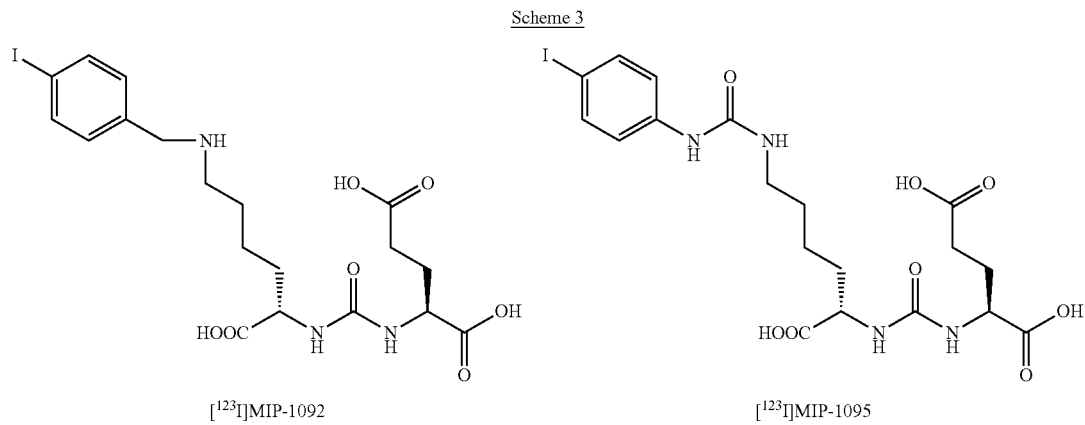

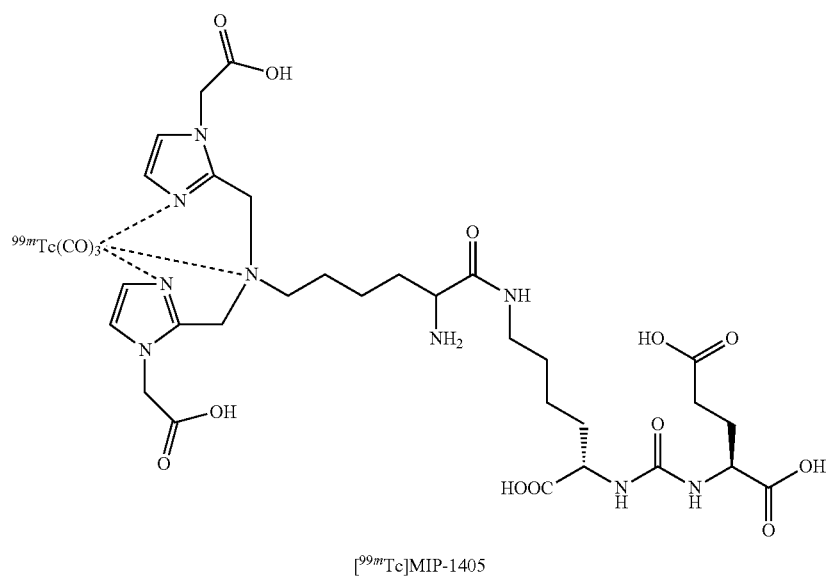

Several $^{11}$C and $^{18}$F labeled PET imaging agents targeting PSMA have also been reported (Scheme 4). Again, these are derivatives of Glu-NH—CO—NH— or Glu-NH—CO—NH-Lys(Ahx), such as [$^{11}$C](S)-2-[3-((R)-1-carboxy-2-methylsulfanyl-ethyl)-ureido]-pentanedioic acid, $^{11}$C-MCG, Two fluorinated version of PSMA-targeting agents, [$^{18}$F] DCFBC: N—[N—[(S)-1,3-dicarboxypropyl]carbamoyl]-4-[$^{18}$F]-fluorobenzyl-L-cysteine, and [$^{18}$F]DCFPyL: 2-(3-(1-carboxy-5-[(6-[$^{18}$F]fluoro-pyridine-3-carbonyl)-amino]-pentyl)-ureido)-pentanedioic acid, have been reported. Both agents showed promising results in imaging patients with metastatic prostate cancer. The preparation of $^{11}$C and $^{18}$F labeled PSMA imaging agents require a near-by cyclotron, because the physical half-life is 20 min and 110 min, respectively. As an alternative, $^{68}$Ga can be used for PET imaging in a laboratory setting without a near-by cyclotron.

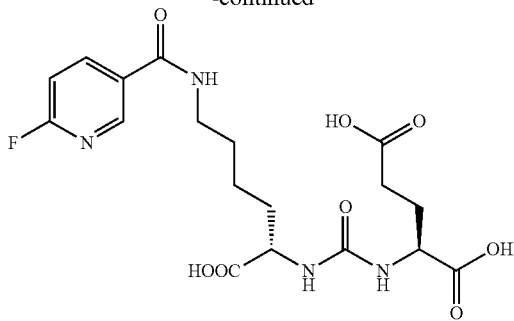

[$^{18}$F]DCFPyL
John Hopkins

Scheme 4

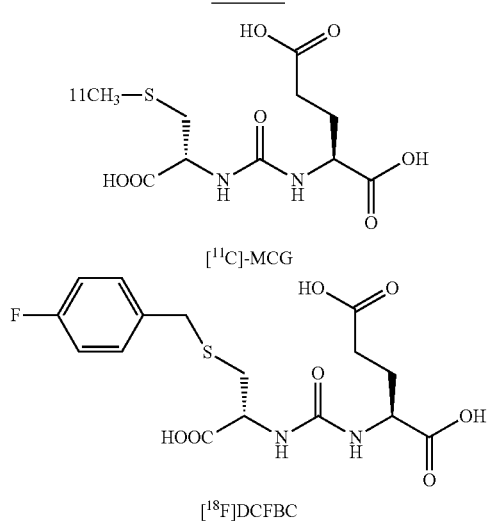

[$^{11}$C]-MCG

[$^{18}$F]DCFBC

In the past few years, [$^{68}$Ga]Glu-NH—CO—NH-Lys (Ahx)-HBED-CC (monomer, [$^{68}$Ga]1a) and its dimer, [$^{68}$Ga](Glu-NH—CO—NH-Lys(Ahx))$_2$-HBED-CC were successfully prepared and showed high PSMA binding (Scheme 5). Although both [$^{68}$Ga]Glu-NH—CO—NH-Lys (Ahx)-HBED-CC (monomer) and [$^{68}$Ga](Glu-NH—CO—NH-Lys(Ahx))$_2$-HBED-CC (dimer) exhibited comparable preclinical data, currently, the most popular PSMA/PET imaging agent that has been successfully applied in humans is [$^{68}$Ga]Glu-NH—CO—NH-Lys(Ahx)-HBED-CC. See Eder M, et al., *Bioconjug. Chem.* 23:688-97 (2012).

Scheme 5

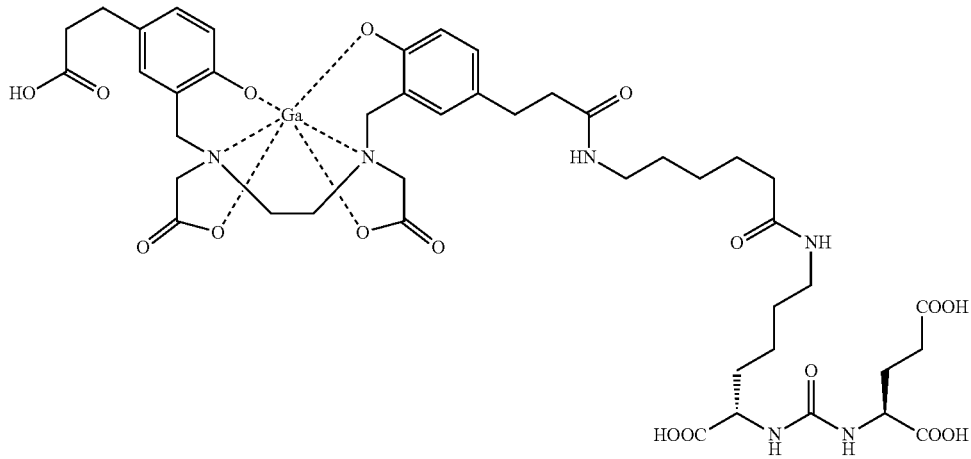

[$^{68}$Ga]Glu-NH—CO—NH-Lys(Ahx)-HBED-CC
Monomer (PSMA-11), [Ga]1a

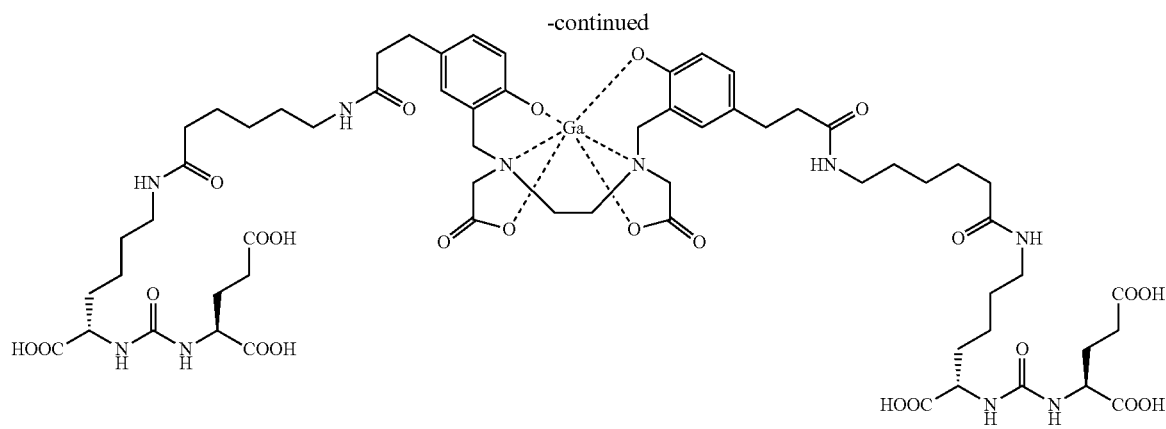

[⁶⁸Ga](Glu-NH—CO—NH-Lys(Ahx))₂-HBED-CC
Dimer

Recently PSMA-617 and DOTAGA-(yl)-fk(sub-KuE) (I&T) were reported (Scheme 6). These two compounds contain different linkers between the chelating moiety and the urea based PSMA targeting moiety. These linkers have various amino acid residues. These PET tracers appear to provide useful diagnostic information in humans. A comparison of PET imaging using [⁶⁸Ga]Ga-PSMA-HBED-CC and [¹⁸F]DCFPyL, in prostate cancer patients has been reported. Additional imaging agents with structure modifications in the linker regions have been reported to have improved tumor targeting properties and pharmacokinetics. See US Published Appl. No. 2016/0228587.

Scheme 6

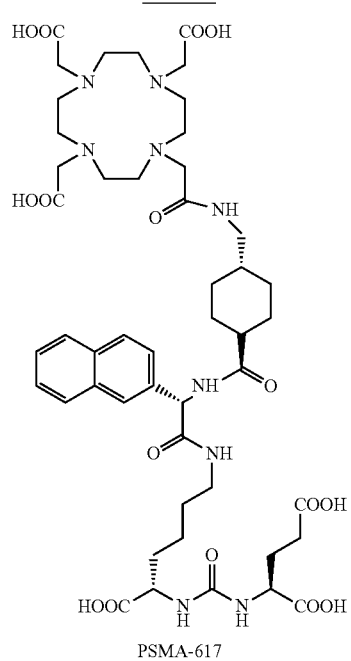

PSMA-617

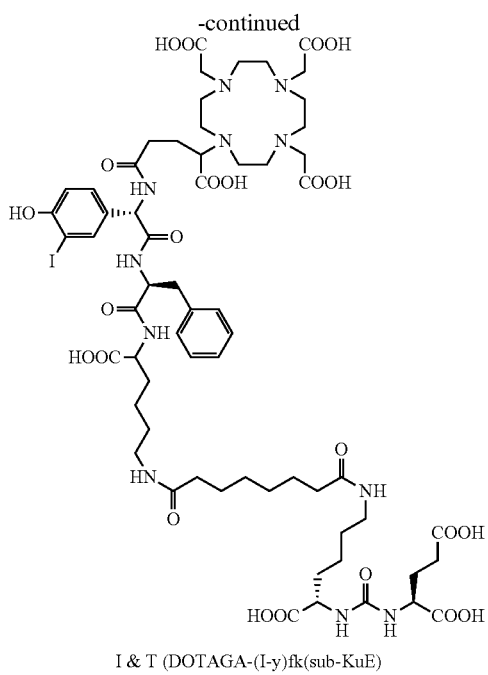

I & T (DOTAGA-(I-y)fk(sub-KuE))

A need continued to exist to further improve the Glu-NH—CO—NH-Lys(Ahx)-HBED-CC amide derivatives as PSMA inhibitor for in vivo imaging and radiation therapy.

BRIEF SUMMARY OF THE INVENTION

In one embodiment, the invention relates to a compound according to Formula I:

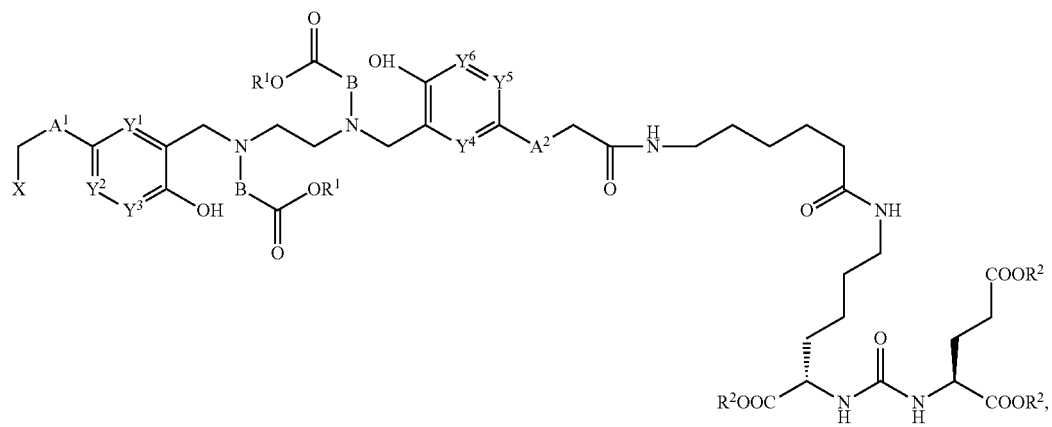

or a pharmaceutically acceptable salt thereof, wherein $A^1$ and $A^2$ are independently a divalent linking moiety comprising 1 to 10 carbon atoms in a chain, a ring, or a combination thereof, wherein at least one carbon atom is optionally replaced with O, —$NR^3$—, or —C(O)—;

B is $CR^4R^5$;

X is selected from the group consisting of:

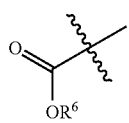

$X_1$

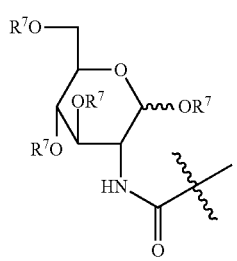

$X_2$

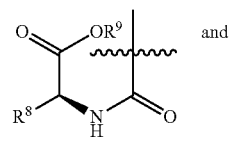 and $X_3$

-continued

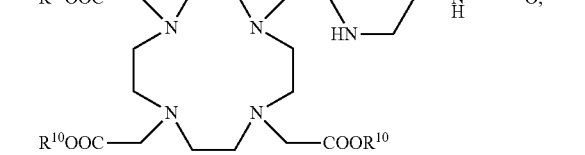

$X_4$ $Y^1$, $Y^2$, $Y^3$, $Y^4$, $Y^5$ and $Y^6$ are independently CH or N;

$R^1$, $R^2$, $R^6$, $R^9$, and $R^{10}$ are independently hydrogen or a carboxylic acid protecting group;

$R^3$ is selected from the group consisting of hydrogen, alkyl, cycloalkyl, heterocycloalkyl, aryl, alkylaryl, and heteroaryl.

$R^4$ and $R^5$ are independently hydrogen, a ($C_1$-$C_6$) alkyl group, an ethylene glycolyl group, or a propylene glycolyl group;

$R^7$ is hydrogen or a ($C_1$-$C_6$) alkanoyl group; and $R^8$ is hydrogen or an α-position substituent of an amino acid, provided that X is not $X_1$ when $A^1$, $A^2$, and B are $CH_2$ and $Y^1$, $Y^2$, $Y^3$, $Y^4$, $Y^5$, and $Y^6$ are CH.

In another embodiment, the invention relates to a compound according to Formula II:

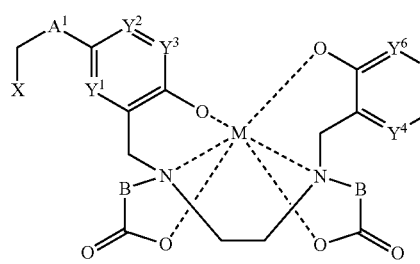
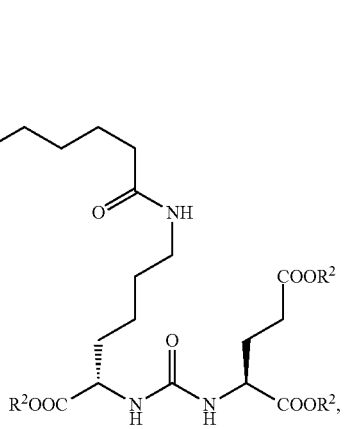

wherein

A¹ and A² are independently a divalent linking moiety comprising 1 to 10 carbon atoms in a chain, a ring, or a combination thereof, wherein at least one carbon atom is optionally replaced with O, —NR³—, or —C(O)—;

B is $CR^4R^5$;

X is selected from the group consisting of:

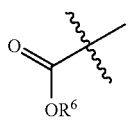
$X_1$

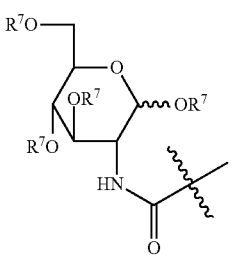
$X_2$

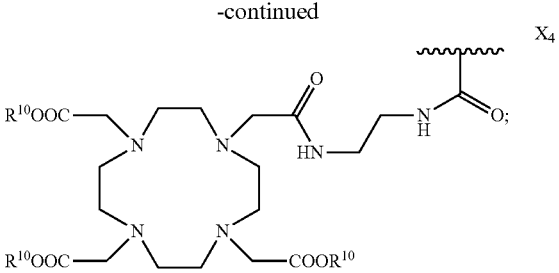

$Y^1$, $Y^2$, $Y^3$, $Y^4$, $Y^5$ and $Y^6$ are independently CH or N;

$R^1$, $R^2$, $R^6$, $R^9$, and $R^{10}$ are independently hydrogen or a carboxylic acid protecting group;

$R^3$ is selected from the group consisting of hydrogen, alkyl, cycloalkyl, heterocycloalkyl, aryl, alkylaryl, and heteroaryl.

$R^4$ and $R^5$ are independently hydrogen, a ($C_1$-$C_6$) alkyl group, an ethylene glycolyl group, or a propylene glycolyl group;

$R^7$ is hydrogen or a ($C_1$-$C_6$) alkanoyl group;

$R^8$ is hydrogen or an α-position substituent of an amino acid; and

M is a metal selected from the group consisting of $^{44}$Sc, $^{47}$Sc, $^{67}$Ga, $^{68}$Ga, $^{72}$As, $^{99m}$Tc, $^{111}$In, $^{90}$Y, $^{97}$Ru, $^{62}$Cu, $^{64}$Cu, $^{52}$Fe, $^{52m}$Mn, $^{140}$La, $^{175}$Yb, $^{153}$Sm, $^{166}$Ho, $^{149}$Pm, $^{177}$Lu, $^{142}$Pr, $^{159}$Gd, $^{213}$Bi, $^{149}$Pm, $^{67}$Cu, $^{111}$Ag, $^{199}$Au, $^{161}$Tb, $^{203}$Pb, and $^{51}$Cr, provided that X is not $X_1$ when $A^1$, $A^2$, and B are $CH_2$ and $Y^1$, $Y^2$, $Y^3$, $Y^4$, $Y^5$ and $Y^6$ are CH.

In another embodiment, the invention relates to a compound according to Formula III:

III

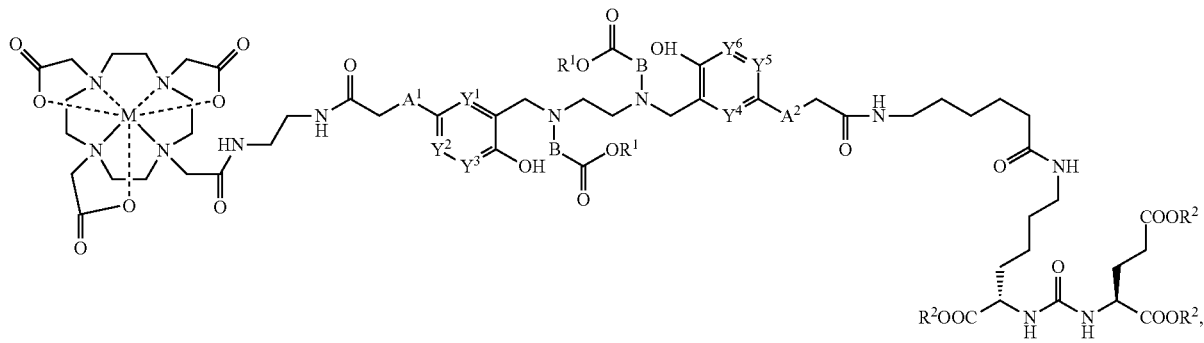

wherein $A^1$ and $A^2$ are independently a divalent linking moiety comprising 1 to 10 carbon atoms in a chain, a ring, or a combination thereof, wherein at least one carbon atom is optionally replaced with O, —$NR^3$—, or —C(O)—;

B is $CR^4R^5$;

$Y^1$, $Y^2$, $Y^3$, $Y^4$, $Y^5$ and $Y^6$ are independently CH or N;

$R^1$ and $R^2$ are independently hydrogen or a carboxylic acid protecting group;

$R^3$ is selected from the group consisting of hydrogen, alkyl, cycloalkyl, heterocycloalkyl, aryl, alkylaryl, and heteroaryl.

$R^4$ and $R^5$ are independently hydrogen, a ($C_1$-$C_6$) alkyl group, an ethylene glycolyl group, or a propylene glycolyl group; and M is a chelating metal selected from the group consisting of $^{44}$Sc, $^{47}$Sc, $^{68}$Ga, $^{99m}$Tc, $^{111}$In, $^{90}$Y, $^{153}$Sm, $^{166}$Ho, $^{177}$Lu, $^{159}$Gd, $^{213}$Bi, $^{149}$Pm, $^{161}$Tb, $^{203}$Pb, and $^{51}$Cr.

In one embodiment, the invention relates to a compound according to Formula IV:

IV

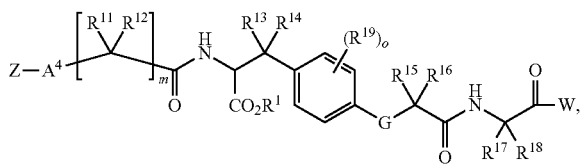

or a pharmaceutically acceptable salt thereof,
wherein
Z is a chelating moiety, or
a group having the structure:

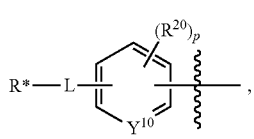

wherein $Y^{10}$ is CH or N;
L is a bond or a divalent linking moiety comprising 1 to 6 carbon atoms in a chain, a ring, or a combination thereof, wherein at least one carbon atom is optionally replaced with O, —$NR^3$—, or —C(O)—;
R* is a positron emitting radioactive isotope;

$R^{20}$ is selected from the group consisting of alkyl, alkoxyl, halide, haloalkyl, and CN;
p is an integer from 0 to 4, wherein when p is greater than 1, each $R^{20}$ is the same or different;
W is a PSMA-targeting ligand;
$A^4$ is a bond or a divalent linking moiety comprising 1 to 10 carbon atoms in a chain, a ring, or a combination thereof, wherein at least one carbon atom is optionally replaced with O, —$NR^3$—, or —C(O)—;
G is O, S, or $NR^3$;
$R^1$ is hydrogen or a carboxylic acid protecting group;
$R^3$ is selected from the group consisting of hydrogen, alkyl, cycloalkyl, heterocycloalkyl, aryl, alkylaryl, and heteroaryl.
$R^{11}$, $R^{12}$, $R^{13}$, $R^{14}$, $R^{15}$, and $R^{16}$ are each independently hydrogen, alkyl, alkoxyl, or halide;
$R^{17}$ and $R^{18}$ are each independently hydrogen, alkyl, aryl, or alkylaryl;
$R^{19}$ is selected from the group consisting of alkyl, alkoxyl, halide, haloalkyl, and CN;
m is an integer from 1 to 6; and
o is an integer from 0 to 4, wherein when o is greater than 1, each $R^{19}$ is the same or different.

In one embodiment, the invention relates to a method for imaging in a subject, comprising administering a radiolabeled compound disclosed herein to the subject; and obtaining an image of the subject or a portion of the subject. In another embodiment, the method for imaging comprises obtaining an image with a device that is capable of detecting positron emission. Additionally, the invention relates to methods of making a compound of Formula I, Formula II, and Formula IV.

DETAILED DESCRIPTION OF THE INVENTION

Figure 1:
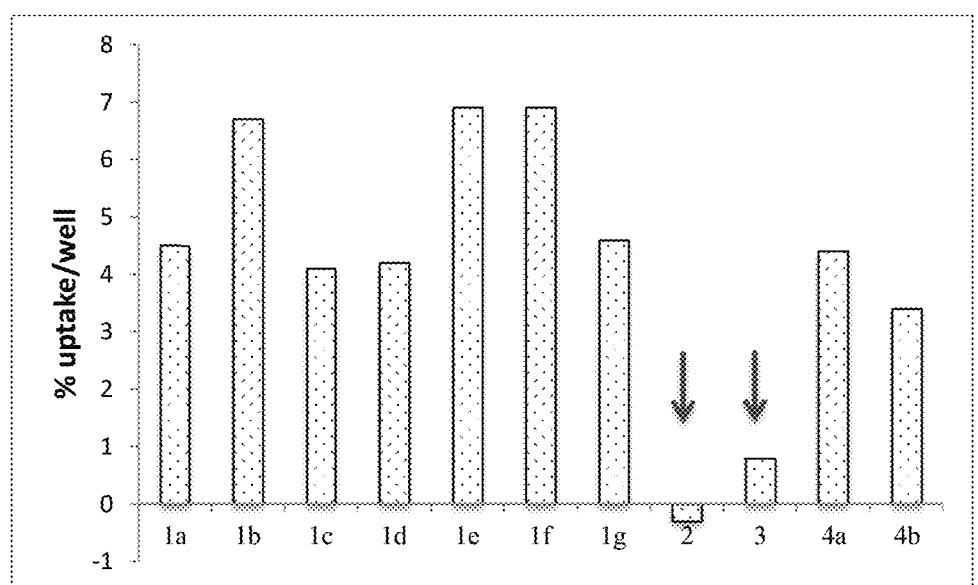
FIG. 1 depicts LNCaP cell uptake studies of HBED-PSMA derivatives for [$^{68}$Ga]1a-g, 2, 3 and 4a-b.
Figure 2A:
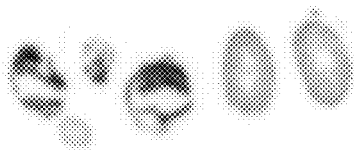
FIG. 2A-2K depict in vitro autoradiography of LNCaP tumor (left side) and mouse kidney sections (right side).
Figure 2B:
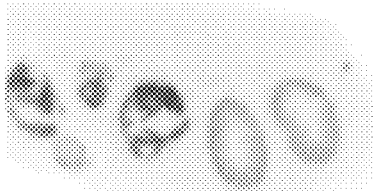
Figure 2C:
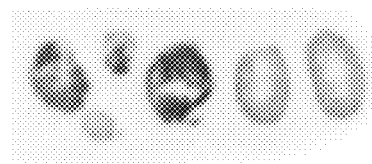
Figure 2D:
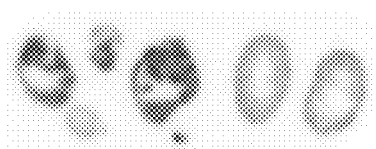
Figure 2E:
Figure 2F:
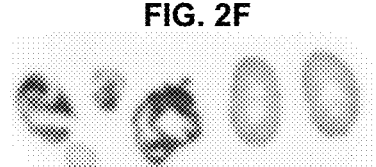
Figure 2G:
Figure 2H:
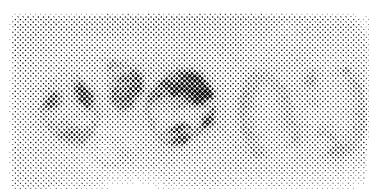
Figure 2I:
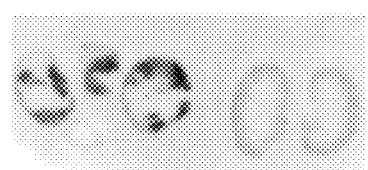
Figure 2J:
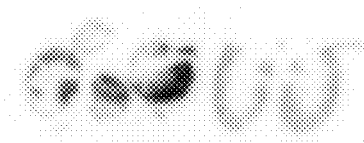
Figure 2K:

An attractive and versatile approach in obtaining radiopharmaceuticals for PET/CT is the use of a $^{68}$Ge/$^{68}$Ga generator to produce $^{68}$Ga ($T_{1/2}$=68 min) PET imaging agents. There are several advantages for using $^{68}$Ga for PET imaging: (1) It is a short-lived positron emitter (half-life 68 min, β+). (2) A $^{68}$Ge/$^{68}$Ga generator readily produces $^{68}$Ga in a laboratory setting without a nearby cyclotron. (3) The parent, $^{68}$Ge, has a physical half-life of 270 days, providing a useful life of 6 to 12 months. (4) There are several commercial vendors now supplying this generator for clinical practice on a routine basis. (5) The coordination chemistry for Ga(III) is highly flexible and large number of Ga chelates with varying stability constants and metal chelating selectivity have been reported; It has been demonstrated that $^{68}$Ga radiopharmaceuticals target various tissues or physiological processes for cancer diagnosis. (6) An important factor to consider is that the emitting β+ energy for $^{18}$F and $^{68}$Ga is 0.63 MeV and 1.90 MeV, respectively. However, despite the difference in the β+ energy, $^{18}$F and $^{68}$Ga radiopharmaceuticals give similar spatial resolution, sensitivity, image contrast, and activity recovery coefficients in human tissue, and they produce comparable clinical images in humans. These factors listed above lend themselves in support of developing $^{68}$Ga radiopharmaceuticals for clinical diagnosis.

In the past two decades there are many reports on using $^{68}$Ga labeled small molecules and peptides for imaging various tumors. Among them [$^{68}$Ga]DOTA-TOC, [$^{68}$Ga]DOTA-TATE, and [$^{68}$Ga]DOTA-NOC are the most commonly employed agents for the detection of neuroendocrine tumors (NET) expressing somatostatin receptors. Additional chelates for making $^{68}$Ga agents, such as NOTA, HBED-CC, TRAP, and many other polyaza carboxylic acids have been reported (Scheme 7). The improved chelates, such as NOTA, NODAGA, and NOTGA, will have the advantage of forming stable $^{68}$Ga labeled complexes at room temperature (i.e. stable in vitro and in vivo), which simplifies preparation and makes it more suitable in a clinical setting. It was previously reported that the stability constants (log $K_d$) for Ga-HBED, Ga-NOTA, and Ga-DOTA were 39, 31, and 21, respectively.

Scheme 7

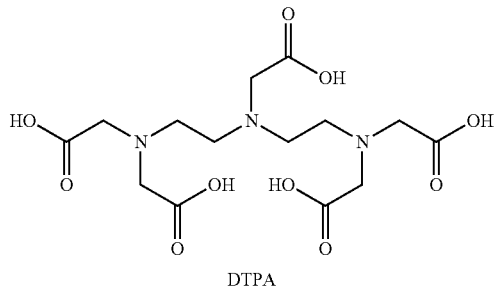

DTPA

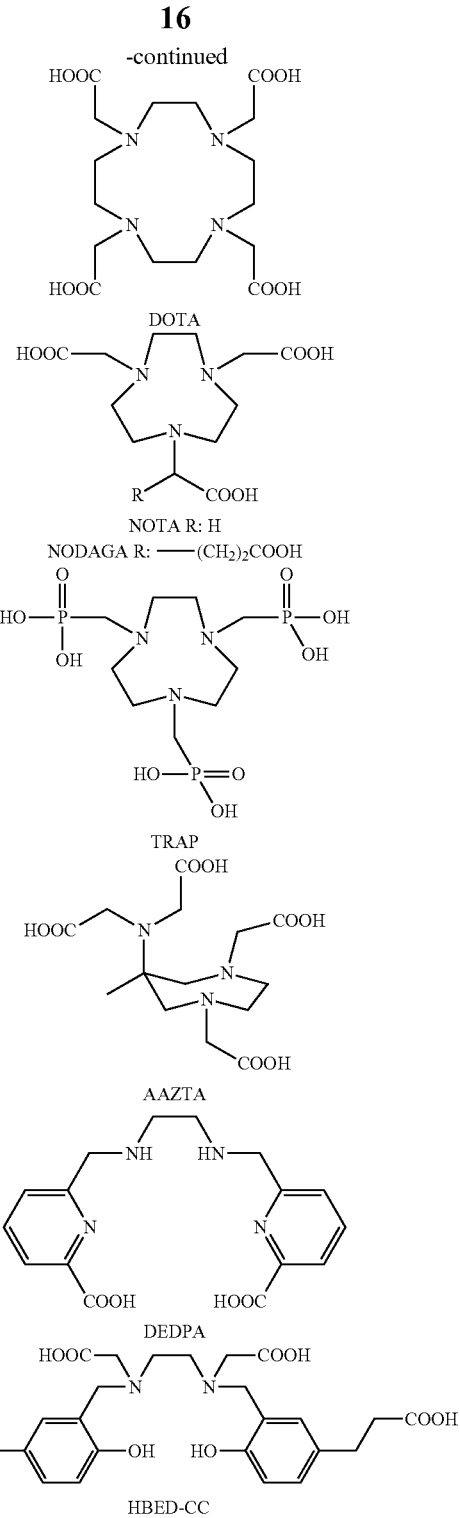

$^{68}$Ga labeled agents provide an alternative approach to producing generator-based PET imaging agents without the need for a nearby cyclotron. Several different versions of $^{68}$Ga labeled PSMA imaging agents have recently been reported. Chelating groups for complexing Ga(III), including DOTA, triazacyclononane-triphosphinate, 1,4,7-triazacyclononane-1,4-bis[methylene(hydroxymethyl)phosphinic acid]-7-[methylene(2-carboxyethyl)phosphinic acid] (NOPO), H$_2$CHXdedpa (cyclohexyl-1,2-[[6-carboxy-pyridin-2-yl]-methylamino]ethane), and (5S,8S,22S,26S)-1- amino-5,8-dibenzyl-4,7,10,19,24-pentaoxo-3,6,9,18,23,25-hexaazaoctacosane-22,26,28-tri-carboxylic acid trifluoroacetate (CHX-A"-DTPA-DUPA-Pep) were reported. All of the Ga-PSMA tagged complexes showed high affinity binding and effective targeting of PSMA expressing tumor models in vitro. However, only limited preclinical data was available for these $^{68}$Ga labeled agents.

New amide derivatives 1b-g (Scheme 8) were prepared. Of particular interest and novelty is the ligand 1g, in which both HBED (for chelating Ga(III)) and DOTA (for chelating other radioactive metal for radiation therapy) moieties are included in one molecule. This approach allows the use of one ligand to label different types of radioactive metals for multiple applications. Additionally, di-pyridyl derivatives 2 and 3, and mono-pyridyl derivatives, 4a and 4b, were also prepared.

Successful PET/CT imaging studies of tumor targeting prostate-specific membrane antigen (PSMA) using $^{68}$Ga labeled Glu-NH—CO—NH-Lys(Ahx)-HBED-CC, $^{68}$Ga]1a, has demonstrated great potential for clinical in diagnosis of prostate cancer; and successful imaging studies using $^{68}$Ga]1a, in humans have been widely reported. Five different series of Glu-NH—CO—NH-Lys(Ahx) amide derivatives have been prepared including HBED-CC derivative containing amino acids, 2-glucosamine and DOTA (1b-g), di-pyridyl derivatives (2 and 3) and mono-pyridyl derivatives (4a and 4b) (Scheme 8). The "cold" ligands, 1b-g, 2, 3, 4a and 4b displayed very good binding affinities ($IC_{50}$=3-35 nM) to the PSMA binding sites. These new ligands, 1b-g, 2, 3, 4a and 4b were labeled with $^{68}$Ga]GaCl$_3$ with high yields and excellent radiochemical purity. Results of in vivo biodistribution studies in mice after an i.v. injection of $^{68}$Ga]1b-g, 4a and 4b suggested that they are specifically localized in tissues express the PSMA sites. So, $^{68}$Ga]1b-g, 4a and 4b are useful as imaging agents for detecting PSMA expression in tumor tissues. The DOTA containing derivative, 1g, can also be separately labeled with $^{177}$Lu, $^{90}$Y and $^{213}$Bi for radiation therapy of PSMA expressing tumors.

Scheme 8

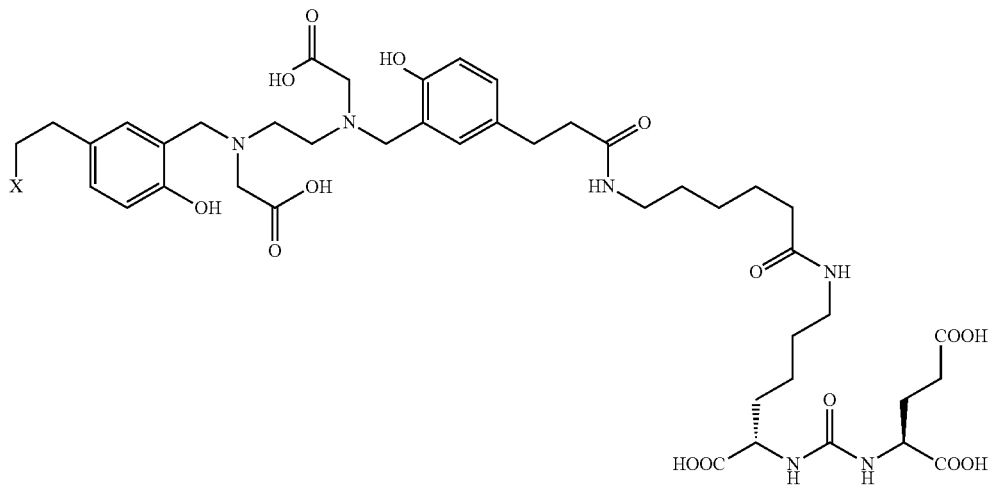

Glu-NH—CO—NH-Lys(Ahx)-HBED-CC derivatives
1a-g

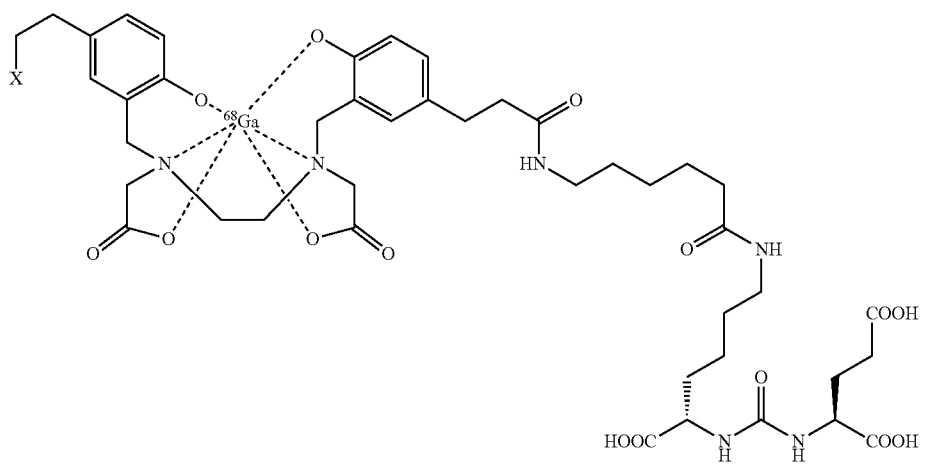

[68]Ga]Glu-NH—CO—NH-Lys(Ahx)-HBED-CC derivatives
[68]Ga]1a-g

-continued
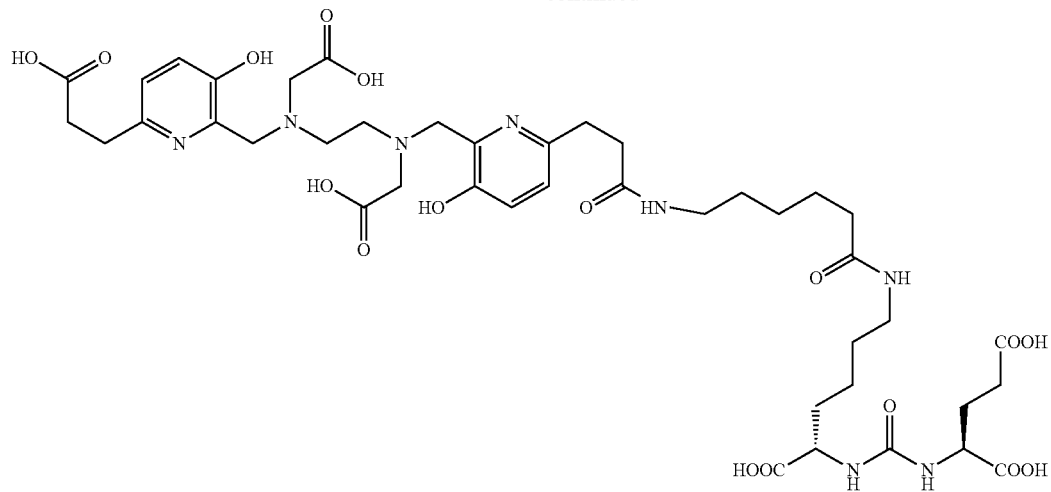
2
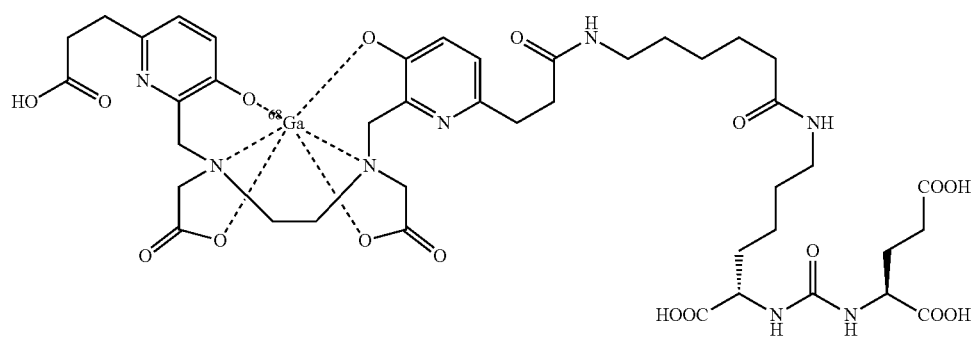
[68Ga]2
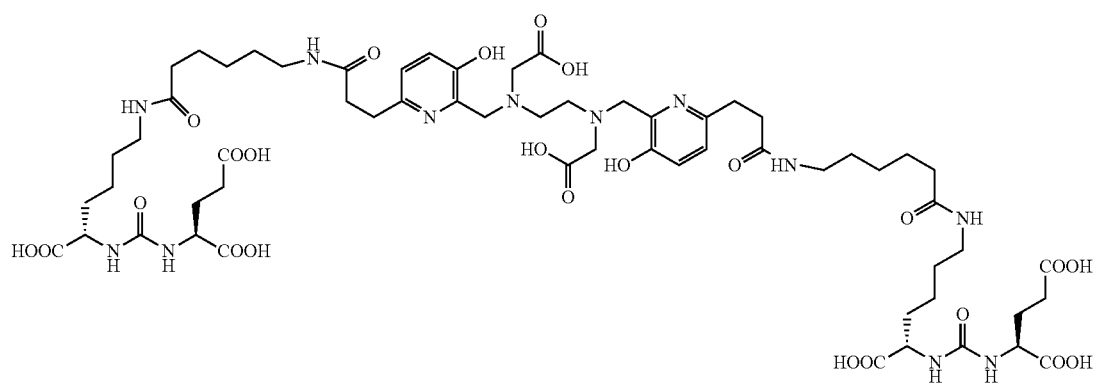
3
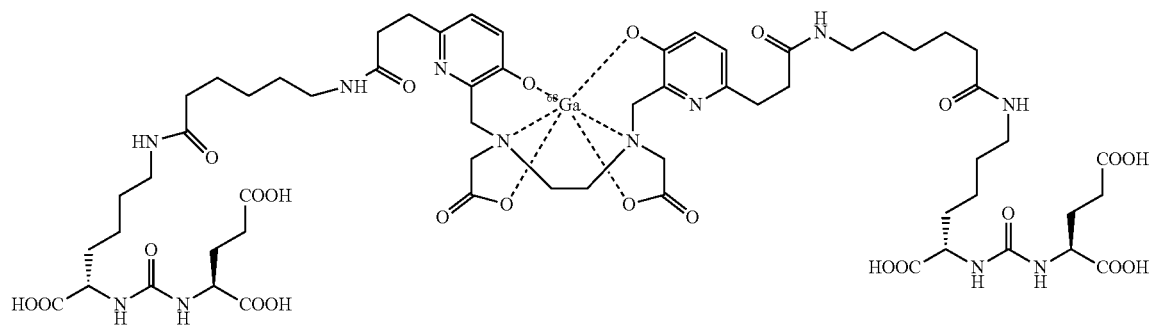
[68Ga]3

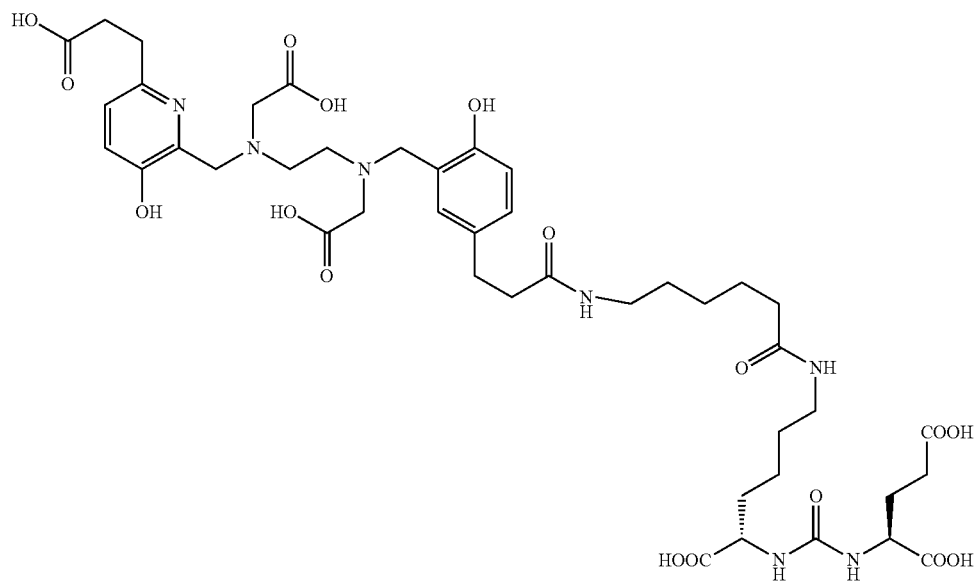
4a
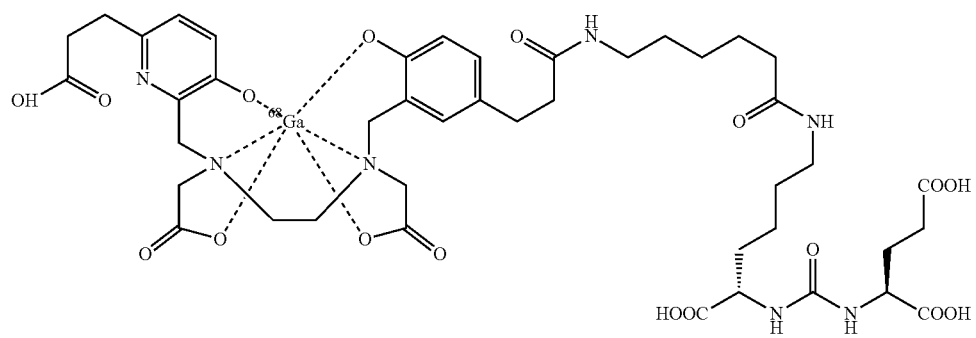
[⁶⁸Ga]4a
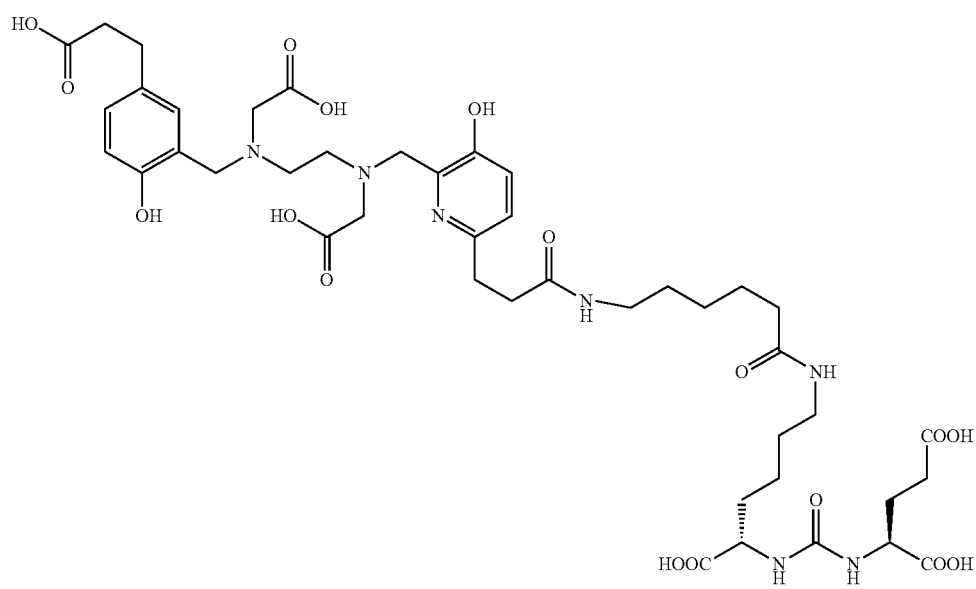
4b

-continued

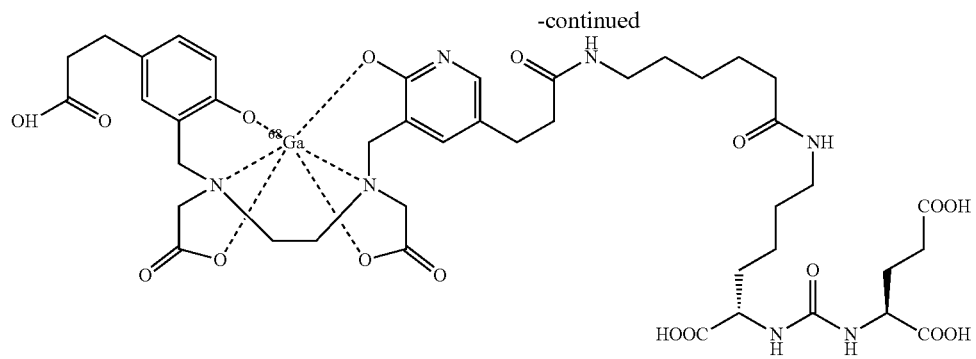

[$^{68}$Ga]4b

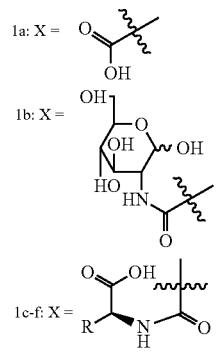

1a: X =
1b: X =
1c-f: X =

1c: R = H
1d: R = CH$_3$
1e: R = CH$_2$COOH
1f: R = (CH$_2$)$_2$COOH

1g: X =

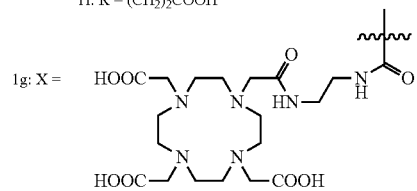

Compounds with a novel phenoxy linker were prepared. This series of PSMA inhibitors including the sub-structure of an urea based PSMA targeting moiety and a novel linker were tested by in vitro binding, tumor cell uptake as well as in vivo biodistribution studies. These PSMA inhibitors showed equal or better binding affinity than [$^{68}$Ga]1a. The novel PSMA inhibitors can have a chelating moiety, such as compounds 5a, 5a', and 5b; or they can have a radioactive group, such as compounds 5c, 5d, 5e, and 5f (Scheme 9).

Scheme 9

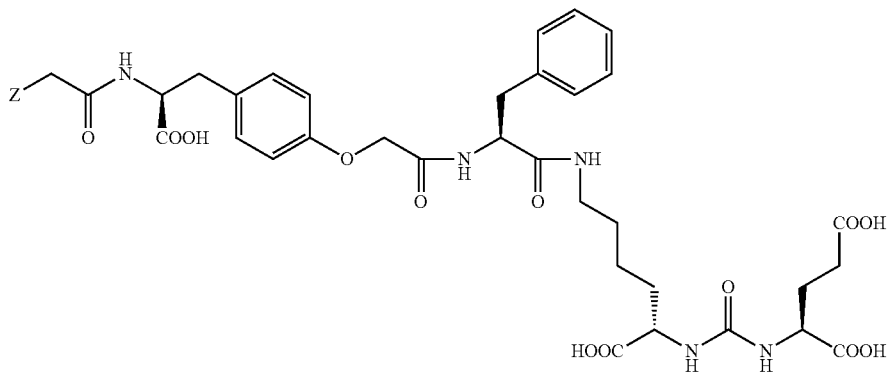

-continued

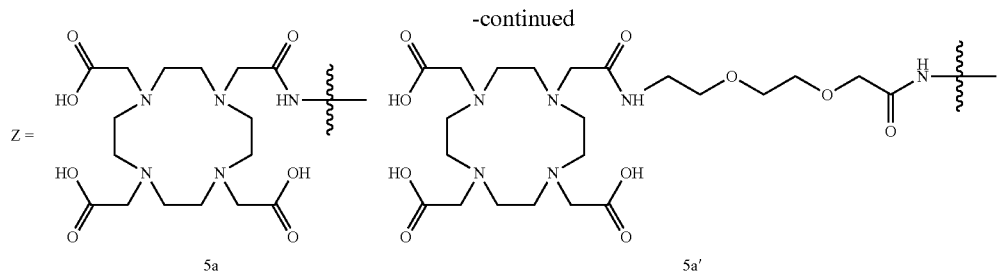

Z =

5a 5a'

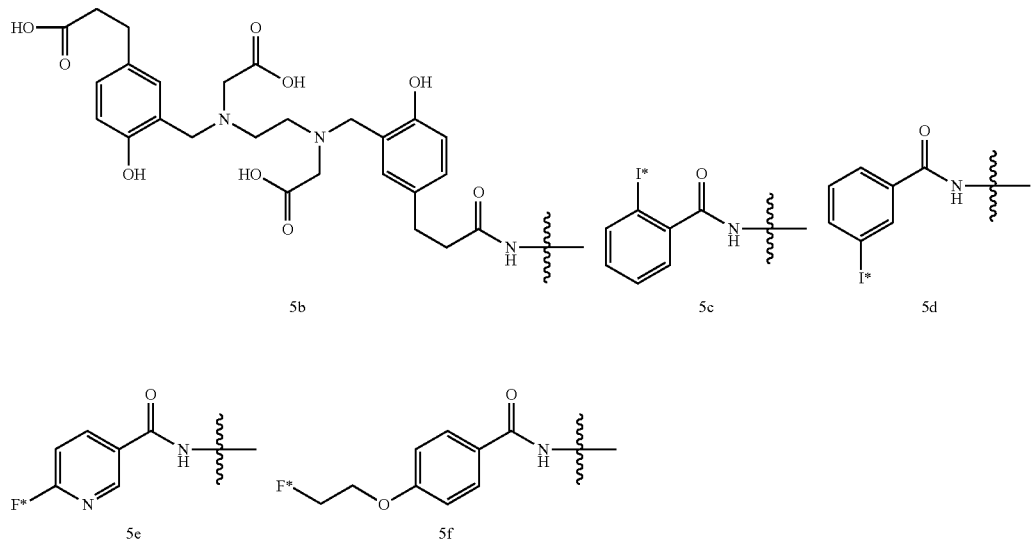

5b 5c 5d 5e 5f

In one embodiment, the invention relates to a compound according to Formula I:

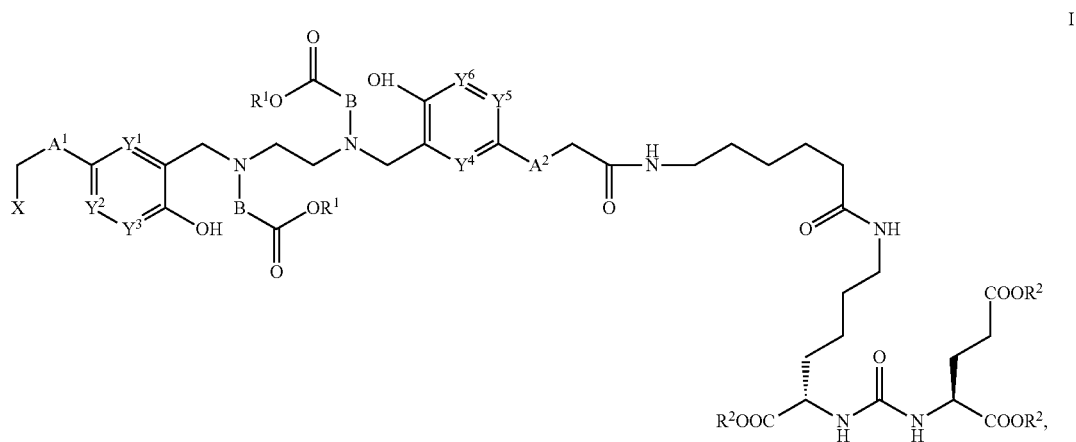

I or a pharmaceutically acceptable salt thereof, wherein $A^1$ and $A^2$ are independently a divalent linking moiety comprising 1 to 10 carbon atoms in a chain, a ring, or a combination thereof, wherein at least one carbon atom is optionally replaced with O, —$NR^3$—, or —C(O)—;

B is $CR^4R^5$;

X is selected from the group consisting of:

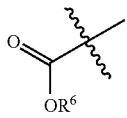

$X_1$

-continued

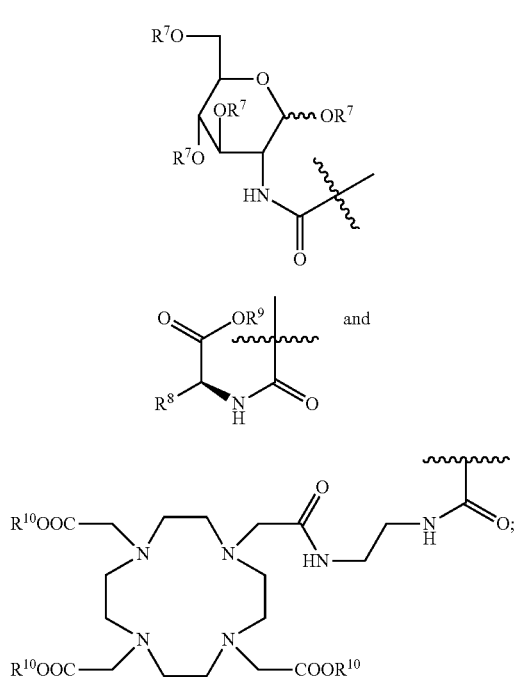

$Y^1$, $Y^2$, $Y^3$, $Y^4$, $Y^5$, and $Y^6$ are independently CH or N;

$R^1$, $R^2$, $R^6$, $R^9$, and $R^{10}$ are independently hydrogen or a carboxylic acid protecting group;

$R^3$ is selected from the group consisting of hydrogen, alkyl, cycloalkyl, heterocycloalkyl, aryl, alkylaryl, and heteroaryl.

$R^4$ and $R^5$ are independently hydrogen, a $(C_1-C_6)$ alkyl group, an ethylene glycolyl group, or a propylene glycolyl group;

$R^7$ is hydrogen or a $(C_1-C_6)$ alkanoyl group; and $R^8$ is hydrogen or an α-position substituent of an amino acid, provided that X is not $X_1$ when $A^1$, $A^2$, and B are $CH_2$ and $Y^1$, $Y^2$, $Y^3$, $Y^4$, $Y^5$, and $Y^6$ are CH.

In another embodiment, the invention relates to a compound according to Formula II:

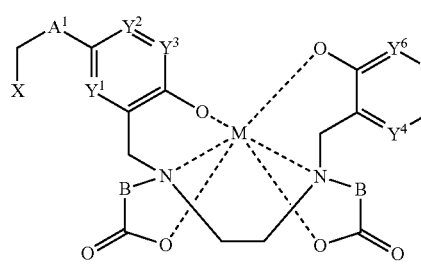

wherein $A^1$ and $A^2$ are independently a divalent linking moiety comprising 1 to 10 carbon atoms in a chain, a ring, or a combination thereof, wherein at least one carbon atom is optionally replaced with O, —$NR^3$—, or —C(O)—;

B is $CR^4R^5$;

X is selected from the group consisting of:

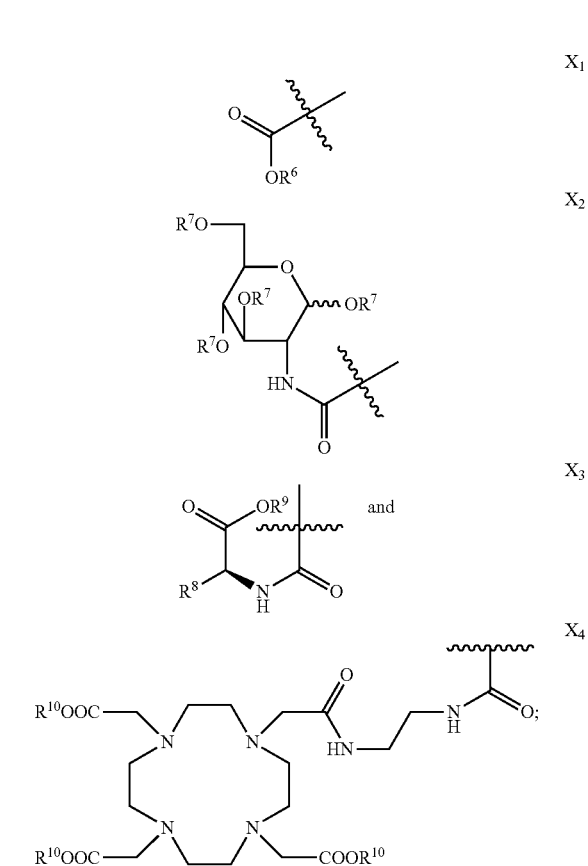

$Y^1$, $Y^2$, $Y^3$, $Y^4$, $Y^5$, and $Y^6$ are independently CH or N;

$R^1$, $R^2$, $R^6$, $R^9$, and $R^{10}$ are independently hydrogen or a carboxylic acid protecting group;

$R^3$ is selected from the group consisting of hydrogen, alkyl, cycloalkyl, heterocycloalkyl, aryl, alkylaryl, and heteroaryl.

II

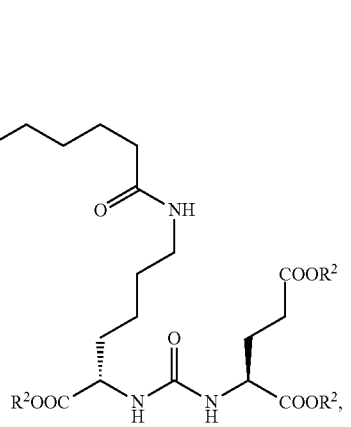

$R^4$ and $R^5$ are independently hydrogen, a $(C_1-C_6)$ alkyl group, an ethylene glycolyl group, or a propylene glycolyl group;

$R^7$ is hydrogen or a ($C_1$-$C_6$) alkanoyl group;

$R^8$ is hydrogen or an α-position substituent of an amino acid; and

M is a metal selected from the group consisting of $^{44}$Sc, $^{47}$Sc, $^{67}$Ga, $^{68}$Ga, $^{99m}$Tc, $^{72}$As, $^{111}$In, $^{90}$Y, $^{97}$Ru, $^{62}$Cu, $^{64}$Cu, $^{52}$Fe, $^{52m}$Mn, $^{140}$La, $^{175}$Yb, $^{153}$Sm, $^{166}$Ho, $^{149}$Pm, $^{177}$Lu, $^{142}$Pr, $^{159}$Gd, $^{213}$Bi, $^{149}$Pm, $^{67}$Cu, $^{111}$Ag, $^{199}$Au, $^{161}$Tb, $^{203}$Pb, $^{51}$Cr, provided that X is not $X_1$ when $A^1$, $A^2$, and B are $CH_2$ and $Y^1$, $Y^2$, $Y^3$, $Y^4$, $Y^5$, and $Y^6$ are CH.

In another embodiment, the invention relates to a compound according to Formula III:

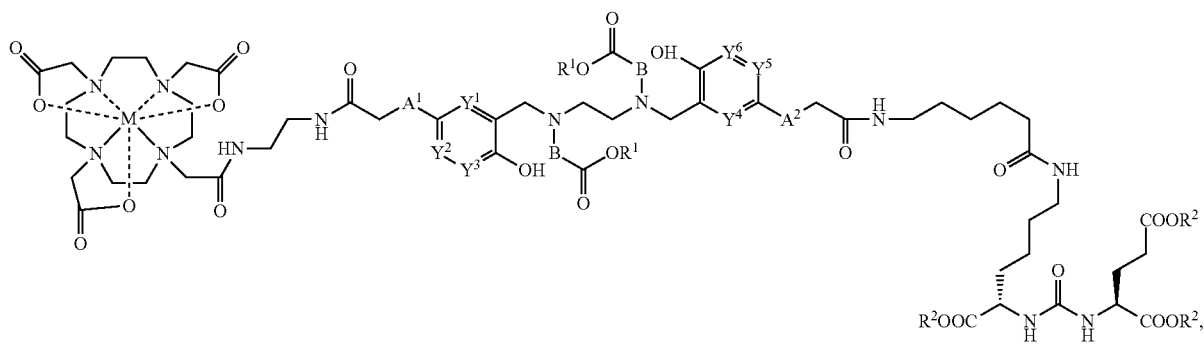

III wherein $A^1$ and $A^2$ are independently a divalent linking moiety comprising 1 to 10 carbon atoms in a chain, a ring, or a combination thereof, wherein at least one carbon atom is optionally replaced with O, —$NR^3$—, or —C(O)—;

B is $CR^4R^5$;

$Y^1$, $Y^2$, $Y^3$, $Y^4$, $Y^5$, and $Y^6$ are independently CH or N;

$R^1$ and $R^2$ are independently hydrogen or a carboxylic acid protecting group;

$R^3$ is selected from the group consisting of hydrogen, alkyl, cycloalkyl, heterocycloalkyl, aryl, alkylaryl, and heteroaryl.

$R^4$ and $R^5$ are independently hydrogen, a ($C_1$-$C_6$) alkyl group, an ethylene glycolyl group, or a propylene glycolyl group; and M is a chelating metal selected from the group consisting of $^{44}$Sc, $^{47}$Sc, $^{68}$Ga, $^{99m}$Tc, $^{111}$In, $^{90}$Y, $^{153}$Sm, $^{166}$Ho, $^{177}$Lu, $^{159}$Gd, $^{213}$Bi, $^{149}$Pm, $^{161}$Tb, $^{203}$Pb, and $^{51}$Cr.

In certain embodiments, the compounds of the present invention are represented by generalized Formulae I, II, and III and the attendant definitions, wherein $A^1$ and $A^2$ are independently a divalent linking moiety comprising 1 to 10 carbon atoms in a chain, a ring, or a combination thereof, wherein at least one carbon atom is optionally replaced with O, —$NR^3$—, or —C(O)—. In another embodiment, $A^1$ and $A^2$ are independently a divalent linking moiety comprising a $C_1$-$C_{10}$ alkylene group wherein at least one carbon atom is optionally replaced with O, —$NR^3$—, or —C(O)—. In another embodiment, $A^1$ and $A^2$ are independently $(CH_2)_n$, wherein n is an integer from 0 to 6. In another embodiment, $A^1$ and $A^2$ are independently $(CH_2)_n$, wherein n is 1, 2, or 3. In another embodiment, $A^1$ and $A^2$ are $CH_2$. Useful examples of the divalent linking moiety include —$CH_2$—, —$CH_2CH_2$—, —$CH_2CH_2CH_2$—, —$OCH_2$—, —$OCH_2CH_2$—, —$OCH_2CH_2CH_2$—, —$NHCH_2$—, —$NHCH_2CH_2$—, —$NHCH_2CH_2CH_2$—, —$COCH_2$—, —$COCH_2CH_2$—, and —$COCH_2CH_2CH_2$.

In certain embodiments, the compounds of the present invention are represented by generalized Formulae I and II and the attendant definitions, wherein X is selected from the group consisting of:

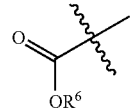

$X_1$

-continued

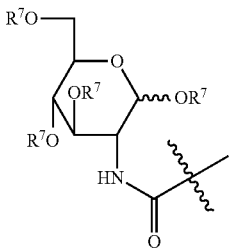

$X_2$

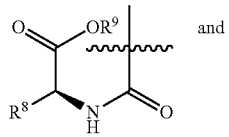

$X_3$ and

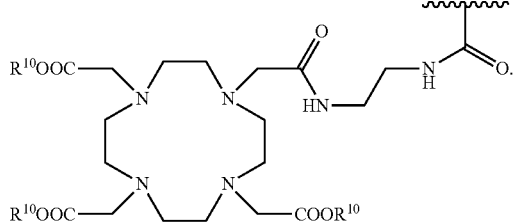

$X_4$

In another embodiment, X is a carboxylic acid group or its derivative ($X_1$). In another embodiment, X contains glucosamine group or its derivative ($X_2$). In another embodiment, X contains an amino acid residue or its derivative (X₃), including glycine, aspartic acid, glutamic acid. In another group, X contains a DOTA moiety (X₄).

Useful $R^6$, $R^9$, and $R^{10}$ groups include a methyl ester, a t-butyl ester, a benzyl ester, and an allyl ester.

In one embodiment, the ring moieties containing $Y^1$, $Y^2$, $Y^3$, $Y^4$, $Y^5$, and $Y^6$ can be derived from, e.g., benzene, pyridine, pyrimidine, pyrazine, pyridazine, and 1,2,4-triazine.

In one embodiment, the invention relates to a compound according to Formula IV:

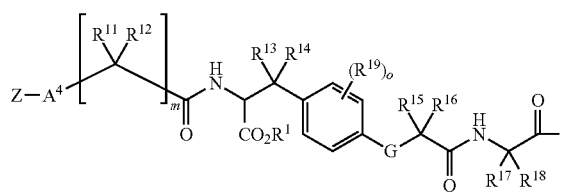

IV or a pharmaceutically acceptable salt thereof, wherein
Z is a chelating moiety, or
a group having the structure:

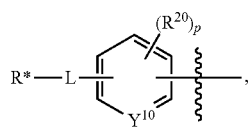

wherein $Y^{10}$ is CH or N;
L is a bond or a divalent linking moiety comprising 1 to 6 carbon atoms in a chain, a ring, or a combination thereof, wherein at least one carbon atom is optionally replaced with O, —NR³—, or —C(O)—;
R* is a positron emitting radioactive isotope;
$R^{20}$ is selected from the group consisting of alkyl, alkoxyl, halide, haloalkyl, and CN;
p is an integer from 0 to 4, wherein when p is greater than 1, each $R^{20}$ is the same or different;
W is a PSMA-targeting ligand;
$A^4$ is a bond or a divalent linking moiety comprising 1 to 10 carbon atoms in a chain, a ring, or a combination thereof, wherein at least one carbon atom is optionally replaced with O, —NR³—, or —C(O)—;
G is O, S, or NR³;
$R^1$ is hydrogen or a carboxylic acid protecting group;
$R^3$ is selected from the group consisting of hydrogen, alkyl, cycloalkyl, heterocycloalkyl, aryl, alkylaryl, and heteroaryl.
$R^{11}$, $R^{12}$, $R^{13}$, $R^{14}$, $R^{15}$, and $R^{16}$ are each independently hydrogen, alkyl, alkoxyl, or halide;
$R^{17}$ and $R^{18}$ are each independently hydrogen, alkyl, aryl, or alkylaryl;
$R^{19}$ is selected from the group consisting of alkyl, alkoxyl, halide, haloalkyl, and CN;
m is an integer from 1 to 6; and
o is an integer from 0 to 4, wherein when o is greater than 1, each $R^{19}$ is the same or different.

In one embodiment, the invention relates to a compound according to Formula IV-a:

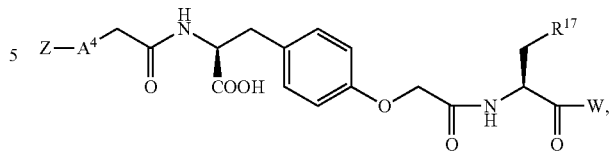

IV-a or a pharmaceutically acceptable salt thereof,
wherein $R^{17}$ is aryl; and wherein $A^4$, Z, and W are as defined herein.

Chelating moieties are known in the art and they refer to metal-binding groups. In some embodiments, Z is a chelating moiety selected from the group consisting of DOTA, HBED-CC, NOTA, NODAGA, TRAP, NOPO, PCTA, DFO, DTPA, CHX-DTPA, AAZTA, DEDPA, and oxo-Do3A. These chelating moieties are derived from 1,4,7,10-tetraazacyclododecane-N,N',N'',N'''-tetraacetic acid (=DOTA), N,N''-bis[2-hydroxy-5-(carboxyethyl)benzyl]ethylenediamine-N,N''-diacetic acid (=HBED-CC), 1,4,7-triazacyclononane-1,4,7-triacetic acid (=NOTA), 2-(4,7-bis(carboxymethyl)-1,4,7-triazonan-1-yl)pentanedioic acid (NODAGA), 2-(4,7,10-tris(carboxymethyl)-1,4,7,10-tetraazacyclododecan-1-yl)pentanedioic acid (DOTAGA), 1,4,7-triazacyclononane phosphinic acid (TRAP), 1,4,7-triazacyclononane-1-[methyl(2-carboxyethyl)phosphinic acid]-4,7-bis[methyl(2-hydroxymethyl)phosphinic acid] (NOPO), 3,6,9,15-tetraazabicyclo[9.3.1.]pentadeca-1(15),11,13-triene-3,6,9-triacetic acid (=PCTA), N'-{5-[Acetyl(hydroxy)amino]pentyl}-N-[5-({4-[(5-aminopentyl)(hydroxy)amino]-4-oxobutanoyl}amino)pentyl]-N-hydroxysuccinamide (DFO), Diethylenetriaminepentaacetic acid (DTPA), Trans-cyclohexyl-diethylenetriaminepentaacetic acid (CHX-DTPA), 1-oxa-4,7,10-triazacyclododecane-4,7,10-triacetic acid (oxo-Do3A), p-isothiocyanatobenzyl-DTPA (SCN-Bz-DTPA), 1-(p-isothiocyanatobenzyl)-3-methyl-DTPA (1B3M), 2-(p-isothiocyanatobenzyl)-4-methyl-DTPA (1M3B), 1-(2)-methyl-4-isocyanatobenzyl-DTPA (MX-DTPA). Chelating moieties are disclosed in US 2016/0228587, which is incorporated by reference herein in its entirety.

Positron emitting radioactive isotopes are known in the art, and they can be, for example, ¹¹C, ¹⁸F, ¹²³I, ¹²⁵I, and ¹³¹I.

PSMA-targeting ligands are known in the art and they refer to groups that can bind to PSMA. PSMA-targeting ligands can be urea-based ligand systems discussed herein.

In some embodiments, the PSMA-targeting ligand W has the structure:

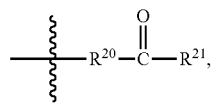

wherein $R^{20}$ and $R^{21}$ are each independently an amino acid residue linked via an amino group thereof to the adjacent —C(O)— group.

In some embodiments, W has the structure:

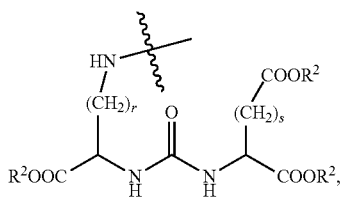

wherein $R^2$ is hydrogen or a carboxylic acid protecting group, r is an integer from 1 to 6, and s is an integer from 1 to 4. In one embodiment, W has the structure:

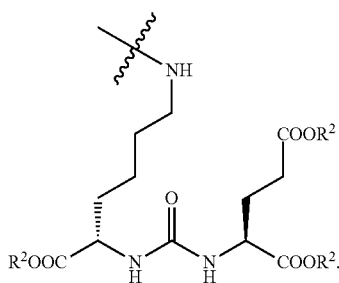

In certain embodiments, the compounds of the present invention are represented by generalized Formulae IV and IV-a, and the attendant definitions.

In some embodiments, L is a bond or a divalent linking moiety comprising 1 to 6 carbon atoms in a chain, a ring, or a combination thereof, wherein at least one carbon atom is optionally replaced with O, $-NR^3-$, or $-C(O)-$. In some embodiment, L is a bond. In another embodiment, L is a divalent linking moiety comprising a $C_1$-$C_6$ alkylene group wherein at least one carbon atom is optionally replaced with O, $-NR^3-$, or $-C(O)-$. In some embodiments, L is $(CH_2)_n$, $-(OCH_2CH_2)_n-$, $-(NHCH_2CH_2)_n-$, or $-C(O)(CH_2)_n-$, wherein n is 1, 2, or 3. In another embodiment, L is $-OCH_2CH_2-$. Other useful examples of the divalent linking moiety include $-CH_2-$, $-CH_2CH_2-$, $-CH_2CH_2CH_2-$, $-OCH_2CH_2CH_2-$, $-NHCH_2CH_2-$, $-NHCH_2CH_2CH_2-$, $-COCH_2-$, $-COCH_2CH_2-$, and $-COCH_2CH_2CH_2-$.

In some embodiments, $A^4$ is a bond, $(CH_2)_n$, $-NHC(O)-$, $-(OCH_2CH_2)_n-$, $-(NHCH_2CH_2)_n-$, $-NH(CO)CH_2-$, $-NHC(O)CH_2(OCH_2CH_2)_n-$, or $-NHC(O)CH_2(NHCH_2CH_2)_n-$, wherein n is 1, 2 or 3. In some embodiments, $A^4$ is a bond, $-(OCH_2CH_2)_n-$, or $-NHC(O)CH_2(OCH_2CH_2)_n-$, wherein n is 1 or 2. In one embodiment, $A^4$ is $-NHC(O)CH_2(OCH_2CH_2)_2-$. In another embodiment, $A^4$ is a bond. In another embodiment, $A^4$ is $-NHC(O)-$.

In some embodiments, $R^{17}$ is an aryl. In one embodiment, $R^{17}$ is optionally substituted phenyl. In another embodiment, $R^{17}$ is optionally substituted naphthyl.

In some embodiments, the invention relates to a complex comprising a compound according to Formula IV chelated to a metal M wherein Z is a chelating moiety. In some embodiments, the metal M is selected from the group consisting of $^{44}$Sc, $^{47}$Sc, $^{203}$Pb, $^{67}$Ga, $^{68}$Ga, $^{72}$As, $^{99m}$Tc, $^{111}$In, $^{90}$Y, $^{97}$Ru, $^{62}$Cu, $^{64}$Cu, $^{52}$Fe, $^{52m}$Mn, $^{140}$La, $^{175}$Yb, $^{153}$Sm, $^{166}$Ho, $^{149}$Pm, $^{177}$Lu, $^{142}$Pr, $^{159}$Gd, $^{213}$Bi, $^{67}$Cu, $^{111}$Ag, $^{199}$Au, $^{161}$Tb, and $^{51}$Cr, $^{99m}$Tc.

In some embodiments, the complex has the structure:

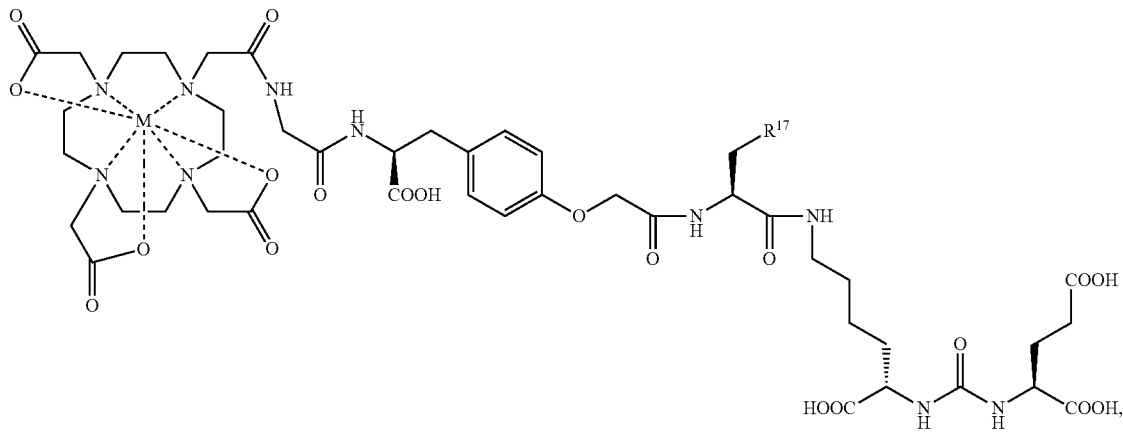

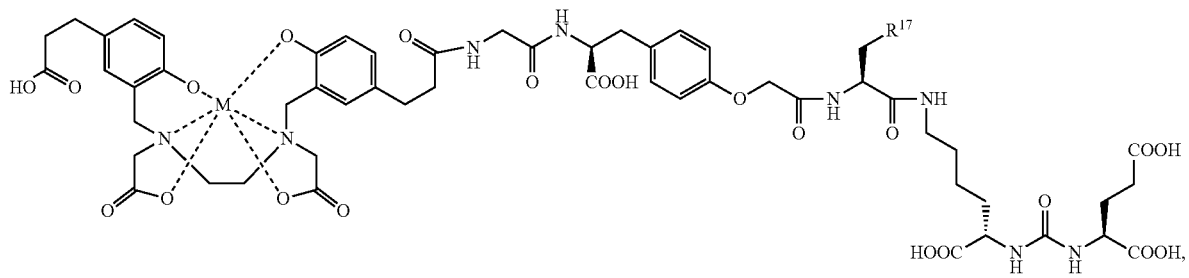

-continued

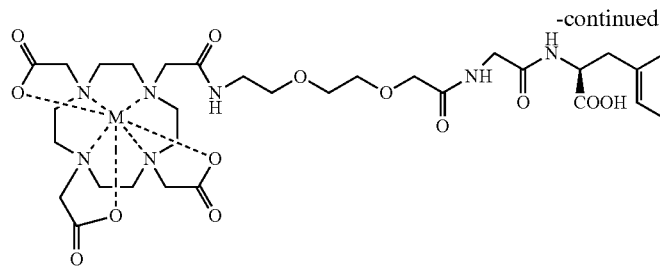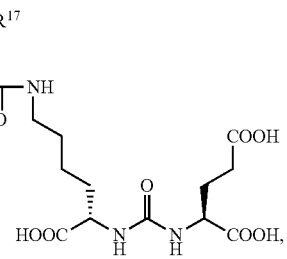

wherein $R^{17}$ is aryl. In some embodiments, $R^{17}$ is phenyl. In some embodiments, M is $^{68}$Ga.

In one embodiment, the invention relates to methods of making a compound of Formulae I, II, and III.

In one embodiment, the present invention provides pharmaceutical compositions comprising a pharmaceutical acceptable carrier and a compound of Formulae I, II, III, and IV. The present invention also provides pharmaceutical compositions comprising a pharmaceutical acceptable carrier and a pharmaceutically acceptable salt of a compound of Formula I. In certain embodiments, the pharmaceutical composition will comprise the reaction precursors necessary generate the compound or salt according to Formula I or subformula thereof upon combination with a radiolabeled precursor.

In one embodiment, the present invention provides a kit formulation, comprising a sterile container containing a compound of Formula I or Formula IV or a pharmaceutically acceptable isotonic solution for i.v. injection thereof, and instructions for diagnostic imaging (for example, $^{68}$Ga) and radiation therapy (for example, $^{90}$Y) use.

The present invention also provides for methods of in vivo imaging, comprising administering an effective amount of a radiometal complex or a radioactive compound disclosed herein to a subject, and detecting the pattern of radioactivity of the complex or compound in the subject. In one embodiment, the invention relates to a method for imaging in a subject, comprising administering a radiolabeled compound disclosed herein to the subject; and obtaining an image of the subject or a portion of the subject. In another embodiment, the method for imaging comprises obtaining an image with a device that is capable of detecting positron emission.

The present invention also provides for methods of in vivo imaging, comprising administering an effective amount of a radiometal complex or a radioactive compound disclosed herein to a subject, and detecting the pattern of radioactivity of the complex or compound in said subject.

Typical subjects to which compounds of the invention may be administered will be mammals, particularly primates, especially humans. For veterinary applications, a wide variety of subjects will be suitable, e.g. livestock such as cattle, sheep, goats, cows, swine and the like; poultry such as chickens, ducks, geese, turkeys, and the like; and domesticated animals particularly pets such as dogs and cats. For diagnostic or research applications, a wide variety of mammals will be suitable subjects including rodents (e.g. mice, rats, hamsters), rabbits, primates, and swine such as inbred pigs and the like. Additionally, for in vitro applications, such as in vitro diagnostic and research applications, body fluids and cell samples of the above subjects will be suitable for use such as mammalian, particularly primate such as human, blood, urine or tissue samples, or blood urine or tissue samples of the animals mentioned for veterinary applications.

Radiopharmaceuticals in accordance with this invention can be positron emitting gallium-68 complexes which, when used in conjunction with a $^{68}$Ge/$^{68}$Ga parent/daughter radionuclide generator system, will allow PET imaging studies, avoiding the expense associated with operation of an in-house cyclotron for radionuclide production.

The complexes are formulated into aqueous solutions suitable for intravenous administration using standard techniques for preparation of parenteral diagnostics. An aqueous solution of the present complexes can be sterilized, for example, by passage through a commercially available 0.2 micron filter. The complexes are typically administered intravenously in an amount effective to provide tissue concentrations of the radionuclide complex sufficient to provide the requisite photon (gamma/positron) flux for imaging the tissue. The dosage level for any given complex of this invention to achieve acceptable tissue imaging depends on its particular biodistribution and the sensitivity of the tissue imaging equipment. Effective dosage levels can be ascertained by routine experimentation. They typically range from about 5 to about 30 millicuries. Where the complexes are gallium-68 complexes for PET imaging of myocardial tissue, adequate photon fluxes can be obtained by intravenous administration of from about 5 to about 30 millicuries of the complex.

The term "amino acid" used herein include both naturally occurring amino acids and unnatural amino acids. Naturally occurring amino acid refers to amino acids that are known to be used for forming the basic constituents of proteins, including alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine, valine, and combinations thereof. Examples of unnatural amino acids include: an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α-hydroxy containing acid; an amino thio acid containing amino acid; an α,α disubstituted amino acid; a β-amino acid; and a cyclic amino acid other than proline.

The term "alkanoyl" used herein refers to the following structure:

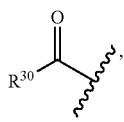

wherein $R^{30}$ is alkyl, cycloalkyl, aryl, (cycloalkyl)alkyl, or arylalkyl, any of which is optionally substituted. The acyl group can be, for example, $C_{1-6}$ alkylcarbonyl (such as, for example, acetyl), arylcarbonyl (such as, for example, benzoyl), levulinoyl, or pivaloyl. In another embodiment, the acyl group is benzoyl.

The term "alkyl" used herein includes both branched and straight-chain saturated aliphatic hydrocarbon groups, having the specified number of carbon atoms. Examples of alkyl include, but are not limited to, methyl, ethyl, n-propyl, i-propyl, n-butyl, s-butyl, t-butyl, n-pentyl, and s-pentyl. Preferred alkyl groups are $C_1$-$C_{10}$ alkyl groups. Typical $C_{1-10}$ alkyl groups include methyl, ethyl, n-propyl, n-butyl, n-pentyl, n-hexyl, n-heptyl, n-octyl, n-nonyl, and n-decyl, isopropyl, sec-butyl, tert-butyl, iso-butyl, iso-pentyl, neo-pentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl, among others. In one embodiment, useful alkyl groups are selected from straight chain $C_{1-6}$ alkyl groups and branched chain $C_{3-6}$ alkyl groups. Typical $C_{1-6}$ alkyl groups include methyl, ethyl, propyl, isopropyl, butyl, sec-butyl, tert-butyl, iso-butyl, pentyl, 3-pentyl, hexyl, among others. In one embodiment, useful alkyl groups are selected from straight chain $C_{2-6}$ alkyl groups and branched chain $C_{3-6}$ alkyl groups. Typical $C_{2-6}$ alkyl groups include ethyl, propyl, isopropyl, butyl, sec-butyl, tert-butyl, iso-butyl, pentyl, 3-pentyl, hexyl among others. In one embodiment, useful alkyl groups are selected from straight chain $C_{1-4}$ alkyl groups and branched chain $C_{3-4}$ alkyl groups. Typical $C_{1-4}$ alkyl groups include methyl, ethyl, propyl, isopropyl, butyl, sec-butyl, tert-butyl, and iso-butyl.

The term "cycloalkyl" used herein includes saturated ring groups, having the specified number of carbon atoms, such as cyclopropyl, cyclobutyl, cyclopentyl, or cyclohexyl. Cycloalkyl groups typically will have 3 to about 12 ring members. In one embodiment, the cycloalkyl has one or two rings. In another embodiment, the cycloalkyl is a $C_3$-$C_8$ cycloalkyl. In another embodiment, the cycloalkyl is a $C_{3-7}$ cycloalkyl. In another embodiment, the cycloalkyl is a $C_{3-6}$ cycloalkyl. Exemplary cycloalkyl groups include cyclopropyl, cyclobutyl, cyclopentyl, cyclohexyl, cycloheptyl, cyclooctyl, norbornyl, decalin, and adamantyl.

The term "heterocycloalkyl" used herein refers to saturated heterocyclic alkyl groups.

The term "aryl" used herein includes $C_{6-14}$ aryl, especially $C_{6-10}$ aryl. Typical $C_{6-14}$ aryl groups include phenyl, naphthyl, phenanthryl, anthracyl, indenyl, azulenyl, biphenyl, biphenylenyl, and fluorenyl groups, more preferably phenyl, naphthyl, and biphenyl groups.

The term "heteroaryl" or "heteroaromatic" used herein refers to groups having 5 to 14 ring atoms, with 6, 10 or 14 π electrons shared in a cyclic array, and containing carbon atoms and 1, 2, or 3 oxygen, nitrogen or sulfur heteroatoms, or 4 nitrogen atoms. In one embodiment, the heteroaryl group is a 5- to 10-membered heteroaryl group. Examples of heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. Typical heteroaryl groups include thienyl (e.g., thien-2-yl and thien-3-yl), furyl (e.g., 2-furyl and 3-furyl), pyrrolyl (e.g., pyrrol-1-yl, 1H-pyrrol-2-yl and 1H-pyrrol-3-yl), imidazolyl (e.g., imidazol-1-yl, 1H-imidazol-2-yl and 1H-imidazol-4-yl), tetrazolyl (e.g., tetrazol-1-yl and tetrazol-5-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, pyrimidin-5-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl). A 5-membered heteroaryl can contain up to 4 heteroatoms. A 6-membered heteroaryl can contain up to 3 heteroatoms. Each heteroatom is independently selected from nitrogen, oxygen and sulfur.

Suitable carboxylic acid protecting group are well known and include, for example, any suitable carboxylic acid protecting group disclosed in Wuts, P. G. M. & Greene, T. W., *Greene's Protective Groups in Organic Synthesis*, 4rd Ed., pp. 16-430 (J. Wiley & Sons, 2007), herein incorporated by reference in its entirety. Those skilled in the art will be familiar with the selection, attachment, and cleavage of protecting groups and will appreciate that many different protective groups are known in the art, the suitability of one protective group or another being dependent on the particular synthetic scheme planned. Suitable carboxylic acid protecting group include, for example, the methyl esters, t-butyl esters, benzyl esters, and allyl esters.

Materials and Methods

General

All reagents and solvents were purchased commercially (Aldrich, Acros, or Alfa Inc.) and were used without further purification, unless otherwise indicated. Solvents were dried through a molecular sieve system (Pure Solve Solvent Purification System; Innovative Technology, Inc.). $^1$H and $^{13}$C NMR spectra were recorded on a Bruker Avance spectrometer at 400 MHz and 100 MHz, respectively, and referenced to NMR solvents as indicated. Chemical shifts are reported in ppm (δ), with a coupling constant, J, in Hz. The multiplicity is defined by singlet (s), doublet (d), triplet (t), broad (br), and multiplet (m). High-resolution mass spectrometry (HRMS) data was obtained with an Agilent (Santa Clara, Calif.) G3250AA LC/MSD TOF system. Thin-layer chromatography (TLC) analyses were performed using Merck (Darmstadt, Germany) silica gel 60 $F_{254}$ plates. Generally, crude compounds were purified by flash column chromatography (FC) packed with silica gel (Aldrich). High performance liquid chromatography (HPLC) was performed on an Agilent 1100 series system. A gamma counter (Cobra II auto-gamma counter, Perkin-Elmer) measured $^{68}$Ga radioactivity. Reactions of non-radioactive chemical compounds were monitored by thin-layer chromatography (TLC) analysis with pre-coated plates of silica gel 60 $F_{254}$. An aqueous solution of [$^{68}$Ga]GaCl$_3$ was obtained from a $^{68}$Ge/$^{68}$Ga generator (Radiomedix Inc.). Solid-phase extraction cartridges (SEP Pak® Light QMA, Oasis® HLB 3cc) were obtained from Waters (Milford, Mass., USA).

Synthesis of example compounds, 1a-g, 2, 3, 4a-b, and 5a-f containing Glu-NH—CO—NH-Lys(Ahx)-HBED-CC group, were prepared by reactions described in the following sections. It is noted that [$^{68}$Ga]1a, (commonly referred to as PSMA-11) is a known PSMA imaging agent, and it is presented as a positive control for binding to PSMA.

Previously reported synthesis of Glu-NH—CO—NH-Lys(Ahx)-HBED-CC (monmer, 1a) and (Glu-NH—CO—NH-Lys(Ahx))$_2$-HBED-CC (dimer) employed a Fe-complex of HBED-CC as the intermediate. The reaction scheme was not very efficient, a new scheme without the use of Fe(III) HBED-CC complex was devised (Scheme 10).

Compound 12, 13, 30, 31 and 32 were synthesized according the following references: Ghassan Bechara, Nadine Leygue, Chantal Galaup, Béatrice Mestre-Voegtlé, Claude Picard. *Tetrahedron*. 2010, 66, 8594-8604; Pijus K. Mandal, John S. McMurray. *J. Org. Chem*. 2007, 72, 6599-6601; Eric Assen B. Kantchev, Guang-Rong Peh, Chi Zhang, Jackie Y. Ying. *Org. Lett*. 2008, 10(18), 3949-3952.

Methyl 3-(4-hydroxyphenyl)propanoate (A) was prepared by O-methylation (esterification) of carboxylic acids in good yield (84%). The methyl ester was treated with MgCl$_2$ and paraformaldehyde to give salicylaldehyde, B, in excellent yield (90%). Condensation of salicylaldehyde with ethylenediamine produced Schiff base without further purification. The corresponding secondary amine, 7, was obtained from the Schiff base after the reduction reaction with Sodium Borohydride in 69% yield. The secondary amines were condensed with excess amount of tert-butyl bromoacetate to afford 8 in 87% yield. The methyl ester group of compound, 8 was selectively removed by NaOH hydrolysis to give acid, 9, in 96% yield. Subsequent HOBt/EDCI promoted coupling reaction with tert-butyl 2-(3-((S)-6-(6-aminohexanamido)-1-tert-butoxy-1-oxohexan-2-yl)ureido)pentanedioate (10) produced protected Glu-NH—CO—NH-Lys(Ahx)-HBED-CC (11a). The intermediates 11b-g were synthesized by coupling reaction of 11a with corresponding amino acids, in 22-63% yield. The tert-butyl protection group was then removed to give 1a-g in 26-79% yield. The precursor, 1a-g employed as the starting material for labeling, and subsequently forming complex with GaCl$_3$ afforded "cold compound" [$^{nat}$Ga]1a-g.

Scheme 12 and 13 outline the synthetic strategy applied to efficiently produce compound 2 and 3. The key intermediate, 20, was successfully prepared through a 9 steps reaction (Scheme 11). Subsequently, HOBt/EDCI promoted coupling reaction with 10 produced protected Glu-NH—CO—NH-Lys(Ahx)-HPyED-CC monomer (21) and dimer (22), followed by a simple acidic de-protection to give final compound 2 and 3.

For the synthesis of the other pyridinyl derivatives linked via amide bonds, the intermediates 28 (Scheme 14) and 35 (Scheme 16) were readily prepared according to similar method. The methyl ester was converted to carboxylic acid by treating with NaOH, which on coupling reaction with 10 provided Glu-NH—CO—NH-Lys(Ahx)-HBE-HPyED-CC (29) and Glu-NH—CO—NH-Lys(Ahx)-HPyED-HBED-CC (36). The protection group was easily removed in the presence of TFA to give 4a and 4b.

Scheme 10

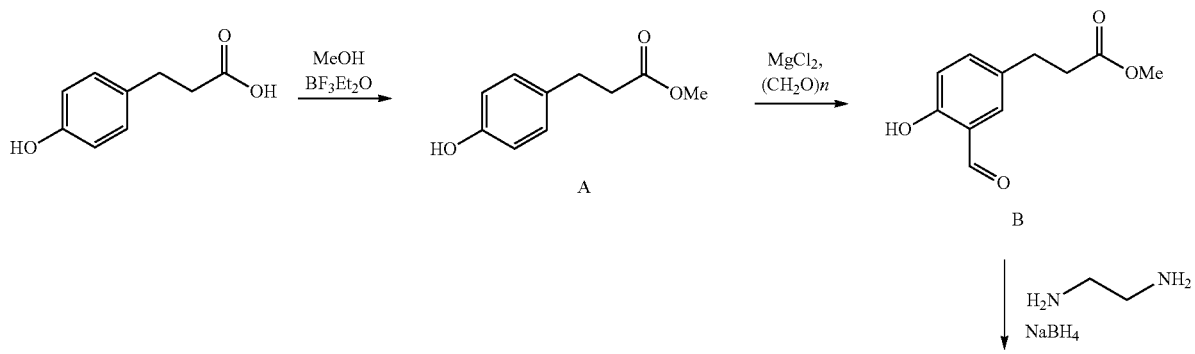

41
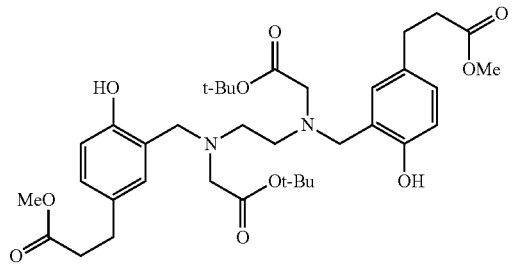
8
42
-continued
K$_2$CO$_3$
tert-Butyl
bromoacetate
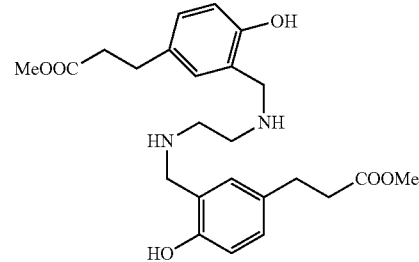
7
NaOH/MeOH ↓
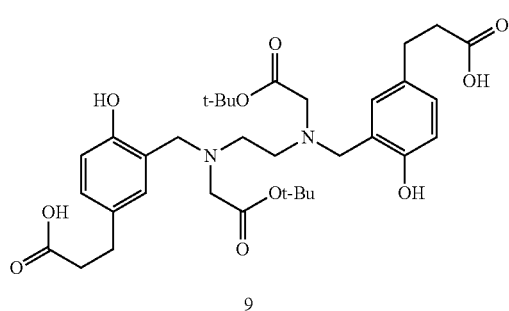
9
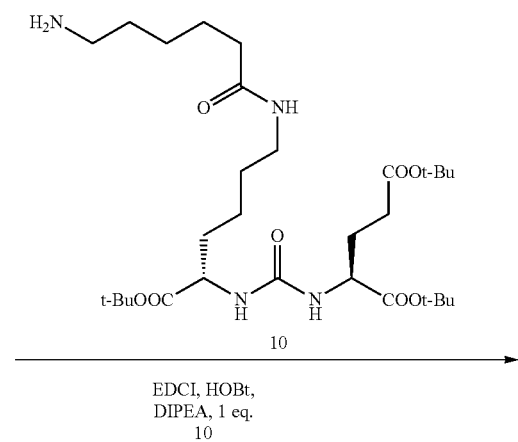
10
EDCI, HOBt,
DIPEA, 1 eq.
10
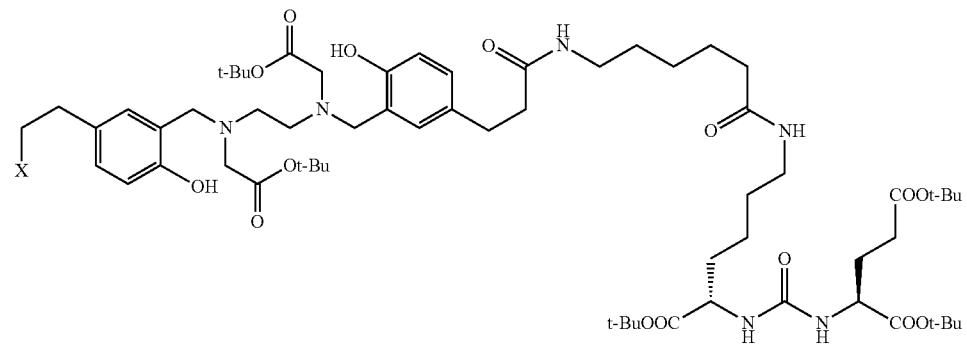
11

-continued
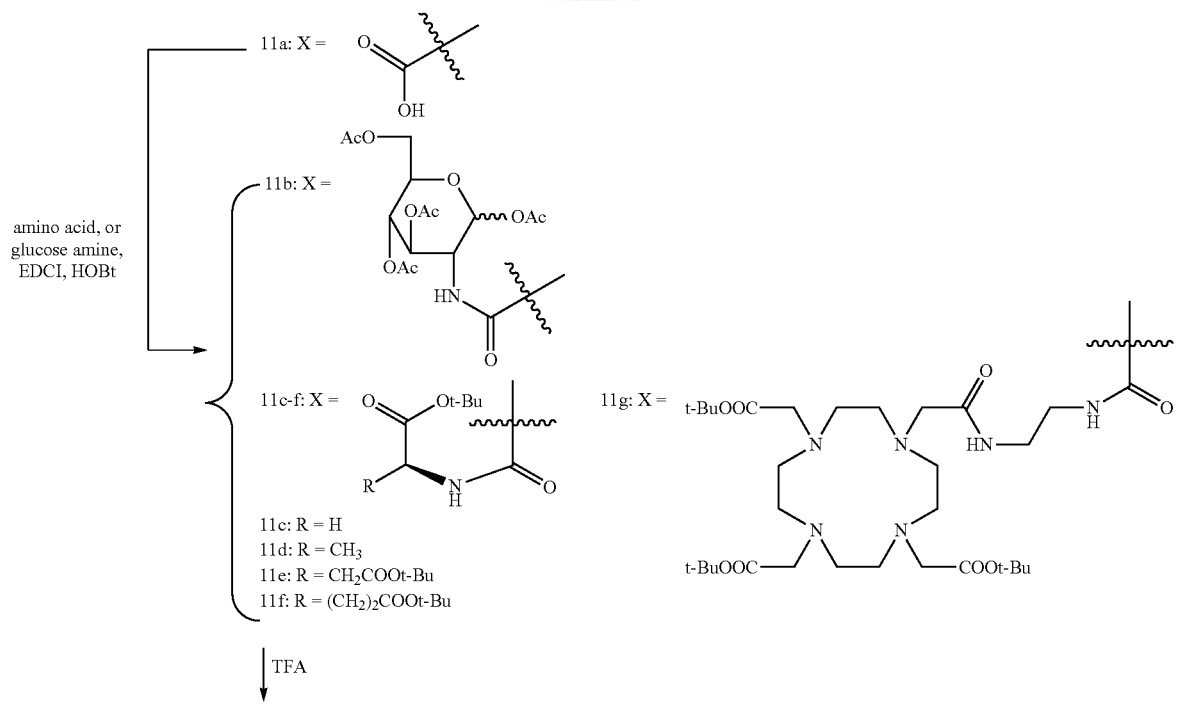
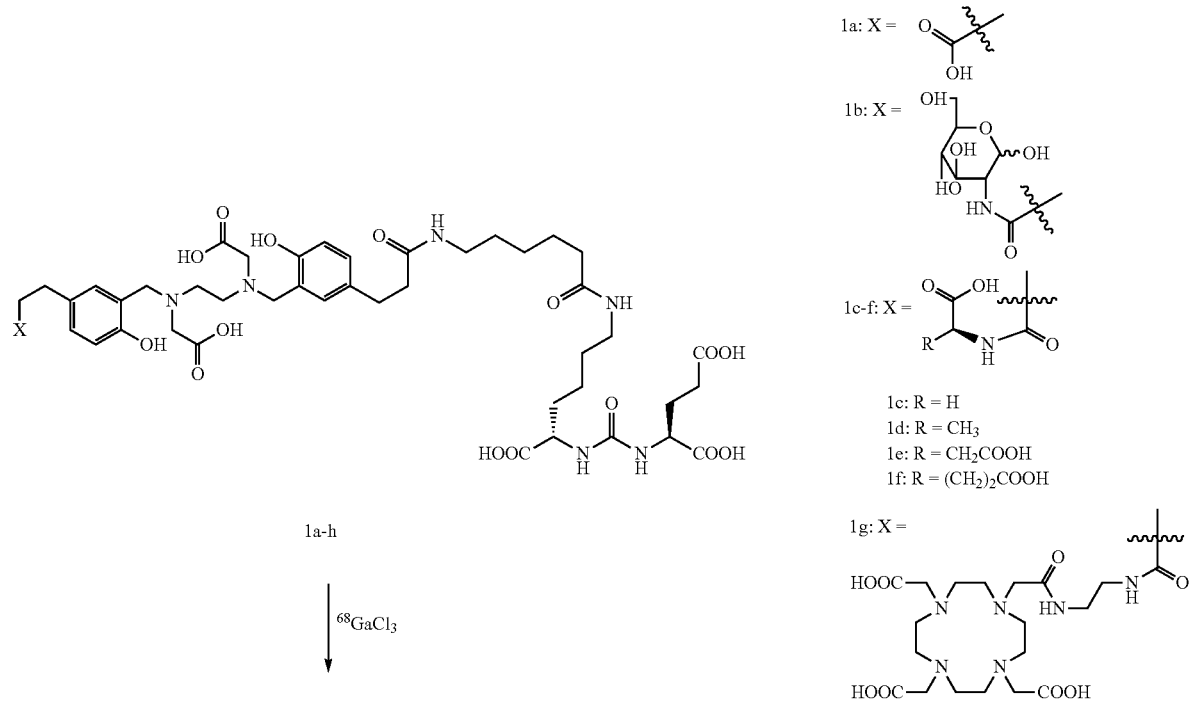

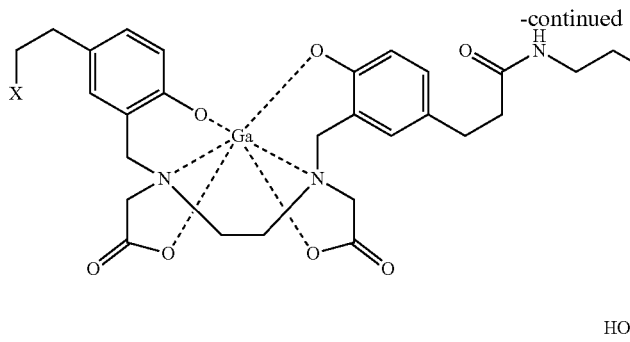
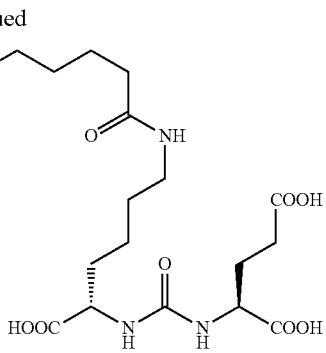

[⁶⁸Ga1a-h]

Example 1

Methyl 3-(4-hydroxyphenyl)propanoate (A)

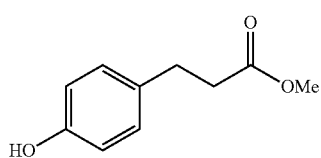

To a solution of 3-(4-hydroxyphenyl)propanoic acid (3 g, 18.1 mmol) in 50 mL MeOH was added $BF_3 \cdot Et_2O$ (0.3 mL). The mixture was stirred at rt for 8 h. The mixture was concentrated, and the residue was purified by flash chromatography (FC) (ethyl acetate (EtOAc)/hexane=2/8) to give 2.72 g white solid A (yield: 84%): ¹HNMR (400 MHz, $CDCl_3$) δ: 7.07 (d, 2H, J=8.4 Hz), 6.76 (d, 2H, J=8.4 Hz), 4.72 (s, 1H), 3.68 (s, 3H), 2.89 (t, 2H, J=7.6 Hz), 2.60 (t, 2H, J=7.6 Hz). HRMS (ESI) calculated for $C_{10}H_{13}O_3$ (M+H⁺), 181.0865; found, 181.0889.

Example 2

Methyl 3-(3-formyl-4-hydroxyphenyl)propanoate (B)

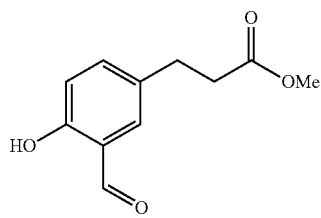

To a solution of A (2.72 g, 15.1 mmol) in 70 mL acetonitrile was added $MgCl_2$ (2.87 g, 30.2 mmol), paraformaldehyde (3.66 g, 120.8 mmol) and $Et_3N$ (6.1 g, 60.4 mmol). The mixture was heated reflux for 8 h. The reaction mixture was then poured into 100 mL 5% HCl and extracted with $Et_2O$ (50 mL×3). The organic layer was dried by anhydrous sodium sulfate ($Na_2SO_4$) and filtered. The filtrate was concentrated, and the residue was purified by flash chromatography (FC) (EtOAc/hexane=2/8) to give 2.84 g white solid B (yield: 90%): ¹HNMR (400 MHz, $CDCl_3$) δ: 7.37-7.40 (m, 2H), 6.93-6.52 (m, 1H), 3.68 (s, 3H), 2.95 (t, 2H, J=7.6 Hz), 2.64 (t, 2H, J=7.6 Hz). HRMS (ESI) calculated for $C_{11}H_{13}O_4$ (M+H⁺), 209.0814; found, 209.0797.

Example 3

Dimethyl 3,3'-(((ethane-1,2-diylbis(azanediyl))bis(methylene))bis(4-hydroxy-3,1-phenylene))dipropanoate (7)

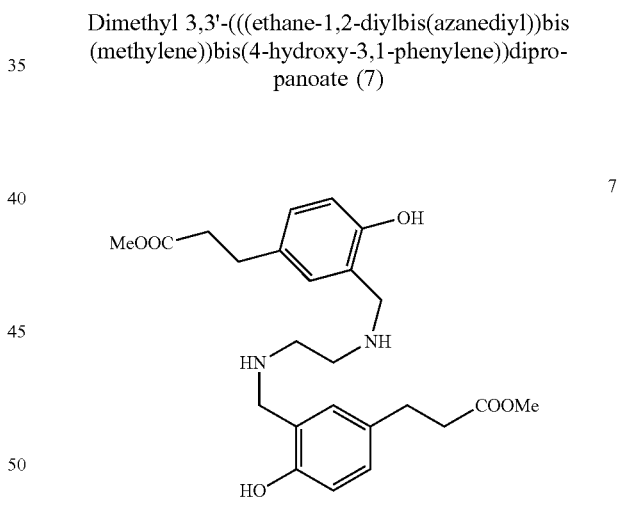

A solution of B (2.84 g, 13.6 mmol) and ethylenediamine (0.372 g, 6.18 mmol) in 60 mL MeOH was heated at 50° C. overnight. The mixture was then cooled with ice-bath. $NaBH_4$ (1.05 g, 27.81) was added portionally. After stirred at rt for 12 h, the mixture was diluted with EtOAc (200 mL), washed with $H_2O$ (50 mL) and brine (50) mL, dried over $Na_2SO_4$, concentrated and purified by FC (DCM/MeOH/$NH_4OH$=90/9/1) to give 2.08 g clear oil 7 (yield: 69%): ¹HNMR (400 MHz, $CDCl_3$) δ: 7.00 (dd, 2H, J=2.0 Hz, J=8.4 Hz), 6.81 (d, 2H, J=2.0 Hz), 6.76 (d, 2H, J=8.4 Hz), 3.97 (s, 2H), 3.67 (s, 6H), 2.83-2.87 (m, 8H), 2.58 (t, 2H, J=7.8 Hz). HRMS (ESI) calculated for $C_{24}H_{33}N_2O_6$ (M+H⁺), 445.2339; found, 445.2326.

Example 4

Dimethyl 3,3'-(((2,2,13,13-tetramethyl-4,11-dioxo-3,12-dioxa-6,9-diazatetradecane-6,9-diyl)bis(methylene))bis(4-hydroxy-3,1-phenylene))dipropanoate (8)

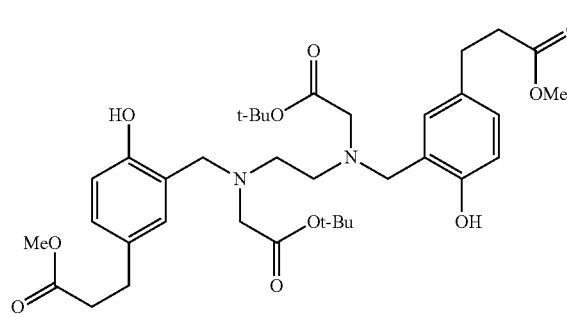

To a solution of 7 (2.08 g, 4.67 mmol) in 50 mL acetonitrile was added tert-butyl bromoacetate (1.91 g, 9.8 mmol) and $Na_2CO_3$ (1.98 g, 18.68 mmol). After heated at 60° C. overnight, EtOAc (200 mL) was added. The mixture was washed with $H_2O$ (50 mL) and brine (50 mL), dried over $Na_2SO_4$, concentrated and purified by FC (EtOAc/hexane=3/7) to give 2.74 g clear oil 8 (yield: 87%): $^1$HNMR (400 MHz, $CDCl_3$) δ: 7.00 (dd, 2H, J=2.0 Hz, J=8.4 Hz), 6.77 (d, 2H, J=8.4 Hz), 6.74 (d, 2H, J=2.0 Hz), 3.70 (s, 4H), 3.67 (s, 6H), 3.17 (s, 4H), 2.83 (t, 4H, J=7.8 Hz), 2.69 (s, 4H), 2.57 (t, 4H, J=7.8 Hz), 1.46 (s, 18H). HRMS (ESI) calculated for $C_{36}H_{53}N_2O_{10}$ (M+H$^+$), 673.3700; found, 673.3680.

Example 5

3,3'-(((2,2,13,13-Tetramethyl-4,11-dioxo-3,12-dioxa-6,9-diazatetradecane-6,9-diyl)bis(methylene))bis(4-hydroxy-3,1-phenylene))dipropanoic acid (9)

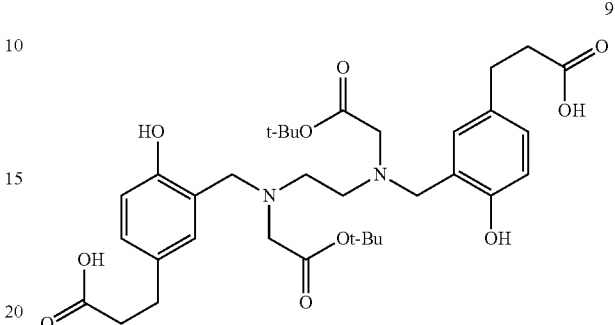

To a solution of 8 (0.673 g, mmol) in 10 mL MeOH/$H_2O$ (1/1) was added NaOH (0.4 g, 10 mmol). After stirred at rt for 4 h, 1 N HCl was added to the mixture till pH=4-5. The resulting mixture was then washed with EtOAc (20 mL×3). The organic layer was collected, washed with brine (20 mL), dried by $Na_2SO_4$ and filtered. The filtrate was concentrated to give 0.62 g white solid 9 (yield: 96%): $^1$HNMR (400 MHz, $CDCl_3$) δ: 7.03 (dd, 2H, J=2.0 Hz, J=8.0 Hz), 6.80 (d, 2H, J=8.0 Hz), 6.71 (d, 2H, J=2.0 Hz), 3.56 (s, 4H), 3.26 (s, 6H), 2.84 (t, 4H, J=7.0 Hz), 2.62 (t, 4H, J=7.0 Hz), 2.56 (s, 4H), 1.48 (s, 18H). HRMS (ESI) calculated for $C_{36}H_{53}N_2O_{10}$ (M+H$^+$), 673.3700; found, 673.3680.

Example 6a 3-(3-(((2-((5-(((7S,11S)-7,11-Bis(tert-butoxycarbonyl)-2,2-dimethyl-4,9,17,24-tetraoxo-3-oxa-8,10,16,23-tetraazahexacosan-26-yl)-2-hydroxybenzyl)(2-(tert-butoxy)-2-oxoethyl)amino)ethyl)(2-(tert-butoxy)-2-oxoethyl)amino)methyl)-4-hydroxyphenyl)propanoic acid (11a)

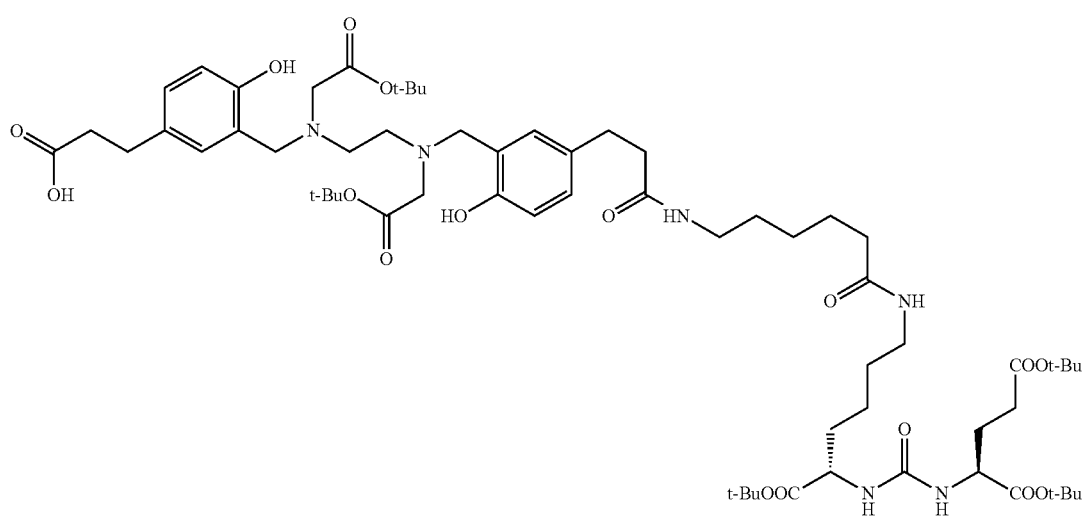

To a solution of 9 (0.62 g, 0.96 mmol) in 10 mL DMF was added Glu-NH—CO—NH-Lys(Ahx)-NH$_2$ (10, 0.519 g, 0.86 mmol), N,N'-dicyclohexylcarbodiimide (EDCI, 0.274 g, 1.44 mol), N-Hydroxybenzotrizole (HOBt, 0.243 g, 1.44 mmol), 4-(dimethylamino)pyridine (DMAP, 0.012 g, 0.1 mmol) and N,N-diisopropylethylamine (DIPEA, 0.495 g, 3.84 mmol). After stirred at rt overnight, the mixture was diluted with EtOAc (50 mL), washed with H$_2$O (15×2 mL) and brine (15) mL, dried over Na$_2$SO$_4$, concentrated and purified by FC (DCM/MeOH/NH$_4$OH=95/5/0.5) to give 0.545 g clear oil 11a (yield: 46.2%): $^1$HNMR (400 MHz, CDCl$_3$) δ: 6.98-7.01 (m, 2H), 6.73-6.77 (m, 4H), 6.55 (t, 1H, J=6.4 Hz), 6.07 (t, 1H, J=6.4 Hz), 5.78-5.82 (m, 2H), 4.28-4.33 (m, 2H), 3.69 (s, 2H), 3.67 (s, 2H), 3.12-3.31 (m, 8H), 2.80-2.86 (m, 4H), 2.68 (s, 4H), 2.62 (t, 2H, J=8.0 Hz), 22.31-2.44 (m, 4H), 2.04-2.18 (m, 3H), 1.77-1.85 (m, 2H), 1.43-1.60 (m, 54H), 1.22-1.28 (m, 2H); HRMS (ESI) calculated for C$_{64}$H$_{103}$N$_6$O$_{17}$ (M+H$^+$), 1227.7380; found, 1227.7309.

Example 6b (3S,7S)-Tri-tert-butyl 22-(3-(((2-(tert-butoxy)-2-oxoethyl)(2-((2-(tert-butoxy)-2-oxoethyl)(2-hydroxy-5-(3-oxo-3-(((3R,4R,5S,6R)-2,4,5-triacetoxy-6-(acetoxymethyl)tetrahydro-2H-pyran-3-yl)amino)propyl)benzyl)amino)ethyl)amino)methyl)-4-hydroxyphenyl)-5,13,20-trioxo-4,6,12,19-tetraazadocosane-1,3,7-tricarboxylate (11b)

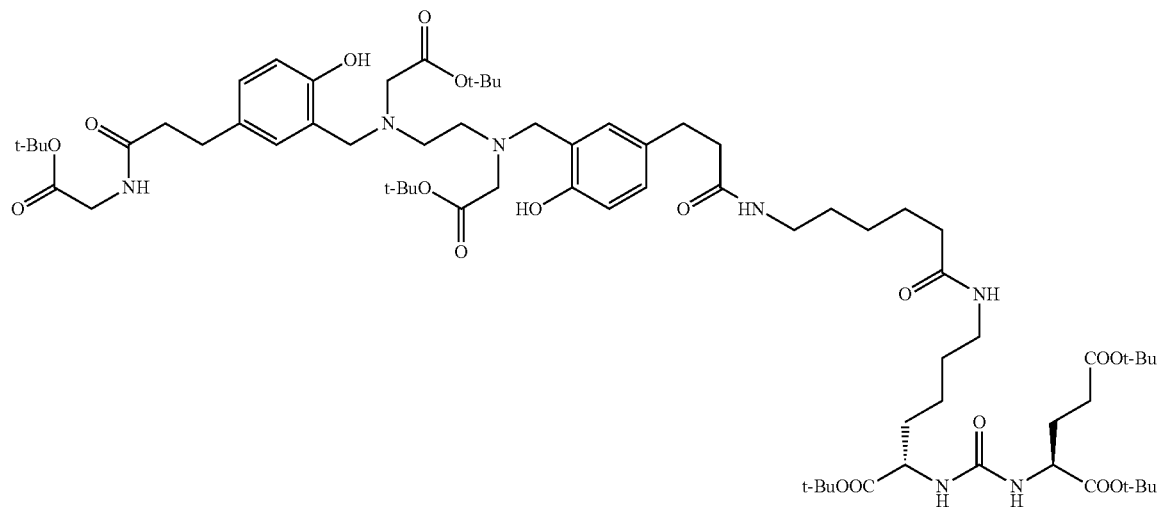

11b

To a solution of 11a (50 mg, 0.04 mmol) in 2 mL DMF was added 1,3,4,6-tetra-O-acetyl-2-amino-2-deoxy-β-D-glucopyranose hydrochloride (23 mg, 0.06 mmol), EDCI (11.5 mg, 0.06 mol), HOBt (10.1 mg, 0.06 mmol), DMAP (0.5 mg, 0.004 mmol) and
DIPEA (15.5 mg, 0.12 mmol). After stirred at rt overnight, the mixture was diluted with EtOAc (20 mL), washed with H$_2$O (10×2 mL) and brine (10) mL, dried over Na$_2$SO$_4$, concentrated and purified by FC (DCM/MeOH/NH$_4$OH=95/5/0.5) to give 39 mg clear oil 11b (yield: 62.6%): $^1$HNMR (400 MHz, CDCl$_3$) δ: 6.98-7.01 (m, 2H), 6.73-6.77 (m, 4H), 6.55 (t, 1H, J=6.4 Hz), 6.07 (t, 1H, J=6.4 Hz), 5.78-5.82 (m, 2H), 4.12-4.30 (m, 6H), 3.67-3.84 (m, 5H), 3.12-3.47 (m, 10H), 2.80-2.86 (m, 4H), 2.68 (s, 4H), 2.62 (t, 2H, J=8.0 Hz), 2.31-2.44 (m, 4H), 2.04-2.18 (m, 3H), 1.77-1.85 (m, 2H), 1.37-1.60 (m, 66H), 1.22-1.28 (m, 2H); HRMS (ESI) calculated for C$_{78}$H$_{122}$N$_7$O$_{25}$ (M+H$^+$), 1556.8490; found, 1556.8360.

Example 6c (3S,7S)-Tri-tert-butyl 22-(3-(((2-(tert-butoxy)-2-oxoethyl)(2-((2-(tert-butoxy)-2-oxoethyl)(5-(3-((2-(tert-butoxy)-2-oxoethyl)amino)-3-oxopropyl)-2-hydroxybenzyl)amino)ethyl)amino)methyl)-4-hydroxyphenyl)-5,13,20-trioxo-4,6,12,19-tetraazadocosane-1,3,7-tricarboxylate (11c)

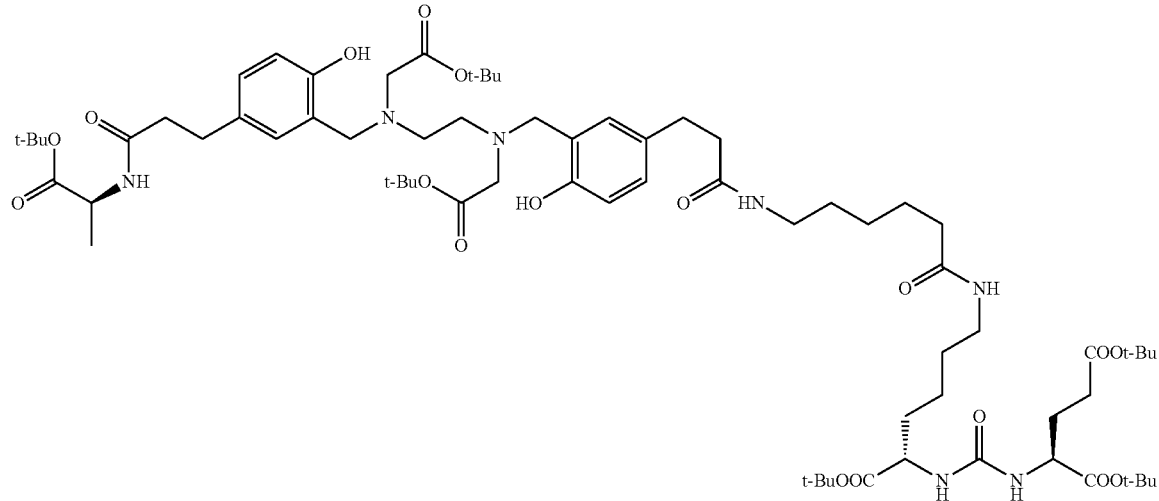

Compound 11c was prepared from 11a (50 mg, 0.04 mmol), glycine t-butyl ester hydrochloride (10 mg, 0.06 mmol), EDCI (11.5 mg, 0.06 mol), HOBt (10.1 mg, 0.06 mmol), DMAP (0.5 mg, 0.004 mmol) and DIPEA (15.5 mg, 0.12 mmol) with the same procedure described for compound 11b. Compound 11c: 20 mg (yield: 37.3%): $^1$HNMR (400 MHz, CDCl$_3$) δ: 6.98-7.01 (m, 2H), 6.73-6.77 (m, 4H), 6.55 (t, 1H, J=6.4 Hz), 6.07 (t, 1H, J=6.4 Hz), 5.78-5.82 (m, 2H), 4.31-4.33 (m, 2H), 4.14 (d, 2H, J=6.8 Hz), 3.67-3.69 (m, 4H), 3.12-3.31 (m, 8H), 2.68-2.86 (m, 8H), 2.44-2.53 (m, 4H), 2.32-2.35 (m, 2H), 2.04-2.18 (m, 3H), 1.77-1.85 (m, 2H), 1.43-1.60 (m, 63H), 1.22-1.28 (m, 2H); HRMS (ESI) calculated for C$_{70}$H$_{114}$N$_7$O$_{18}$ (M+H$^+$), 1340.8220; found, 1340.8227.

Example 6d (3S,7S)-Tri-tert-butyl 22-(3-(((2-((5-(3-(((S)-1-(tert-butoxy)-1-oxopropan-2-yl)amino)-3-oxopropyl)-2-hydroxybenzyl)(2-(tert-butoxy)-2-oxoethyl)amino)ethyl)(2-(tert-butoxy)-2-oxoethyl)amino)methyl)-4-hydroxyphenyl)-5,13,20-trioxo-4,6,12,19-tetraazadocosane-1,3,7-tricarboxylate (11d)

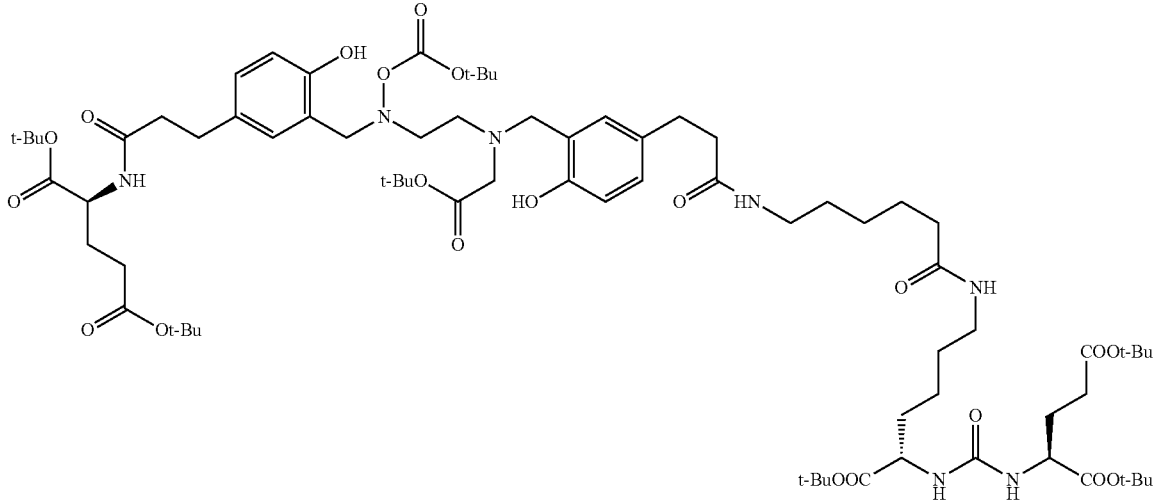

Compound 11d was prepared from 11a (50 mg, 0.04 mmol), alanine tert-butyl ester hydrochloride (10.9 mg, 0.06 mmol), EDCI (11.5 mg, 0.06 mol), HOBt (10.1 mg, 0.06 mmol), DMAP (0.5 mg, 0.004 mmol) and DIPEA (15.5 mg, 0.12 mmol) with the same procedure described for compound 11b. Compound 11d: 19 mg (yield: 35.1%): $^1$HNMR (400 MHz, CDCl$_3$) δ: 6.98-7.01 (m, 2H), 6.73-6.77 (m, 4H), 6.55 (t, 1H, J=6.4 Hz), 6.07 (t, 1H, J=6.4 Hz), 5.78-5.82 (m, 2H), 4.31-4.45 (m, 3H), 3.67-3.69 (m, 4H), 3.12-3.31 (m, 8H), 2.81-2.86 (m, 8H), 2.44-2.53 (m, 4H), 2.32-2.35 (m, 2H), 2.04-2.18 (m, 3H), 1.77-1.85 (m, 2H), 1.43-1.60 (m, 66H), 1.22-1.28 (m, 2H); HRMS (ESI) calculated for $C_{71}H_{116}N_7O_{18}$ (M+H$^+$), 1354.8377; found, 1354.8431.

Example 6e (3S,7S)-Tri-tert-butyl 22-(3-(((2-(tert-butoxy)-2-oxoethyl)(2-((2-(tert-butoxy)-2-oxoethyl)(5-(3-(((S)-1,4-di-tert-butoxy-1,4-dioxobutan-2-yl)amino)-3-oxopropyl)-2-hydroxybenzyl)amino)ethyl)amino)methyl)-4-hydroxyphenyl)-5,13,20-trioxo-4,6,12,19-tetraazadocosane-1,3,7-tricarboxylate (11e)

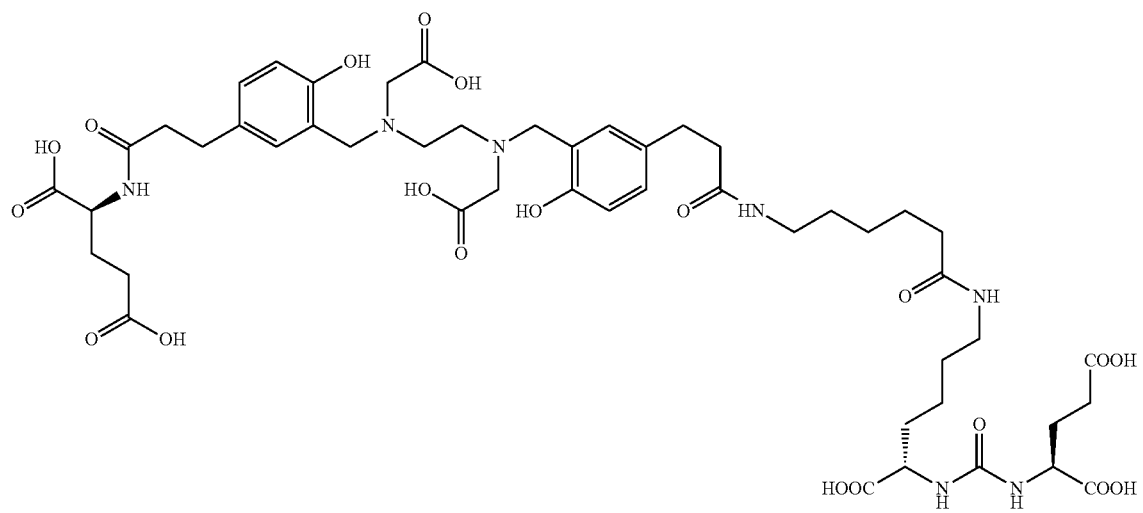

Compound 11e was prepared from 11a (50 mg, 0.04 mmol), L-aspartic acid di-tert-butyl ester hydrochloride (14.4 mg, 0.06 mmol), EDCI (11.5 mg, 0.06 mol), HOBt (10.1 mg, 0.06 mmol), DMAP (0.5 mg, 0.004 mmol) and DIPEA (15.5 mg, 0.12 mmol) with the same procedure described for compound 11b. Compound 11e: 31 mg (yield: 35.1%): $^1$HNMR (400 MHz, CDCl$_3$) δ: 6.98-7.01 (m, 2H), 6.73-6.77 (m, 4H), 6.55 (t, 1H, J=6.4 Hz), 6.07 (t, 1H, J=6.4 Hz), 5.78-5.82 (m, 2H), 4.66-4.68 (m, 1H), 4.28-4.33 (m, 2H), 3.67-3.69 (m, 4H), 3.12-3.31 (m, 8H), 2.81-2.86 (m, 8H), 2.44-2.68 (m, 6H), 2.32-2.35 (m, 2H), 2.04-2.18 (m, 3H), 1.77-1.85 (m, 2H), 1.43-1.60 (m, 72H), 1.22-1.28 (m, 2H); HRMS (ESI) calculated for $C_{76}H_{124}N_7O_{20}$ (M+H$^+$), 1454.8901; found, 1454.8998.

Example 6f (3S,7S)-Tri-tert-butyl 22-(3-(((2-(tert-butoxy)-2-oxoethyl)(2-((2-(tert-butoxy)-2-oxoethyl)(5-(3-(((S)-1,5-di-tert-butoxy-1,5-dioxopentan-2-yl)amino)-3-oxopropyl)-2-hydroxybenzyl)amino)ethyl)amino) methyl)-4-hydroxyphenyl)-5,13,20-trioxo-4,6,12,19-tetraazadocosane-1,3,7-tricarboxylate (11f)

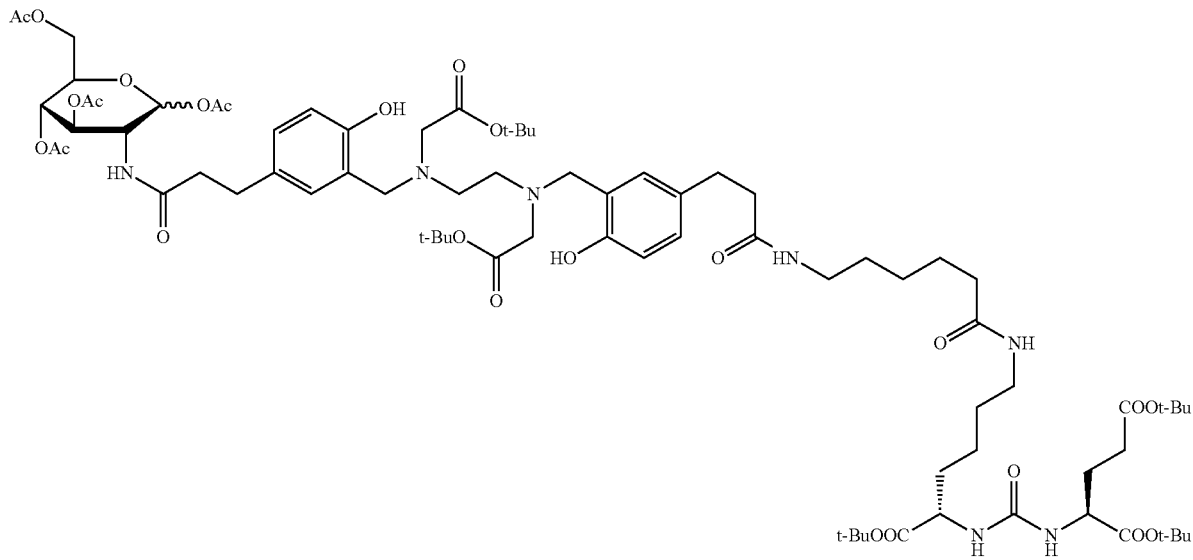

11f

Compound 11f was prepared from 11a (50 mg, 0.04 mmol), L-glutamic acid di-tert-butyl ester hydrochloride (17.7 mg, 0.06 mmol), EDCI (11.5 mg, 0.06 mol), HOBt (10.1 mg, 0.06 mmol), DMAP (0.5 mg, 0.004 mmol) and DIPEA (15.5 mg, 0.12 mmol) with the same procedure described for compound 11b. Compound 11f: 31 mg (yield: 35.1%): $^1$HNMR (400 MHz, CDCl$_3$) δ: 6.98-7.01 (m, 2H), 6.73-6.77 (m, 4H), 6.55 (t, 1H, J=6.4 Hz), 6.07 (t, 1H, J=6.4 Hz), 5.78-5.82 (m, 2H), 4.46-4.51 (m, 1H), 4.28-4.33 (m, 2H), 3.67-3.69 (m, 4H), 3.12-3.31 (m, 8H), 2.81-2.86 (m, 8H), 2.04-2.57 (m, 13H), 1.77-1.85 (m, 2H), 1.43-1.60 (m, 72H), 1.22-1.28 (m, 2H); HRMS (ESI) calculated for C$_{77}$H$_{126}$N$_7$O$_{20}$ (M+H$^+$), 1468.9058; found, 1468.9239.

Example 6g tert-Butyl-(S)-6-(6-(3-(3-(((2-(tert-butoxy)-2-oxo-ethyl)(2-((2-(tert-butoxy)-2-oxoethyl)(2-hydroxy-5-(3-oxo-3-((2-(2-(4,7,10-tris(2-(tert-butoxy)-2-oxo-ethyl)-1,4,7,10-tetraazacyclododecan-1-yl) acetamido)ethyl)amino)propyl)benzyl)amino)ethyl) amino) methyl)-4-hydroxyphenyl)propanamido) hexanamido)-2-(3-((S)-1,5-di-tert-butoxy-1,5-dioxopentan-2-yl)ureido)hexanoate (11g)

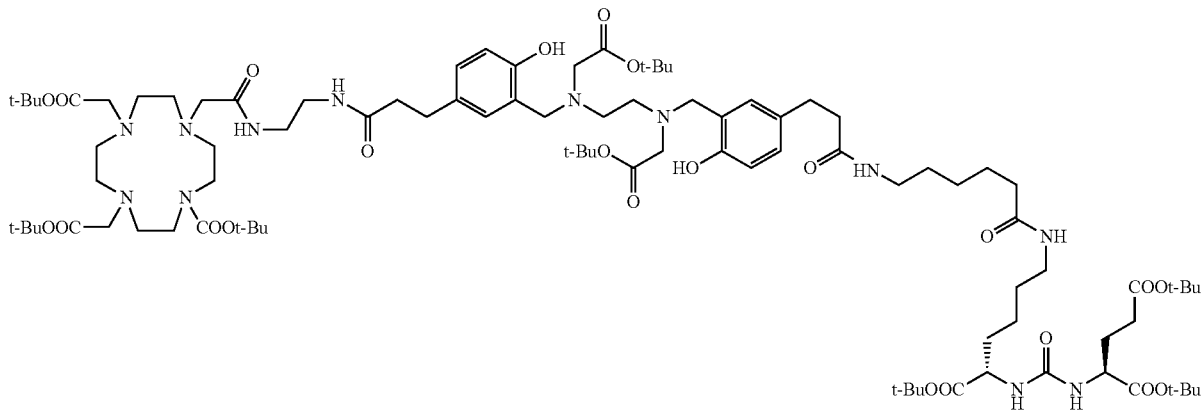

11g

Compound 11g was prepared from 11a (60 mg, 0.049 mmol), 2-aminoethyl-mono-amide-DOTA-tris-tBu ester (34 mg, 0.049 mmol), EDCI (14 mg, 0.074 mol), HOBt (12.4 mg, 0.074 mmol), and DIPEA (25.2 mg, 0.196 mmol) with the same procedure described for compound 11b. Compound 11g: 20 mg (yield: 22.4%): HRMS (ESI) calculated for $C_{94}H_{159}N_{12}O_{23}$ (M+H$^+$), 1824.1641; found, 1824.1629.

Example 7b (3S,7S)-22-(3-((((Carboxymethyl)(2-((carboxymethyl)(2-hydroxy-5-(3-oxo-3-(((3R,4R,5S,6R)-2,4,5-trihydroxy-6-(hydroxymethyl)tetrahydro-2H-pyran-3-yl)amino)propyl)benzyl)amino)ethyl)amino)methyl)-4-hydroxyphenyl)-5,13,20-trioxo-4,6,12,19-tetraazadocosane-1,3,7-tricarboxylic acid (1b)

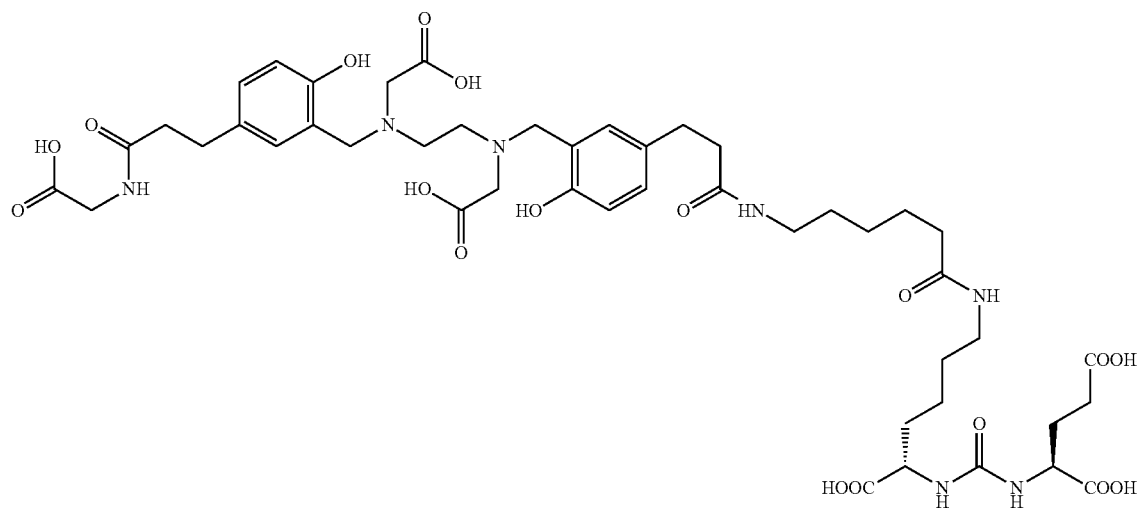

1b

A solution of 11b (39 mg, 0.025 mmol) in 0.9 mL trifluoroacetic acid (TFA) and 0.1 mL dimethyl sulfide was stirred at rt for 3 h. The reaction mixture was evaporated in vacuo, and the residue was recrystallized from Ether/EtOH to give 13.2 mg white solid 1b (yield: 47.4%): $^1$HNMR (400 MHz, MeOD) δ: 7.09-7.13 (m, 4H), 6.80 (d, 2H, J=8.8 Hz), 4.24-4.33 (m, 3H), 4.15 (s, 2H), 4.09 (s, 2H), 3.66-3.85 (m, 9H), 3.16 (t, 2H, J=6.6 Hz), 3.11 (t, 2H, J=6.6 Hz), 2.80-2.84 (m, 4H), 2.39-2.51 (m, 6H), 2.13-2.17 (m, 3H), 1.82-1.94 (m, 2H), 1.42-1.67 (m, 9H), 1.23-1.29 (m, 2H); HRMS (ESI) calculated for $C_{50}H_{74}N_7O_{21}$ (M+H$^+$), 1108.4938; found, 1108.1940.

Example 7c (3S,7S)-22-(3-((((Carboxymethyl)(2-((carboxymethyl)(5-(3-((carboxymethyl)amino)-3-oxopropyl)-2-hydroxybenzyl)amino)ethyl)amino)methyl)-4-hydroxyphenyl)-5,13,20-trioxo-4,6,12,19-tetraazadocosane-1,3,7-tricarboxylic acid (1c)

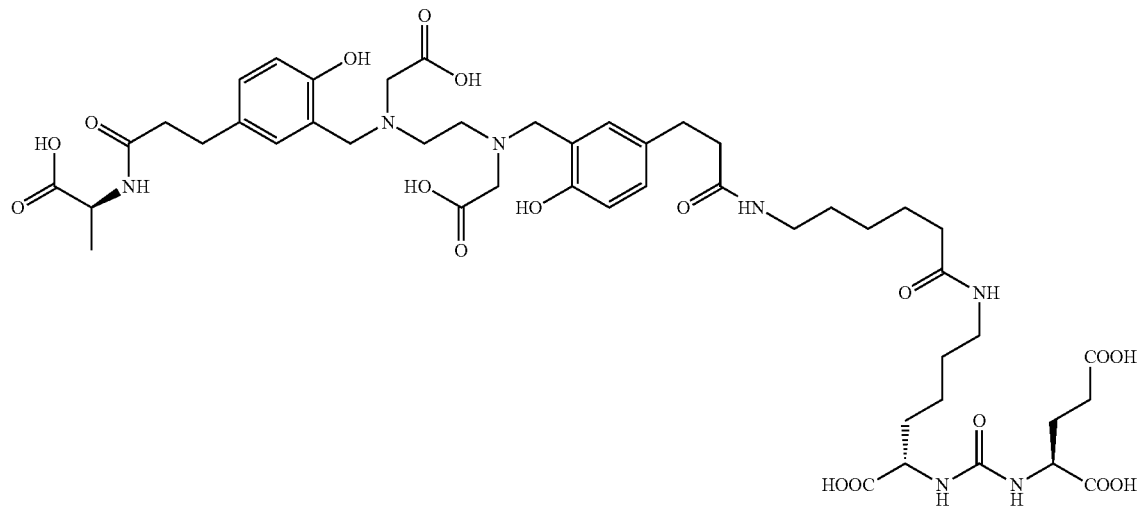

Compound 1c was prepared from 11c (20 mg, 0.015 mmol) in 0.9 mL trifluoroacetic acid (TFA) and 0.1 mL dimethyl sulfide, with the same procedure described for compound 1b. Compound 1c: 6.3 mg (yield: 41.8%): $^1$HNMR (400 MHz, MeOD) δ: 7.08-7.13 (m, 4H), 6.80 (d, 2H, J=8.8 Hz), 4.24-4.33 (m, 3H), 4.14 (s, 2H), 4.08 (s, 2H), 3.88 (s, 2H), 3.68 (s, 2H), 3.63 (s, 2H), 3.17 (t, 2H, J=6.8 Hz), 3.09 (t, 2H, J=6.8 Hz), 2.80-2.87 (m, 4H), 2.39-2.53 (m, 6H), 2.13-2.17 (m, 3H), 1.82-1.94 (m, 2H), 1.42-1.67 (m, 9H), 1.23-1.29 (m, 2H); HRMS (ESI) calculated for $C_{46}H_{66}N_7O_{18}$ (M+H$^+$), 1004.4464; found, 1004.4498.

Example 7d (3S,7S)-22-(3-(((2-((5-(3-(((S)-1-Carboxyethyl)amino)-3-oxopropyl)-2-hydroxybenzyl)(carboxymethyl)amino)ethyl)(carboxymethyl)amino)methyl)-4-hydroxyphenyl)-5,13,20-trioxo-4,6,12,19-tetraazadocosane-1,3,7-tricarboxylic acid (1d)

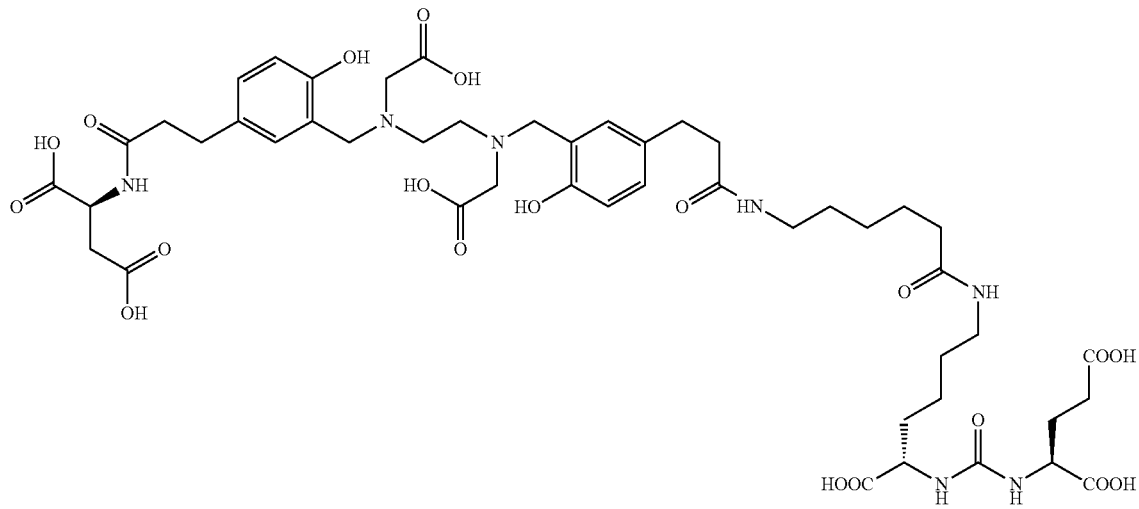

Compound 1d was prepared from 11d (20 mg, 0.014 mmol) in 0.9 mL trifluoroacetic acid (TFA) and 0.1 mL dimethyl sulfide, with the same procedure described for compound 1b. Compound 1d: 8.3 mg (yield: 58.2%): $^1$HNMR (400 MHz, MeOD) δ: 7.05-7.13 (m, 4H), 6.80 (d, 2H, J=8.8 Hz), 4.24-4.33 (m, 3H), 4.12 (s, 2H), 4.09 (s, 2H), 3.88 (s, 2H), 3.68 (s, 2H), 3.63 (s, 2H), 3.17 (t, 2H, J=6.8 Hz), 3.10 (t, 2H, J=6.8 Hz), 2.80-2.87 (m, 4H), 2.40-2.53 (m, 6H), 2.13-2.17 (m, 3H), 1.81-1.94 (m, 2H), 1.42-1.67 (m, 12H), 1.23-1.29 (m, 2H); HRMS (ESI) calculated for $C_{47}H_{68}N_7O_{18}$ (M+H$^+$), 1018.4621; found, 1018.4707.

Example 7e (3S,7S)-22-(3-((((Carboxymethyl)(2-((carboxymethyl)(5-(3-(((S)-1,2-dicarboxyethyl)amino)-3-oxopropyl)-2-hydroxybenzyl)amino)ethyl)amino) methyl)-4-hydroxyphenyl)-5,13,20-trioxo-4,6,12,19-tetraazadocosane-1,3,7-tricarboxylic acid (1e)

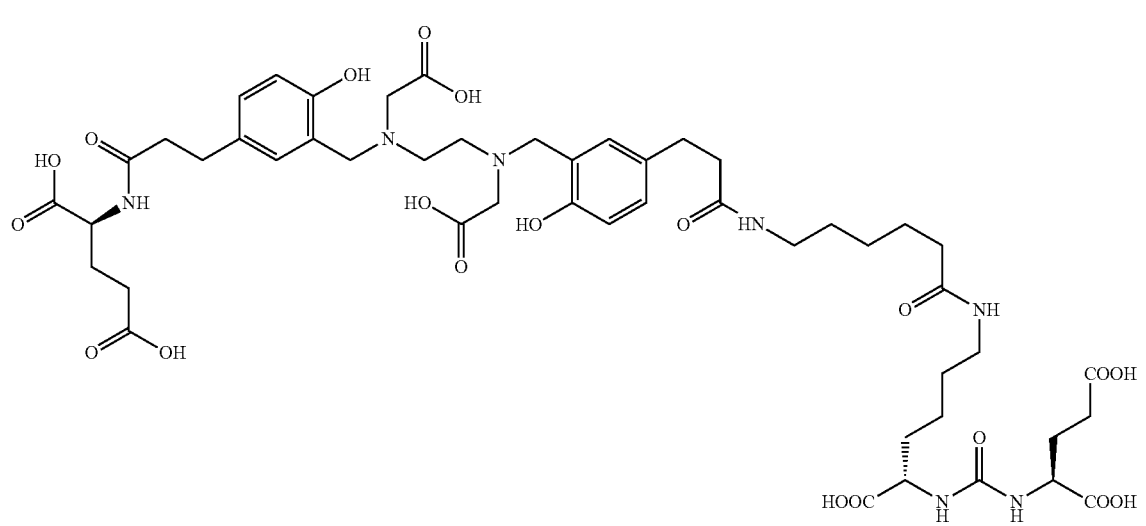

1e

Compound 1e was prepared from 11e (30 mg, 0.0206 mmol) in 0.9 mL trifluoroacetic acid (TFA) and 0.1 mL dimethyl sulfide, with the same procedure described for compound 1b. Compound 1e: 5.7 mg (yield: 26.1%): $^1$HNMR (400 MHz, MeOD) δ: 7.05-7.13 (m, 4H), 6.80 (d, 2H, J=8.8 Hz), 4.72 (t, 1H, J=6.0 Hz), 4.24-4.33 (m, 2H), 4.16 (s, 2H), 4.08 (s, 2H), 3.71 (s, 2H), 3.64 (s, 2H), 3.17 (t, 2H, J=6.8 Hz), 3.11 (t, 2H, J=6.8 Hz), 2.76-2.85 (m, 6H), 2.39-2.52 (m, 6H), 2.13-2.17 (m, 3H), 1.81-1.94 (m, 2H), 1.42-1.67 (m, 9H), 1.23-1.29 (m, 2H); HRMS (ESI) calculated for $C_{48}H_{68}N_7O_{20}$ (M+H$^+$), 1062.4519; found, 1062.4549.

Example 7f (3S,7S)-22-(3-((((Carboxymethyl)(2-((carboxymethyl)(5-(3-(((S)-1,3-dicarboxypropyl)amino)-3-oxopropyl)-2-hydroxybenzyl)amino)ethyl)amino)methyl)-4-hydroxyphenyl)-5,13,20-trioxo-4,6,12,19-tetraazadocosane-1,3,7-tricarboxylic acid (1f)

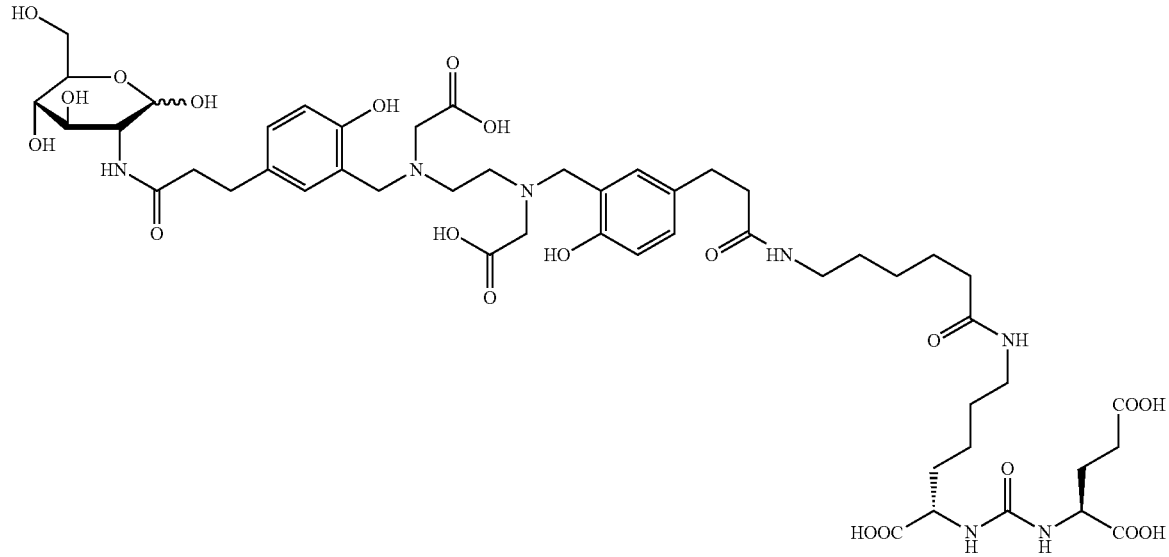

1f

Compound 1f was prepared from 11f (40 mg, 0.027 mmol) in 0.9 mL trifluoroacetic acid (TFA) and 0.1 mL dimethyl sulfide, with the same procedure described for compound 1b. Compound 1f: 13.5 mg (yield: 46.4%): $^1$HNMR (400 MHz, MeOD) δ: 7.09-7.13 (m, 4H), 6.81 (dd, 2H, J=4.4 Hz, J=8.8 Hz), 4.41 (dd, 1H, J=4.8 Hz, J=9.2 Hz), 4.24-4.33 (m, 2H), 4.15 (s, 2H), 4.09 (s, 2H), 3.71 (s, 2H), 3.65 (s, 2H), 3.17 (t, 2H, J=6.8 Hz), 3.11 (t, 2H, J=6.8 Hz), 2.80-2.85 (m, 4H), 2.39-2.52 (m, 6H), 2.27-2.31 (m, 2H), 2.10-2.17 (m, 4H), 1.81-1.94 (m, 3H), 1.42-1.67 (m, 9H), 1.23-1.29 (m, 2H); HRMS (ESI) calculated for $C_{49}H_{70}N_7O_{20}$ (M+H$^+$), 1076.4676; found, 1076.4877.

Example 7g (3S,7S)-22-(3-(((carboxymethyl)(2-((carboxymethyl)(2-hydroxy-5-(3-oxo-3-((2-(2-(4,7,10-tris(carboxymethyl)-1,4,7,10-tetraazacyclododecan-1-yl)acetamido)ethyl)amino)propyl) benzyl)amino)ethyl)amino)methyl)-4-hydroxyphenyl)-5,13,20-trioxo-4,6,12,19-tetraazadocosane-1,3,7-tricarboxylic acid (1g)

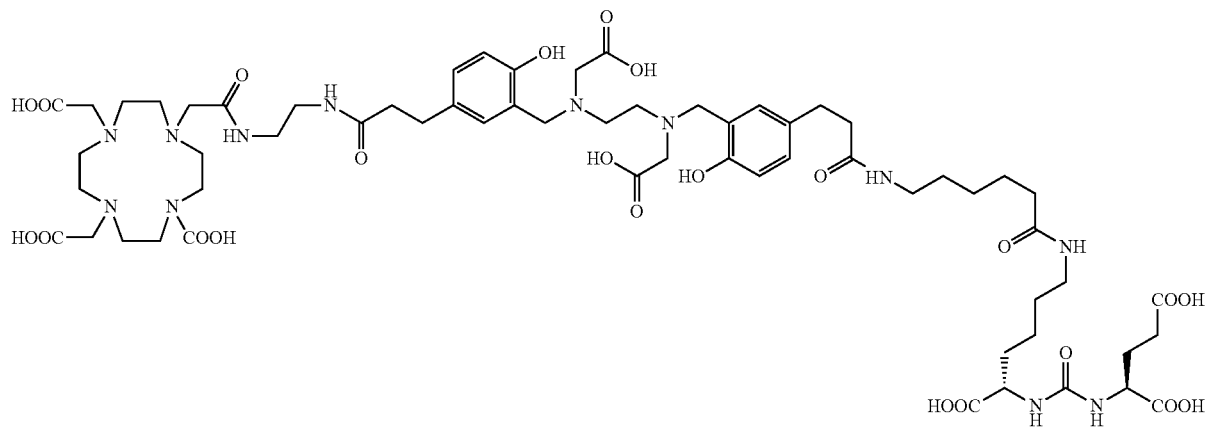

1g

Compound 1g was prepared from 11g (20 mg, 0.011 mmol) in 0.9 mL trifluoroacetic acid (TFA) and 0.1 mL dimethyl sulfide, with the same procedure described for compound 1b. Compound 1g: 12 mg (yield: 79.3%): $^1$HNMR (400 MHz, MeOD) δ: 7.12 (d, 1H, J=2.0 Hz), 7.10 (d, 1H, J=2.0 Hz), 7.07-7.09 (m, 2H), 6.80 (dd, 2H, J=2.0 Hz, J=8.0 Hz), 4.24-4.33 (m, 2H), 4.14 (s, 2H), 4.11 (s, 2H), 3.89 (s, 4H), 3.77 (s, 2H), 3.59-3.62 (m, 6H), 3.45-3.38 (m, 8H), 3.15-3.22 (m, 10H), 3.11 (t, 2H, J=6.8 Hz), 2.80-2.85 (m, 4H), 2.39-2.53 (m, 6H), 2.13-2.17 (m, 3H) 1.82-1.94 (m, 2H), 1.42-1.67 (m, 9H), 1.23-1.29 (m, 2H); HRMS (ESI) calculated for $C_{62}H_{95}N_{12}O_{23}$ (M+H$^+$), 1375.6633, found, 1375.6654.
Scheme 11
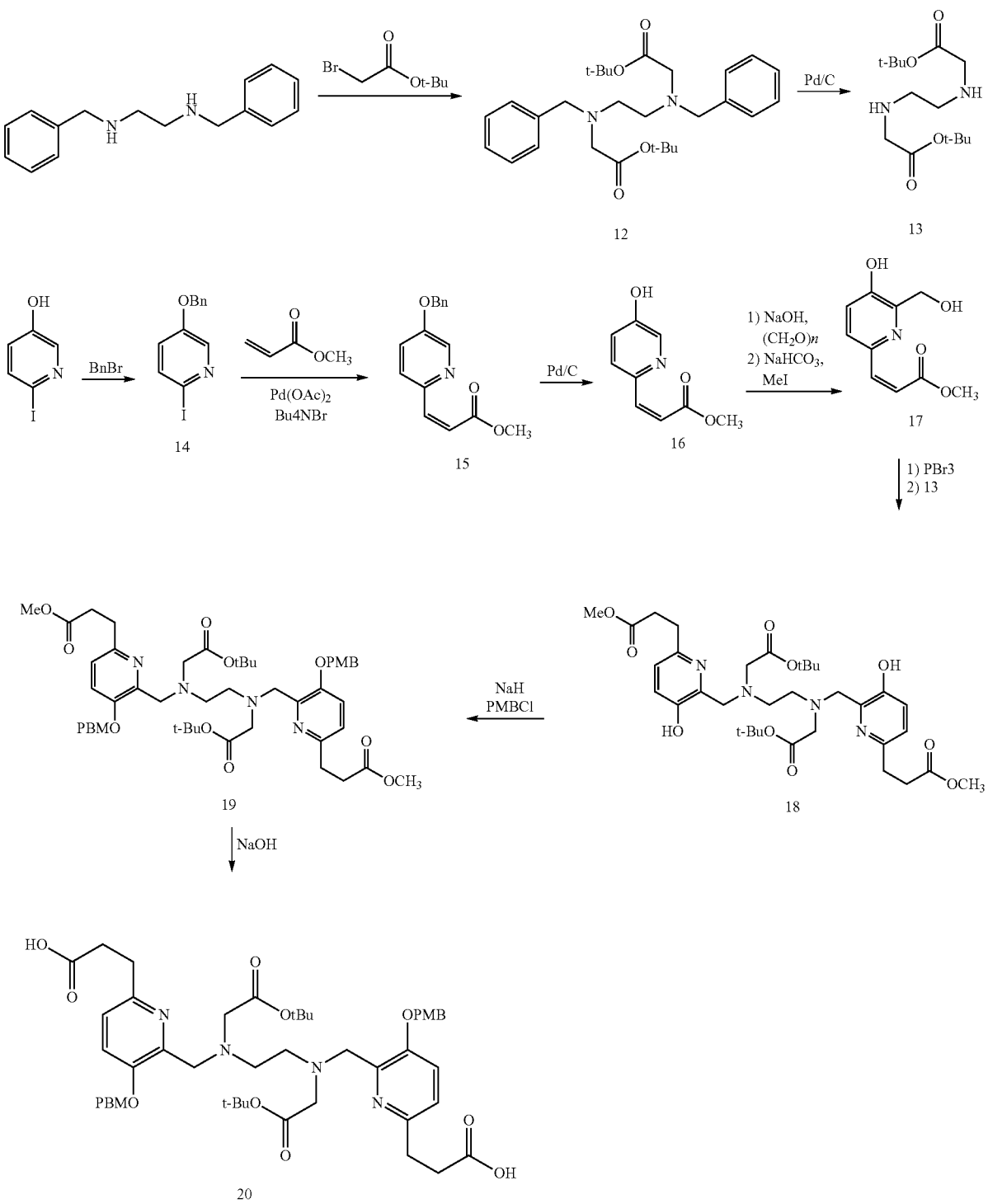

Example 8

5-(Benzyloxy)-2-iodopyridine (14).

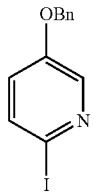

14

NaH (60% in mineral oil, 211 mg, 7 mmol) was placed in a two-neck flask and washed with hexane. 20 mL DMF was added to form a suspension. A solution of 5-hydroxy-2-bromopyridine (779 mg, 3.5 mmol) in 10 mL DMF was added dropwise at 0° C. After stirring at rt for 30 min, the mixture was cooled to 0° C., and benzyl bromide (898 mg, 5.25 mmol) was added dropwise, and the reaction mixture was stirred at rt overnight. The mixture was then poured into 50 mL cold sat. $NH_4Cl$, and extracted with DCM (50 mL×2). The organic layer was washed with $H_2O$ (30 mL) and brine (30 mL), dried over $Na_2SO_4$, concentrated and purified by FC (EtOAc/hexane=2/8) to give 1.08 g clear oil 14 (yield: 99%).

Example 9

(Z)-Methyl 3-(5-(benzyloxy)pyridin-2-yl)acrylate (15)

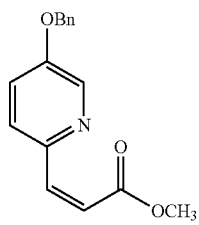

15

A mixture of 14 (4.67 g, 21.6 mmol), methyl acrylate (7.39 g, 43.2 mmol), potassium carbonate ($K_2CO_3$, 7.45 g, 54 mmol), tetrabutylammonium bromide (13.9 g, 43.2 mmol), and palladium acetate ($Pd(OAc)_2$, 263.5 mg, 1.08 mmol) in 100 mL DMF was deoxygenated by purging into nitrogen for 15 min and then heated at 120° C. for overnight. The mixture was cooled to RT, diluted with 300 mL EtOAc and washed with $H_2O$ (80 mL×2) as well as brine (80 mL). The organic layer was dried by $Na_2SO_4$ and filtered. The filtrate was concentrated, and the residue was purified by FC (EtOAc/hexane=2/8) to give 3.86 g colorless oil 15 (yield: 66.2%): HRMS (ESI) calculated for $C_{16}H_{16}NO3$ (M+H$^+$), 270.1130; found, 270.1109.

Example 10

Methyl 3-(5-hydroxypyridin-2-yl)propanoate (16)

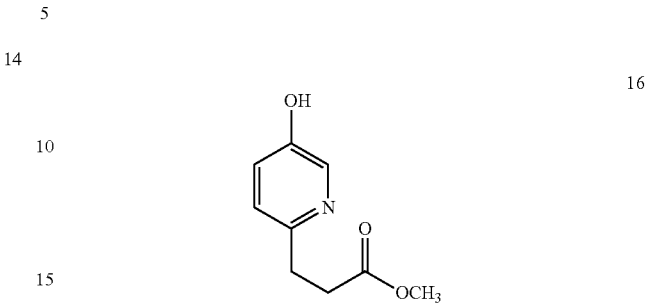

16

A mixture of 15 (3.86 g, 14.3 mmol) and Pd/C (500 mg) in 50 mL MeOH was stirred at rt under $H_2$ for 4 h. The resulting mixture was filtered and the filtrate was concentrated to give 2.6 g colorless oil 16 (yield: 100%): HRMS (ESI) calculated for $C_9H_{12}NO_3$ (M+H$^+$), 182.0817; found, 182.0740.

Example 11

Methyl 3-(5-hydroxy-6-(hydroxymethyl)pyridin-2-yl)propanoate (17)

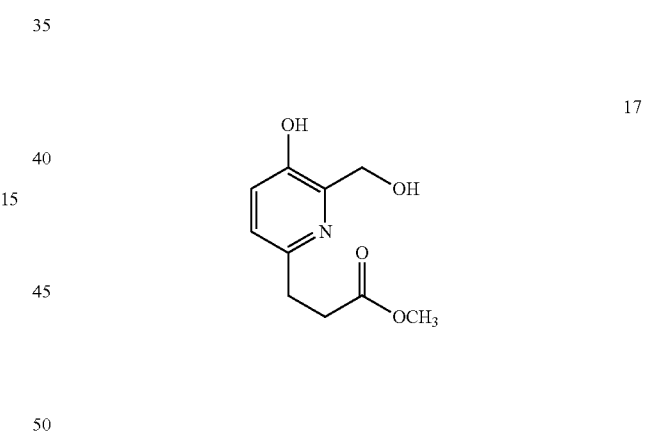

17

To a solution of 16 (480 mg, 2.7 mmol) in 15 mL $H_2O$ was added NaOH (216 mg, 5.4 mmol) and paraformaldehyde (486 mg, 16.2 mmol). After stirring at 90° C. for 6 h, the mixture was cooled with ice-bath. The pH was adjusted to 7 with 1 N HCl. The solvent was removed in vacuo. 20 mL DMF was then added to the residue, followed by iodomethane (2.3 g, 16.2 mmol) and sodium bicarbonate (1.36 g, 16.2 mmol). After stirred at rt for overnight, the mixture was then poured into 100 mL EtOAc and washed with $H_2O$ (30 mL×2) as well as brine (30 mL). The organic layer was dried by $Na_2SO_4$ and filtered. The filtrate was concentrated, and the residue was purified by FC (DCM/MeOH/$NH_4OH$=90/9/1) to give 440 mg white solid 17 (yield: 76.9%): HRMS (ESI) calculated for $C_{10}H_{14}NO_4$ (M+H$^+$), 212.0923; found, 212.0933.

Example 12

Dimethyl 3,3'-(6,6'-((2,2,13,13-tetramethyl-4,11-dioxo-3,12-dioxa-6,9-diazatetradecane-6,9-diyl)bis(methylene))bis(5-hydroxypyridine-6,2-diyl))dipropanoate (18)

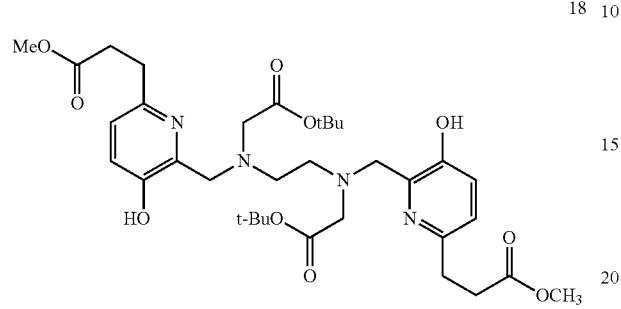

To a solution of 17 (190 mg, 0.90 mmol) in 5 mL chloroform was added phosphorus tribromide (121 mg, 0.45 mmol) dropwise under ice-bath. The mixture was warmed to rt and maintained for 3 h. The resulting mixture was then cooled to 0° C. DIPEA (462 mg, 3.58 mmol) was added followed by 13 (102.5 mg, 0.356 mmol). The ice-bath was then removed. The mixture was stirred at rt overnight. The solvent was removed in vacuo and the residue was purified by FC (DCM/MeOH/NH$_4$OH=85/15/1.5) to give 140 mg colorless oil 18 (yield: 58.3%): HRMS (ESI) calculated for $C_{34}H_{51}N_4O_{10}$ (M+H$^+$), 675.3605; found, 675.3545.

Example 13

Dimethyl 3,3'-(6,6'-((2,2,13,13-tetramethyl-4,11-dioxo-3,12-dioxa-6,9-diazatetradecane-6,9-diyl)bis(methylene))bis(5-((4-methoxybenzyl)oxy)pyridine-6,2-diyl))dipropanoate (19)

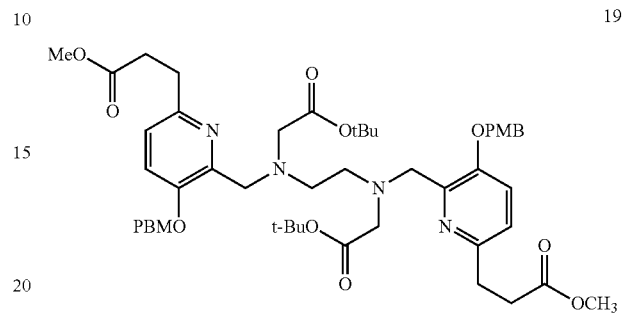

To a solution of 18 (140 mg, 0.21 mmol) in 5 mL DMF was added 4-methoxybenzyl (130 mg, 0.83 mmol) and NaH (33.2 mg, 0.83 mmol) at 0° C. The mixture was the warmed to rt and maintained for 6 h. The resulting mixture was then poured into 30 mL EtOAc and washed with H$_2$O (10 mL×2) as well as brine (10 mL). The organic layer was dried by Na$_2$SO$_4$ and filtered. The filtrate was concentrated, and the residue was purified by FC (DCM/MeOH/NH$_4$OH=90/9/1) to give 61.8 mg white solid 19 (yield: 32.6%): HRMS (ESI) calculated for $C_{50}H_{67}N_4O_{12}$ (M+H$^+$), 915.4755; found, 915.4689.

Scheme 12

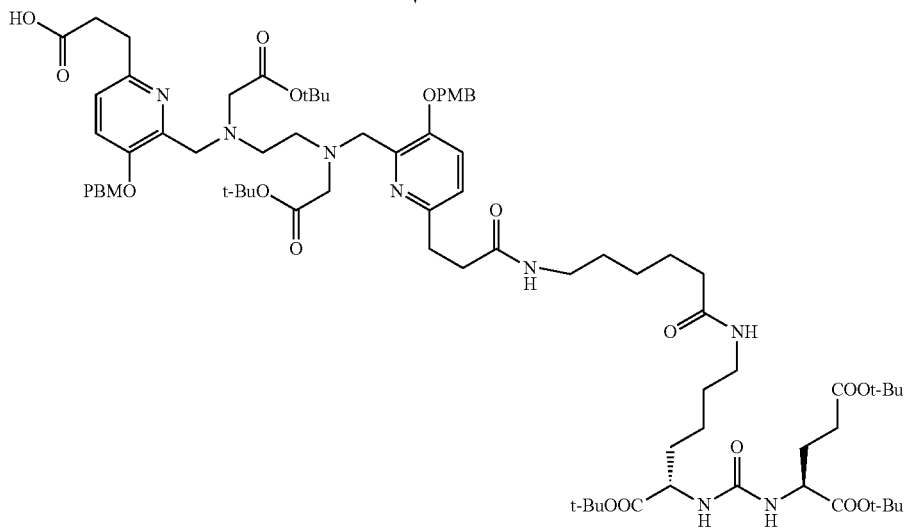

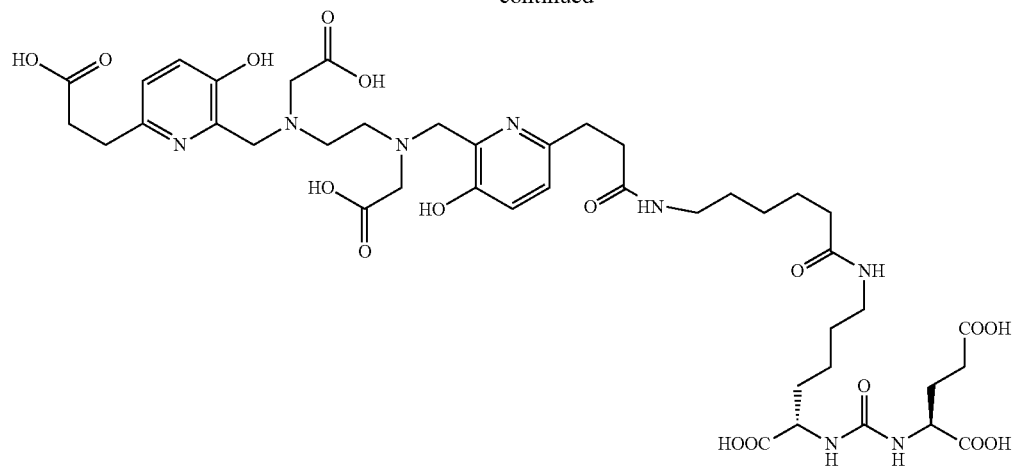
2 | $^{68}$Ga(III)Cl$_3$
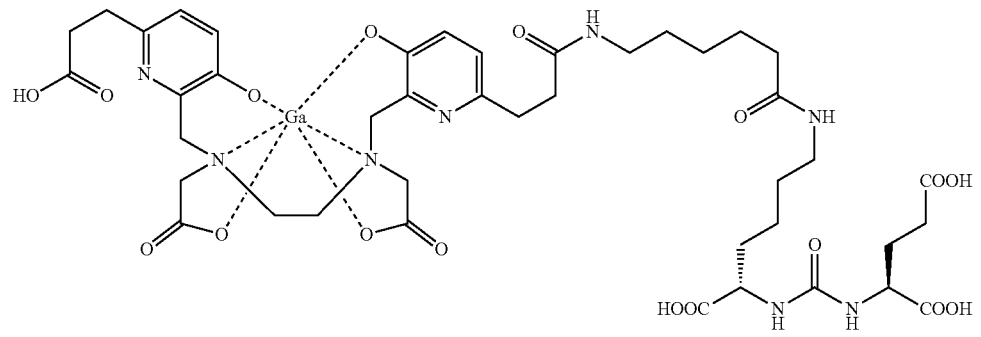
$^{68}$Ga 2
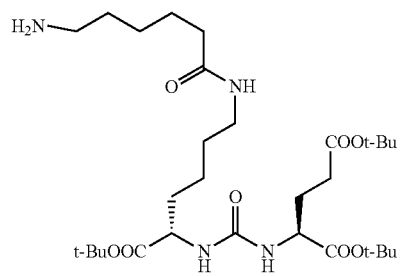
10

Example 14

3,3'-(6,6'-((2,2,13,13-Tetramethyl-4,11-dioxo-3,12-dioxa-6,9-diazatetradecane-6,9-diyl)bis(methylene))bis(5-((4-methoxybenzyl)oxy)pyridine-6,2-diyl))dipropanoic acid (20)

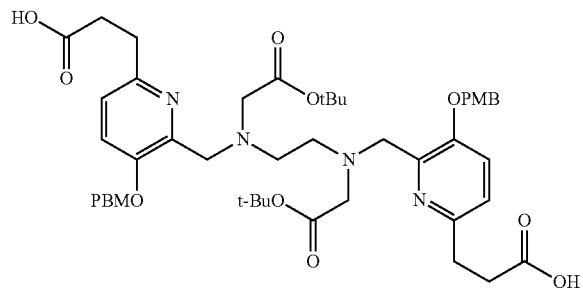

20

To a solution of 19 (61.8 mg, 0.068 mmol) in 2 mL MeOH was added 2 mL NaOH (1 N). After stirred at rt for 4 h, 1 N HCl was added to the mixture till pH=4-5. The resulting mixture was then extracted with EtOAc (20 mL×3). The organic layer was collected, washed with brine (20 mL), dried by $Na_2SO_4$ and filtered. The filtrate was concentrated to give 47.7 mg white solid 20 (yield: 79.1%): HRMS (ESI) calculated for $C_{48}H_{63}N_4O_{12}$ (M+H$^+$), 887.4442; found, 887.4342.

Example 15 tert-Butyl-3-(6-(((2-(((6-((7S,11S)-7,11-bis(tert-butoxycarbonyl)-2,2-dimethyl-4,9,17,24-tetraoxo-3-oxa-8,10,16,23-tetraazahexacosan-26-yl)-3-((4-methoxybenzyl)oxy)pyridin-2-yl)methyl)(2-(tert-butoxy)-2-oxoethyl)amino)ethyl)(2-(tert-butoxy)-2-oxoethyl)amino)methyl)-5-((4-methoxybenzyl)oxy)pyridin-2-yl)propanoate (21) and (S,2S,2'S)-6,6'-((6,6'-((3,3'-(6,6'-((2,2,13,13-tetramethyl-4,11-dioxo-3,12-dioxa-6,9-diazatetradecane-6,9-diyl)bis(methylene))bis(5-((4-methoxybenzyl)oxy)pyridine-6,2-diyl))bis(propanoyl))bis(azanediyl))bis(hexanoyl))bis(azanediyl))bis(tert-butyl-2-(3-((S)-1,5-di-tert-butoxy-1,5-dioxopentan-2-yl)ureido)hexanoate) (22)

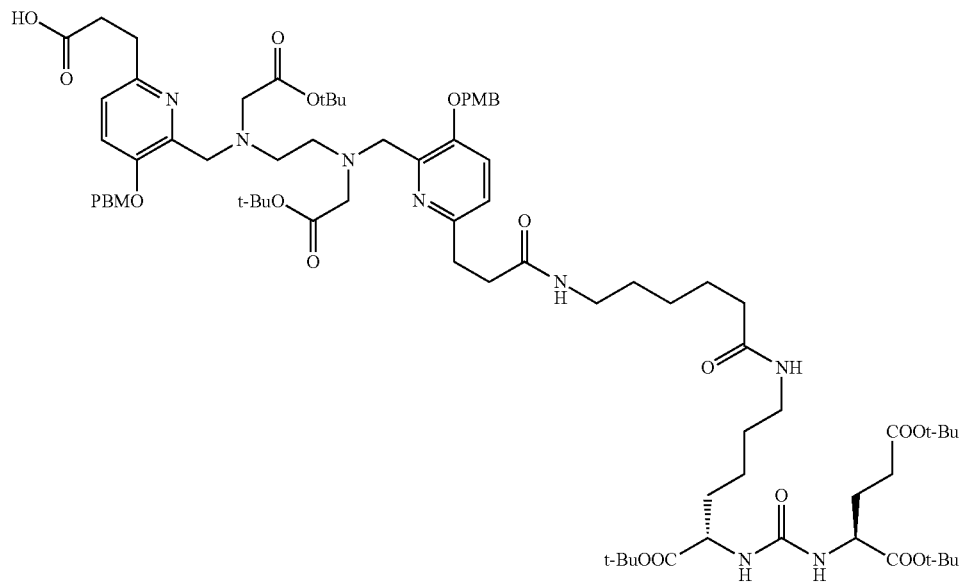

21

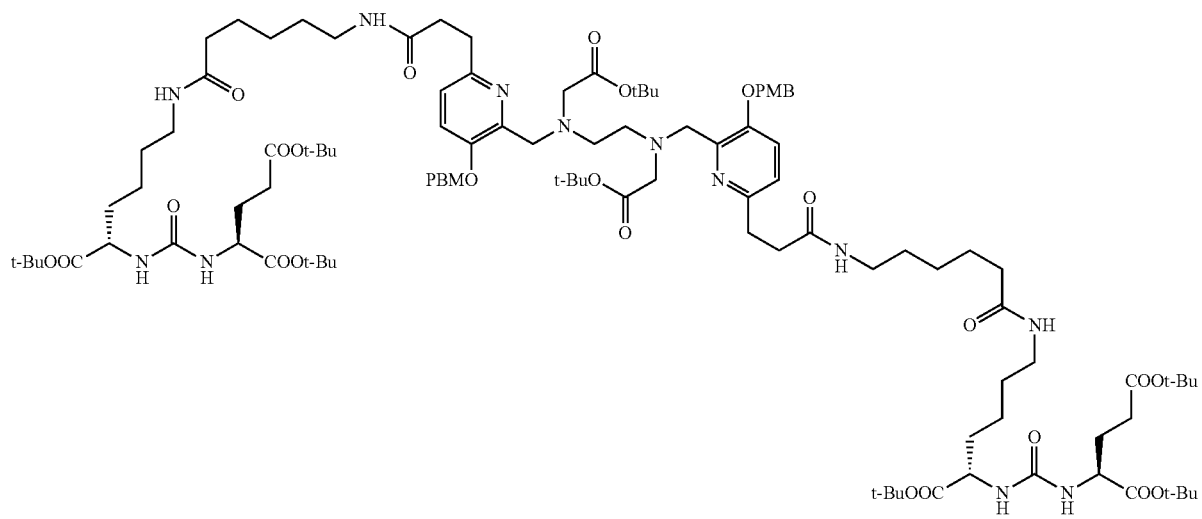

22

To a solution of 20 (47.7 mg, 0.054 mmol) in 4 mL DMF was added 10 (32.7 mg, 0.054 mmol), N,N'-dicyclohexylcarbodiimide (EDCI, 15.4 mg, 0.081 mol), N-Hydroxybenzotrizole (HOBt, 13.7 mg, 0.081 mmol), and DIPEA (20.9 mg, 0.162 mmol). After stirred at rt overnight, the mixture was diluted with EtOAc (30 mL), washed with $H_2O$ (10×2 mL) and brine (10 mL), dried over $Na_2SO_4$, concentrated and purified by FC (DCM/MeOH/$NH_4OH$=90/9/1) to give 19 mg clear oil 21 (yield: 23.9%) and 10 mg 22 (yield: 9.1%): Compound 21: HRMS (ESI) calculated for $C_{78}H_{117}N_8O_{19}$ (M+H$^+$), 1469.8435; found, 1469.8511; Compound 22: HRMS (ESI) calculated for $C_{108}H_{171}N_{12}O_{28}$ (M+H$^+$), 2052.2427; found, 2052.2408.

Example 16

(3S,7S)-22-(6-(((2-(((6-(2-Carboxyethyl)-3-hydroxypyridin-2-yl)methyl) (carboxymethyl)amino)ethyl) (carboxymethyl)amino)methyl)-5-hydroxypyridin-2-yl)-5,13,20-trioxo-4,6,12,19-tetraazadocosane-1,3,7-tricarboxylic acid (2)

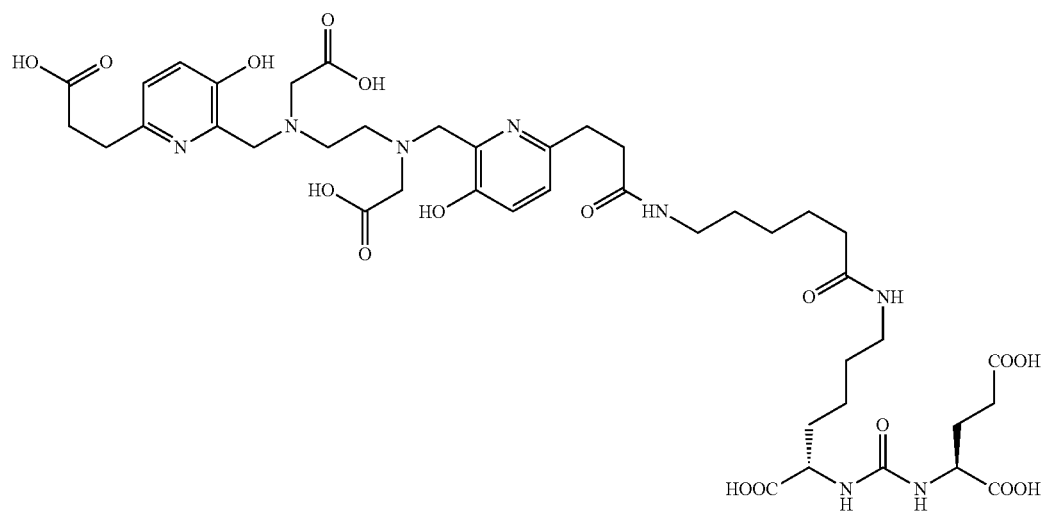

2

A solution of 21 (19 mg, 0.013 mmol) in 0.9 mL trifluoroacetic acid (TFA) and 0.1 mL dimethyl sulfide was stirred at rt for 3 h. The reaction mixture was evaporated in vacuo, and the residue was recrystallized from Ether/EtOH to give 10 mg white solid 2 (yield: 81.0%): $^1$HNMR (400 MHz, MeOD) δ: 7.65-7.74 (m, 4H), 4.40 (s, 2H), 4.35 (s, 2H), 4.29-4.33 (m, 1H), 4.20-4.24 (m, 1H), 3.80 (s, 2H), 3.74 (s, 2H), 3.44-3.45 (m, 4H), 3.14-3.29 (m, 8H), 2.91 (t, 2H, J=7.0 Hz), 2.74 (t, 2H, J=7.2 Hz), 2.55 (t, 2H, J=7.2 Hz), 2.19-2.26 (m, 3H), 1.99-2.04 (m, 1H), 1.86-1.88 (m, 1H), 1.73-1.77 (m, 1H), 1.45-1.61 (m, 8H), 1.25-1.29 (m, 2H); HRMS (ESI) calculated for $C_{42}H_{61}N_8O_{17}$ (M+H$^+$), 949.4155; found, 949.4116.

Scheme 13

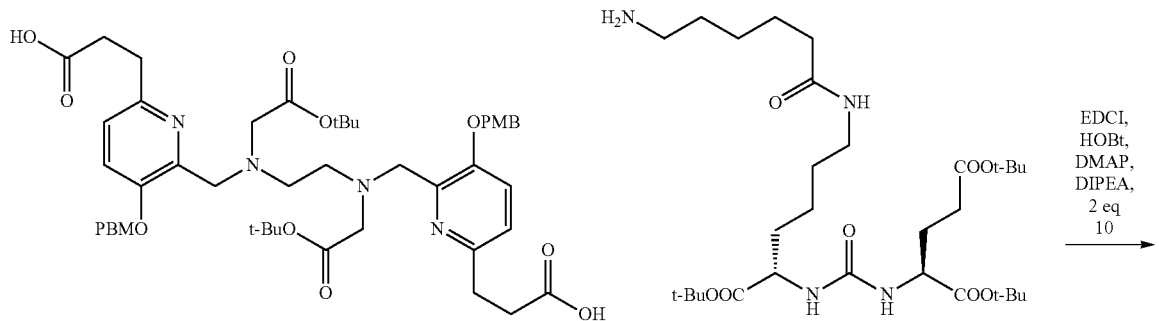

77 78
-continued
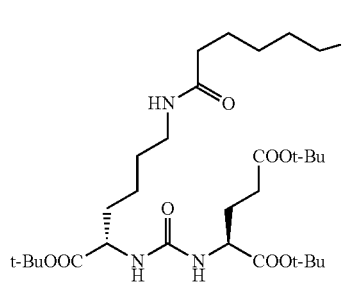
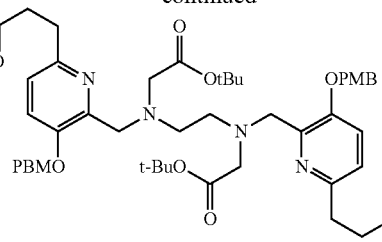
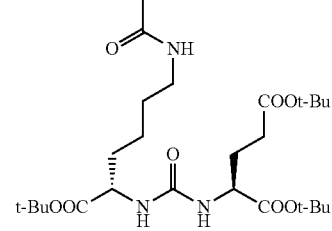
22
↓ TFA
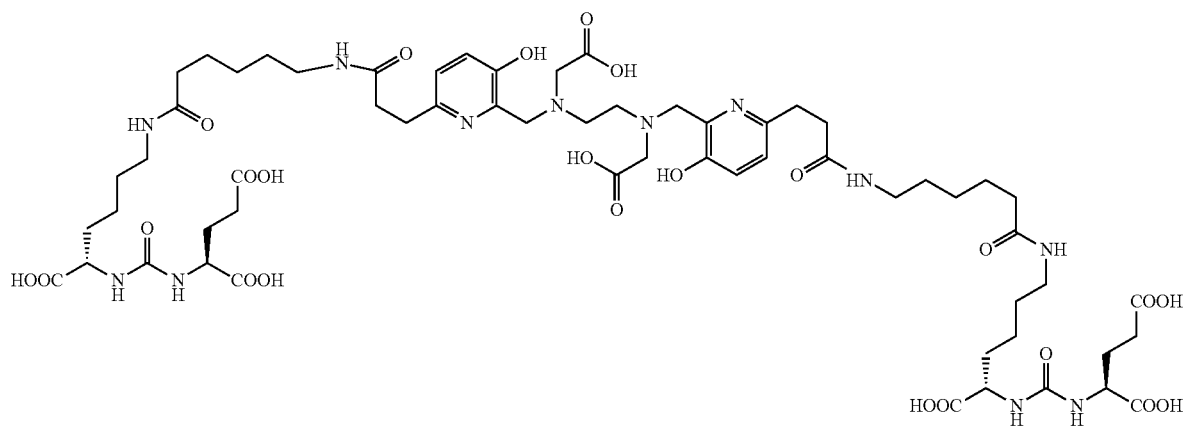
3
↓ ⁶⁸Ga(III)Cl₃
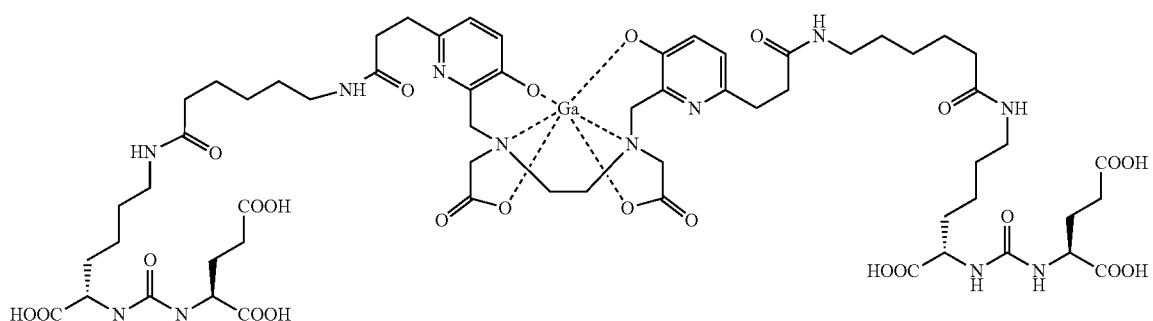
⁶⁸Ga 3

Example 17

(3S,3'S,7S,7'S)-22,22'-(6,6'-((Ethane-1,2-diylbis((carboxymethyl)azanediyl)) bis(methylene))bis(5-hydroxypyridine-6,2-diyl))bis(5,13,20-trioxo-4,6,12,19-tetraazadocosane-1,3,7-tricarboxylic acid) (3)

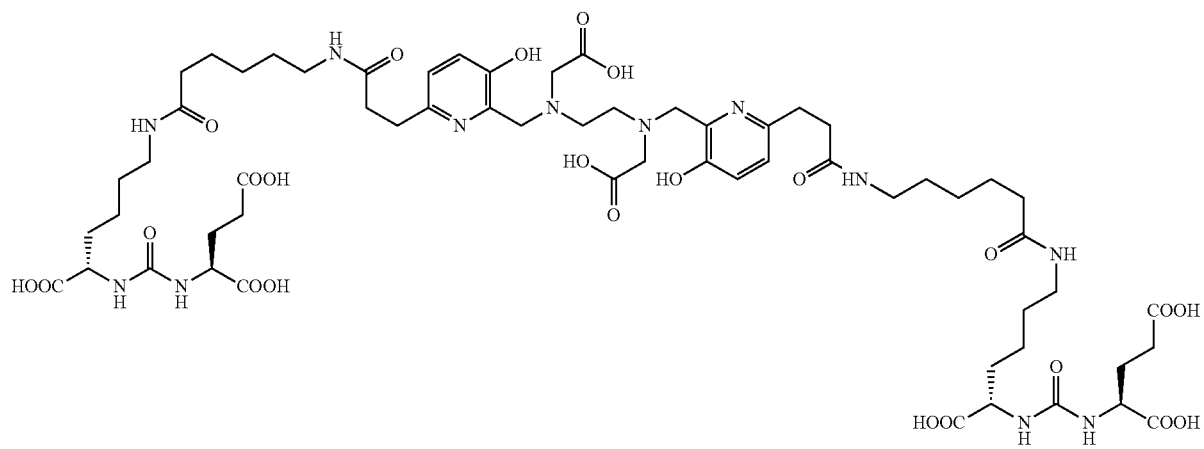

3

Compound 3 was prepared from 22 (10 mg, 0.0049 mmol) in 0.9 mL trifluoroacetic acid (TFA) and 0.1 mL dimethyl sulfide, with the same procedure described for compound 2. Compound 3: 3.6 mg (yield: 53.9%): $^1$HNMR (400 MHz, MeOD) δ: 7.68 (d, 2H, J=8.4 Hz), 7.62 (d, 2H, J=8.4 Hz), 4.30-4.35 (m, 6H), 4.21-4.23 (m, 2H), 3.72 (s, 4H), 3.46 (s, 4H), 3.15-3.23 (m, 12H), 2.71-2.75 (m, 4H), 2.54-2.58 (m, 4H), 2.20-2.27 (m, 6H), 1.99-2.04 (m, 2H), 1.86-1.88 (m, 2H), 1.73-1.77 (m, 2H), 1.45-1.61 (m, 16H), 1.25-1.29 (m, 4H); HRMS (ESI) calculated for $C_{60}H_{91}N_{12}O_{24}$ (M+H$^+$), 1363.6269; found, 1363.6332.

Scheme 14

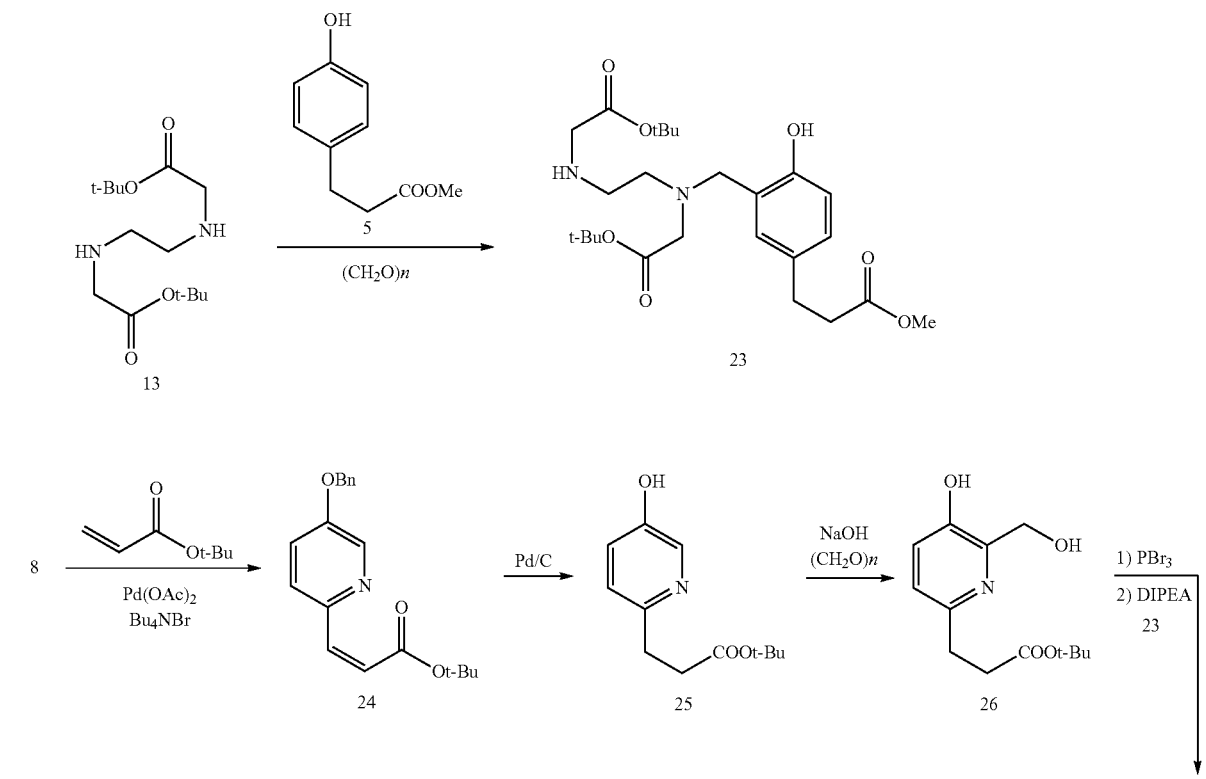

81
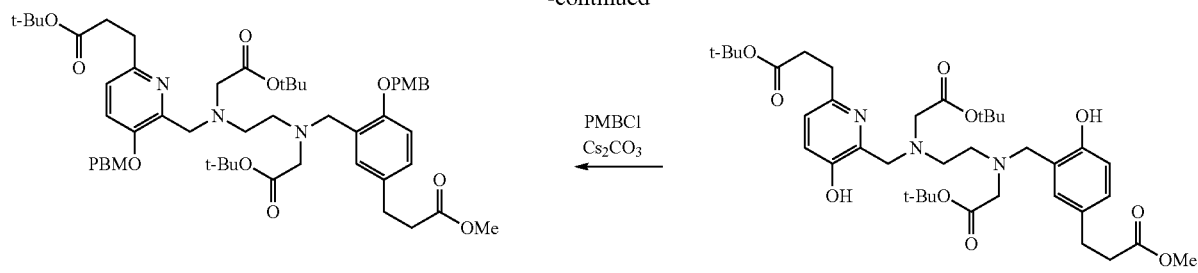
82
-continued
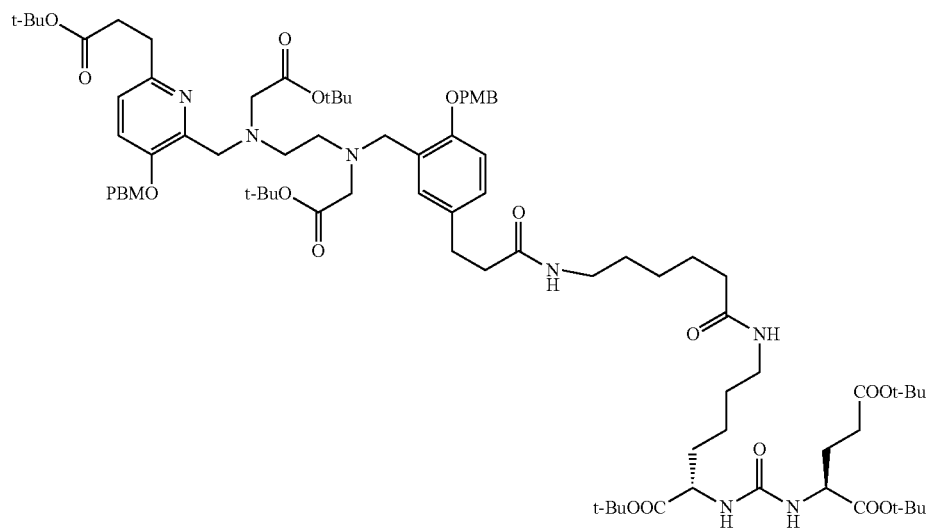
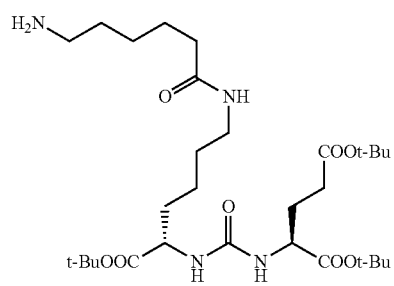

Example 18

Methyl 3-(3-(((2-(tert-butoxy)-2-oxoethyl)(2-((2-(tert-butoxy)-2-oxoethyl)amino)ethyl) amino)methyl)-4-hydroxyphenyl)propanoate (23)

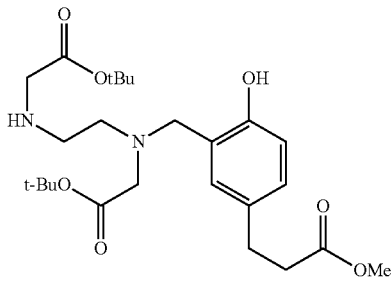

23

To a solution of 13 (1.7 g, 5.9 mmol) in 75 mL EtOH and 75 mL toluene was added 5 (885 mg, 4.92 mmol) and paraformaldehyde (1.06 g, 35.3 mmol) at rt. The mixture was heated under reflux for overnight. The mixture was concentrated, and the residue was purified by flash chromatography (FC) (EtOAc/hexane=2/8) to give 850 mg colorless oil 23 (yield: 36%): HRMS (ESI) calculated for $C_{25}H_{41}N_2O_7$ (M+H$^+$), 481.2914; found, 481.2963.

Example 19

(Z)-tert-Butyl 3-(5-(benzyloxy)pyridin-2-yl)acrylate (24)

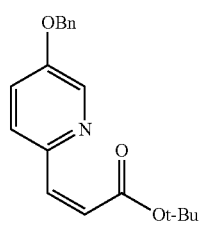

24

A mixture of 14 (5.56 g, 17.8 mmol), tert-butyl acrylate (4.58 g, 35.7 mmol), potassium carbonate ($K_2CO_3$, 4.92 g, 35.7 mmol), tetrabutylammonium bromide (11.5 g, 35.7 mmol), and palladium acetate (Pd(OAc)$_2$, 217 mg, 0.89 mmol) in 75 mL DMF was deoxygenated by purging into nitrogen for 15 min and then heated at 120° C. for overnight. The mixture was cooled to RT, diluted with 250 mL EtOAc and washed with H$_2$O (60 mL×2) as well as brine (60 mL). The organic layer was dried by Na$_2$SO$_4$ and filtered. The filtrate was concentrated, and the residue was purified by FC (EtOAc/hexane=2/8) to give 2.15 g colorless oil 24 (yield: 38.7%): HRMS (ESI) calculated for $C_{19}H_{22}NO_3$ (M+H$^+$), 312.1600; found, 312.1672.

Example 20

Methyl 3-(5-hydroxypyridin-2-yl)propanoate (25)

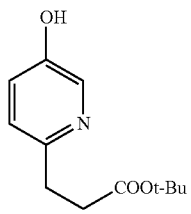

25

A mixture of 24 (2.15 g, 6.89 mmol) and Pd/C (430 mg) in 50 mL MeOH was stirred at rt under H$_2$ for 4 h. The resulting mixture was filtered and the filtrate was concentrated to give 1.54 g colorless oil 25 (yield: 100%): HRMS (ESI) calculated for $C_{12}H_{18}NO_3$ (M+H$^+$), 224.1287; found, 224.1208.

Example 21 tert-Butyl 3-(5-hydroxy-6-(hydroxymethyl)pyridin-2-yl)propanoate (26)

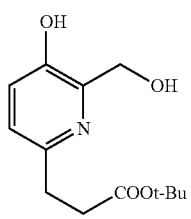

26

To a solution of 25 (2.15 g, 9.6 mmol) in 50 mL H$_2$O was added NaOH (422 mg, 10.56 mmol) and paraformaldehyde (1.73 g, 57.6 mmol). After stirring at 90° C. for 3 h, the mixture was cooled with ice-bath. The pH was adjusted to 7 with 1 N HCl. The solvent was removed in vacuo. The residue was purified by FC (DCM/MeOH/NH$_4$OH=90/9/1) to give 1.3 g white solid 26 (yield: 53.3%): HRMS (ESI) calculated for $C_{13}H_{20}NO_4$ (M+H$^+$), 254.1392; found, 254.1436.

Example 22 tert-Butyl 3-(6-(((2-(tert-butoxy)-2-oxoethyl)(2-((2-(tert-butoxy)-2-oxoethyl)(2-hydroxy-5-(3-methoxy-3-oxopropyl)benzyl)amino)ethyl)amino)methyl)-5-hydroxypyridin-2-yl)propanoate (27)

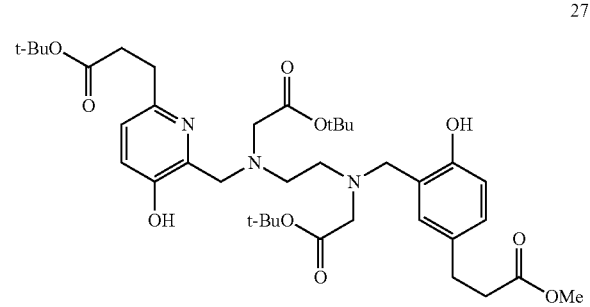 [SMILES: COC(=O)CCc1ccc(O)c(CN(CCN(CC(=O)OC(C)(C)C)Cc2nc(CCC(=O)OC(C)(C)C)ccc2O)CC(=O)OC(C)(C)C)c1]

27

To a solution of 26 (153 mg, 0.6 mmol) in 5 mL chloroform was added phosphorus tribromide (81.4 mg, 0.3 mmol) dropwise under ice-bath. The mixture was warmed to rt and maintained for 3 h. The resulting mixture was then cooled to 0° C. DIPEA (384 mg, 3 mmol) was added followed by 23 (241 mg, 0.5 mmol). The ice-bath was then removed. The mixture was stirred at rt overnight. The solvent was removed in vacuo and the residue was purified by FC (DCM/MeOH/NH$_4$OH=85/15/1.5) to give 25 mg colorless oil 27 (yield: 7%): HRMS (ESI) calculated for $C_{38}H_{58}N_3O_{10}$ (M+H$^+$), 716.4122; found, 716.4169.

Example 23 tert-Butyl 3-(6-(((2-(tert-butoxy)-2-oxoethyl)(2-((2-(tert-butoxy)-2-oxoethyl)(5-(3-methoxy-3-oxopropyl)-2-((4-methoxybenzyl)oxy)benzyl)amino)ethyl)amino)methyl)-5-((4-methoxybenzyl)oxy)pyridin-2-yl)propanoate (28)

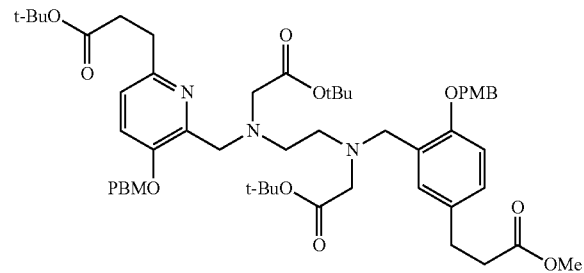

28

To a solution of 27 (23 mg, 0.032 mmol) in 2 mL DMF was added 4-methoxybenzyl (17.4 mg, 0.064 mmol) and Cs$_2$CO$_3$ (20.93 mg, 0.064 mmol) at 0° C. The mixture was the warmed to rt and maintained for 4 h. The resulting mixture was then poured into 30 mL EtOAc and washed with H$_2$O (10 mL×2) as well as brine (10 mL). The organic layer was dried by Na$_2$SO$_4$ and filtered. The filtrate was concentrated, and the residue was purified by FC (DCM/MeOH/NH$_4$OH=90/9/1) to give 25 mg clear oil 28 (yield: 81.5%): HRMS (ESI) calculated for $C_{54}H_{74}N_3O_{12}$ (M+H$^+$), 956.5272; found, 956.5240.

Example 24

(S)-6-(6(3-(3-(((2-(tert-Butoxy)-2-oxoethyl)(2-((2-(tert-butoxy)-2-oxoethyl)((6-(3-(tert-butoxy)-3-oxopropyl)-3-((4-methoxybenzyl)oxy)pyridin-2-yl)methyl)amino)ethyl) amino)methyl)-4-((4-methoxybenzyl)oxy)phenyl)propanamido)hexanamido)-2-(3-((S)-1,5-di-tert-butoxy-1,5-dioxopentan-2-yl)ureido)hexanoic acid (29)

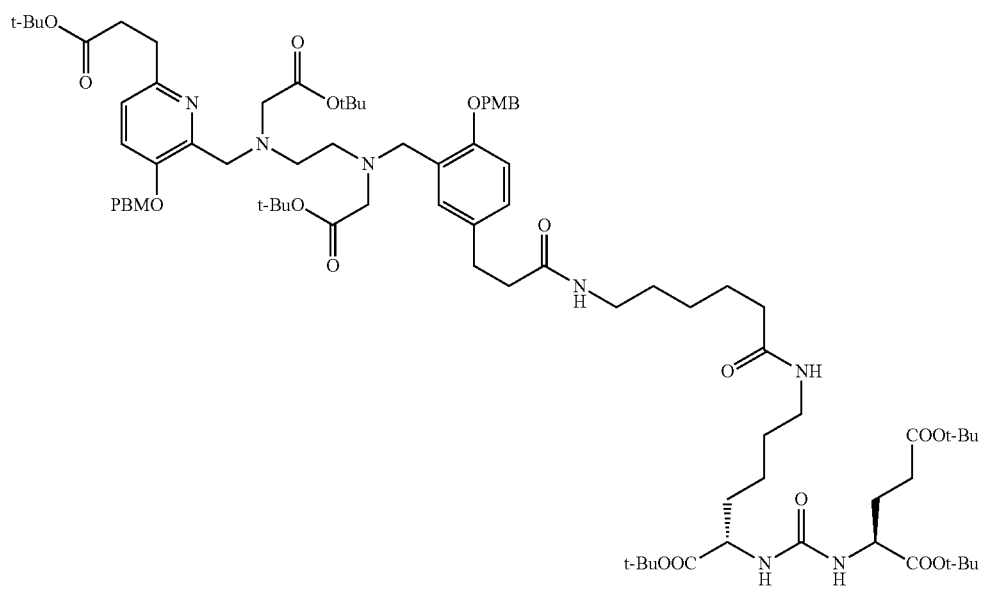

29

To a solution of 28 (25 mg, 0.026 mmol) in 1 mL MeOH was added 1 mL NaOH (1 N). After stirred at rt for 4 h, 1 N HCl was added to the mixture till pH=4-5. The resulting mixture was then extracted with EtOAc (10 mL×3). The organic layer was collected, washed with brine (10 mL), dried by $Na_2SO_4$ and filtered. The filtrate was concentrated to give 23 mg white solid. 2 mL DMF was then added to the residue, followed by Glu-NH—CO—NH-Lys(Ahx)-$NH_2$ (10, 19.1 mg, 0.032 mmol), N,N'-dicyclohexylcarbodiimide (EDCI, 7.57 mg, 0.040 mol), N-Hydroxybenzotrizole (HOBt, 6.7 mg, 0.040 mmol), and DIPEA (6.84 mg, 0.053 mmol). After stirred at rt overnight, the mixture was diluted with EtOAc (30 mL), washed with $H_2O$ (10×2 mL) and brine (10 mL), dried over $Na_2SO_4$, concentrated and purified by FC (DCM/MeOH/$NH_4OH$=90/9/1) to give 15 mg clear oil 29 (yield: 37.7%): HRMS (ESI) calculated for $C_{83}H_{126}N_7O_{19}$ (M+H$^+$), 1524.9108; found, 1524.9088.

Scheme 15

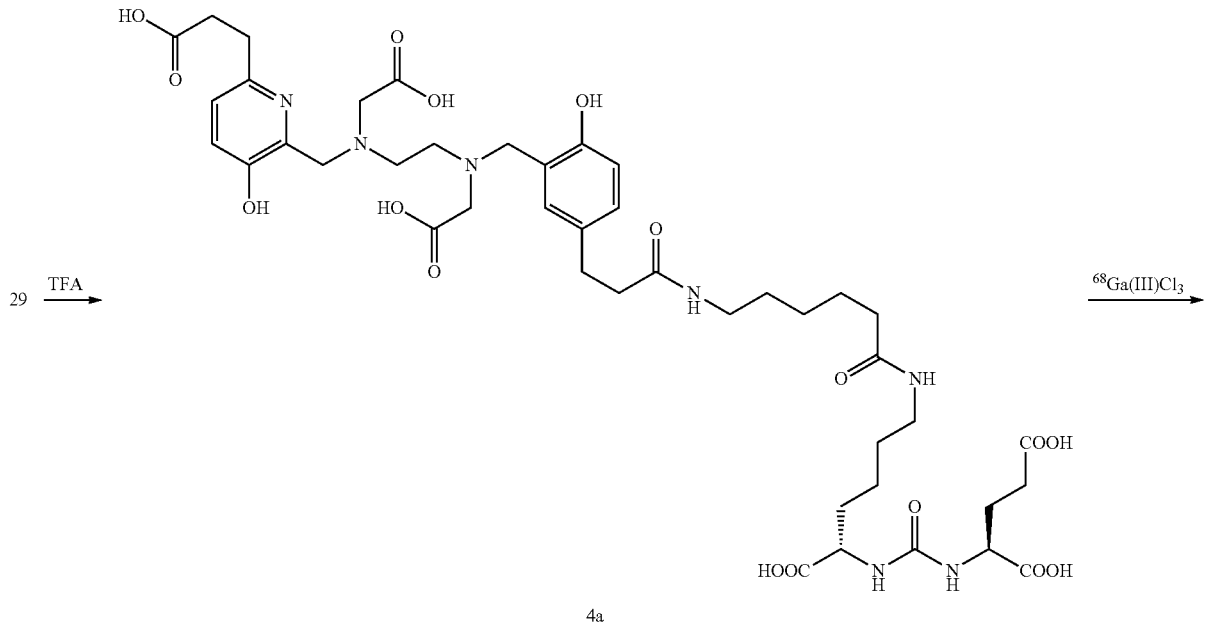

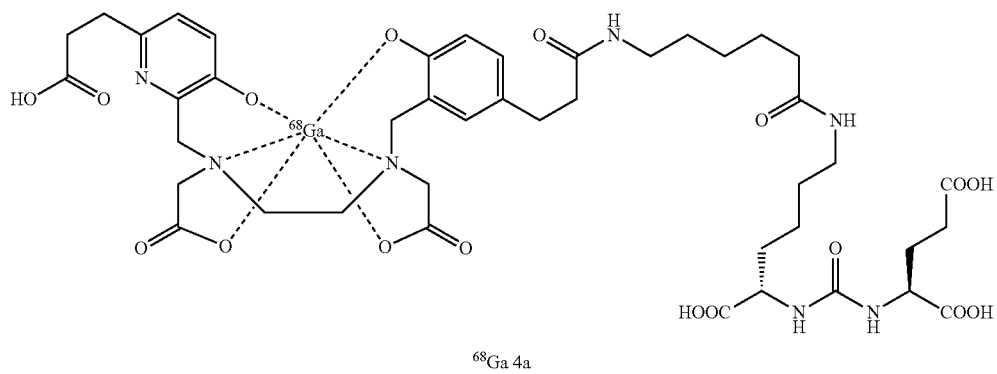

$^{68}$Ga 4a

Example 25

(3S,7S)-22-(3-(((2-(((6-(2-Carboxyethyl)-3-hydroxy-pyridin-2-yl)methyl)(carboxymethyl)amino)ethyl)(carboxymethyl)amino)methyl)-4-hydroxyphenyl)-5,13,20-trioxo-4,6,12,19-tetraazadocosane-1,3,7-tricarboxylic acid (4a)

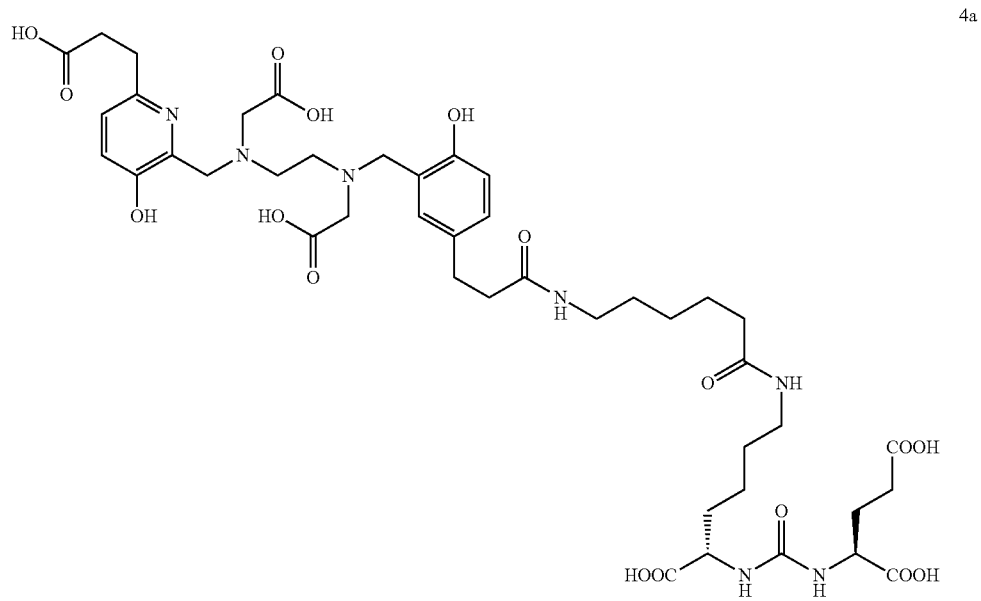 [SMILES: O=C(O)CCc1ccc(O)c(CN(CCN(CC(=O)O)Cc2cc(CCC(=O)NCCCCCC(=O)NCCCC[C@H](NC(=O)N[C@@H](CCC(=O)O)C(=O)O)C(=O)O)ccc2O)CC(=O)O)n1]

4a

Compound 4a was prepared from 29 (15 mg, 0.0098 mmol) in 0.9 mL trifluoroacetic acid (TFA) and 0.1 mL dimethyl sulfide, with the same procedure described for compound 2. Compound 4a: 4.5 mg (yield: 48.4%): $^1$HNMR (400 MHz, MeOD) δ: 7.68-7.71 (m, 1H), 7.58-7.65 (m, 1H), 7.09-7.21 (m, 2H), 6.82 (dd, 1H, J=6.4 Hz, J=8.4 Hz), 4.43 (2H), 4.20-4.36 (m, 4H), 3.87 (s, 2H), 3.48-3.51 (m, 6H), 3.10-3.21 (m, 6H), 2.83-2.86 (m, 4H), 2.39-2.46 (m, 4H), 2.11-2.19 (m, 3H), 1.82-1.94 (m, 2H), 1.42-1.67 (m, 9H), 1.23-1.29 (m, 2H); HRMS (ESI) calculated for $C_{43}H_{62}N_7O_{17}$ (M+H$^+$), 948.4202; found, 948.4173.

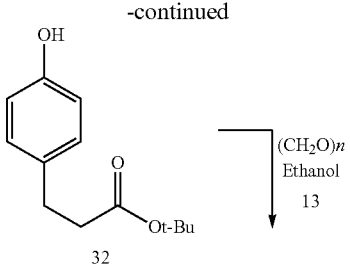

Scheme 16

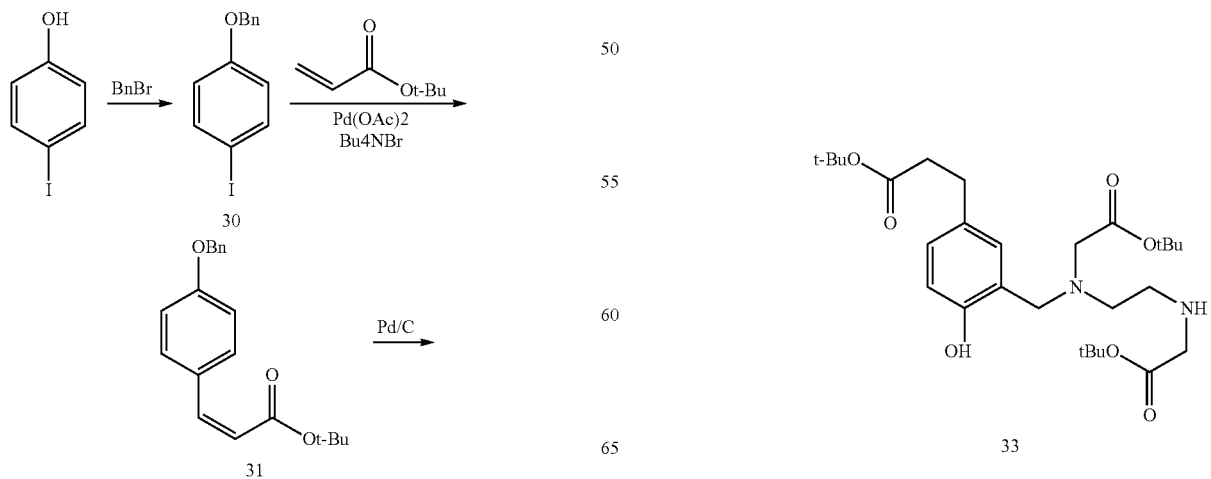

Example 26 tert-Butyl 3-(3-(((2-(tert-butoxy)-2-oxoethyl)(2-((2-(tert-butoxy)-2-oxoethyl)amino) ethyl)amino) methyl)-4-hydroxyphenyl)propanoate (33)

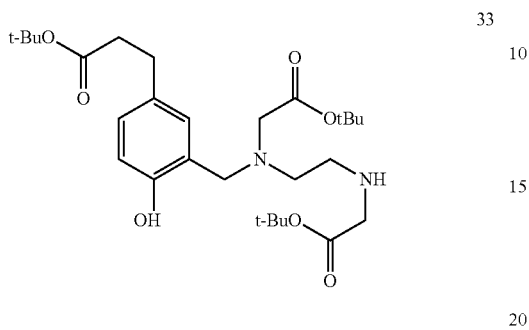

33

To a solution of 32 (565 mg, 2.54 mmol) in 30 mL EtOH was added 13 (880 mg, 3 mmol) and paraformaldehyde (762 mg, 25.4 mmol) at rt. The mixture was heated under reflux for 6 h. The mixture was concentrated, and the residue was purified by flash chromatography (FC) (DCM/MeOH/NH$_4$OH=90/9/1) to give 900 mg colorless oil 33 (yield: 67.7%): HRMS (ESI) calculated for C$_{28}$H$_{47}$O$_7$ (M+H$^+$), 523.3383; found, 523.3484.

Scheme 17

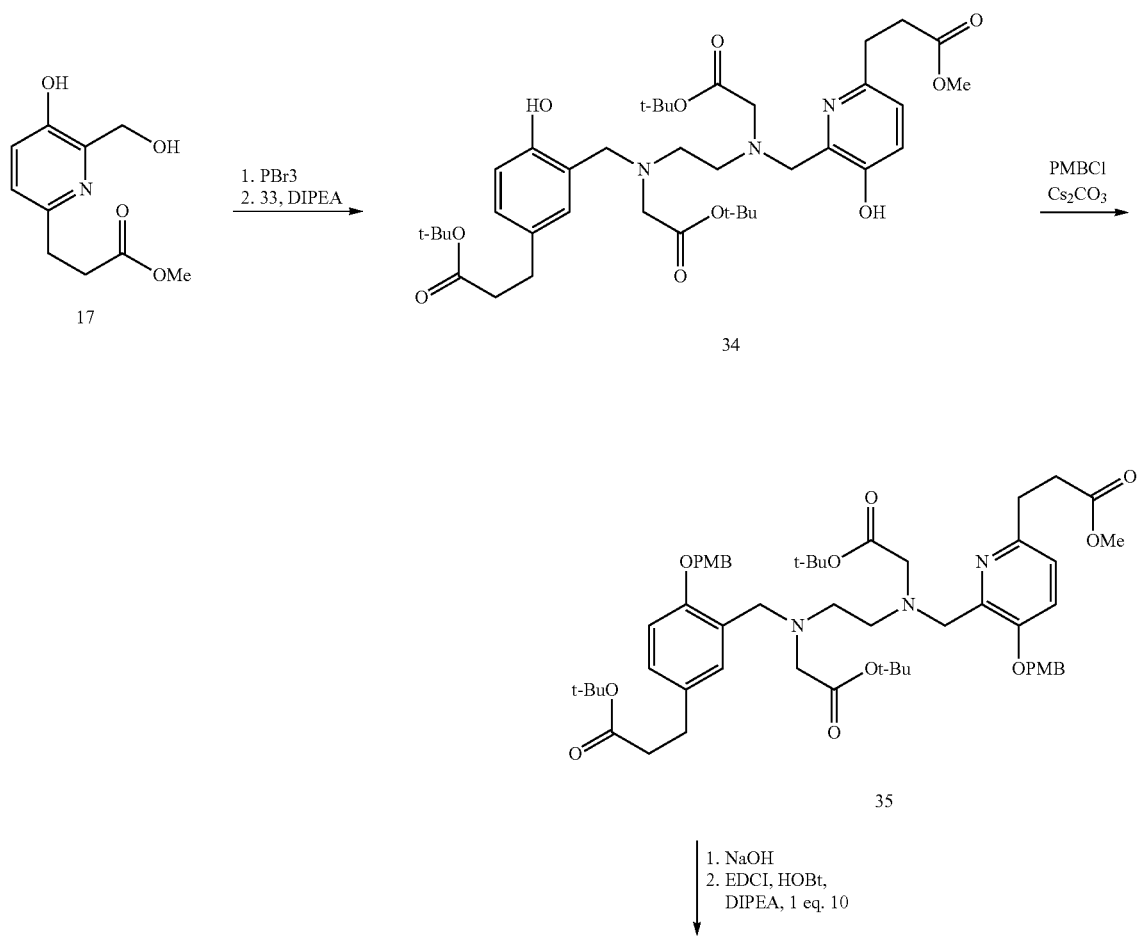

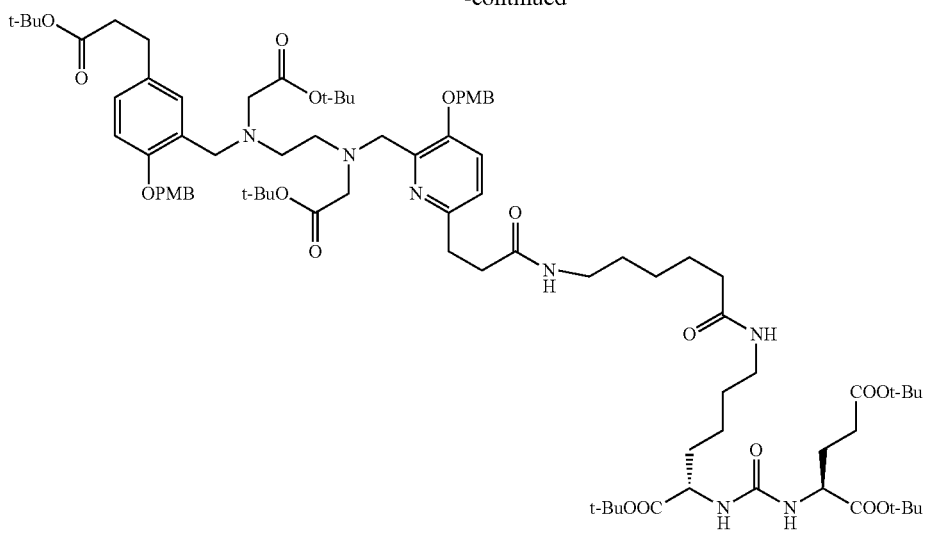
36
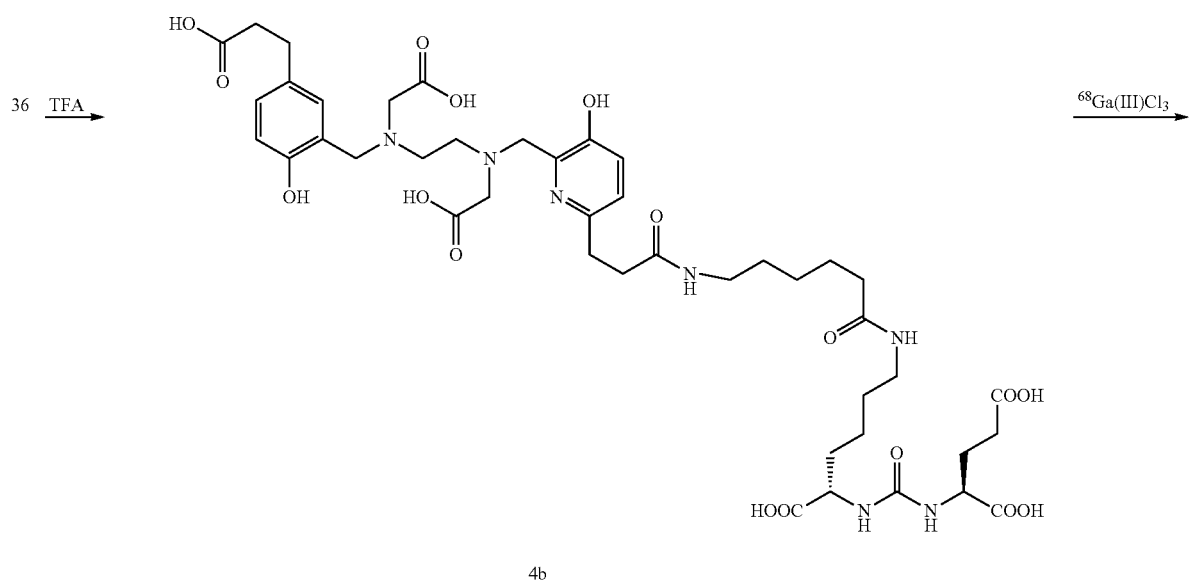
4b
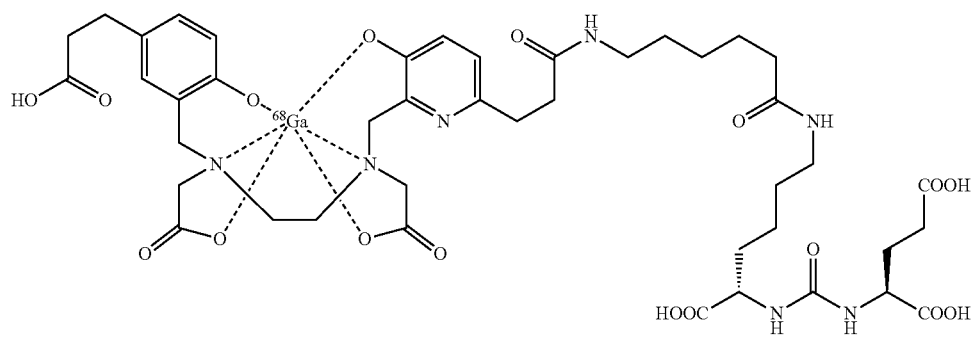
⁶⁸Ga 4b

Example 27 tert-Butyl 3-(3-(((2-(tert-butoxy)-2-oxoethyl)(2-((2-(tert-butoxy)-2-oxoethyl)((3-hydroxy-6-(3-methoxy-3-oxopropyl)pyridin-2-yl)methyl)amino)ethyl)amino)methyl)-4-hydroxyphenyl)propanoate (34)

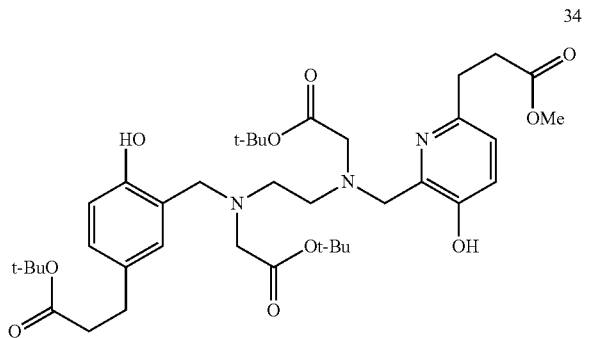 [SMILES: COC(=O)CCc1ccc(O)c(CN(CCN(CC(=O)OC(C)(C)C)Cc2cc(CCC(=O)OC(C)(C)C)ccc2O)CC(=O)OC(C)(C)C)n1]

To a solution of 17 (150 mg, 0.71 mmol) in 5 mL chloroform was added phosphorus tribromide (95.6 mg, 0.35 mmol) dropwise under ice-bath. The mixture was warmed to rt and maintained for 3 h. The resulting mixture was then cooled to 0° C. DIPEA (547 mg, 4.24 mmol) was added followed by 33 (295 mg, 0.57 mmol). The ice-bath was then removed. The mixture was stirred at rt overnight. The solvent was removed in vacuo and the residue was purified by FC (DCM/MeOH/NH$_4$OH=90/9/1) to give 120 mg colorless oil 34 (yield: 29.6%): HRMS (ESI) calculated for C$_{38}$H$_{58}$N$_3$O$_{10}$ (M+H$^+$), 716.4122; found, 716.4241.

Example 28 tert-Butyl 3-(3-(((2-(tert-butoxy)-2-oxoethyl)(2-((2-(tert-butoxy)-2-oxoethyl)((6-(3-methoxy-3-oxopropyl)-3-((4-methoxybenzyl)oxy)pyridin-2-yl)methyl)amino)ethyl)amino)methyl)-4-((4-methoxybenzyl)oxy)phenyl)propanoate (35)

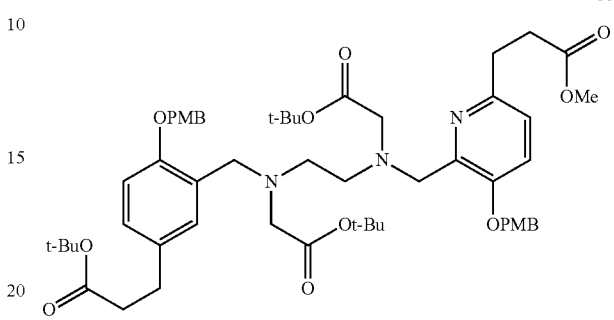

To a solution of 34 (120 mg, 0.17 mmol) in 5 mL DMF was added 4-methoxybenzyl (105 mg, 0.67 mmol) and Cs$_2$CO$_3$ (217.8 mg, 0.67 mmol) at 0° C. The mixture was the warmed to rt and maintained for 6 h. The resulting mixture was then poured into 30 mL EtOAc and washed with H$_2$O (10 mL×2) as well as brine (10 mL). The organic layer was dried by Na$_2$SO$_4$ and filtered. The filtrate was concentrated, and the residue was purified by FC (DCM/MeOH/NH$_4$OH=90/9/1) to give 80 mg colorless oil 35 (yield: 49.8%): HRMS (ESI) calculated for C$_{54}$H$_{74}$N$_3$O$_{12}$ (M+H$^+$), 956.5272; found, 956.5322.

Example 29

(3S,7S)-tri-tert-Butyl 22-(6-(((2-(tert-butoxy)-2-oxoethyl)(2-((2-(tert-butoxy)-2-oxoethyl)(5-(3-(tert-butoxy)-3-oxopropyl)-2-((4-methoxybenzyl)oxy)benzyl)amino)ethyl) amino)methyl)-5-((4-methoxybenzyl)oxy)pyridin-2-yl)-5,13,20-trioxo-4,6,12,19-tetraazadocosane-1,3,7-tricarboxylate (36)

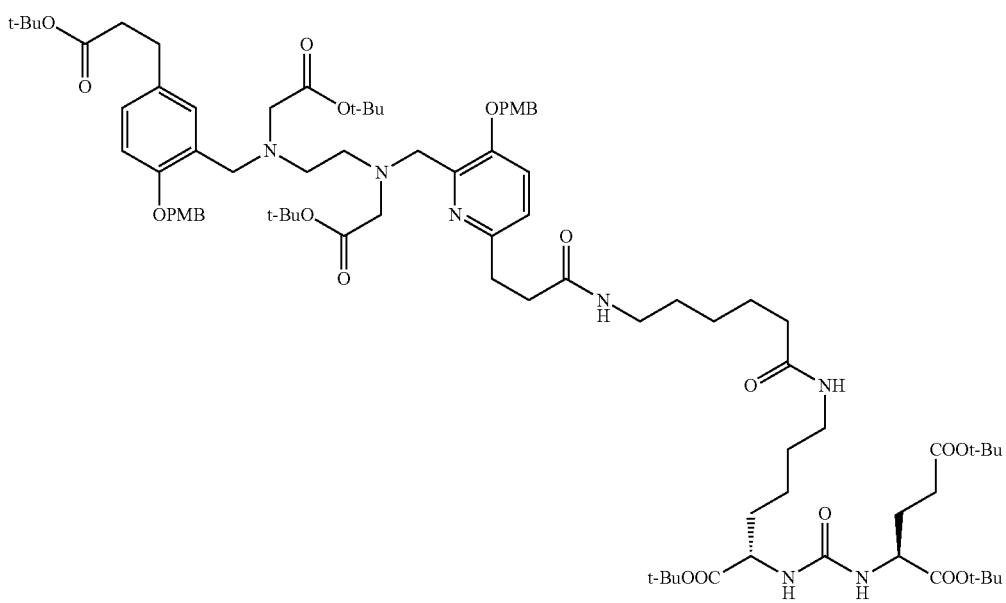

To a solution of 35 (80 mg, 0.084 mmol) in 2 mL MeOH was added 2 mL NaOH (1 N). After stirred at rt for 4 h, 1 N HCl was added to the mixture till pH=4-5. The resulting mixture was then extracted with EtOAc (20 mL×3). The organic layer was collected, washed with brine (20 mL), dried by $Na_2SO_4$ and filtered. The filtrate was concentrated to give 65 mg white solid. 4 mL DMF was then added to the residue, followed by Glu-NH—CO—NH-Lys(Ahx)-$NH_2$ (10, 41.4 mg, 0.069 mmol), N,N'-dicyclohexylcarbodiimide (EDCI, 19.7 mg, 0.104 mol), N-Hydroxybenzotrizole (HOBt, 17.5 mg, 0.104 mmol), and DIPEA (26.7 mg, 0.207 mmol). After stirred at rt overnight, the mixture was diluted with EtOAc (30 mL), washed with $H_2O$ (10×2 mL) and brine (10 mL), dried over $Na_2SO_4$, concentrated and purified by FC (DCM/MeOH/$NH_4OH$=90/9/1) to give 20 mg clear oil 36 (yield: 15.6%): HRMS (ESI) calculated for $C_{83}H_{126}N_7O_{19}$ (M+H$^+$), 1524.9108; found, 1524.9266.

Example 30

(3S,7S)-22-(6-(((2-((5-(2-Carboxyethyl)-2-hydroxybenzyl)(carboxymethyl)amino)ethyl) (carboxymethyl)amino)methyl)-5-hydroxypyridin-2-yl)-5,13,20-trioxo-4,6,12,19-tetraazadocosane-1,3,7-tricarboxylic acid (4b)

A solution of 36 (20 mg, 0.013 mmol) in 1 mL trifluoroacetic acid (TFA) was stirred at rt for 3 h. The reaction mixture was evaporated in vacuo, and the residue was washed with $Et_2O$ and purified by semi-prep HPLC to give 6.7 mg white solid 4b (yield: 54.4%): $^1$HNMR (400 MHz, MeOD) δ: 7.79 (d, 1H, J=8.4 Hz), 7.62 (d, 1H, J=8.4 Hz), 7.20-7.27 (m, 2H), 6.84 (d, 1H, J=8.4 Hz), 4.55 (s, 2H), 4.23-4.33 (m, 4H), 3.98 (s, 2H), 3.53 (s, 4H), 3.16-3.25 (m, 6H), 2.83-2.87 (m, 2H), 2.74-2.77 (m, 2H), 2.38-2.59 (m, 4H), 2.11-2.19 (m, 3H), 1.82-1.94 (m, 2H), 1.42-1.67 (m, 9H), 1.23-1.29 (m, 2H); HRMS (ESI) calculated for $C_{43}H_{62}N_7O_{17}$ (M+H$^+$), 948.4202; found, 948.4137.

Example 31

Radiolabeling

Gallium-68 eluted in 0.05 N HCl solution was obtained from a $^{68}$Ge/$^{68}$Ga generator (iTG, Germany). To prepare the new ligands with HBED-PSMA derivatives as precursors for $^{68}$Ga labeling, stock solutions of 1 mg in 1 mL 0.1 N NaOAc were prepared and used for each radiolabelling study. Labeling of $^{68}$Ga was performed after adding $^{68}$Ga solution and 2N NaOAc solution to ligands. Optimal reaction parameters were determined through various pH levels (2-7) and at a ligand concentration ranging from 0.6-3.0 μM. For in vivo studies, a higher amount of radioactivity of $^{68}$Ga labeled agents was needed. The labeling was performed in aq. NaOAc buffer (120 μL, 2.0 M) by adding a ligand solution (20 μL, 1 mg/mL) to $^{68}$Ga solution (4 mL in 0.05 N HCl). The final pH of the solution was 4.10.

Influence of other metal ions on labeling of [$^{68}$Ga]1a-g, 2, 3 and 4a-b was tested by performing the optimized labeling reaction in the presence of various potential metal contaminants, such as $Zn^{+2}$, $Fe^{+3}$, $Cu^{+2}$ and $Sn^{+2}$. Labeling was performed in aq. NaOAc buffer (30 μL, 0.2 M) by combining the ligand solution (5 μL, 0.1 mg/mL), $^{68}$Ga solution (100 μL in 0.05 N HCl) and 15 μL of stock solution of the respective metal chloride necessary to obtain the desired final contaminant concentration.

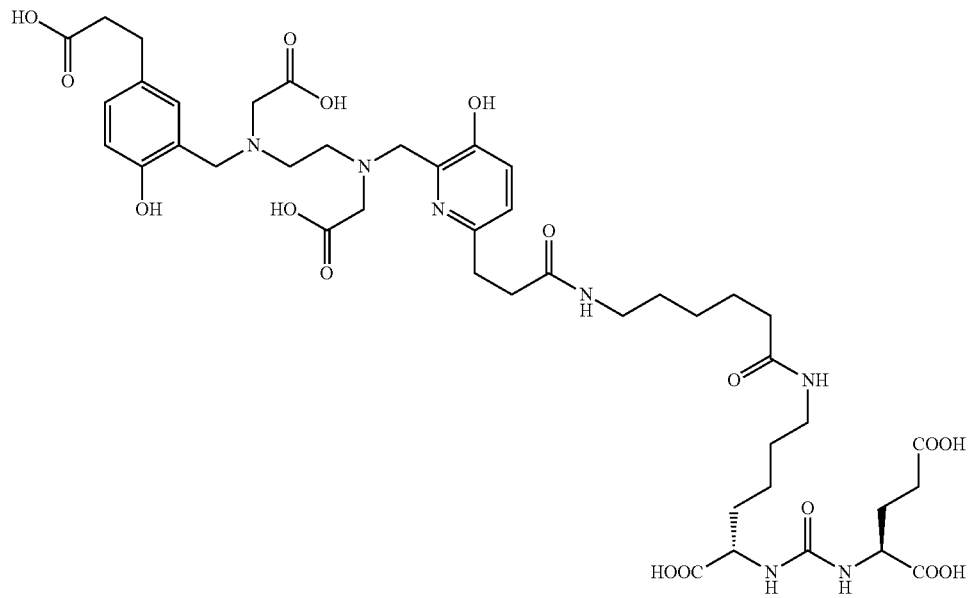

4b

Radiolabeling yields were determined after maintaining the reaction mixture at room temperature for 10 min. Radiochemical yields for [$^{68}$Ga]1a-g, 2, 3 and 4a-b, were determined by HPLC. The HPLC system was developed using a Gemini C18 column (solvent A: MeOH; solvent B: 0.1% TFA in water) with the gradient: 0-6 min (0-100% A); flow rate 2 mL/min. The $^{68}$Ga complexation of all ligands, [$^{68}$Ga]1a-g, 2, 3 and 4a-b, resulted in high radiochemical yields of 90-99% after 10 min reaction time at room temperature. As a consequence, radiotracers were subsequently used for in vitro and in vivo experiments without further purification.

A proper metal ion, such as Lu(III) chloride, can be identified for selective radiolabeling of the DOTA moiety of compound 1g based on difference in the metal's complexing capability and stability constants for metal complexes with DOTA and HBED. The conditions for the selective radio-labeling can be routinely optimized under a similar reaction condition as described above for $^{68}$Ga(III), except that the reception required heating the reaction mixture of $^{177}$Lu(III) and the ligand, 1g, at 95° C. for 30 min. The reaction for making [$^{177}$Lu]1g proceeded smoothly with an excellent radiochemical yield (>99%).

Preparation of the intermediate compound 43 was based on the following chemical reactions (Scheme 18).

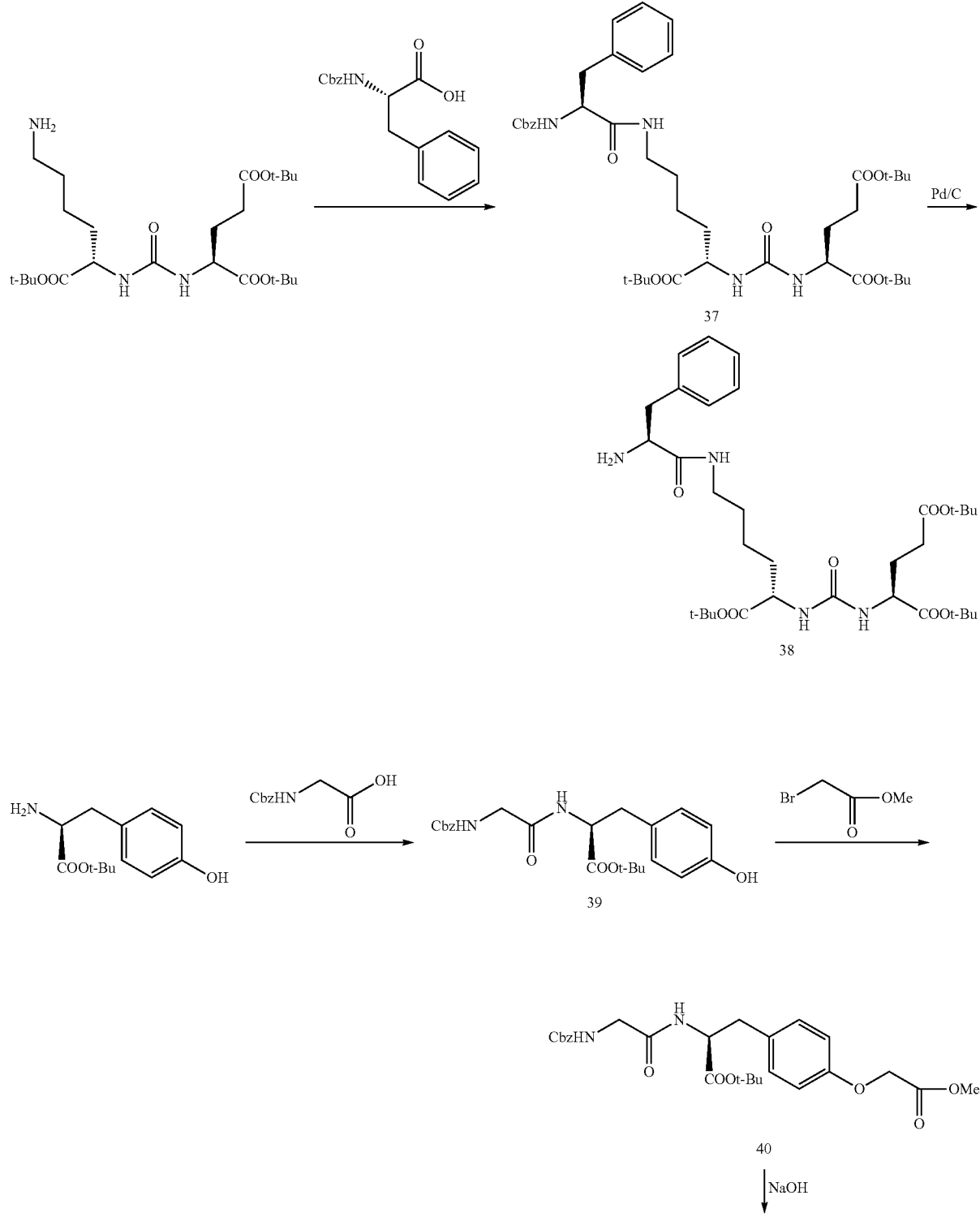

Scheme 18

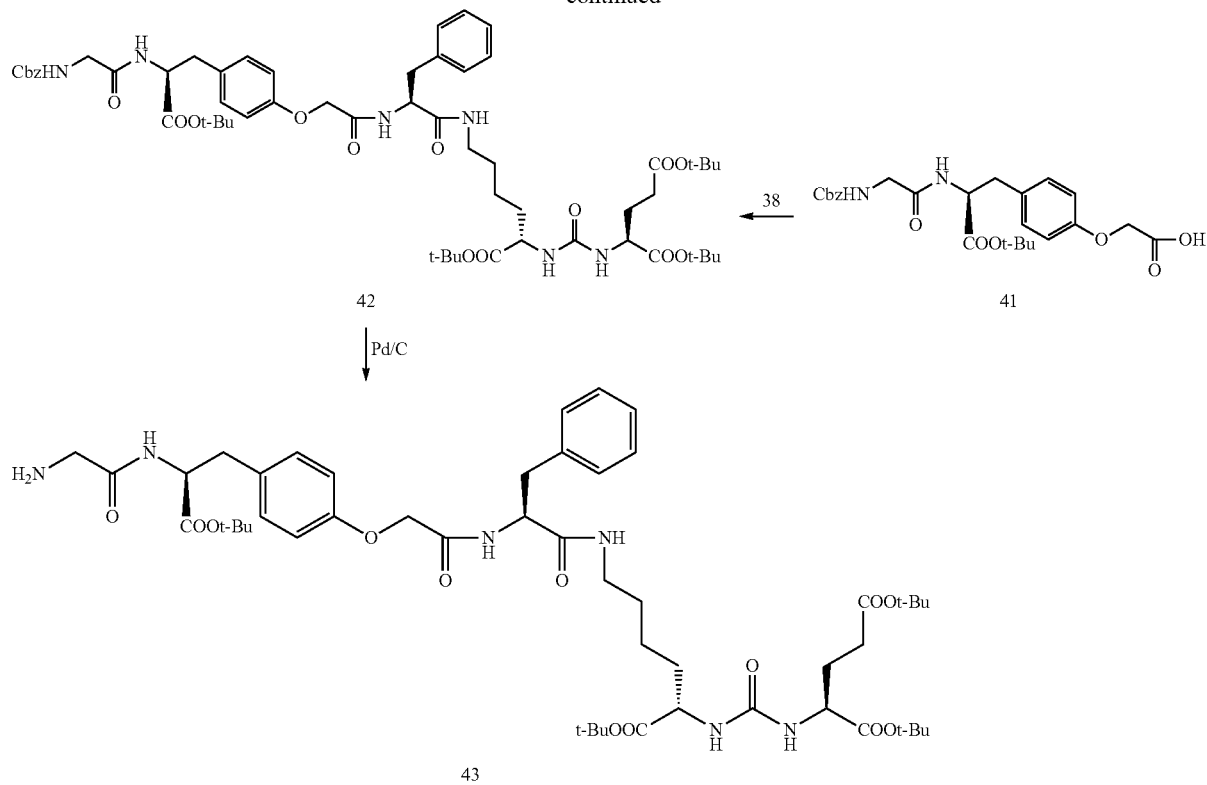

Example 32

(5S,12S,16S)-Tri-tert-butyl 5-benzyl-3,6,14-trioxo-1-phenyl-2-oxa-4,7,13,15-tetraazaoctadecane-12,16,18-tricarboxylate. (37)

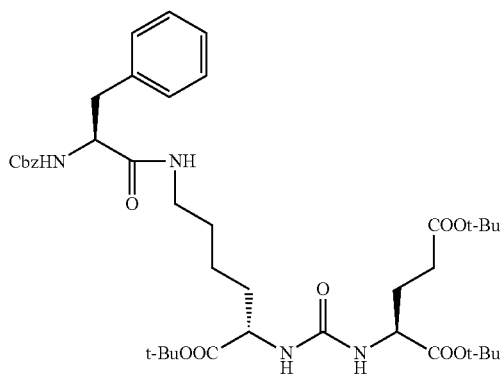

To a solution of Z-Phe-OH (218.3 mg, 0.55 mmol) in 20 mL DCM, triethylamine (Et₃N, 101 mg, 1 mmol, (S)-di-tert-butyl-2-(3-((S)-6-amino-1-tert-butoxy-1-oxohexan-2-yl)ureido)pentanedioate (248 mg, 0.5 mmol) HOBt (10 mg) and EDCI (197 mg, 1.1 mmol) were added at room temperature for overnight. The solvent was removed and the residue was purified by FC (DCM/MeOH/NH₄OH=95/5/0.5) to give 37 as a colorless oil (yield: 250 mg, 65%): ¹HNMR (400 MHz, CDCl₃) δ: 7.29-7.34 (m, 5H), 7.17-7.23 (m, 5H), 6.88 (br s, 1H), 6.11 (br s, 1H), 5.99 (br s, 1H), 5.65 (br s, 1H), 4.99-5.10 (m, 2H), 4.40-4.97 (m, 2H), 4.29-4.34 (m, 1H), 3.42 (br s, 1H), 2.96-3.08 (m, 3H), 2.32-2.37 (m, 2H), 2.03-2.12 (m, 1H), 1.78-1.89 (m, 1H), 1.66-1.73 (m, 1H), 1.57-1.66 (m, 1H), 1.27-1.52 (m, 31H). HRMS calcd. for $C_{41}H_{60}N_4O_{10}$ 768.4309, found 769.4491 $[M+H]^+$.

Example 33

(S)-Di-tert-butyl 2-(3-((S)-6-((S)-2-amino-3-phenyl-propanamido)-1-(tert-butoxy)-1-oxohexan-2-yl)ureido)pentanedioate. (38)

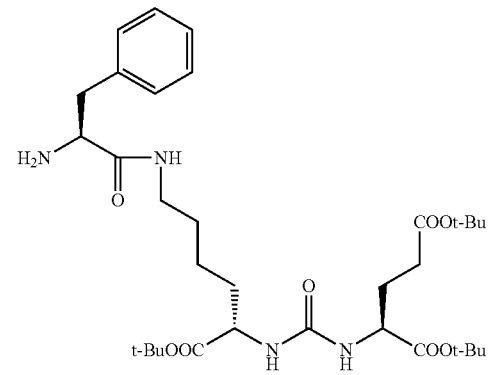

A mixture of 37 (250 mg, 0.325 mmol) and Pd/C (50 mg) in 10 mL EtOH was stirred at room temperature under H₂ for overnight. The reaction mixture was then filtered. The filtrate was concentrated to give 38 as a colorless oil (yield: 200 mg, 96.9%): ¹HNMR (400 MHz, CDCl₃) δ: 7.21-7.35 (m, 5H), 5.52-5.58 (m, 2H), 4.27-4.38 (m, 2H), 3.59-3.62 (m, 1H), 3.17-3.36 (m, 3H), 2.66-2.72 (m, 1H), 2.24-2.39 (m, 2H), 2.02-2.11 (m, 1H),), 1.78-1.89 (m, 1H), 1.66-1.73 (m, 1H), 1.57-1.66 (m, 1H), 1.27-1.52 (m, 31H). HRMS calcd. for $C_{33}H_{54}N_4O_8$ 634.3942, found 635.4011 [M+H]⁺.

Example 34

(S)-tert-Butyl 2-(2-(((benzyloxy)carbonyl)amino) acetamido)-3-(4-hydroxyphenyl)propanoate. (39)

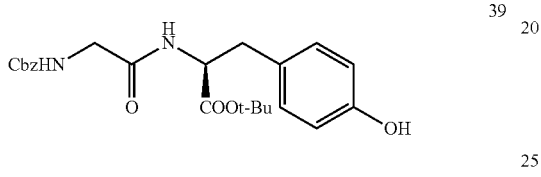

39

To a solution of 2-(((benzyloxy)carbonyl)amino)acetic acid (0.836 g, 4 mmol) in 5 mL DMF, N,N-diisopropylethylamine (DIPEA, 1.55 g, 12 mmol), 1-hydroxybenzotriazole hydrate (HOBt, 6 mmol, 1.01 g), N-(3-dimethylaminopropyl)-N-ethylcarbodiimide hydrochloride (EDCI, 1.14 g, 6 mmol) and (R)-tert-butyl 2-amino-3-(4-hydroxyphenyl)propanoate (0.949 g, 4 mmol) were added at 0° C. The mixture was stirred at room temperature for overnight before 30 mL EtOAc was added to the reaction mixture. It was then washed with H₂O (10 mL×2) and brine (10 mL), dried over MgSO₄, and filtered. The filtrate was concentrated, and the residue was purified by FC (DCM/MeOH/NH₄OH=95/5/0.5) to give 39 as a white solid (yield: 1.66 g, 96.7%): ¹HNMR (400 MHz, CDCl₃) δ: 7.33-7.38 (m, 5H), 6.99 (d, 2H, J=8.0 Hz), 6.71 (d, 2H, J=8.0 Hz), 6.32 (br s, 1H), 5.31 (br s, 1H), 5.14 (s, 2H), 4.83 (d, 1H, J=6.0 Hz), 3.80-3.93 (m, 2H), 3.03 (d, 2H, J=5.2 Hz), 1.43 (s, 9H). HRMS calcd. for $C_{23}H_{28}N_2O_6$ 428.1947, found 429.2014 [M+H]⁺.

Example 35

(S)-tert-Butyl 2-(2-(((benzyloxy)carbonyl)amino) acetamido)-3-(4-(2-methoxy-2-oxoethoxy)phenyl) propanoate. (40)

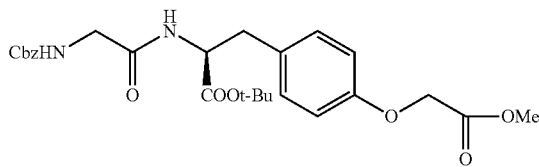

40

To a solution of 39 (1.66 g, 3.88 mmol) in 40 mL ACN, methyl bromoacetate (1.66 g, 8.51 mmol) and K₂CO₃ (1.07 g, 7.76 mmol) were added. The mixture was then stirred at room temperature for 3 h and filtered. The filtrate was concentrated, and the residue was purified by FC (EtOAc/hexane=1/1) to give 40 as a colorless oil (yield: 1.76 g, 90.5%). ¹HNMR (400 MHz, CDCl₃) δ: 7.32-7.37 (m, 5H), 7.10 (d, 2H, J=8.4 Hz), 6.81 (d, 2H, J=8.4 Hz), 6.32 (br s, 1H), 5.31 (br s, 1H), 5.14 (s, 2H), 4.69-4.74 (m, 1H), 4.60 (s, 2H), 3.80-3.93 (m, 5H), 3.04 (d, 2H, J=6.4 Hz), 1.43 (s, 9H). HRMS calcd. for $C_{26}H_{32}N_2O_8$ 500.2159, found 501.2043 [M+H]⁺.

Example 36

(S)-2-(4-(2-(2-(((Benzyloxy)carbonyl)amino)acetamido)-3-(tert-butoxy)-3-oxopropyl)phenoxy)acetic acid. (41)

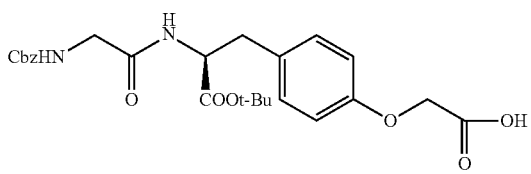

41

A solution of 40 (1.76 g, 3.51 mmol) in 20 mL MeOH/NaOH (1 N) (V/V=1/1) was stirred at room temperature for 2 h. HCl (1 N) was then added to the reaction mixture to pH=4-5. The resulting mixture was extracted with EtOAc (50 mL×3). The organic layer was then dried over MgSO₄ and filtered. The filtrate was concentrated, and the residue was purified by FC (DCM/MeOH/NH₄OH=90/9/1) to give 41 as a white solid (yield: 0.91 g, 53.2%). ¹HNMR (400 MHz, CDCl₃) δ: 7.32-7.37 (m, 5H), 7.05 (d, 2H, J=8.4 Hz), 6.81 (d, 2H, J=8.4 Hz), 6.50 (br s, 1H), 5.48 (br s, 1H), 5.14 (s, 2H), 4.70-4.75 (m, 1H), 4.59 (s, 2H), 3.84 (s, 2H), 3.04 (d, 2H, J=6.4 Hz), 1.43 (s, 9H). HRMS calcd. for $C_{25}H_{30}N_2O_8$ 486.2002, found 487.1999 [M+H]⁺.

Example 37

(4S,11S,15S)-Tri-tert-butyl 4-benzyl-1-(4-((S)-2-(2-(((benzyloxy)carbonyl)amino)acetamido)-3-(tert-butoxy)-3-oxopropyl)phenoxy)-2,5,13-trioxo-3,6,12,14-tetraazaheptadecane-11,15,17-tricarboxylate. (42)

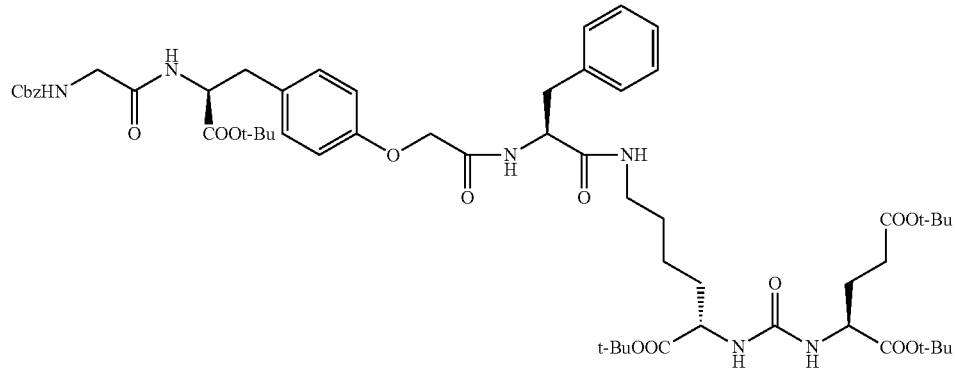

42

To a 41 (559 mg, 1.2 mmol) in 15 mL DMF, DIPEA (309.6 mg, 2.4 mmol), HOBt (304 mg, 1.8 mmol), 38 (762 mg, 1.2 mmol) and EDCI (342 mg, 1.8 mmol) were added at 0° C. The mixture was stirred at room temperature for overnight before 30 mL EtOAc was added to the reaction mixture. It was then washed with $H_2O$ (10 mL×2) and brine (10 mL), dried over $MgSO_4$, and filtered. The filtrate was concentrated, and the residue was purified by FC (DCM/MeOH/$NH_4OH$=95/5/0.5) to give 42 as a white solid (yield: 987 mg, 74.6%): $^1$HNMR (400 MHz, $CDCl_3$) δ: 7.32-7.37 (m, 5H), 7.19-7.24 (m, 5H), 6.97 (d, 2H, J=7.6 Hz), 6.70 (d, 2H, J=8.4 Hz), 6.22 (br s, 1H), 6.01 (br s, 1H), 5.63 (d, 1H, J=6.8 Hz), 5.06-5.13 (m, 2H), 4.83-4.91 (m, 1H), 4.69-4.70 (m, 2H), 4.31-4.38 (m, 2H), 4.19-4.28 (m, 2H), 3.86 (dd, 2H, J=5.2 Hz, J=17.2 Hz), 3.36-3.44 (m, 1H), 2.99-3.16 (m, 4H), 2.84-2.91 (m, 1H), 2.32-2.37 (m, 2H), 2.03-2.12 (m, 1H), 1.78-1.89 (m, 1H), 1.66-1.73 (m, 1H), 1.57-1.66 (m, 1H), 1.27-1.52 (m, 40H). HRMS calcd. for $C_{29}H_{42}N_3O_{15/2}$ (½M+H)$^+$: 552.2998, found 552.3054.

Example 38

(4S,11S,15S)-Tri-tert-butyl 1-(4-((S)-2-(2-aminoacetamido)-3-(tert-butoxy)-3-oxopropyl)phenoxy)-4-benzyl-2,5,13-trioxo-3,6,12,14-tetraazaheptadecane-11,15,17-tricarboxylate. (43)

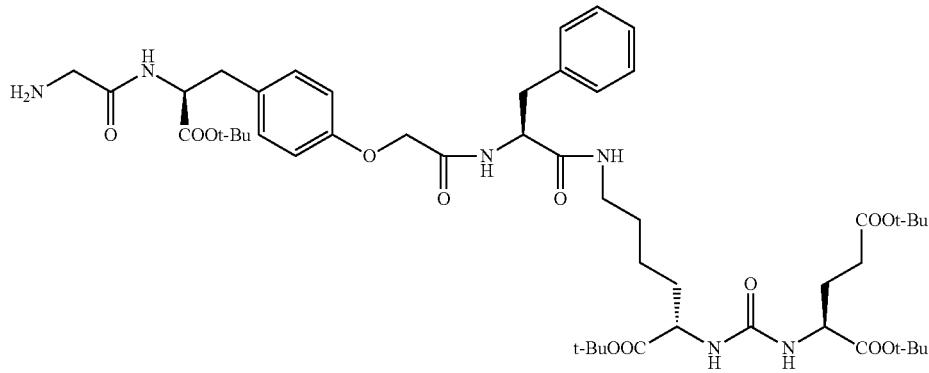

43

A mixture of 42 (987 mg, 0.895 mmol) and Pd/C (200 mg) in 10 mL EtOH was stirred at room temperature under $H_2$ for overnight. The reaction mixture was then filtered. The filtrate was concentrated to give 43 as a colorless oil (yield: 788 mg, 91.2%): $^1$HNMR (400 MHz, $CD_3OD$) δ: 7.20-7.30 (m, 5H), 7.17 (d, 2H, J=8.4 Hz), 6.87 (d, 2H, J=8.8 Hz), 4.66-4.69 (m, 1H), 4.43-4.59 (m, 3H), 4.21 (dd, 1H, J=5.2 Hz, J=8.6 Hz), 4.13 (dd, 1H, J=5.2 Hz, J=8.6 Hz), 3.26 (d, 2H, J=3.2 Hz), 2.93-3.17 (m, 6H), 2.32-2.37 (m, 2H), 2.03-2.12 (m, 1H), 1.78-1.89 (m, 1H), 1.66-1.73 (m, 1H), 1.57-1.66 (m, 1H), 1.27-1.52 (m, 40H). HRMS calcd. for $C_{33}H_{54}N_4O_8$ 634.3942, found 635.4011 $[M+H]^+$.

Preparation of compound 5a was based on the following chemical reactions (Scheme 19).

Scheme 19

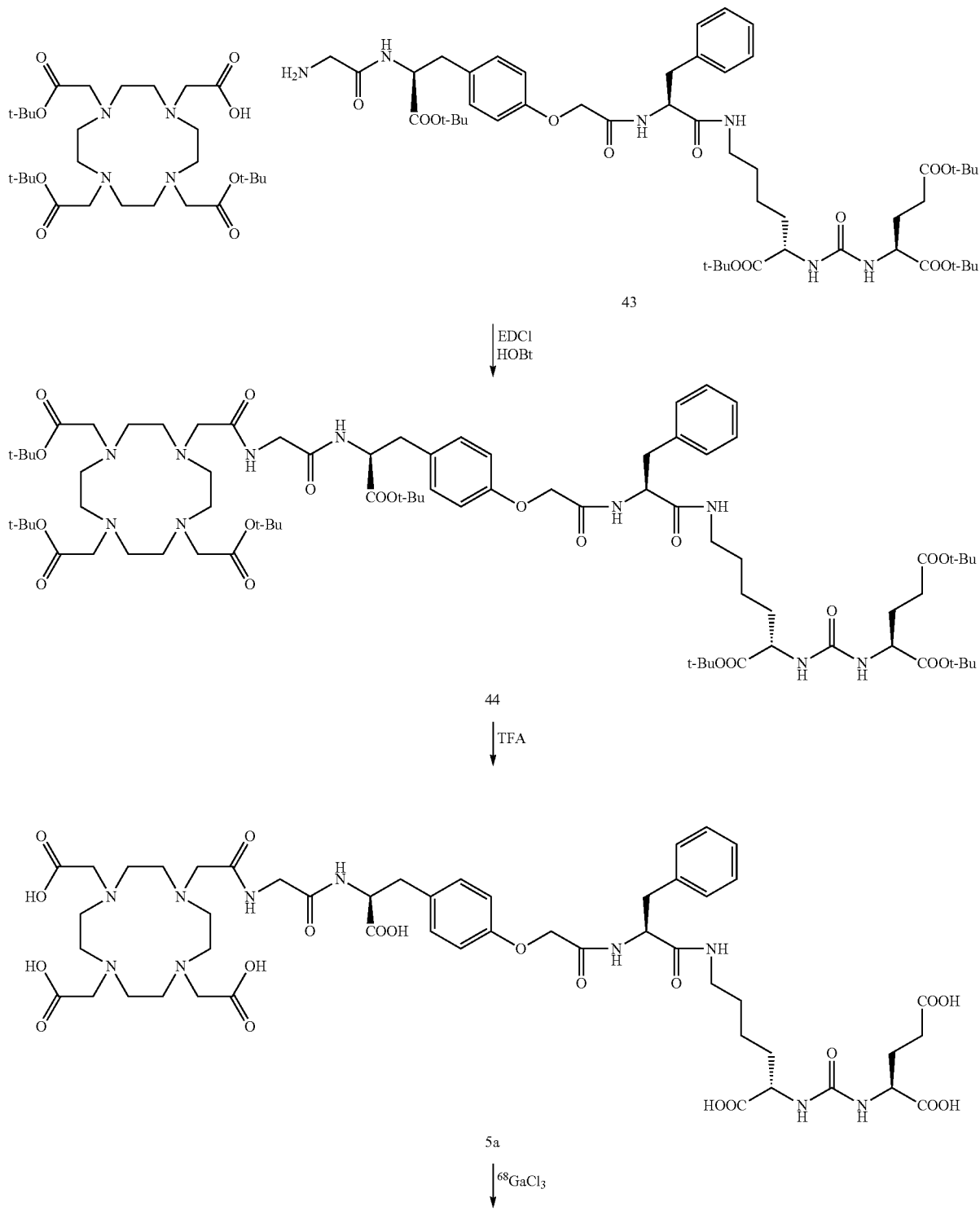

-continued

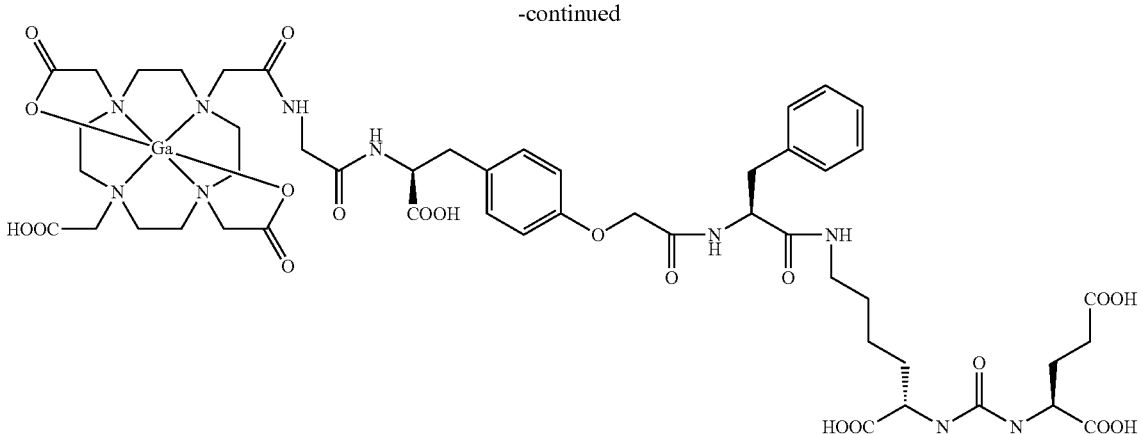

[⁶⁸Ga]5a

Example 39

(4S,11S,15S)-Tri-tert-butyl4-benzyl-1-(4-((S)-3-(tert-butoxy)-3-oxo-2-(2-(2-(4,7,10-tris(2-(tert-butoxy)-2-oxoethyl)-1,4,7,10-tetraazacyclododecan-1-yl)acetamido)acetamido) propyl)phenoxy)-2,5,13-trioxo-3,6,12,14-tetraazaheptadecane-11,15,17-tricarboxylate. (44)

44

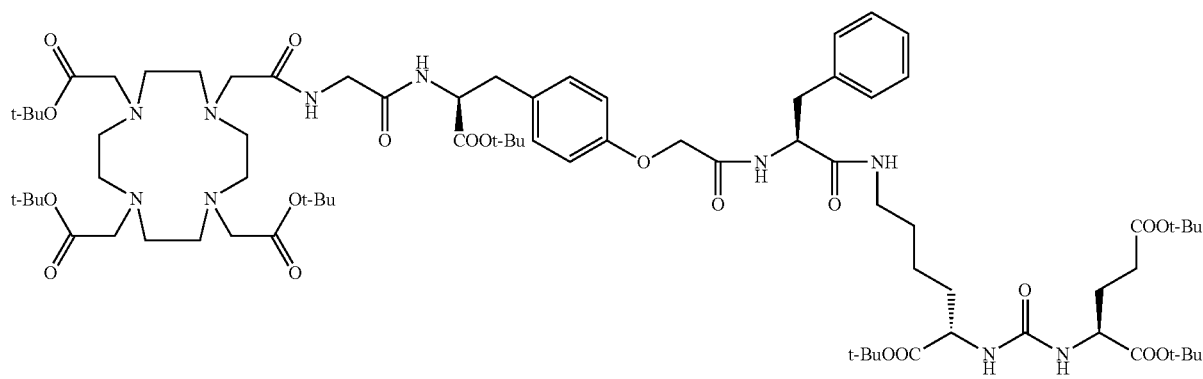

To a DOTA-tris-tBu ester (28.6 mg, 0.05 mmol) in 2 mL DMF, DIPEA (24.8 mg, 0.192 mmol), HOBt (16.2 mg, 0.096 mmol), 43 (50 mg, 0.048 mmol) and EDCI (18.2 mg, 0.096 mmol) were added at 0° C. The mixture was stirred at room temperature for overnight, then 15 mL EtOAc was added to above solution. It was then washed with $H_2O$ (5 mL×2) and brine (5 mL), dried over $MgSO_4$, and filtered. The filtrate was concentrated, and the residue was purified by FC (DCM/MeOH/$NH_4OH$=95/5/0.5) to give 43 as a colorless oil (yield: 26 mg, 35.6%): HRMS calcd. for $C_{39}H_{64}N_5O_{10}$ (½M+H)⁺: 762.4653, found 762.4787.

Example 40

(4S,11S,15S)-4-Benzyl-1-(4-((S)-2-carboxy-2-(2-(2-(4,7,10-tris(carboxymethyl)-1,4,7,10-tetraazacyclododecan-1-yl)acetamido)acetamido)ethyl)phenoxy)-2,5,13-trioxo-3,6,12,14-tetraazaheptadecane-11,15,17-tricarboxylic acid. (5a)

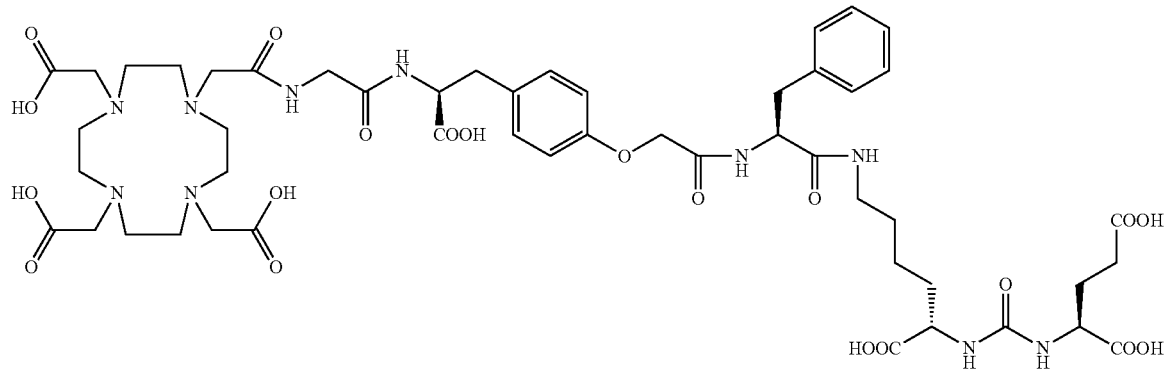

5a

A solution of substrate 44 (26 mg, 0.017 mmol) in 1 mL trifluoroacetic acid (TFA) was stirred at room temperature for 5 h. The reaction mixture was evaporated in vacuo, and the residue was recrystallized from Ether/EtOH. The resulting white solid was dissolved in 1 mL MeOH and purified by prep-HPLC (A: 0.1% TFA in $H_2O$, B: MeOH, 0-18 min, 0%-80% B) to give 5.3 mg white solid 5a (yield: 27.6%): $^1$HNMR (400 MHz, $CD_3OD$) δ: $^1$HNMR (400 MHz, $CD_3OD$) δ: 7.19-7.27 (m, 5H), 7.15 (d, 2H, J=8.4 Hz), 6.85 (d, 2H, J=8.4 Hz), 4.64-4.6 (m, 2H), 4.43-4.53 (m, 2H), 4.29-4.33 (m, 1H), 4.21-4.24 (m, 1H), 3.71-4.01 (m, 8H), 3.27-3.43 (m, 16H), 3.07-3.19 (m, 6H), 2.94-3.02 (m, 2H), 2.38-2.43 (m, 2H), 2.09-2.18 (m, 1H), 1.77-1.93 (m, 2H), 1.59-1.64 (m, 1H), 1.30-1.48 (m, 4H); HRMS (ESI) calculated for $C_{25}H_{36}N_5O_{10}$(½M+H$^+$), 566.2642, found, 566.2545.

Preparation of compound 5b was based on the following chemical reactions (Scheme 20).

Scheme 20

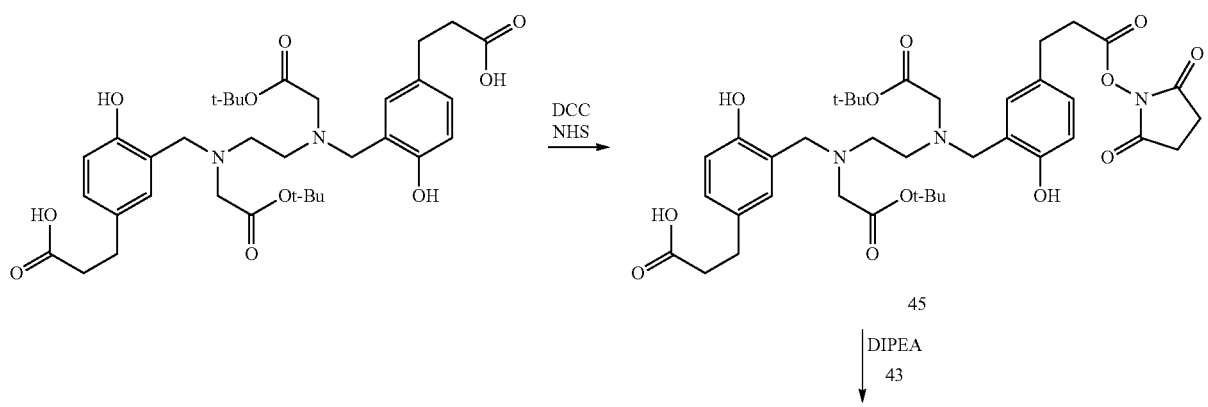

45

↓ DIPEA

43

-continued
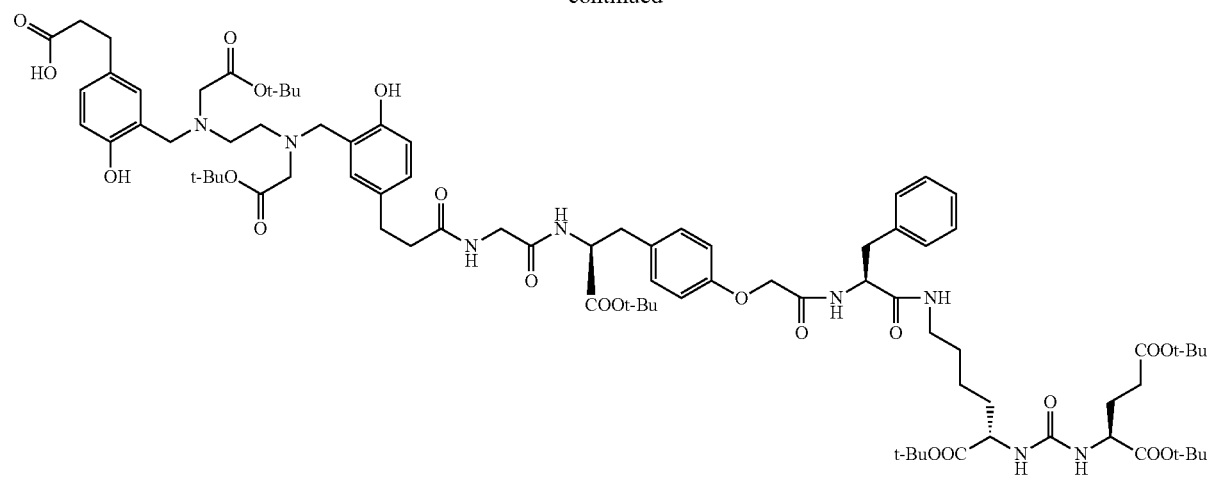
46
↓ TFA
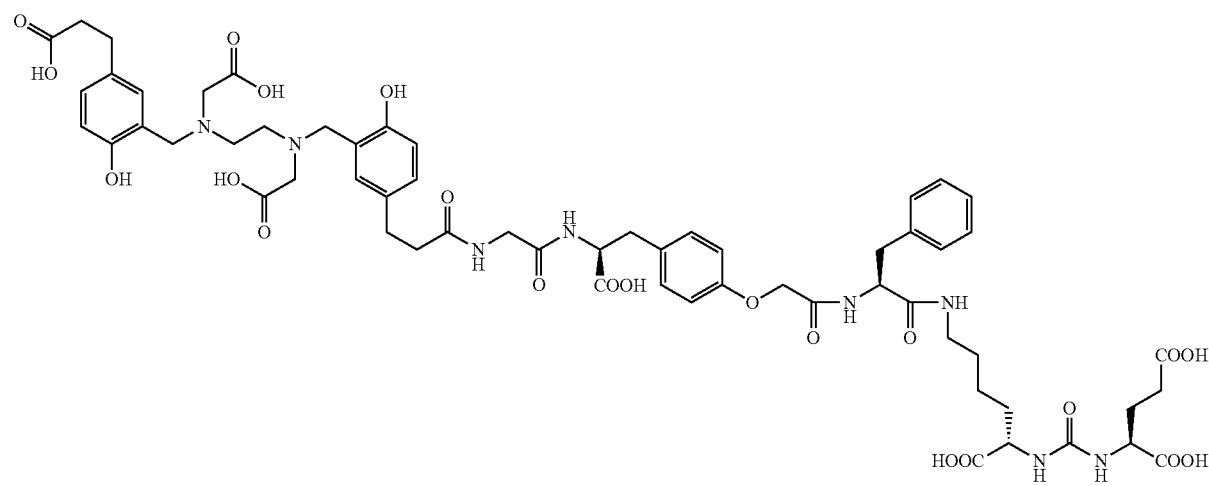
5b
↓ $^{68}GaCl_3$
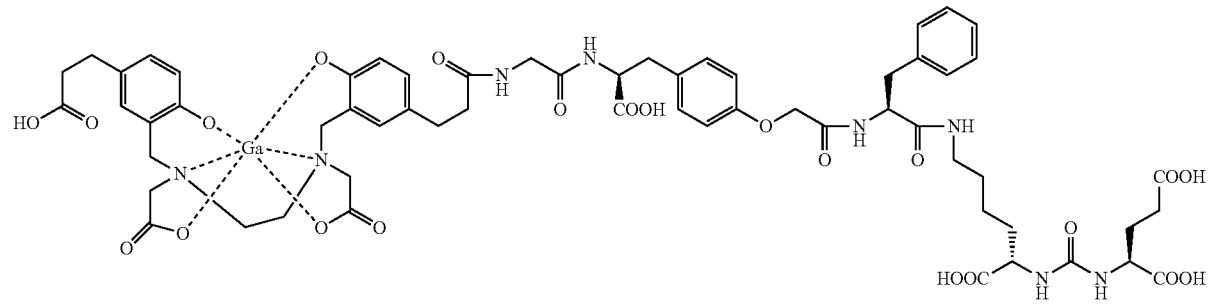
[$^{68}$Ga]5b

Example 41

3-(3-(((2-((5-(3-((2-(((S)-3-(4-(((4S,11S,15S)-4-Benzyl-11,15-bis(tert-butoxycarbonyl)-20,20-dimethyl-2,5,13,18-tetraoxo-19-oxa-3,6,12,14-tetraazahenicosyl)oxy)phenyl)-1-(tert-butoxy)-1-oxopropan-2-yl)amino)-2-oxoethyl)amino)-3-oxopropyl)-2-hydroxybenzyl)(2-(tert-butoxy)-2-oxoethyl)amino)ethyl)(2-(tert-butoxy)-2-oxoethyl)amino)methyl)-4-hydroxyphenyl)propanoic acid. (46)

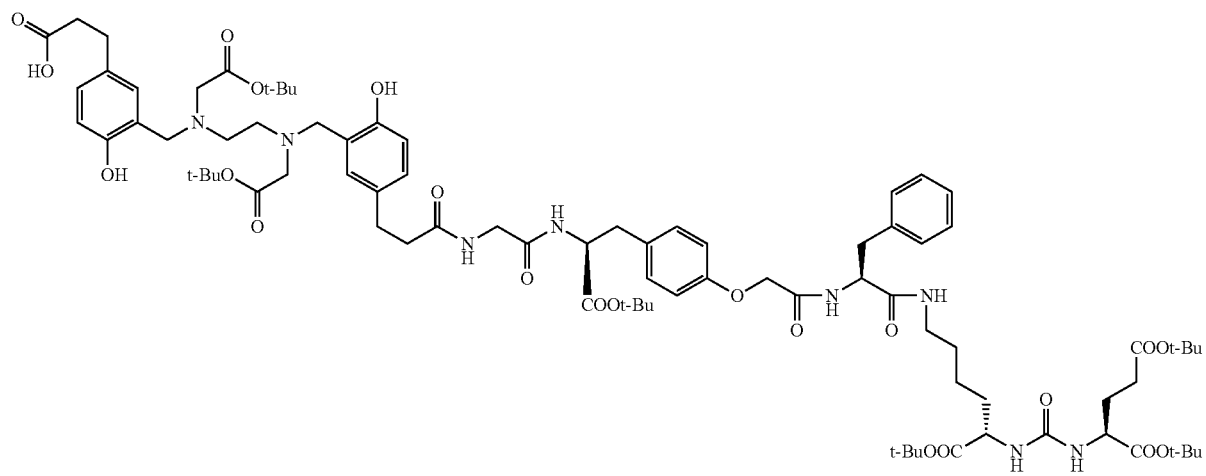

46

To a solution of HBED-CC (59.8 mg, 0.092 mmol) in 2 mL DMF was added DCC (19.0 mg, 0.092 mmol) and NHS (10.6 mg, 0.092 mmol) at 0° C. The mixture was stirred at room temperature for 6 h before 15 mL EtOAc was added to the reaction mixture. It was then washed with $H_2O$ (5 mL×2) and brine (5 mL), dried over $MgSO_4$, and filtered. The filtrate was concentrated, and the residue (45) was directly used without purification. 3 mL DMF was added to the residue, followed by DIPEA (11.9 mg, 0.092 mmol) and 43 (45 mg, 0.046 mmol). The mixture was stirred at room temperature for overnight. 15 mL EtOAc was added to the reaction mixture. It was then washed with $H_2O$ (5 mL×2) and brine (5 mL), dried over $MgSO_4$, and filtered. The filtrate was concentrated, and the residue was purified by FC (DCM/MeOH/$NH_4OH$=95/5/0.5) to give 46 as a colorless oil (yield: 38 mg, 51.8%): $^1$HNMR (400 MHz, $CDCl_3$) δ: 7.20-7.24 (m, 5H), 6.99-7.04 (m, 4H), 6.63-6.78 (m, 6H), 5.66 (d, 1H, J=8.4 Hz), 4.93 (br s, 1H), 4.72-4.75 (m, 1H), 4.26-4.40 (m, 3H), 3.79-3.84 (m, 2H), 3.57 (s, 4H), 3.41-3.45 (m, 1H), 3.24 (s, 2H), 3.21 (s, 2H), 2.89-3.17 (m, 6H), 2.78-2.85 (m, 4H), 2.45-2.63 (m, 8H), 2.32-2.37 (m, 2H), 2.03-2.12 (m, 1H), 1.78-1.89 (m, 1H), 1.66-1.73 (m, 1H), 1.57-1.66 (m, 1H), 1.27-1.52 (m, 58H); HRMS calcd. for $C_{42}H_{62}N_4O_{11}$ (½M+H)$^+$: 798.4415, found 798.4492.

Example 42

(4S,11S,15S)-4-Benzyl-1-(4-((S)-2-carboxy-2-(2-(3-(3-(((2-((5-(2-carboxyethyl)-2-hydroxybenzyl)(carboxymethyl)amino)ethyl)(carboxymethyl)amino)methyl)-4-hydroxyphenyl)propanamido)acetamido)ethyl)phenoxy)-2,5,13-trioxo-3,6,12,14-tetraazaheptadecane-11,15,17-tricarboxylic acid. (5b)

Example 43

⁶⁸Ga-Labeling of 5b 0.5-1 mL eluant in 0.05 M HCl of ⁶⁸Ge/⁶⁸Ga generator (ITG) and 25 μL 2 NaOAc were added and mixed with the precursor 5b (2-4 nmol) and incubated at 60° C. After 10 min, labeling efficiency and radiochemical purity were determined using Radio-HPLC. Radiochemical purity of

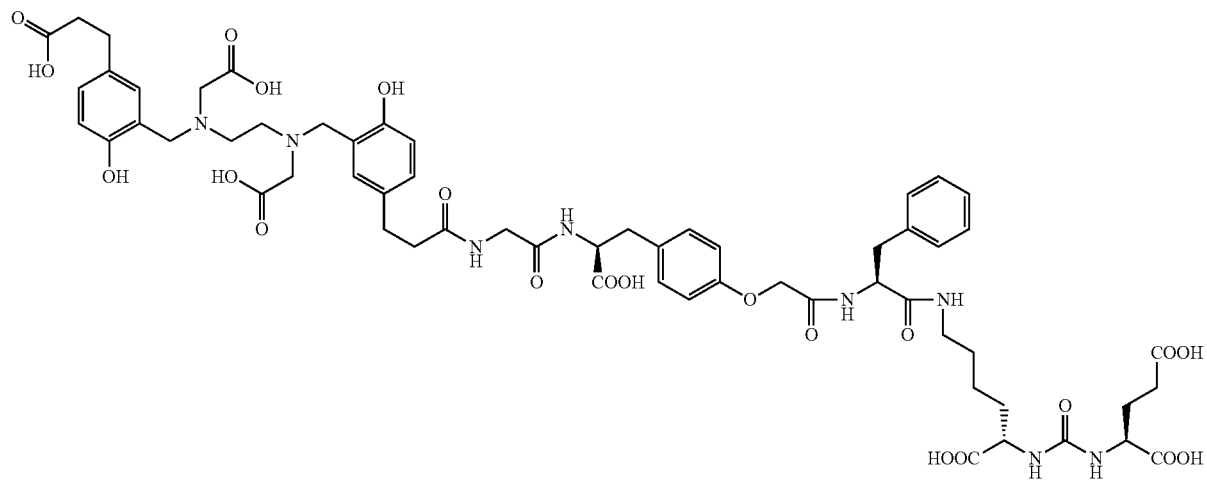

5b

Compound 5d (yield: 11.3 mg, 37.7%) was prepared from 46 (38 mg, 0.0238 mmol) and 1 mL TFA, following the same procedure described for compound 5a. ¹HNMR (400 MHz, CD₃OD) δ: 7.09-7.29 (m, 11H), 6.79-6.86 (m, 4H), 4.64-4.69 (m, 2H), 4.41-4.54 (m, 2H), 4.31-4.34 (m, 1H), 4.24-4.27 (m, 1H), 4.12 (s, 2H), 4.10 (s, 2H), 3.78-3.87 (m, 2H), 3.67 (s, 4H), 3.30 (s, 4H), 3.07-3.18 (4H), 2.93-3.03 (m, 2H), 2.81-2.85 (m, 4H), 2.49-2.58 (m, 4H), 2.39-2.44 (m, 2H), 2.11-2.19 (m, 1H), 1.87-1.95 (m, 1H), 1.77-1.83 (m, 1H), 1.58-1.67 (m, 1H), 1.31-1.47 (m, 4H); ¹³C NMR (100 MHz, DMSO-d₆) δ 175.02, 174.63, 174.31, 174.20, 173.29, 172.29, 170.81, 170.56, 169.37, 167.84, 157.78, 156.83, 155.01, 154.94, 137.94, 132.41, 132.32, 131.86, 130.59, 130.41, 129.66, 128.54, 126.82, 115.84, 114.80, 65.37, 54.13, 53.99, 52.73, 52.11, 49.92, 35.99, 32.20, 29.92, 27.96, 23.07, 18.98. HRMS calcd. for $C_{30}H_{38}N_4O_{11}$ (½M+H)⁺: 630.2537, found 630.3151.

⁶⁸Ga-labelled conjugate was ≥98%. Therefore, the tracer was diluted and used in vitro and in vivo experiments without further purification. Specific activities of the ⁶⁸Ga-labeled PSMA inhibitors were 500 to 1000 Ci/mmol. Analytical reversed-phase high performance liquid chromatography (RP-HPLC) was performed on a Luna C18 (5 μm, 150×4.6 mm) column using an Agilent gradient HPLC System. The [⁶⁸Ga]P16-093 was eluted applying different gradients of 0.1% (v/v) trifluoroacetic acid (TFA) in H₂O and 0.1% TFA (v/v) in MeOH at a constant flow of 2 mL/min (0-6 min, from 100% H₂O with 0.1% TFA to 100% MeOH with 0.1% TFA and then back to 100% H₂O with 0.1% TFA 6-8 min). The radiolabeling yields were consistently >90% and radiochemical purity >98%.

Compounds 5c and 5d were prepared based on the following chemical reactions (Scheme 21).

Scheme 21

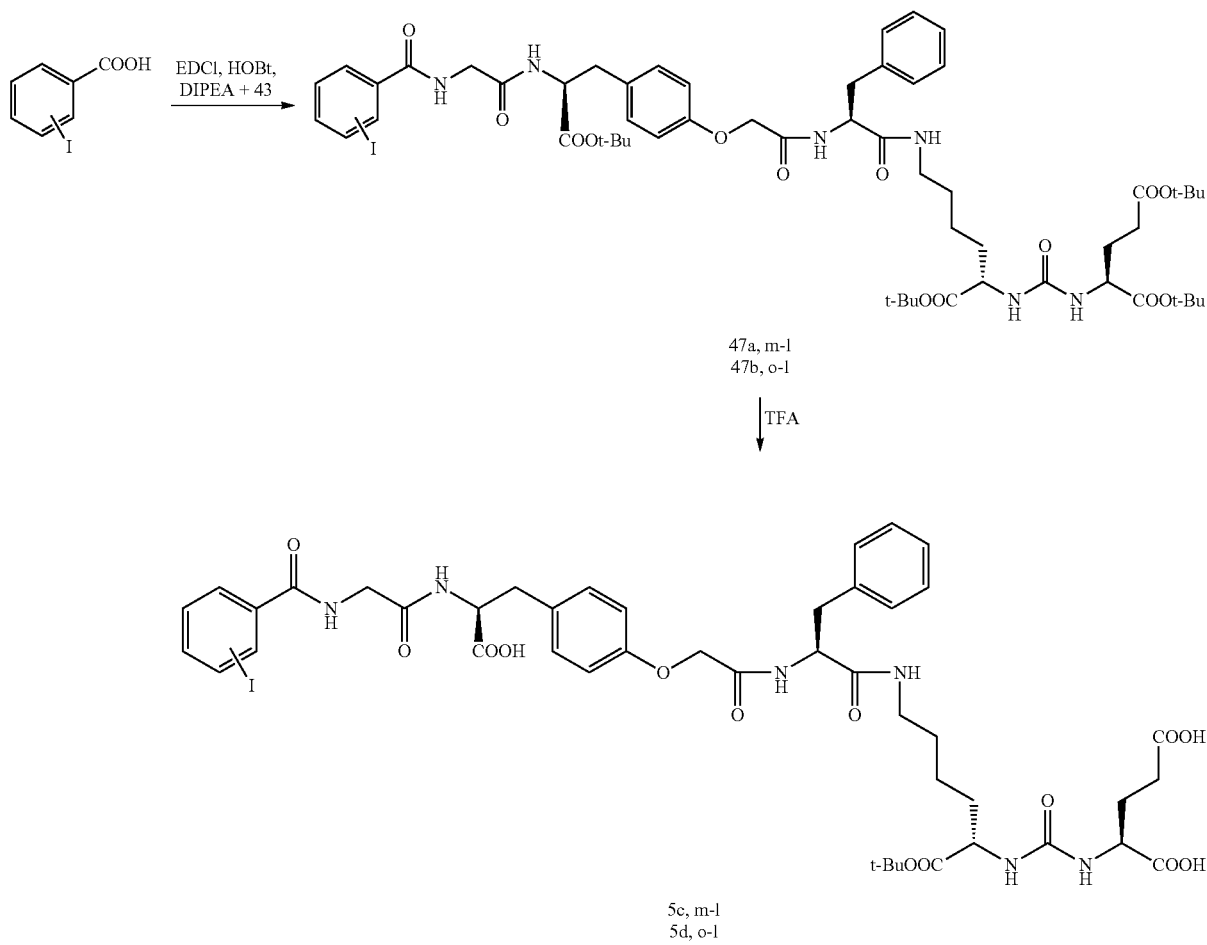

Example 44

(4S,11S,15S)-Tri-tert-butyl 4-benzyl-1-(4-((S)-3-tert-butoxy-2-(2-(3-iodobenzamido)acetamido)-3-oxopropyl)phenoxy)-2,5,13-trioxo-3,6,12,14-tetraazaheptadecane-11,15,17-tricarboxylate (47a)

To a 3-iodobenzoic acid (112 mg, 0.048 mmol) in 2 mL DMF, DIPEA (24.8 mg, 0.192 mmol), HOBt (16.2 mg, 0.096 mmol), EDCI (18.2 mg, 0.096 mmol) and 43 (50 mg, 0.048 mmol) were added at 0° C. The mixture was stirred at room temperature for overnight before 15 mL EtOAc was added to the reaction mixture. It was then washed with H₂O

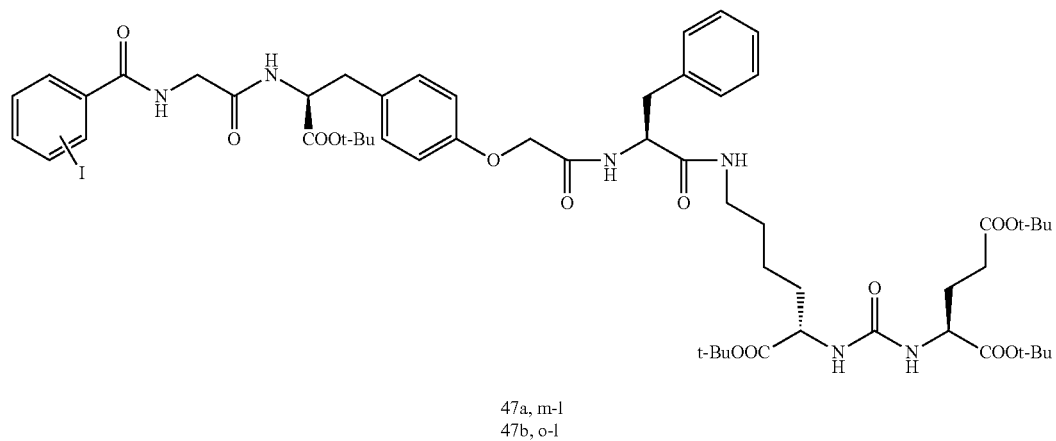

(5 mL×2) and brine (5 mL), dried over MgSO$_4$, and filtered. The filtrate was concentrated, and the residue was purified by FC (DCM/MeOH/NH$_4$OH=95/5/0.5) to give 43 as a colorless oil (yield: 40 mg, 69.4%): $^1$HNMR (400 MHz, CDCl3) δ: 8.11 (s, 1H), 7.81-7.84 (m, 1H), 7.68 (d, 1H, J=7.6 Hz), 7.25-7.27 (m, 5H), 7.14 (t, 1H, J=8.0 Hz), 6.92 (d, 2H, J=8.4 Hz), 6.64 (d, 2H, J=8.4 Hz), 5.65 (d, 1H, J=8.4 Hz), 5.18 (br s, 1H), 4.97 (br s, 1H), 4.80-4.85 (m, 1H), 4.49-4.52 (m, 1H), 4.25-4.30 (m, 1H), 4.11-4.15 (m, 1H), 3.95 (dd, 1H, J=4.0 Hz, J=17.2 Hz), 3.58 (br s, 1H), 3.34-3.39 (m, 1H), 3.18-3.25 (m, 2H), 3.02-3.12 (m, 2H), 2.85-2.90 (m, 1H), 2.28-2.42 (m, 2H), 2.08-2.14 (m, 1H), 1.81-1.90 (m, 1H), 1.66-1.73 (m, 1H), 1.57-1.66 (m, 1H), 1.27-1.52 (m, 40H); HRMS calcd. for C$_{57}$H$_{80}$IN$_6$O$_{14}$ (M+H)$^+$: 1199.4777, found 1199.4886.

Example 45

(4S,11S,15S)-Tri-tert-butyl 4-benzyl-1-(4-((S)-3-tert-butoxy-2-(2-(2-iodobenzamido)acetamido)-3-oxopropyl)phenoxy)-2,5,13-trioxo-3,6,12,14-tetraazaheptadecane-11,15,17-tricarboxylate (47b)

Compound 47b (yield: 25 mg, 43.4%) was prepared from 43 (50 mg, 0.048 mmol), following the same procedure described for compound 47a. 7.86 (d, 1H, J=8.0 Hz), 7.38-7.39 (m, 2H), 7.19-7.27 (m, 5H), 7.03-7.13 (m, 3H), 6.73-6.79 (m, 2H), 6.22 (br s, 1H), 5.99-6.00 (m, 1H), 5.73-5.75 (m, 1H), 5.66 (d, 1H, J=8.0 Hz), 4.93 (br s, 1H), 4.74-4.82 (m, 2H), 4.21-4.46 (m, 3H), 4.04-4.11 (m, 1H), 3.48 (br s, 1H), 3.38-3.41 (m, 1H), 3.04-3.20 (m, 4H), 2.88-2.99 (m, 1H), 2.28-2.42 (m, 2H), 2.08-2.14 (m, 1H), 1.81-1.90 (m, 1H), 1.66-1.73 (m, 1H), 1.57-1.66 (m, 1H), 1.27-1.52 (m, 40H); HRMS calcd. for C$_{57}$H$_{80}$I N$_6$O$_{14}$ (M+H)$^+$: 1199.4777, found: 1199.4845.

Example 46

(4S,11S,15S)-4-Benzyl-1-(4-((S)-2-carboxy-2-(2-(3-iodobenzamido)acetamido) ethyl)phenoxy)-2,5,13-trioxo-3,6,12,14-tetraazaheptadecane-11,15,17-tricarboxylic acid (5c)

$^1$HNMR (400 MHz, CD$_3$OD) δ: 8.19-8.20 (m, 1H), 7.87-7.93 (m, 2H), 7.81-7.84 (m, 1H), 7.11-7.28 (m, 7H), 6.77 (d, 2H, J=8.4 Hz), 4.64-4.72 (m, 2H), 4.42 (dd, 2H, J=14.8 Hz, J=34.8 Hz), 4.29-4.33 (m, 1H), 4.22-4.25 (m, 1H), 4.01 (d, 2H, J=2.8 Hz), 3.07-3.17 (m, 4H), 2.96-3.02 (m, 2H), 2.38-2.42 (m, 2H), 2.09-2.17 (m, 1H), 1.75-1.93 (m, 2H), 1.56-1.65 (m, 1H), 1.40-1.46 (m, 2H), 1.31-1.37 (m, 2H); HRMS calcd. for C$_{41}$H$_{48}$IN$_6$O$_{14}$ (M+H)$^+$: 975.2273, found: 975.2386.

Example 47

(4S,11S,15S)-4-Benzyl-1-(4-((S)-2-carboxy-2-(2-(2-iodobenzamido)acetamido) ethyl)phenoxy)-2,5,13-trioxo-3,6,12,14-tetraazaheptadecane-11,15,17-tricarboxylic acid (5d)

A solution of substrate (60 mg, 0.05 mmol) in 1 mL trifluoroacetic acid (TFA) was stirred at room temperature for 5 h. The reaction mixture was evaporated in vacuo, and the residue was recrystallized from Ether/EtOH give 29 mg white solid (yield: 59.5%): $^1$HNMR (400 MHz, CD$_3$OD) δ: $^1$HNMR (400 MHz, CD$_3$OD) δ: 7.94-8.00 (m, 1H), 7.88-7.90 (m, 1H), 7.37-7.44 (m, 2H), 7.14-7.28 (m, 7H), 6.83 (d, 2H, J=8.8 Hz), 4.63-4.73 (m, 2H), 4.44 (dd, 2H, J=14.8 Hz, J=34.8 Hz), 4.29-4.33 (m, 1H), 4.22-4.25 (m, 1H), 4.01 (dd, 2H, J=16.6 Hz, J=26.5 Hz), 3.06-3.20 (m, 4H), 2.96-3.04 (m, 2H), 2.38-2.42 (m, 2H), 2.09-2.17 (m, 1H), 1.75-1.93 (m, 2H), 1.56-1.65 (m, 1H), 1.40-1.46 (m, 2H), 1.31-1.37 (m, 2H); HRMS calcd. for C$_{41}$H$_{48}$I N$_6$O$_{14}$+H)$^+$: 975.2273, found: 975.2281.

Example 48

3-(Tributylstannyl)benzoic acid (48)

A mixture of 3-iodobenzoic acid (248 mg, 1 mmol), Pd(PPh$_3$)$_4$ (115.8 mg, 0.1 mmol) and Bis(tributyltin) (2.9 g, 5 mmol) in 8 mL toluene was deoxygenated by purging into nitrogen for 15 min and then heated at 95° C. for 4 h. The solvent was removed, and the residue was purified by FC

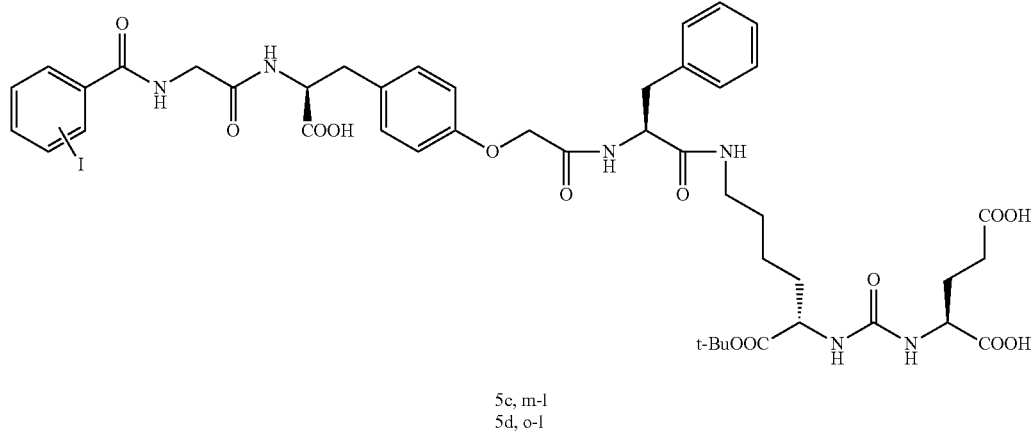

5c, m-I
5d, o-I

A solution of substrate (40 mg, 0.033 mmol) in 1 mL trifluoroacetic acid (TFA) was stirred at room temperature for 5 h. The reaction mixture was evaporated in vacuo, and the residue was recrystallized from Ether/EtOH give 25 mg white solid (yield: 77.8%): $^1$HNMR (400 MHz, CD$_3$OD) δ:

(EtOH/hexane=4/6) to give 48 as a colorless oil (yield: 40 mg, 69.4%): $^1$HNMR (400 MHz, CDCl$_3$) δ: 8.16-8.25 (m, 1H), 8.02-8.04 (m, 1H), 7.66-7.76 (m, 1H), 7.41-7.45 (m, 1H), 1.46-1.64 (m, 6H), 1.30-1.41 (m, 6H), 1.02-1.20 (m, 6H), 0.89-0.95 (m, 9H).

Example 49

(4S,11S,15S)-Tri-tert-butyl 4-benzyl-1-(4-((S)-3-tert-butoxy-3-oxo-2-(2-(3-(tributylstannyl)benzamido)acetamido)propyl)phenoxy)-2,5,13-trioxo-3,6,12,14-tetraazaheptadecane-11,15,17-tricarboxylate (6a)

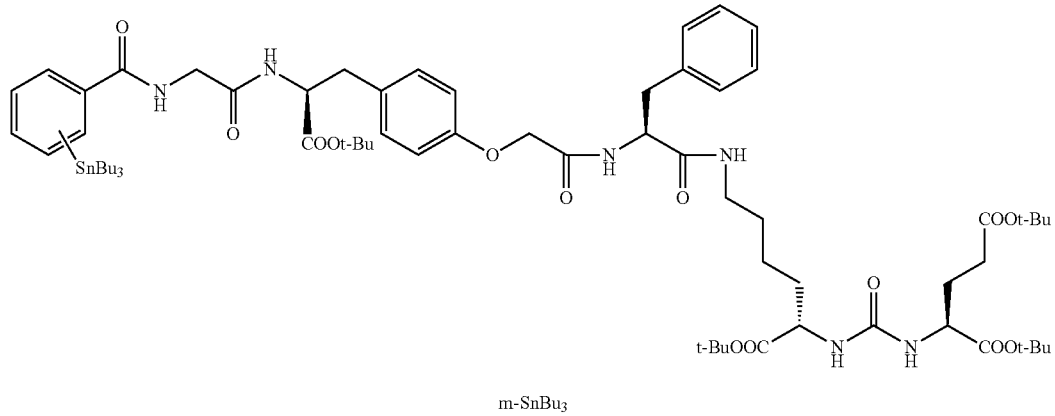

6a m-SnBu₃

To a solution of 48 (59.8 mg, 0.092 mmol) in 2 mL THF was added DCC (19.0 mg, 0.092 mmol) and NHS (10.6 mg, 0.092 mmol) at 0° C. The mixture was stirred at room temperature for 6 h before 15 mL EtOAc was added to the reaction mixture. It was then washed with H₂O (5 mL×2) and brine (5 mL), dried over MgSO₄, and filtered. The filtrate was concentrated, and the residue was directly used without purification. 3 mL DMF was added to the residue, followed by DIPEA (11.9 mg, 0.092 mmol) and 43 (50 mg, 0.046 mmol). The mixture was stirred at room temperature for overnight. 15 mL EtOAc was added to the reaction mixture. It was then washed with H₂O (5 mL×2) and brine (5 mL), dried over MgSO₄, and filtered. The filtrate was concentrated, and the residue was purified by FC (DCM/MeOH/NH₄OH=95/5/0.5) to give 6a as a colorless oil (yield: 39 mg, 62.2%): $^1$HNMR (400 MHz, CDCl₃) δ: 7.90-8.00 (m, 1H), 7.58-7.63 (m, 2H), 7.33-7.37 (m, 1H), 7.19-7.29 (m, 5H), 6.95 (d, 2H, J=8.4 Hz), 6.46 (d, 2H, J=8.4 Hz), 5.72 (d, 1H, J=8.4 Hz), 5.18 (br s, 1H), 4.81-4.85 (m, 2H), 4.45-4.50 (m, 1H), 4.28-4.33 (m, 1H), 4.11-4.15 (m, 1H), 4.00-4.05 (m, 1H), 3.64 (br s, 1H), 3.39-3.41 (m, 1H), 3.03-3.22 (m, 4H), 2.90-2.92 (m, 1H), 2.29-2.44 (m, 2H), 2.07-2.15 (m, 1H), 1.81-1.90 (m, 1H), 1.27-1.66 (m, 52H), 1.02-1.20 (m, 6H), 0.89-0.95 (m, 9H); HRMS calcd. for $C_{79}H_{106}N_6O_{14}Sn$ (M+H)⁺: 1363.6867, found 1363.7005.

Compound 5e was prepared based on the following chemical reactions (Scheme 22).

Scheme 22

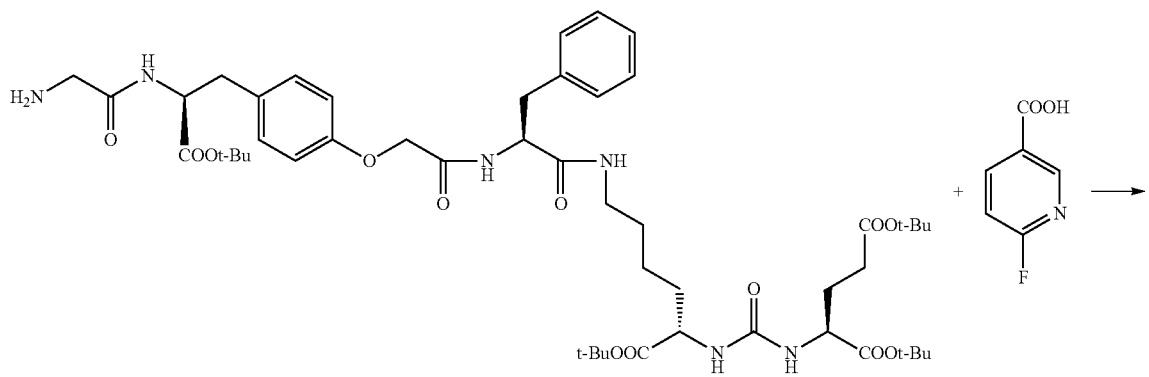

43

-continued

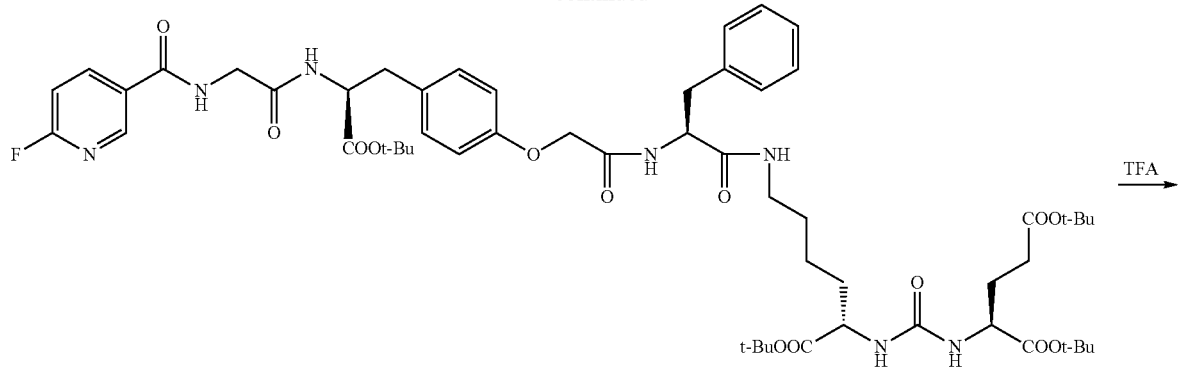

49

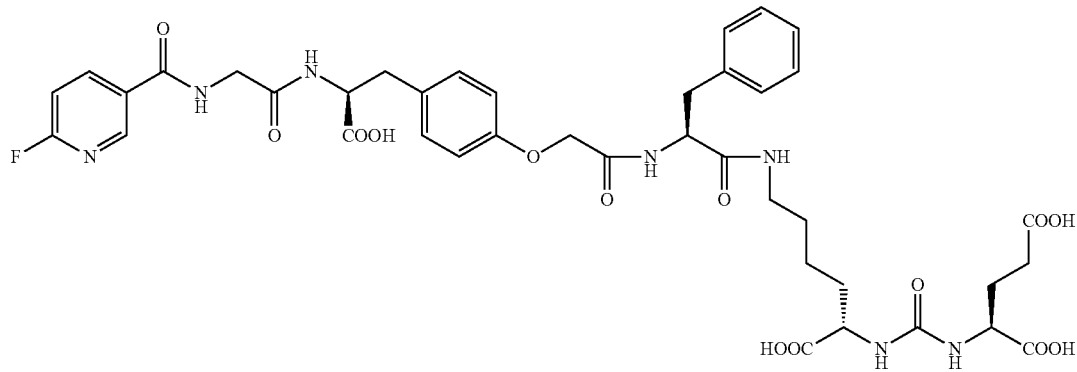

5e

Example 50

Synthesis of Compound 49

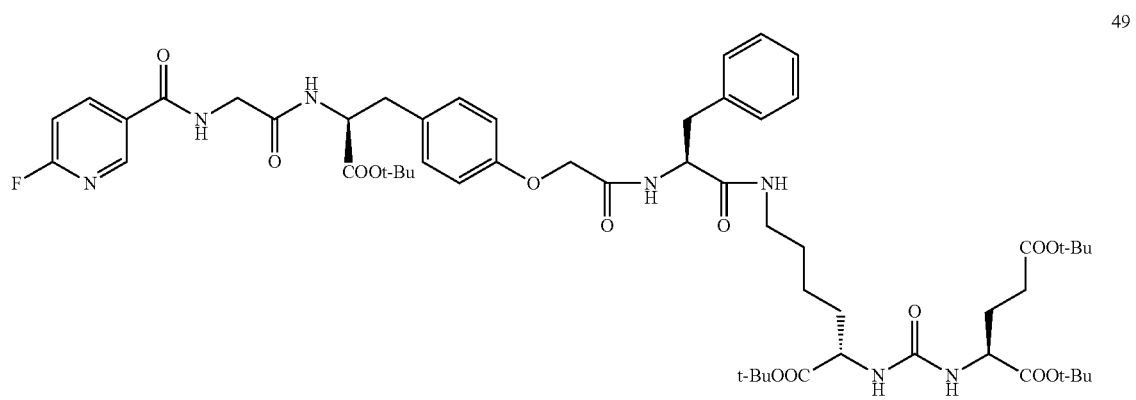

49

To a stirred DMF (20 mL) solution of compound 43 (200 mg, 2.1 mmol), and 6-Fluoropyridine-3-carboxylic acid (28 mg, 2 mmol), Et$_3$N (2 ml), HOBt (10 mg), HBTU (148 mg, 4 mmol) were added sequentially. The reaction was stirred at room temperature for 2 h, the solution was extracted by ethyl acetate, washed by brine, dried by Na$_2$SO$_4$. The solution was removed by rotary evaporation to obtain viscous oil, which was purification by combiflash (DCM: Methanol:NH$_3$H$_2$O 90:9:1) to give the title compound 49 as colorless oil (138 mg, 61.2%). $^1$HNMR (400 MHz, CDCl$_3$) δ: 8.60 (d, J=2.28 Hz, 1H), 8.48-8.41 (m, 2H), 8.14-8.10 (m, 2H), 7.92 (s, 1H), 6.94 (dd, J=2.8, 2.8 Hz, 1H), 6.85 (d, J=8.4 Hz, 2H), 5.72 (d, J=8.4 Hz, 1H), 5.39-5.33 (m, 2H), 4.87-4.84 (m, 1H), 4.55-4.50 (m, 1H), 4.30-4.25 (m, 1H), 4.17 (s, 1H), 4.03-3.91 (m, 2H), 3.45-3.42 (m, 1H), 3.33-3.26 (m, 2H), 3.18-3.13 (m, 2H), 3.06 (dd, J=4.0, 4.0 Hz, 1H), 2.95-2.88 (m, 1H), 2.44-2.28 (m, 2H), 2.17-2.08 (m, 1H), 1.93-1.83 (m, 1H), 1.54 (s, 9H), 1.45 (s, 18H), 1.28 (s, 9H). $^{13}$CNMR (100 MHz, CDCl$_3$) δ: 175.57, 172.37, 172.13, 172.08, 170.07, 169.94, 168.59, 166.30, 165.43, 163.88, 157.50, 155.94, 148.33, 140.48, 140.39, 137.02, 130.65, 129.43, 128.74, 128.30, 127.46, 127.41, 126.63, 114.07, 109.35, 108.99, 82.65, 82.11, 81.25, 80.35, 77.38. 77.07, 76.75, 65.88, 54.43, 53.83, 52.76, 52.43, 42.94, 39.91, 39.00, 36.74, 33.11, 31.67, 28.92, 28.57. 28.21, 28.11, 27.99, 27.90, 22.61. HRMS calcd. For C$_{56}$H$_{78}$FN$_7$O$_{14}$, 1091.5591. found 1092.5743 [M+H]$^+$.

Example 51

Synthesis of Compound 5e

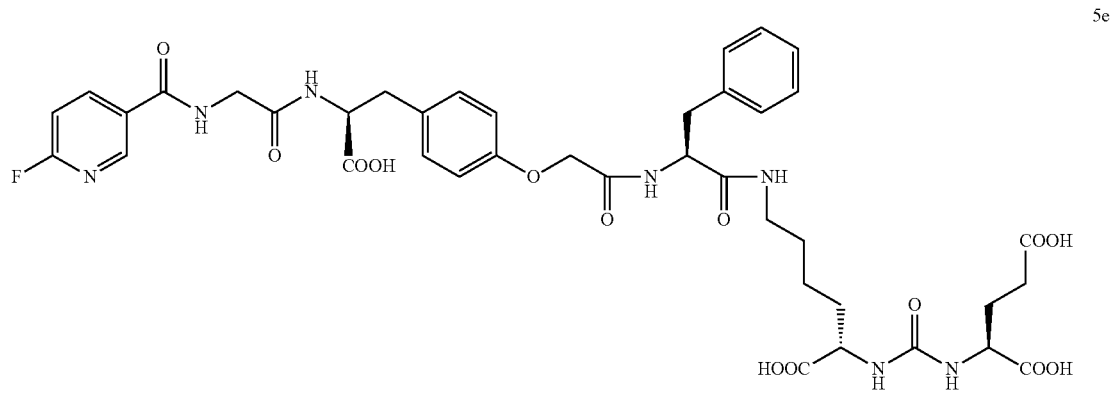 [SMILES: O=C(O)CC[C@H](NC(=O)N[C@@H](CCCCNC(=O)[C@H](Cc1ccccc1)NC(=O)COc1ccc(C[C@H](NC(=O)CNC(=O)c2ccc(F)nc2)C(=O)O)cc1)C(=O)O)C(=O)O]

5e

To a stirred solution of compound 49 (120 mg, 0.11) in 10 mL TFA was stirred at room temperature for overnight. The mixture was then removed under vacuum, and ether was added into the residue to give white product 5e (95 mg, 100%). $^1$HNMR (400 MHz, DMSO-d6) δ: 8.93 (t, J=5.6 Hz, 1H), 8.71 (d, J=2.4 Hz, 1H), 8.41-8.36 (m, 1H), 8.25 (d, J=8.0 Hz, 1H), 8.06 (d, J=8.0 Hz, 2H), 7.31 (dd, J=2.4, 2.4 Hz, 1H), 7.24-7.18 (m, 5H), 7.10 (d, J=8.4 Hz, 2H), 6.72 (d, J=8.4 Hz, 2H), 6.33-6.28 (m, 5H), 4.52 (d, J=5.2 Hz, 1H), 4.4 (s, 3H), 4.1-4.0 (m, 3H), 3.97-3.82 (m, 4H), 3.11-3.04 (m, 3H), 3.01-2.96 (m, 5H), 2.89-2.80 (m, 3H), 2.27-2.21 (m, 2H), 1.92-1.89 (m, 1H), 1.73-1.61 (m, 2H), 1.52-1.48 (m, 1H), 1.35-1.33 (m, 2H), 1.25-1.19 (m, 2H). $^{13}$CNMR (100 MHz, DMSO-d6) δ: 175.02, 174.63, 174.20, 173.30, 170.81, 169.04, 167.84, 164.35, 157.77, 156.84, 148.00, 141.99, 141.90, 137.95, 130.61, 130.45, 129.66, 128.55, 126.82, 114.79, 110.10, 109.72, 67.06, 54.16, 53.99, 52.73, 52.11, 42.99, 36.37, 32.20, 30.34, 29.12, 27.96, 23.06 HRMS calcd. For $C_{40}H_{46}FN_7O_{14}$ 867.3087 found 868.3088 $[M+H]^+$.

Radiolabeling of 5e can be produced by the scheme describe below (Scheme 23).

Scheme 23

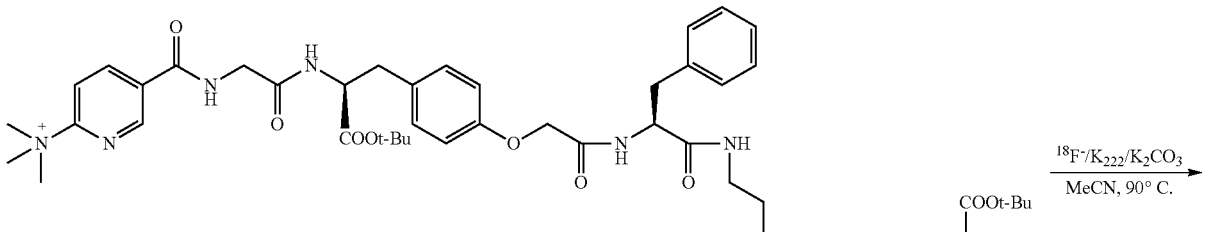

50

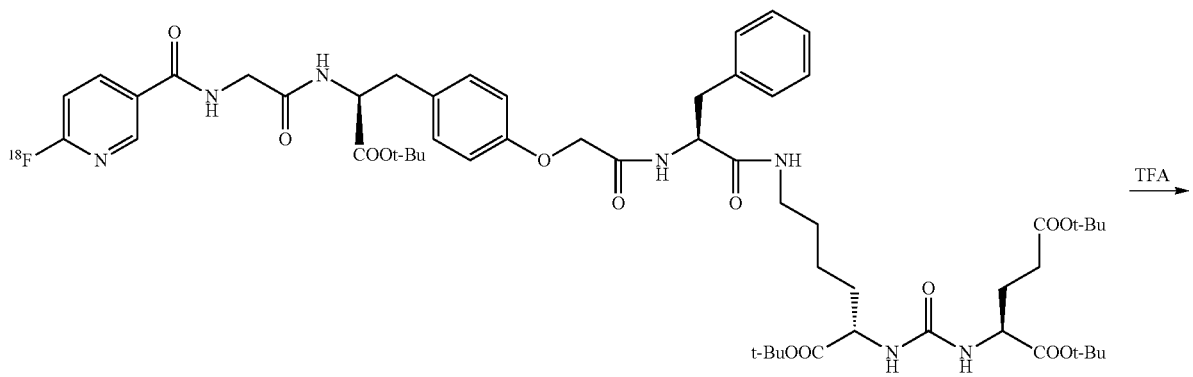

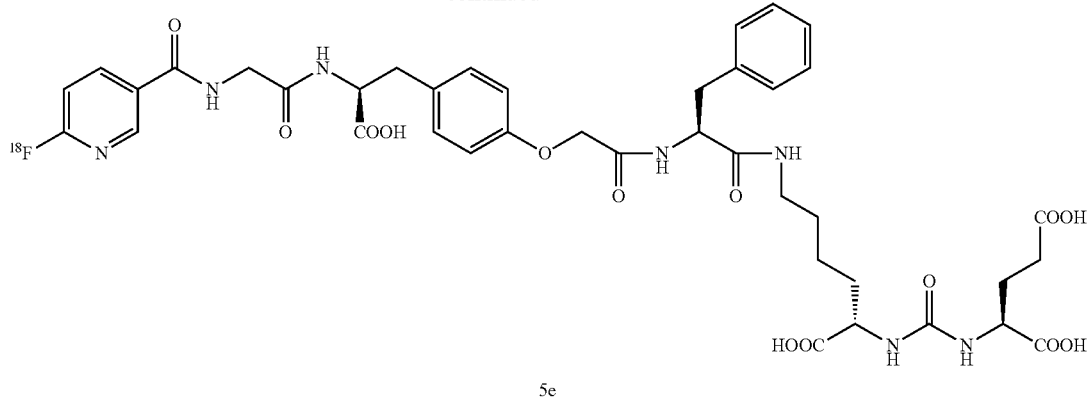
5e
Compound 5f was prepared based on the following chemical reactions (Scheme 24). Radiolabeling of 5f can be performed by known methods.
Scheme 24
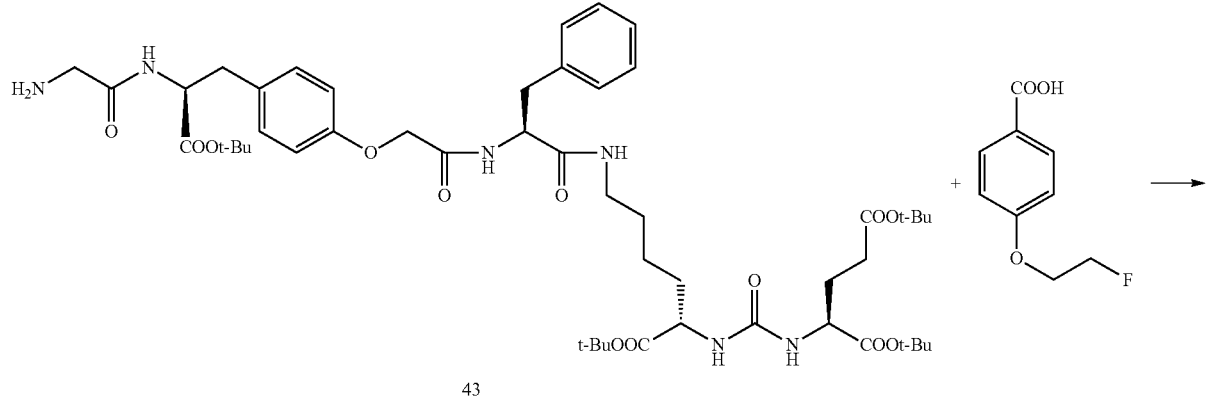
43
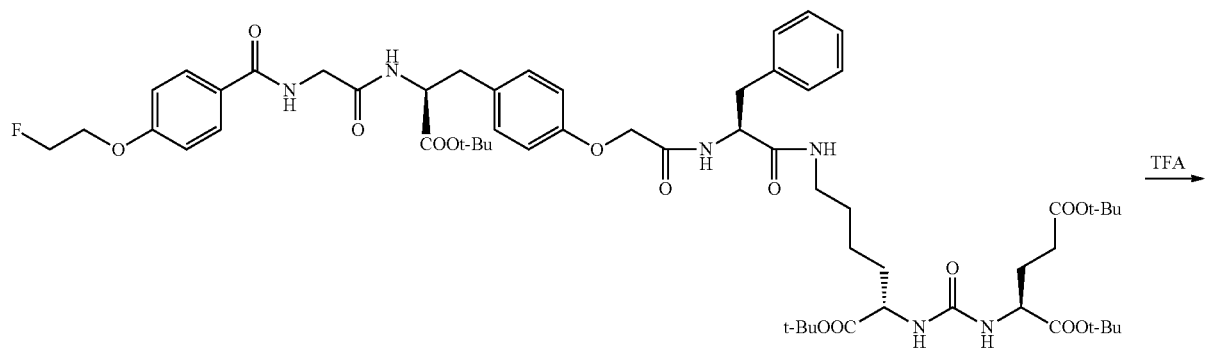
TFA

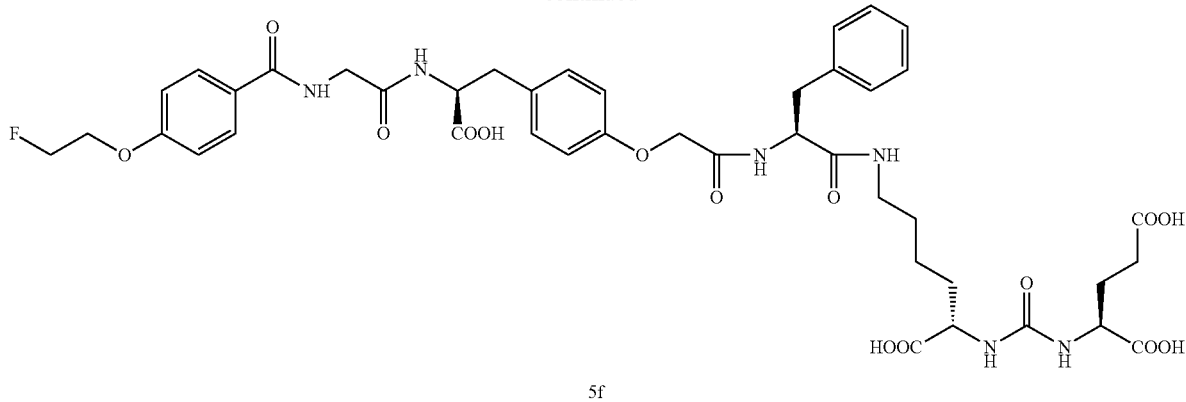

5f

Example 52

$^{68}$Ga Labeling of 5a and 5b

The $^{68}$Ge/$^{68}$Ga-generator (ITG, Germany) was eluted with 4 mL of 0.01N HCl. Typically, 2 nmol of 5a or 5b was added to a mixture of 25 μL 2 N NaOAc and 500 μL [$^{68}$Ga]GaCl$_3$ eluate. The pH of the labelling solution was adjusted using various strength of NaOAc solution. The reaction mixture was incubated for 10 min at 90° C. for 5a and at room temperature for 5b. The radiochemical purity (RCP) was determined via analytical RP-HPLC.

Labeling with [$^{68}$Ga]GaCl$_3$ typically yields more than 97% radiochemical purity both 5a and 5b. The effects of ligand amount, time, pH and temperature on labeling were tested.

5b was labeled quantitatively with [$^{68}$Ga]GaCl$_3$ in the condition of pH 3.2~4.6, as low as 2 nmole of ligand and longer than 4 min at room temperature. For the labeling of 5a, heating at 70-90° C. for 5 min was needed.

Biological Evaluation

Example 53

In Vitro Competitive Binding Assay to Determine IC$_{50}$ to PSMA

In order to determine the binding affinity, in vitro competitive binding assays were performed. The LNCaP cells were incubated with 150,000 cpm of [$^{125}$I]MIP-1095 in the presence of 10 different concentrations of competing drugs. After incubation at 37° C. for 1 h, the bound and free radioactivity were separated by vacuum filtration through GF/B filter paper using a Brandel M-24R cell harvester followed by washing twice. Non-specific binding was defined with 10 μM PMPA. The cell bound radioactivity was measured with a gamma counter, 2470 Wizard$^2$ (Perkin-Elmer, IL). The IC$_{50}$ values were calculated by fitting the data using a nonlinear regression algorithm (GraphPad Software).

The PSMA binding affinities were determined in a competitive binding assay using LNCaP human prostate carcinoma cells and the known high affinity PSMA ligand, [$^{125}$I]MIP-1095 as the radioligand. The IC$_{50}$ values for the metal-free PSMA-inhibiting ligands and known PSMA inhibitors are summarized in Table 1. Data are expressed as mean±SD (n=4).

TABLE 1

PSMA binding affinities of cold ligands (IC$_{50}$, nM)

| Ligand | IC$_{50}$ (nM) |
|---|---|
| 1a (PSMA-11) | 16.6 ± 2.4 |
| 1b | 53.3 ± 30.9 |
| 1c | 25.6 ± 9.4 |
| 1d | 26.8 ± 6.3 |
| 1e | 29.5 ± 11.0 |
| 1f | 37.2 ± 18.6 |
| 1g | 70.2 ± 29.1 |
| 2 | 40.4 ± 18.3 |
| 3 | 132 ± 11 |
| 4a | 67.4 ± 30.3 |
| 4b | 40.5 ± 20.5 |
| 5a | 36.1 ± 18.1 |
| 5b | 11.6 ± 5.2 |
| [$^{nat}$Ga]5b | 16.5 ± 3.1 |
| 5c | 5.0 ± 1.9 |
| 5d | 5.3 ± 2.2 |
| 5e | 6.0 ± 1.8 |
| MIP-1095 | 4.6 ± 1.4 |
| 2-PMPA | 147 ± 44 |
| ZJ-43 | 74 ± 29 |

Scheme 25

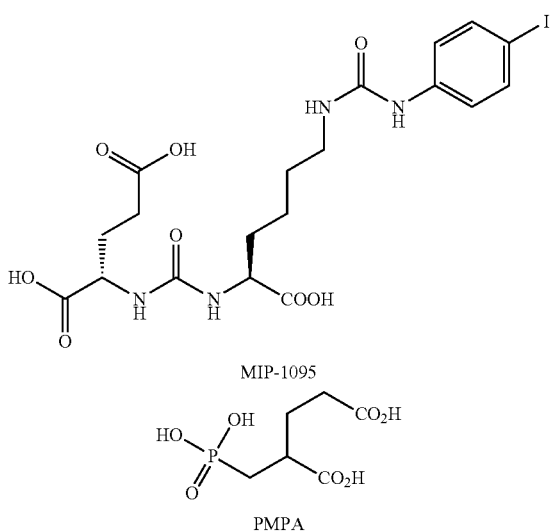

MIP-1095

PMPA

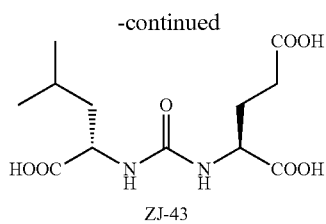

ZJ-43

Compound 5b has a little improved affinity to PSMA-11 with $IC_{50}$ values of 11.6±5.2 nM and 16.6±2.4 nM, respectively. Known PSMA inhibitors, ZJ-43 and 2-PMPA showed much lower binding affinities than compound 5b. Introduction of gallium into 5b did not cause a change in inhibitory activity of compound 5b, demonstrating higher binding affinity to PSMA comparable to the unchelated compound.

Example 54

In Vitro Binding Signals of $^{68}$Ga Labeled Ligands

To compare the binding affinity and specificity of [$^{68}$Ga] labeled ligands, cell binding studies with hot ligands were performed. 100 µL of freshly harvested PSMA cells (3 different cell numbers: 4×10$^5$, 2×10$^5$, 1×10$^5$) were incubated with 100 µL hot ligand and 50 µL PBS for TB or 50 µL 1a (PSMA11) (10 µM) for non-specific binding (NSB). After incubation at 37° C. for 60 min, the cell bound fractions were collected using a cell harvester (Brandel, MD). After washing twice with 5 mL ice-cold washing buffer, the cell-bound radioactivity was measured with a gamma counter (Wizard, Perkin Elmer).

TABLE 2

Binding signals of Ga-68 radiolabeled ligands in LNCaP tumor homogenates

| | Total binding (TB) | Nonspecific binding (NSB) | Specific binding (SB) SB = TB − NSB |
|---|---|---|---|
| 1a(PSMA11) | 13.5 | 1.2 | 12.3 |
| 1b | 10.8 | 2.0 | 8.8 |
| 1c | 13.4 | 1.6 | 11.8 |
| 1d | 12.6 | 1.4 | 11.2 |
| 1e | 14.8 | 1.6 | 13.2 |
| 1f | 13.5 | 1.5 | 12.0 |
| 1g | 10.5 | 1.5 | 9.0 |
| 2 | 9.2 | 5.1 | 4.1 |
| 3 | 10.0 | 4.2 | 5.8 |
| 4a | 13.4 | 1.4 | 12.0 |
| 4b | 10.3 | 1.5 | 8.8 |
| 5a | 3.30 | 0.47 | 2.83 |
| 5b | 10.73 | 0.18 | 10.54 |

All tracers ([$^{68}$Ga]1a-g, 2, 3, 4a-b and 5a-b) showed specific binding to LNCaP tumor homogenates (Table 2). However, [$^{68}$Ga]2 and [$^{68}$Ga]3 showed high nonspecific binding and lower specific binding. The specific bindings of [$^{68}$Ga]1b-g, [$^{68}$Ga]4a, [$^{68}$Ga]4b and [$^{68}$Ga]5b were comparable to that of the known compound, [$^{68}$Ga]1a (PSMA11). The results suggest that these new HBED-PSMA derivatives may be useful imaging agents for PSMA expressing tumors.

Example 55

Cell Uptake Comparisons

Cell uptake studies were performed using PSMA expressing LNCaP cells. Cells were grown in 6 well plates for 2 days. After incubation with $^{68}$Ga-labeled ligands for 1 hr at 37° C., media were removed. After washing twice with 3 mL PBS buffer, cells were lysed with 0.1 N NaOH. Lysed cells were wiped with filter paper and radioactivity in filter paper was measured with a gamma counter.

As shown in FIG. 1, most of the tracers, [$^{68}$Ga]1b-g, and 4a-b, showed better or comparable cell uptakes to [$^{68}$Ga]1a. The LNCaP cells over express PSMA receptor binding sites, the level of binding, % uptake/well, was an indicator of PSMA binding, the higher the better. [$^{68}$Ga]1a, a known PSMA imaging agent (PSMA-11), was used as a control. It was found that ([$^{68}$Ga]1b-g and 4a-b displayed excellent uptake comparable or better than that of [$^{68}$Ga]1a. However, [$^{68}$Ga]2 and 3, (indicated by arrows) the di-pyridyl derivatives, showed low cell uptakes, suggesting that these two ligand displayed the least binding under the assaying conditions. It is likely that [$^{68}$Ga]2 and 3 are not stable in the test media.

Example 56

In Vitro Autoradiography of LNCaP Tumor and Mouse Kidney Sections

LNCaP tumor and mouse kidneys were cut at 20 µm on a cryostat, thaw-mounted onto slides. Slides are incubated with radiotracers (3 µCi/ml) in PBS for 30 min and washed with PBS twice for 3 min each. After drying, the slides put into a plate for exposure for 30 min. Images were acquired with Typhoon FLA 7000 (GE Healthcare).

To validate the PSMA binding, in vitro autoradiography studies using LNCaP tumor and mouse kidney sections were carried out. Autoradiography studies demonstrated all radioligands have good binding to LNCaP tumors and kidneys. Incubation with 2-PMPA, a known PSMA inhibitor, blocked radiotracers' binding to tumor and kidney. These data confirm that all tracers ([$^{68}$Ga]1a-g, 2, 3 and 4a-b) bind to PSMA in prostate tumors and PSMA expressed in kidneys.

FIGS. 2A-2K show in vitro autoradiography of LNCaP tumor (left side) and mouse kidney sections (right side). The new [$^{68}$Ga]1b-g, 2, 3 and 4a-b, target compounds, displayed high binding to PSMA expressed in LNCaP tumors and mouse kidneys. These new PSMA target compounds, display high uptake in the sections. [$^{68}$Ga]1a (PSMA-11) was used as a control.

Example 57

Small Animal Imaging with a microPET

Male athymic mice (CD-1 nude, 5-6 weeks old) were obtained from Charles River, and were allowed to acclimatize at the vivarium for 1 week prior to implanting tumors. Mice were provided with food and water ad libitum. LNCaP tumors were induced on the left shoulder by sub-cutaneous (s.c.) injection of 5.0×10$^6$ cells in a 200 µL cell suspension of a 1:1 v/v mixture of media with reconstituted basement membrane (BD Matrigel™, Collaborative Biomedical Products Inc., Bedford, Mass.). Similarly, PC-3 tumors were induced on the right shoulder by s.c. injection of 2.0×10$^6$ cells. Palpable LNCaP tumors developed after a period of 4-5 weeks.

Dynamic small animal PET (APET) imaging studies of LNCaP (left shoulder) and PC-3 (right shoulder) tumor bearing nude mouse were performed with [$^{68}$Ga]1a and [$^{68}$Ga]4a. PET imaging studies were performed on a Phillips Mosaic small animal PET scanner, which has an imaging field of view of 11.5 cm. Under isoflurane anesthesia (1-2%, 1 L/min oxygen), the tumor-bearing nude mouse was injected with 0.5 mCi activity by an intravenous injection into the lateral tail vein. Data acquisition began at 30 min after the injection. Dynamic scans were conducted over a period of 1 h (5 min/frame; image voxel size 0.5 mm$^3$). Mouse was visually monitored for breathing, and a heating pad was used to maintain body temperature throughout the entire procedure. Images were reconstructed and a region of interest (ROI) analysis was performed using AMIDE software (http://amide.sourceforge.net/).

Figure 3A:
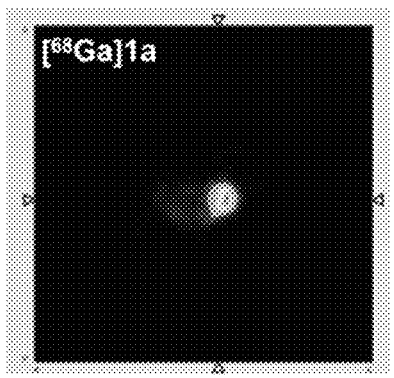
FIGS. 3A-3F depicts sagittal, transaxial and coronal sections of APET images of nude mouse with LNCaP tumor at left shoulder and PC-3 tumor at right shoulder at 60 min post i.v. injection of [$^{68}$Ga]1a (FIGS. 3A-3C) and [$^{68}$Ga]4a (FIG. 3D-3F).
Figure 3B:
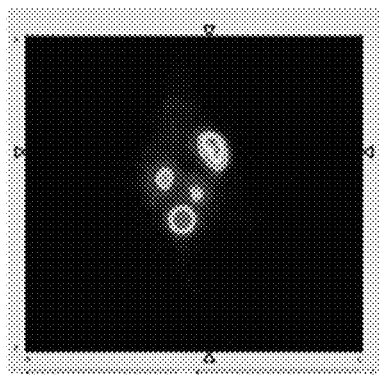
Figure 3C:
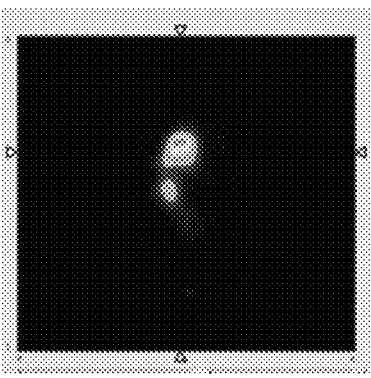
Figure 3D:
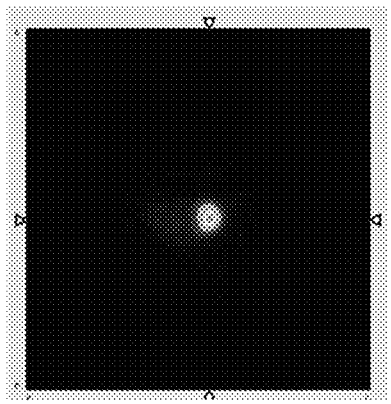
Figure 3E:
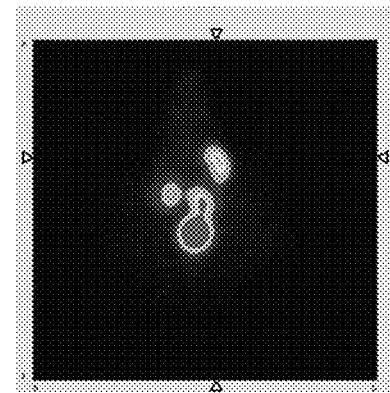
Figure 3F:
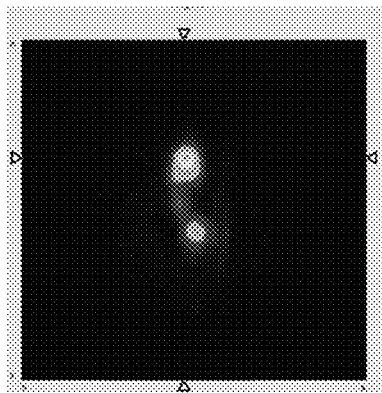

Representative animal PET images of LNCaP xenograft mice between 60 to 75 min after i.v. injection of [$^{68}$Ga]1a, and [$^{68}$Ga]4a are shown in FIGS. 3A-3F. Only LNCaP tumor was clearly visualized with all tracers with good tumor-to-background contrasts. PSMA negative tumor, PC-3 did not show any uptakes of radiotracers. The results showed that tumor xenografts, in which high expression of PSMA (LNCaP tumor), showed the highest uptake and retention. These agents also exhibited high kidney uptake and predominant renal excretion. FIGS. 3A-3F show sagittal, transaxial and coronal sections of APET images of nude mouse with LNCaP tumor at left shoulder and PC-3 tumor at right shoulder between 60 to 75 min post i.v. injection of [$^{68}$Ga]1a (FIGS. 3A-3C) and [$^{68}$Ga]4a (FIG. 3D-3F). The data confirmed that the PSMA positive tumor on the left shoulder displayed high uptake and retention at 60 min post i.v. injection.

Example 58

Cell Binding and Internalization

The cellular uptake and internalization kinetics of the [$^{68}$Ga]1a, [$^{68}$Ga]5a and [$^{68}$Ga]5b were determined using PSMA-expressing LNCaP cells. Furthermore, to be able to discriminate between total cellular activity (sum of membrane-associated and internalized activity) and internalized activity, all incubations were followed by a washing step with mild acid at 4° C. to remove specifically cell-surface bound radioligand by displacement.

LNCaP cells (in 6-well plates in triplicates) were incubated in RPMI-1640 medium with [$^{68}$Ga]1a, [$^{68}$Ga]5a or [$^{68}$Ga]5b for 0-2 h at 37° C. At the indicated time, the medium was removed and the cells were washed twice and then incubated with a mild acid buffer (50 mM glycine, 150 mM NaCl, pH 3.0) at 4° C. for 5 min. The supernatant (containing cell surface-bound radioactivity) was pooled and the cell pellet (containing internalized radioactivity) was collected with filter paper and then radioactivity in supernatant and cell pellet was counted on a gamma counter.

TABLE 3

Cell binding and internalization of radiotracers

| Time (min) | [$^{68}$Ga]1a | [$^{68}$Ga]5a | [$^{68}$Ga]5b |
|---|---|---|---|
| (A) Cell surface binding activity (% ID/10$^6$ cells) | | | |
| 5 | 3.21 ± 0.74 | 1.67 ± 0.24 | 2.50 ± 0.79 |
| 15 | 3.61 ± 0.47 | 1.92 ± 0.24 | 2.87 ± 0.10 |
| 30 | 2.95 ± 0.36 | 1.96 ± 0.27 | 3.54 ± 0.62 |
| 60 | 3.22 ± 0.81 | 1.89 ± 0.13 | 3.74 ± 0.33 |
| 90 | 3.41 ± 0.17 | 2.33 ± 0.01 | 5.03 ± 0.41 |
| 120 | 3.35 ± 0.04 | 2.03 ± 0.23 | 4.69 ± 0.45 |
| (B) Internalized activity (% ID/10$^6$ cells) | | | |
| 5 | 0.49 ± 0.21 | 0.21 ± 0.04 | 1.58 ± 0.30 |
| 15 | 2.51 ± 0.19 | 1.14 ± 0.21 | 4.08 ± 0.01 |
| 30 | 4.30 ± 0.72 | 2.55 ± 0.42 | 8.29 ± 0.54 |
| 60 | 7.43 ± 1.27 | 3.70 ± 0.44 | 12.5 ± 0.46 |
| 90 | 8.34 ± 0.16 | 5.40 ± 0.13 | 20.0 ± 2.54 |
| 120 | 8.82 ± 0.45 | 5.43 ± 1.20 | 18.9 ± 1.61 |

LNCaP cells were incubated with [$^{68}$Ga]1a, [$^{68}$Ga]5a and [$^{68}$Ga]5b for up to 2 h at 37° C. to determine whether the compound is internalized by endocytosis. The cells were then washed with a mild acid buffer to remove extracellularly bound compound. The cell surface binding and the acid-insensitive binding, or internalized compound, to LNCaP cells are shown in Table 3. The cellular binding and internalization of [$^{68}$Ga]1a, [$^{68}$Ga]5a and [$^{68}$Ga]5b showed a time-dependent increase over the time and reached plateau between 60 and 90 min. The internalized activity of [$^{68}$Ga]5b was much higher than those of [$^{68}$Ga]1a and [$^{68}$Ga]5a.

Figure 4:
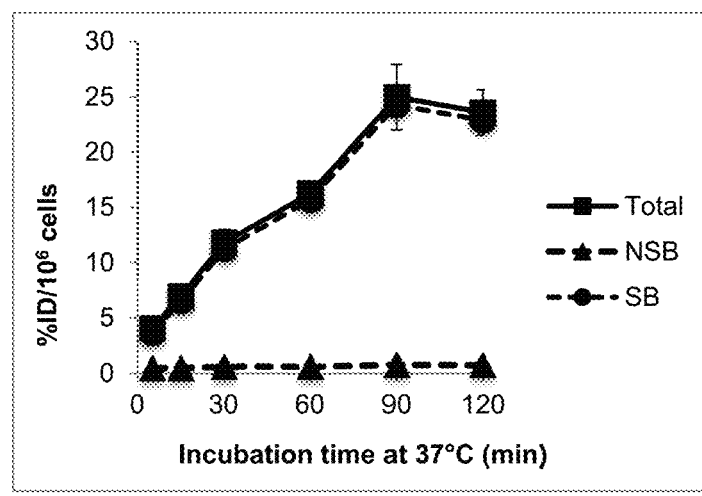
FIG. 4 depicts kinetics of [$^{68}$Ga]5b uptakes in PSMA expressing LNCaP cells.

FIG. 4 shows the kinetics of [$^{68}$Ga]5b uptakes in PSMA expressing LNCaP cells. Non specific binding (NSB) was evaluated by blocking with 20 μM PMPA. Specificity of cell uptake (SB) was calculated by subtracting the respective signals resulting from PMPA blocking. Values are expressed as % of applied radioactivity bound to 10$^6$ cells. The data clearly suggested that the non specific binding (NSB) was extremely low and the binding of [$^{68}$Ga]5b to the cells was contribution from the specific binding to PSMA.

Example 59

Biodistribution of [$^{68}$Ga]Labeled Ligand in PSMA Positive Tumor Bearing Nude Mice In a dish contained 5×10$^6$ cells of LNCaP in 50% Matrigel (Becton Dickinson, Heidelberg, Germany) were subcutaneously inoculated into the left shoulder of male 5- to 6-week-old CD-1 nu/nu mice (Charles River Laboratories). The tumors were allowed to grow for 8 weeks until approximately 0.5 cm$^3$ in size.

The $^{68}$Ga-radiolabeled compounds were injected via tail vein (25 μCi per mouse; 0.1-0.2 nmol). At 1 h after injection, the animals were sacrificed. Organs of interest were dissected and weighed. The radioactivity was measured with a gamma counter and calculated as % ID/g.

TABLE 4

Organ distribution (1 h post-injection) of [$^{68}$Ga]radiotracers in LNCaP tumor bearing nude mice (% dose/g, AVG ± SD, n = 3)

| | [$^{68}$Ga]1a | [$^{68}$Ga]5a | [$^{68}$Ga]5b |
|---|---|---|---|
| Blood | 0.37 ± 0.07 | 0.36 ± 0.05 | 0.46 ± 0.04 |
| Heart | 0.59 ± 0.14 | 0.19 ± 0.04 | 0.51 ± 0.12 |
| Muscle | 0.58 ± 0.24 | 0.21 ± 0.15 | 0.34 ± 0.07 |
| Lung | 2.44 ± 1.03 | 0.46 ± 0.13 | 2.27 ± 0.37 |
| Kidney | 176 ± 5.66 | 23.5 ± 8.96 | 156 ± 22.7 |
| Spleen | 18.48 ± 3.02 | 0.70 ± 0.38 | 11.09 ± 3.35 |
| Pancreas | 1.38 ± 0.63 | 0.20 ± 0.05 | 0.97 ± 0.23 |
| Liver | 0.62 ± 0.24 | 0.36 ± 0.10 | 0.78 ± 0.09 |
| Skin | 1.14 ± 0.58 | 0.33 ± 0.17 | 1.16 ± 0.57 |
| Brain | 0.04 ± 0.01 | 0.03 ± 0.01 | 0.05 ± 0.01 |
| Bone | 0.21 ± 0.05 | 0.11 ± 0.04 | 0.27 ± 0.07 |
| LNCaP tumor | 10.07 ± 3.32 | 5.15 ± 1.86 | 11.26 ± 2.61 |

[$^{68}$Ga]5b showed the high tumor and kidney uptake. In addition, [$^{68}$Ga]5b was cleared in other organs much better than [$^{68}$Ga]1a. Although [$^{68}$Ga]5a demonstrated lower tumor uptake, but its kidney retention was the lowest, which is desirable for a therapeutic drug. For example, [$^{177}$Lu]5a can be used as a therapeutic drug.

Example 60

Biodistribution of [$^{68}$Ga] Radiotracers in Normal Mice

Normal CD-1 male mice were injected via the tail vein with 35 μCi of [$^{68}$Ga] radiotracers (0.2 nmole of ligand). Each four mice were sacrificed by cervical dislocation at 2, 30, 60 and 120 min p.i. All organs were removed and blood was also collected. Each organ was weighed, and the tissue radioactivity was measured with an automated gamma counter (Wizard, Perkin Elmer). The % ID/g was calculated by comparison with samples of a standard dilution of the initial dose. All measurements were corrected for decay.

The kidneys and spleen are the most prominent organs in the biodistribution, because PSMA is expressed naturally in kidneys and spleen in mouse and because [$^{68}$Ga]5b is also excreted through kidneys. The tracer was cleared quickly and well except kidneys and spleen. No significant tracer activity is seen in other tissue.

Additional biodistribution studies for [$^{177}$Lu]1g were performed in normal mice. The lutetium-177 is an isotope with a longer half-life ($T_{1/2}$, 6.73 days) and weak beta emission for radiotherapy. Initial uptakes in the kidneys, as an indicator for PSMA binding, were comparable to that of [$^{68}$Ga]1g, suggesting that the Lu-DOTA has no effect on the tumor targeting. The results suggested that both $^{68}$Ga and $^{177}$Lu can be used to label 1g, and [$^{68}$Ga]1g and [$^{177}$Lu]1g will retain a high tumor PSMA targeting.

TABLE 5

Biodistribution of [$^{68}$Ga]1a-g, 2, 3 and 4a-b and [$^{177}$Lu]1g in normal male mice (% dose/g, n = 3)

[$^{68}$Ga]1a

| | 2 min | 30 min | 60 min | 120 min |
|---|---|---|---|---|
| Blood | 7.75 ± 1.60 | 0.54 ± 0.08 | 0.33 ± 0.07 | 0.12 ± 0.03 |
| Heart | 3.32 ± 0.51 | 0.27 ± 0.09 | 0.34 ± 0.07 | 0.23 ± 0.19 |
| Muscle | 1.68 ± 0.20 | 0.32 ± 0.01 | 0.19 ± 0.02 | 0.12 ± 0.03 |
| Lung | 5.29 ± 0.82 | 1.14 ± 0.17 | 0.93 ± 0.14 | 0.77 ± 0.17 |
| Kidney | 40.5 ± 7.81 | 108 ± 23.7 | 91.1 ± 11.6 | 83.9 ± 13.6 |
| Spleen | 7.46 ± 0.84 | 2.95 ± 0.36 | 4.39 ± 0.42 | 5.07 ± 2.68 |
| Pancreas | 1.91 ± 0.17 | 0.76 ± 0.11 | 0.59 ± 0.10 | 0.64 ± 0.23 |
| Liver | 11.0 ± 0.99 | 0.35 ± 0.03 | 6.09 ± 0.86 | 2.56 ± 0.80 |
| Skin | 2.42 ± 0.38 | 0.95 ± 0.20 | 0.44 ± 0.05 | 0.31 ± 0.12 |
| Brain | 0.25 ± 0.02 | 0.03 ± 0.00 | 0.02 ± 0.00 | 0.01 ± 0.00 |
| Bone | 1.77 ± 0.16 | 0.24 ± 0.08 | 0.23 ± 0.02 | 0.21 ± 0.05 |

| | [$^{68}$Ga]1b | | [$^{68}$Ga]1c | |
|---|---|---|---|---|
| | 2 min | 60 min | 2 min | 60 min |
| Blood | 7.86 ± 2.12 | 0.76 ± 0.30 | 8.55 ± 0.07 | 0.58 ± 0.07 |
| Heart | 3.45 ± 1.10 | 0.45 ± 0.06 | 3.48 ± 0.31 | 0.43 ± 0.14 |
| Muscle | 1.62 ± 0.48 | 0.36 ± 0.05 | 2.16 ± 0.34 | 0.60 ± 0.13 |
| Lung | 5.32 ± 1.79 | 1.24 ± 0.07 | 5.42 ± 0.23 | 0.90 ± 0.16 |
| Kidney | 48.1 ± 14.8 | 136 ± 13.3 | 47.2 ± 2.68 | 83.5 ± 14.7 |
| Spleen | 3.75 ± 1.20 | 4.15 ± 1.72 | 3.58 ± 0.48 | 1.63 ± 0.20 |
| Pancreas | 1.77 ± 0.65 | 0.98 ± 0.25 | 2.20 ± 0.04 | 1.13 ± 0.17 |
| Liver | 2.25 ± 0.82 | 0.36 ± 0.06 | 2.91 ± 0.15 | 0.79 ± 0.15 |
| Skin | 2.08 ± 0.57 | 0.72 ± 0.20 | 3.00 ± 0.40 | 1.07 ± 0.16 |
| Brain | 0.22 ± 0.06 | 0.03 ± 0.01 | 0.28 ± 0.04 | 0.03 ± 0.01 |
| Bone | 1.77 ± 0.47 | 0.63 ± 0.08 | 2.30 ± 0.07 | 1.24 ± 0.19 |

| | [$^{68}$Ga]1d | | [$^{68}$Ga]1e | |
|---|---|---|---|---|
| | 2 min | 60 min | 2 min | 60 min |
| Blood | 7.44 ± 1.40 | 0.44 ± 0.06 | 7.47 ± 0.33 | 0.45 ± 0.14 |
| Heart | 3.18 ± 0.48 | 0.42 ± 0.01 | 3.12 ± 0.17 | 0.28 ± 0.05 |
| Muscle | 1.96 ± 0.08 | 0.50 ± 0.07 | 2.01 ± 0.09 | 0.33 ± 0.07 |
| Lung | 4.96 ± 0.67 | 1.10 ± 0.13 | 5.08 ± 0.13 | 1.14 ± 0.30 |
| Kidney | 50.3 ± 8.32 | 141.7 ± 0.82 | 46.6 ± 3.01 | 113 ± 28.5 |
| Spleen | 3.40 ± 0.91 | 5.11 ± 0.97 | 3.69 ± 0.45 | 3.03 ± 0.90 |
| Pancreas | 1.83 ± 0.40 | 1.02 ± 0.18 | 1.80 ± 0.17 | 0.74 ± 0.19 |
| Liver | 2.36 ± 0.27 | 0.68 ± 0.11 | 2.00 ± 0.09 | 0.35 ± 0.09 |
| Skin | 2.30 ± 0.20 | 0.81 ± 0.11 | 2.46 ± 0.32 | 0.67 ± 0.06 |
| Brain | 0.23 ± 0.04 | 0.03 ± 0.00 | 0.25 ± 0.07 | 0.02 ± 0.00 |
| Bone | 2.01 ± 0.24 | 0.70 ± 0.09 | 2.33 ± 0.05 | 0.52 ± 0.06 |

[$^{68}$Ga]1f

| | 2 min | 60 min |
|---|---|---|
| Blood | 7.77 ± 1.51 | 0.97 ± 0.24 |
| Heart | 3.23 ± 0.64 | 0.52 ± 0.07 |
| Muscle | 1.81 ± 0.07 | 0.60 ± 0.04 |
| Lung | 5.07 ± 1.01 | 1.37 ± 0.15 |
| Kidney | 45.0 ± 12.57 | 120 ± 5.65 |
| Spleen | 3.80 ± 0.97 | 2.98 ± 1.86 |
| Pancreas | 1.72 ± 0.41 | 1.13 ± 0.17 |
| Liver | 2.43 ± 0.60 | 0.79 ± 0.13 |
| Skin | 2.44 ± 0.16 | 0.98 ± 0.10 |
| Brain | 0.25 ± 0.02 | 0.04 ± 0.01 |
| Bone | 2.33 ± 0.38 | 1.08 ± 0.05 |

[$^{68}$Ga]1g

| | 2 min | 30 min | 60 min | 120 min |
|---|---|---|---|---|
| Blood | 7.62 ± 0.08 | 0.68 ± 0.09 | 0.41 ± 0.02 | 0.25 ± 0.04 |
| Heart | 2.82 ± 0.21 | 0.49 ± 0.15 | 0.27 ± 0.03 | 0.16 ± 0.01 |
| Muscle | 1.72 ± 0.18 | 0.48 ± 0.04 | 0.30 ± 0.08 | 0.23 ± 0.04 |
| Lung | 5.19 ± 0.19 | 2.13 ± 0.39 | 1.33 ± 0.06 | 0.85 ± 0.16 |
| Kidney | 50.9 ± 5.81 | 110 ± 13.4 | 116 ± 23.2 | 95.0 ± 11.2 |
| Spleen | 5.06 ± 0.78 | 5.28 ± 2.18 | 4.77 ± 2.37 | 2.48 ± 0.91 |
| Pancreas | 1.73 ± 0.09 | 0.73 ± 0.19 | 0.48 ± 0.05 | 0.39 ± 0.04 |
| Liver | 2.00 ± 0.05 | 0.47 ± 0.06 | 0.43 ± 0.05 | 0.30 ± 0.01 |
| Skin | 2.00 ± 0.21 | 1.13 ± 0.25 | 0.92 ± 0.11 | 0.66 ± 0.10 |
| Brain | 0.29 ± 0.06 | 0.06 ± 0.03 | 0.03 ± 0.01 | 0.02 ± 0.00 |
| Bone | 1.51 ± 0.17 | 0.22 ± 0.11 | 0.28 ± 0.03 | 0.28 ± 0.03 |

[$^{177}$Lu]1g

| | 0.5 hr | 1 hr | 6 hr | 24 hr |
|---|---|---|---|---|
| Blood | 0.64 ± 0.22 | 0.15 ± 0.05 | 0.01 ± 0.00 | 0.01 ± 0.00 |
| Heart | 0.28 ± 0.09 | 0.14 ± 0.01 | 0.02 ± 0.01 | 0.01 ± 0.00 |
| Muscle | 0.27 ± 0.07 | 0.11 ± 0.03 | 0.03 ± 0.00 | 0.01 ± 0.00 |
| Lung | 0.80 ± 0.38 | 0.45 ± 0.13 | 0.11 ± 0.00 | 0.03 ± 0.01 |
| Kidney | 40.6 ± 10.5 | 30.3 ± 3.50 | 17.8 ± 4.07 | 4.02 ± 1.34 |
| Spleen | 0.78 ± 0.37 | 0.92 ± 0.24 | 0.28 ± 0.08 | 0.04 ± 0.00 |
| Pancreas | 0.40 ± 0.07 | 0.32 ± 0.183 | 0.08 ± 0.03 | 0.02 ± 0.01 |
| Liver | 0.23 ± 0.02 | 0.12 ± 0.02 | 0.07 ± 0.01 | 0.03 ± 0.00 |
| Skin | 0.56 ± 0.12 | 0.21 ± 0.04 | 0.06 ± 0.00 | 0.04 ± 0.01 |
| Brain | 0.03 ± 0.01 | 0.01 ± 0.00 | 0.01 ± 0.00 | 0.01 ± 0.00 |
| Bone | 0.22 ± 0.05 | 0.11 ± 0.01 | 0.12 ± 0.01 | 0.12 ± 0.01 |

[$^{68}$Ga]2

| | 2 min | 30 min | 60 min | 120 min |
|---|---|---|---|---|
| Blood | 8.92 ± 0.75 | 1.18 ± 0.15 | 0.89 ± 0.10 | 0.78 ± 0.04 |
| Heart | 3.40 ± 0.45 | 0.51 ± 0.03 | 0.33 ± 0.02 | 0.28 ± 0.02 |
| Muscle | 2.00 ± 0.25 | 0.46 ± 0.03 | 0.24 ± 0.01 | 0.18 ± 0.01 |
| Lung | 5.18 ± 0.52 | 1.07 ± 0.12 | 0.72 ± 0.16 | 0.45 ± 0.01 |
| Kidney | 56.4 ± 8.05 | 108 ± 8.66 | 67.8 ± 15.57 | 26.9 ± 6.13 |
| Spleen | 3.57 ± 0.20 | 1.33 ± 0.08 | 0.84 ± 0.24 | 0.36 ± 0.04 |
| Pancreas | 1.85 ± 0.17 | 0.76 ± 0.12 | 0.44 ± 0.08 | 0.30 ± 0.04 |
| Liver | 2.01 ± 0.08 | 0.33 ± 0.01 | 0.25 ± 0.06 | 0.22 ± 0.01 |
| Skin | 3.07 ± 0.05 | 0.88 ± 0.08 | 0.46 ± 0.10 | 0.29 ± 0.03 |
| Brain | 0.24 ± 0.02 | 0.05 ± 0.00 | 0.03 ± 0.00 | 0.03 ± 0.01 |
| Bone | 2.18 ± 0.08 | 0.48 ± 0.02 | 0.43 ± 0.01 | 0.60 ± 0.03 |

[$^{68}$Ga]3

| | 2 min | 30 min | 60 min | 120 min |
|---|---|---|---|---|
| Blood | 8.94 ± 1.57 | 3.19 ± 0.72 | 1.52 ± 0.44 | 1.00 ± 0.30 |
| Heart | 4.34 ± 1.15 | 0.93 ± 0.22 | 0.82 ± 0.22 | 0.84 ± 0.20 |
| Muscle | 2.02 ± 0.74 | 1.53 ± 0.68 | 1.01 ± 0.29 | 1.13 ± 0.50 |

TABLE 5-continued

Biodistribution of [$^{68}$Ga]1a-g, 2, 3 and 4a-b and [$^{177}$Lu]1g in normal male mice (% dose/g, n = 3)

| | | | | |
|---|---|---|---|---|
| Lung | 7.49 ± 2.71 | 1.38 ± 0.17 | 1.29 ± 0.31 | 0.97 ± 0.12 |
| Kidney | 56.2 ± 6.53 | 94.4 ± 13.7 | 61.3 ± 5.97 | 30.3 ± 8.87 |
| Spleen | 5.14 ± 1.49 | 4.35 ± 0.37 | 1.75 ± 0.17 | 1.71 ± 0.56 |
| Pancreas | 2.89 ± 0.61 | 1.36 ± 0.32 | 1.34 ± 0.45 | 1.21 ± 0.19 |
| Liver | 3.42 ± 0.11 | 1.71 ± 0.05 | 1.81 ± 0.14 | 2.00 ± 0.20 |
| Skin | 2.63 ± 0.48 | 1.48 ± 0.34 | 2.35 ± 0.34 | 1.22 ± 0.20 |
| Brain | 0.33 ± 0.06 | 0.09 ± 0.01 | 0.06 ± 0.04 | 0.05 ± 0.02 |
| Bone | 3.53 ± 0.96 | 1.70 ± 0.20 | 2.34 ± 1.08 | 3.56 ± 1.08 |

[$^{68}$Ga]4a

| | 2 min | 30 min | 60 min | 120 min |
|---|---|---|---|---|
| Blood | 8.59 ± 0.82 | 0.95 ± 0.33 | 0.30 ± 0.03 | 0.20 ± 0.10 |
| Heart | 3.62 ± 0.34 | 0.56 ± 0.21 | 0.31 ± 0.14 | 0.21 ± 0.03 |
| Muscle | 2.68 ± 0.30 | 0.61 ± 0.10 | 0.35 ± 0.07 | 0.20 ± 0.03 |
| Lung | 5.45 ± 0.44 | 1.55 ± 0.30 | 1.18 ± 0.14 | 0.83 ± 0.21 |
| Kidney | 60.7 ± 2.89 | 148 ± 5.73 | 181 ± 26.81 | 128 ± 25.0 |
| Spleen | 3.64 ± 0.16 | 3.51 ± 1.69 | 2.83 ± 1.49 | 2.83 ± 1.25 |
| Pancreas | 2.35 ± 0.12 | 0.89 ± 0.12 | 1.09 ± 0.27 | 1.02 ± 0.26 |
| Liver | 2.22 ± 0.23 | 0.39 ± 0.12 | 0.23 ± 0.01 | 0.18 ± 0.05 |
| Skin | 2.84 ± 0.19 | 0.99 ± 0.16 | 0.45 ± 0.07 | 0.30 ± 0.02 |
| Brain | 0.27 ± 0.04 | 0.04 ± 0.01 | 0.03 ± 0.00 | 0.02 ± 0.00 |
| Bone | 2.33 ± 0.21 | 0.37 ± 0.10 | 0.24 ± 0.02 | 0.23 ± 0.06 |

TABLE 6

Biodistribution of [$^{68}$Ga]5b in normal CD-1 male mice (% dose/g, avg ± SD, n = 3)

| | 2 min | 30 min | 60 min | 120 min |
|---|---|---|---|---|
| Blood | 7.94 ± 0.52 | 1.13 ± 0.13 | 0.48 ± 0.11 | 0.27 ± 0.07 |
| Heart | 4.33 ± 0.11 | 0.98 ± 0.06 | 0.40 ± 0.09 | 0.22 ± 0.06 |
| Muscle | 1.97 ± 0.16 | 0.67 ± 0.05 | 0.31 ± 0.07 | 0.16 ± 0.01 |
| Lung | 5.75 ± 0.26 | 2.63 ± 0.08 | 1.28 ± 0.31 | 0.61 ± 0.07 |
| Kidneys | 50.32 ± 3.31 | 73.96 ± 5.56 | 62.77 ± 12.55 | 49.00 ± 4.76 |
| Spleen | 3.86 ± 0.57 | 1.70 ± 0.44 | 1.71 ± 0.66 | 1.39 ± 0.38 |
| Pancreas | 2.18 ± 0.04 | 0.80 ± 0.09 | 0.52 ± 0.02 | 0.32 ± 0.02 |
| Liver | 2.97 ± 0.24 | 0.95 ± 0.11 | 0.54 ± 0.09 | 0.37 ± 0.06 |
| Skin | 2.38 ± 0.10 | 1.14 ± 0.15 | 0.58 ± 0.19 | 0.26 ± 0.02 |
| Brain | 0.19 ± 0.02 | 0.05 ± 0.01 | 0.03 ± 0.00 | 0.02 ± 0.00 |
| Bone | 2.16 ± 0.11 | 0.60 ± 0.02 | 0.38 ± 0.04 | 0.26 ± 0.01 |
| Stomach | 0.81 ± 0.29 | 0.31 ± 0.07 | 0.17 ± 0.06 | 0.22 ± 0.05 |
| Small intestine | 2.46 ± 0.15 | 1.03 ± 0.07 | 0.74 ± 0.17 | 0.45 ± 0.12 |
| Large intestine | 1.20 ± 0.20 | 0.37 ± 0.04 | 0.31 ± 0.21 | 0.54 ± 0.16 |
| Fat | 2.08 ± 0.27 | 1.45 ± 0.13 | 0.73 ± 0.11 | 0.35 ± 0.04 |
| Testes | 0.96 ± 0.15 | 1.14 ± 0.21 | 0.82 ± 0.06 | 0.68 ± 0.06 |
| Seminal vesicles | 1.47 ± 0.25 | 1.13 ± 0.19 | 0.94 ± 0.22 | 0.64 ± 0.10 |
| Tail | 8.08 ± 0.78 | 2.92 ± 0.95 | 1.73 ± 0.55 | 0.55 ± 0.04 |
| Body leftover | 2.30 ± 0.05 | 0.98 ± 0.05 | 0.52 ± 0.11 | 0.27 ± 0.01 |

Example 61

Small Animal microPET Imaging in Tumor Bearing Nude Mice

To illustrate the usefulness of [$^{68}$Ga]5b as a PET tracer for PSMA imaging, microPET studies with tumor bearing nude mice were performed. This study was performed in a small animal imaging facility Male CD-1-nu/nu mice were implanted subcutaneously with 5×106 LNCaP cells and PC-3 cells. When the tumors reached approximately 5-10 mm in diameter, the mice were used for microPET imaging. Mice bearing LNCaP tumor and PC-3 tumors were injected via the tail vein with ~0.5 mCi of [$^{68}$Ga]5b. Imaging studies were carried out under general anesthesia of the animals, induced with inhalation of 10% and maintained with inhalation of 6.5% isoflurane in 30% oxygen/air. Animals were positioned prone in the scanner. Whole body scan was performed for 15 min from 60 min post-injection of radiotracers. PET images were generated using the AMIDE software. MicroPET images obtained in LNCaP and PC-3 tumor xenografts from 60 min to 75 min after injection of [$^{68}$Ga]5b are shown in FIGS. 5A-5C.

Figure 5A:
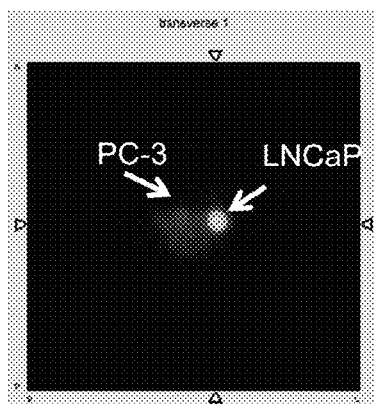
FIG. 5A-5C depict microPET images of tumor (LNCaP PSMA+ and PC-3 PSMA−) bearing mice between 60 min to 75 min after injection of [$^{68}$Ga]5b.
Figure 5B:
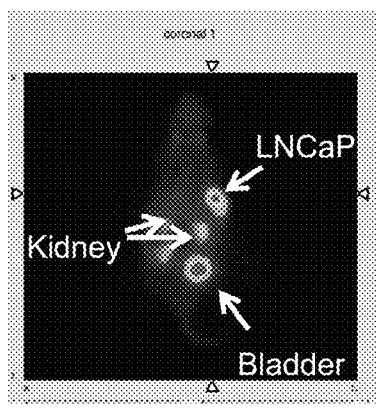
Figure 5C:
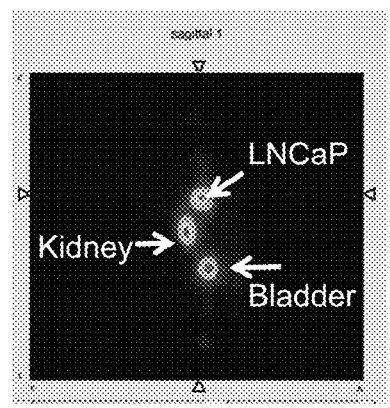

FIGS. 5A, 5B, and 5C show microPET images of tumor (LNCaP PSMA+ and PC-3 PSMA−) bearing mice between 60 min to 75 min after injection of [$^{68}$Ga]5b.

Intense [$^{68}$Ga]5b uptake was seen only in the kidneys, bladder and PSMA positive LNCaP tumor. PSMA negative PC-3 tumors did not show any uptakes of [$^{68}$Ga]5b. The intense renal uptake was partially due to specific binding of the radiotracer to proximal renal tubules as well as to excretion of this hydrophilic compound.

Blocking of [$^{68}$Ga]5b with 2-PMPA was performed in the same mouse. CD-1 nu/nu mouse bearing LNCaP and PC-3 tumor xenografts was injected with [$^{68}$Ga]5b alone or with 2-PMPA (2 mg/kg), a structurally unrelated PSMA inhibitor, to demonstrate that binding to LNCaP tumors was specific to PSMA.

Figure 6A:
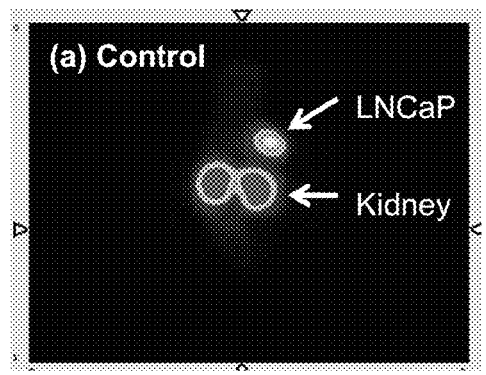
FIGS. 6A and 6B depict coronal microPET images of LNCaP (left shoulder) and PC-3 (right shoulder) tumors bearing mouse after injection of (a) [$^{68}$Ga]5b only and (b) [$^{68}$Ga]5b with 2-PMPA.
Figure 6B:
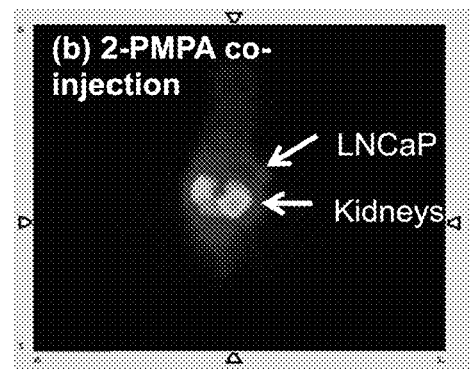

FIGS. 6A and 6B show coronal microPET images (1 h p.i. for 15 min) of LNCaP (left shoulder) and PC-3 (right shoulder) tumors bearing mouse after injection of (a) [$^{68}$Ga]5b only and (b) [$^{68}$Ga]5b with 2-PMPA (2 mg/kg, co-injection).

Representative animal PET images of LNCaP xenograft mice between 60 to 75 min after i.v. injection of [$^{68}$Ga]1a, and [$^{68}$Ga]5b are shown in FIGS. 5A-5C. Only LNCaP tumor was clearly visualized with all tracers with good tumor-to-background contrasts. PSMA negative tumor, PC-3 did not show any uptakes of radiotracers. The results showed that tumor xenografts, in which high expression of PSMA (LNCaP tumor), showed the highest uptake and retention. These agents also exhibited high kidney uptake and predominant renal excretion. FIGS. 5A-5C show sagittal, transaxial and coronal sections of APET images of nude mouse with LNCaP tumor at left shoulder and PC-3 tumor at right shoulder between 60 to 75 min post i.v. injection of [$^{68}$Ga]1a and [$^{68}$Ga]5b. The data confirmed that the PSMA positive tumor on the left shoulder displayed high uptake and retention at 60 min post i.v. injection. Uptake was high in PSMA expressing kidney and LNCaP tumor xenograft.

Also evident was renal excretion through the bladder. [$^{68}$Ga]5b localized to the PSMA-expressing LNCaP tumor, but not to the PSMA-deficient PC-3 tumor. Further, binding was abolished in the LNCaP tumor and kidney tissue when a 2 mg/kg dose of 2-PMPA was co-injected, indicating that binding was indeed saturable and specific to PSMA. These results clearly indicate that [$^{68}$Ga]5b is suitable as a tracer for PSMA imaging in prostate cancer with PET.

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

REFERENCES

[1] Stasiuk G J and Long N J. The ubiquitous DOTA and its derivatives: the impact of 1,4,7,10-tetraazacyclododecane-1,4,7,10-tetraacetic acid on biomedical imaging. Chem. Commun. (Camb.) 2013; 49:2732-46.

[2] Roosenburg S, Laverman P, Joosten L, Cooper M S, Kolenc-Peitl P K, Foster J M, et al. PET and SPECT imaging of a radiolabeled minigastrin analogue conjugated with DOTA, NOTA, and NODAGA and labeled with (64)Cu, (68)Ga, and (111)In. Mol. Pharm. 2014; 11:3930-7.

[3] Notni J, Simecek J, and Wester H J. Phosphinic acid functionalized polyazacycloalkane chelators for radiodiagnostics and radiotherapeutics: unique characteristics and applications. ChemMedChem 2014; 9:1107-15.

[4] Baum R P, Kulkarni H R, Muller D, Satz S, Danthi N, Kim Y S, et al. First-In-Human Study Demonstrating Tumor-Angiogenesis by PET/CT Imaging with (68)Ga-NODAGA-THERANOST, a High-Affinity Peptidomimetic for alphavbeta3 Integrin Receptor Targeting. Cancer Biother. Radiopharm. 2015; 30:152-9.

[5] Eisenwiener K P, Prata M I, Buschmann I, Zhang H W, Santos A C, Wenger S, et al. NODAGATOC, a new chelator-coupled somatostatin analogue labeled with [67/68Ga] and [111In] for SPECT, PET, and targeted therapeutic applications of somatostatin receptor (hsst2) expressing tumors. Bioconjug. Chem. 2002; 13:530-41.

[6] Eder M, Wangler B, Knackmuss S, LeGall F, Little M, Haberkorn U, et al. Tetrafluorophenolate of HBED-CC: a versatile conjugation agent for 68Ga-labeled small recombinant antibodies. Eur. J. Nucl. Med. Mol. Imaging 2008; 35:1878-86.

[7] Schafer M, Bauder-Wust U, Leotta K, Zoller F, Mier W, Haberkorn U, et al. A dimerized urea-based inhibitor of the prostate-specific membrane antigen for 68Ga-PET imaging of prostate cancer. EJNMMI Res 2012; 2:23.

[8] Price E W and Orvig C. Matching chelators to radiometals for radiopharmaceuticals. Chem. Soc. Rev. 2014; 43:260-90.

[9] Boros E, Ferreira C L, Yapp D T, Gill R K, Price E W, Adam M J, et al. RGD conjugates of the H2dedpa scaffold: synthesis, labeling and imaging with 68Ga. Nucl. Med. Biol. 2012; 39:785-94.

[10] Manzoni L, Belvisi L, Arosio D, Bartolomeo M P, Bianchi A, Brioschi C, et al. Synthesis of Gd and (68)Ga complexes in conjugation with a conformationally optimized RGD sequence as potential MRI and PET tumor-imaging probes. ChemMedChem 2012; 7:1084-93.

[11] Waldron B P, Parker D, Burchardt C, Yufit D S, Zimny M, and Roesch F. Structure and stability of hexadentate complexes of ligands based on AAZTA for efficient PET labelling with gallium-68. Chem. Commun. (Camb.) 2013; 49:579-81.

[12] Pomper M G, Musachio J L, Zhang J, Scheffel U, Zhou Y, Hilton J, et al. 11C-MCG: synthesis, uptake selectivity, and primate PET of a probe for glutamate carboxypeptidase II (NAALADase). Mol. Imaging 2002; 1:96-101.

[13] Rowe S P, Gage K L, Faraj S F, Macura K J, Cornish T C, Gonzalez-Roibon N, et al. (1)(8)F-DCFBC PET/CT for PSMA-Based Detection and Characterization of Primary Prostate Cancer. J. Nucl. Med. 2015; 56:1003-10.

[14] Cho S Y, Gage K L, Mease R C, Senthamizhchelvan S, Holt D P, Jeffrey-Kwanisai A, et al. Biodistribution, tumor detection, and radiation dosimetry of 18F-DCFBC, a low-molecular-weight inhibitor of prostate-specific membrane antigen, in patients with metastatic prostate cancer. J. Nucl. Med. 2012; 53:1883-91.

[15] Chen Y, Pullambhatla M, Foss C A, Byun Y, Nimmagadda S, Senthamizhchelvan S, et al. 2-(3-{1-Carboxy-5-[(6-[18F]fluoro-pyridine-3-carbonyl)-amino]-pentyl}-ureido)-pen tanedioic acid, [18F]DCFPyL, a PSMA-based PET imaging agent for prostate cancer. Clin. Cancer Res. 2011; 17:7645-53.

[16] Szabo Z, Mena E, Rowe S P, Plyku D, Nidal R, Eisenberger M A, et al. Initial Evaluation of [(18)F]DCFPyL for Prostate-Specific Membrane Antigen (PSMA)-Targeted PET Imaging of Prostate Cancer. Mol. Imaging Biol. 2015; 17:565-74.

[17] Eder M, Eisenhut M, Babich J, and Haberkorn U. PSMA as a target for radiolabelled small molecules. Eur. J. Nucl. Med. Mol. Imaging 2013; 40:819-23.

[18] Eder M, Neels O, Mueller M, Bauder-Wuest U, Remde Y, Schaefer M, et al. Novel preclinical and radiopharmaceutical aspects of [68Ga]Ga-PSMA-HBED-CC: a new PET tracer for imaging of prostate cancer. Pharmaceuticals 2014; 7:779-96.

[19] Eiber M, Maurer T, Souvatzoglou M, Beer A J, Ruffani A, Haller B, et al. Evaluation of Hybrid 68Ga-PSMA Ligand PET/CT in 248 Patients with Biochemical Recurrence After Radical Prostatectomy. J. Nucl. Med. 2015; 56:668-74.

[20] Benesova M, Schafer M, Bauder-Wust U, Afshar-Oromieh A, Kratochwil C, Mier W, et al. Preclinical Evaluation of a Tailor-Made DOTA-Conjugated PSMA Inhibitor with Optimized Linker Moiety for Imaging and Endoradiotherapy of Prostate Cancer. J. Nucl. Med. 2015; 56:914-20.

[21] Kabasakal L, AbuQbeitah M, Aygun A, Yeyin N, Ocak M, Demirci E, et al. Pre-therapeutic dosimetry of normal organs and tissues of Lu-PSMA-617 prostate-specific membrane antigen (PSMA) inhibitor in patients with castration-resistant prostate cancer. Eur. J. Nucl. Med. Mol. Imaging 2015.

[22] Afshar-Oromieh A, Hetzheim H, Kratochwil C, Benesova M, Eder M, Neels O C, et al. The novel theranostic PSMA-ligand PSMA-617 in the diagnosis of prostate cancer by PET/CT: biodistribution in humans, radiation dosimetry and first evaluation of tumor lesions. J. Nucl. Med. 2015.

[23] Weineisen M, Schottelius M, Simecek J, Baum R P, Yildiz A, Beykan S, et al. 68Ga- and 177Lu-Labeled PSMA I&T: Optimization of a PSMA-Targeted Theranostic Concept and First Proof-of-Concept Human Studies. J. Nucl. Med. 2015; 56:1169-76.

[24] Herrmann K, Bluemel C, Weineisen M, Schottelius M, Wester H J, Czernin J, et al. Biodistribution and radiation dosimetry for a probe targeting prostate-specific membrane antigen for imaging and therapy. J. Nucl. Med. 2015; 56:855-61.

[25] Ristau B T, O'Keefe D S, and Bacich D J. The prostate-specific membrane antigen: lessons and current clinical implications from 20 years of research. Urol Oncol 2014; 32:272-9.

[26] Barinka C, Rojas C, Slusher B, and Pomper M. Glutamate carboxypeptidase II in diagnosis and treatment of neurologic disorders and prostate cancer. Curr. Med. Chem. 2012; 19:856-70.

[27] Pavlicek J, Ptacek J, Cerny J, Byun Y, Skultetyova L, Pomper M G, et al. Structural characterization of P1'-diversified urea-based inhibitors of glutamate carboxypeptidase II. Bioorg. Med. Chem. Lett. 2014; 24:2340-5.

[28] Davis M I, Bennett M J, Thomas L M, and Bjorkman P J. Crystal structure of prostate-specific membrane antigen, a tumor marker and peptidase. Proc. Natl. Acad. Sci. U.S.A 2005; 102:5981-6.

[29] Akhtar N H, Pail O, Saran A, Tyrell L, and Tagawa S T. Prostate-Specific Membrane Antigen-Based Therapeutics. Advances in Urology 2012; 2012:9.

[30] Osborne J R, Akhtar N H, Vallabhajosula S, Anand A, Deh K, and Tagawa S T. Prostate-specific membrane antigen-based imaging. Urol Oncol 2013; 31:144-54.

[31] Franc B L, Cho S Y, Rosenthal S A, Cui Y, Tsui B, Vandewalker K M, et al. Detection and localization of carcinoma within the prostate using high resolution transrectal gamma imaging (TRGI) of monoclonal antibody directed at prostate specific membrane antigen (PSMA)—proof of concept and initial imaging results. Eur. J. Radiol. 2013; 82:1877-84.

[32] Tagawa S T, Milowsky M I, Morris M, Vallabhajosula S, Christos P, Akhtar N H, et al. Phase II study of Lutetium-177-labeled anti-prostate-specific membrane antigen monoclonal antibody J591 for metastatic castration-resistant prostate cancer. Clin. Cancer Res. 2013; 19:5182-91.

[33] Osborne J R, Green D A, Spratt D E, Lyashchenko S, Fareedy S B, Robinson B D, et al. A prospective pilot study of (89)Zr-J591/prostate specific membrane antigen positron emission tomography in men with localized prostate cancer undergoing radical prostatectomy. J. Urol. 2014; 191:1439-45.

[34] Holland J P, Divilov V, Bander N H, Smith-Jones P M, Larson S M, and Lewis J S. 89Zr-DFO-J591 for immunoPET of prostate-specific membrane antigen expression in vivo. J. Nucl. Med. 2010; 51:1293-300.

[35] Li Y, Tian Z, Rizvi S M, Bander N H, and Allen B J. In vitro and preclinical targeted alpha therapy of human prostate cancer with Bi-213 labeled J591 antibody against the prostate specific membrane antigen. Prostate Cancer Prostatic Dis 2002; 5:36-46.

[36] Hao G, Kumar A, Dobin T, Öz O K, Hsieh J-T, and Sun X. A Multivalent Approach of Imaging Probe Design To Overcome an Endogenous Anion Binding Competition for Noninvasive Assessment of Prostate Specific Membrane Antigen. Mol. Pharm. 2013; 10:2975-85.

[37] Humblet V, Misra P, Bhushan K R, Nasr K, Ko Y S, Tsukamoto T, et al. Multivalent scaffolds for affinity maturation of small molecule cell surface binders and their application to prostate tumor targeting. J. Med. Chem. 2009; 52:544-50.

[38] Misra P, Humblet V, Pannier N, Maison W, and Frangioni J V. Production of multimeric prostate-specific membrane antigen small-molecule radiotracers using a solid-phase 99mTc preloading strategy. J. Nucl. Med. 2007; 48:1379-89.

[39] Lapi S E, Wahnishe H, Pham D, Wu L Y, Nedrow-Byers J R, Liu T, et al. Assessment of an 18F-labeled phosphoramidate peptidomimetic as a new prostate-specific membrane antigen-targeted imaging agent for prostate cancer. J. Nucl. Med. 2009; 50:2042-8.

[40] Nedrow-Byers J R, Moore A L, Ganguly T, Hopkins M R, Fulton M D, Benny P D, et al. PSMA-targeted SPECT agents: mode of binding effect on in vitro performance. Prostate 2013; 73:355-62.

[41] Nedrow-Byers J R, Jabbes M, Jewett C, Ganguly T, He H, Liu T, et al. A phosphoramidate-based prostate-specific membrane antigen-targeted SPECT agent Prostate 2012; 72:904-12.

[42] Kozikowski A P, Zhang J, Nan F, Petukhov P A, Grajkowska E, Wroblewski J T, et al. Synthesis of urea-based inhibitors as active site probes of glutamate carboxypeptidase II: efficacy as analgesic agents. J. Med. Chem. 2004; 47:1729-38.

[43] Rong S B, Zhang J, Neale J H, Wroblewski J T, Wang S, and Kozikowski A P. Molecular modeling of the interactions of glutamate carboxypeptidase II with its potent NAAG-based inhibitors. J. Med. Chem. 2002; 45:4140-52.

[44] Nan F, Bzdega T, Pshenichkin S, Wroblewski J T, Wroblewska B, Neale J H, et al. Dual function glutamate-related ligands: discovery of a novel, potent inhibitor of glutamate carboxypeptidase II possessing mGluR3 agonist activity. J. Med. Chem. 2000; 43:772-4.

[45] Banerjee S R, Pullambhatla M, Foss C A, Nimmagadda S, Ferdani R, Anderson C J, et al. (64)Cu-labeled inhibitors of prostate-specific membrane antigen for PET imaging of prostate cancer. J. Med. Chem. 2014; 57:2657-69.

[46] Castanares M A, Mukherjee A, Chowdhury W H, Liu M, Chen Y, Mease R C, et al. Evaluation of prostate-specific membrane antigen as an imaging reporter. J. Nucl. Med. 2014; 55:805-11.

[47] Banerjee S R and Pomper M G. Clinical applications of Gallium-68. Appl. Radiat. Isot. 2013; 76:2-13.

[48] Banerjee S R, Pullambhatla M, Byun Y, Nimmagadda S, Green G, Fox J J, et al. 68Ga-labeled inhibitors of prostate-specific membrane antigen (PSMA) for imaging prostate cancer. J. Med. Chem. 2010; 53:5333-41.

[49] Vallabhajosula S, Nikolopoulou A, Babich J W, Osborne J R, Tagawa S T, Lipai I, et al. 99mTc-labeled small-molecule inhibitors of prostate-specific membrane antigen: pharmacokinetics and biodistribution studies in healthy subjects and patients with metastatic prostate cancer. J. Nucl. Med. 2014; 55:1791-8.

[50] Barrett J A, Coleman R E, Goldsmith S J, Vallabhajosula S, Petry N A, Cho S, et al. First-in-man evaluation of 2 high-affinity PSMA-avid small molecules for imaging prostate cancer. J. Nucl. Med. 2013; 54:380-7.

[51] Maresca K P, Hillier S M, Femia F J, Keith D, Barone C, Joyal J L, et al. A series of halogenated heterodimeric inhibitors of prostate specific membrane antigen (PSMA) as radiolabeled probes for targeting prostate cancer. J. Med. Chem. 2009; 52:347-57.

[52] Zechmann C M, Afshar-Oromieh A, Armor T, Stubbs J B, Mier W, Hadaschik B, et al. Radiation dosimetry and first therapy results with a (124)I/(131)I-labeled small molecule (MIP-1095) targeting PSMA for prostate cancer therapy. Eur. J. Nucl. Med. Mol. Imaging 2014; 41:1280-92.

[53] Dietlein M, Kobe C, Kuhnert G, Stockter S, Fischer T, Schomäcker K, et al. Comparison of [18F]DCFPyL and [68Ga]Ga-PSMA-HBED-CC for PSMA-PET Imaging in Patients with Relapsed Prostate Cancer. Mol. Imaging Biol. 2015; 17:575-84.

[54] Rowe S P, Gorin M A, Hammers H J, Som Javadi M, Hawasli H, Szabo Z, et al. Imaging of metastatic clear cell renal cell carcinoma with PSMA-targeted F-DCFPyL PET/CT. Ann. Nucl. Med. 2015.

[55] Huang S S, Wang X, Zhang Y, Doke A, DiFilippo F P, and Heston W D. Improving the biodistribution of PSMA-targeting tracers with a highly negatively charged linker. Prostate 2014; 74:702-13.

[56] Smith D L, Breeman W A, and Sims-Mourtada J. The untapped potential of Gallium 68-PET: the next wave of (6)(8)Ga-agents. Appl. Radiat. Isot. 2013; 76:14-23.

[57] Burke B P, Clemente G S, and Archibald S J. Recent advances in chelator design and labelling methodology for (68) Ga radiopharmaceuticals. J Labelled Comp Radiopharm 2014; 57:239-43.

[58] Velikyan I. Prospective of (68)Ga-radiopharmaceutical development Theranostics 2013; 4:47-80.

[59] Breeman W A, de Blois E, Sze Chan H, Konijnenberg M, Kwekkeboom D J, and Krenning E P. (68)Ga-labeled DOTA-peptides and (68)Ga-labeled radiopharmaceuticals for positron emission tomography: current status of research, clinical applications, and future perspectives. Semin. Nucl. Med. 2011; 41:314-21.

[60] Rosch F. Past, present and future of 68Ge/68Ga generators. Appl. Radiat. Isot. 2013; 76:24-30.

[61] Velikyan I. 68Ga-Based Radiopharmaceuticals: Production and Application Relationship. Molecules 2015; 20:12913-43.

[62] Sanchez-Crespo A. Comparison of Gallium-68 and Fluorine-18 imaging characteristics in positron emission tomography. Appl. Radiat. Isot. 2013; 76:55-62.

[63] Velikyan I, Sundin A, Sorensen J, Lubberink M, Sandstrom M, Garske-Roman U, et al. Quantitative and qualitative intrapatient comparison of 68Ga-DOTATOC and 68Ga-DOTATATE: net uptake rate for accurate quantification. J. Nucl. Med. 2014; 55:204-10.

[64] Sandstrom M, Velikyan I, Garske-Roman U, Sorensen J, Eriksson B, Granberg D, et al. Comparative biodistribution and radiation dosimetry of 68Ga-DOTATOC and 68Ga-DOTATATE in patients with neuroendocrine tumors. J. Nucl. Med. 2013; 54:1755-9.

[65] Beiderwellen K J, Poeppel T D, Hartung-Knemeyer V, Buchbender C, Kuehl H, Bockisch A, et al. Simultaneous 68Ga-DOTATOC PET/MRI in patients with gastroenteropancreatic neuroendocrine tumors: initial results. Invest. Radiol. 2013; 48:273-9.

[66] Eder M, Neels O, Muller M, Bauder-Wust U, Remde Y, Schafer M, et al. Novel Preclinical and Radiopharmaceutical Aspects of [68Ga]Ga-PSMA-HBED-CC: A New PET Tracer for Imaging of Prostate Cancer. Pharmaceuticals (Basel) 2014; 7:779-96.

[67] Mjos K D and Orvig C. Metallodrugs in medicinal inorganic chemistry. Chem. Rev. 2014; 114:4540-63.

[68] Velikyan I, Maecke H, and Langstrom B. Convenient preparation of 68Ga-based PET-radiopharmaceuticals at room temperature. Bioconjug. Chem. 2008; 19:569-73.

[69] Motekaitis R J, Rogers B E, Reichert D E, Martell A E, and Welch M J. Stability and Structure of Activated Macrocycles. Ligands with Biological Applications. Inorg. Chem. 1996; 35:3821-7.

[70] Mease R C, Foss C A, and Pomper M G. PET imaging in prostate cancer: focus on prostate-specific membrane antigen. Curr. Top. Med. Chem. 2013; 13:951-62.

[71] Eder M, Schafer M, Bauder-Wust U, Hull W E, Wangler C, Mier W, et al. 68Ga-complex lipophilicity and the targeting property of a urea-based PSMA inhibitor for PET imaging. Bioconjug. Chem. 2012; 23:688-97.

[72] Verburg F A, Krohn T, Heinzel A, Mottaghy F M, and Behrendt F F. First evidence of PSMA expression in differentiated thyroid cancer using [(68)Ga]PSMA-HBED-CC PET/CT. Eur. J. Nucl. Med. Mol. Imaging 2015; 42:1622-3.

[73] Ahmadzadehfar H, Rahbar K, Kurpig S, Bogemann M, Claesener M, Eppard E, et al. Early side effects and first results of radioligand therapy with (177)Lu-DKFZ-617 PSMA of castrate-resistant metastatic prostate cancer: a two-centre study. EJNMMI Res 2015; 5:114.

[74] Weineisen M, Simecek J, Schottelius M, Schwaiger M, and Wester H J. Synthesis and preclinical evaluation of DOTAGA-conjugated PSMA ligands for functional imaging and endoradiotherapy of prostate cancer. EJNMMI Res 2014; 4:63.

[75] Weineisen M, Schottelius M, Simecek J, Baum R P, Yildiz A, Beykan S, et al. 68Ga- and 177Lu-Labeled PSMA I& T: Optimization of a PSMA-Targeted Theranostic Concept and First Proof-of-Concept Human Studies. J. Nucl. Med. 2015; 56:1169-76.

[76] Simecek J, Notni J, Kapp T G, Kessler H, and Wester H J. Benefits of NOPO as chelator in gallium-68 peptides, exemplified by preclinical characterization of (68)Ga—NOPO-c(RGDfK). Mol. Pharm. 2014; 11:1687-95.

[77] Simecek J, Hermann P, Havlickova J, Herdtweck E, Kapp T G, Engelbogen N, et al. A cyclen-based tetraphosphinate chelator for the preparation of radiolabeled tetrameric bioconjugates. Chemistry 2013; 19:7748-57.

[78] Simecek J, Hermann P, Wester H J, and Notni J. How is (68)Ga labeling of macrocyclic chelators influenced by metal ion contaminants in (68)Ge/(68)Ga generator eluates? ChemMedChem 2013; 8:95-103.

[79] Simecek J, Zemek O, Hermann P, Notni J, and Wester H J. Tailored Gallium(III) Chelator NOPO: Synthesis, Characterization, Bioconjugation, and Application in Preclinical Ga-68-PET Imaging. Mol. Pharm. 2013.

[80] Ramogida C F, Cawthray J F, Boros E, Ferreira C L, Patrick B O, Adam M J, et al. H2CHXdedpa and H4CHXoctapa-Chiral Acyclic Chelating Ligands for (67/68)Ga and (111)In Radiopharmaceuticals. Inorg. Chem. 2015; 54:2017-31.

[81] Baur B, Solbach C, Andreolli E, Winter G, Machulla H J, and Reske S N. Synthesis, Radiolabelling and In Vitro Characterization of the Gallium-68-, Yttrium-90- and Lutetium-177-Labelled PSMA Ligand, CHX-A"-DTPA-DUPA-Pep. Pharmaceuticals (Basel) 2014; 7:517-29.

[82] Afshar-Oromieh A, Avtzi E, Giesel F L, Holland-Letz T, Linhart H G, Eder M, et al. The diagnostic value of PET/CT imaging with the 68Ga-labelled PSMA ligand HBED-CC in the diagnosis of recurrent prostate cancer. Eur. J. Nucl. Med. Mol. Imaging 2014:Ahead of Print.

[83] Afshar-Oromieh A, Haberkorn U, Schlemmer H P, Fenchel M, Eder M, Eisenhut M, et al. Comparison of PET/CT and PET/MRI hybrid systems using a 68Ga-labelled PSMA ligand for the diagnosis of recurrent prostate cancer: initial experience. Eur. J. Nucl. Med. Mol. Imaging 2014; 41:887-97.

[84] Maurer T, Beer A J, Wester H J, Kubler H, Schwaiger M, and Eiber M. Positron emission tomography/magnetic resonance imaging with 68Gallium-labeled ligand of prostate-specific membrane antigen: promising novel option in prostate cancer imaging? Int. J. Urol. 2014; 21:1286-8.

[85] Chakraborty P S, Tripathi M, Agarwal K K, Kumar R, Vijay M K, and Bal C. Metastatic Poorly Differentiated Prostatic Carcinoma With Neuroendocrine Differentiation: Negative on 68Ga-PSMA PET/CT. Clin. Nucl. Med. 2015; 40:e163-6.

[86] Eiber M, Nekolla S G, Maurer T, Weirich G, Wester H J, and Schwaiger M. Ga-PSMA PET/MR with multimodality image analysis for primary prostate cancer. Abdom. Imaging 2014.

[87] Afshar-Oromieh A, Avtzi E, Giesel F L, Holland-Letz T, Linhart H G, Eder M, et al. The diagnostic value of PET/CT imaging with the (68)Ga-labelled PSMA ligand HBED-CC in the diagnosis of recurrent prostate cancer. Eur. J. Nucl. Med. Mol. Imaging 2015; 42:197-209.

[88] Delker A, Fendler W P, Kratochwil C, Brunegraf A, Gosewisch A, Gildehaus F J, et al. Dosimetry for Lu-DKFZ-PSMA-617: a new radiopharmaceutical for the treatment of metastatic prostate cancer. Eur. J. Nucl. Med. Mol. Imaging 2015.

[89] Sun Y, Anderson C J, Pajeau T S, Reichert D E, Hancock R D, Motekaitis R J, et al. Indium (III) and gallium (III) complexes of bis(aminoethanethiol) ligands with different denticities: stabilities, molecular modeling, and in vivo behavior. J. Med. Chem. 1996; 39:458-70.

[90] Mandal P K and McMurray J S. Pd—C-Induced Catalytic Transfer Hydrogenation with Triethylsilane. J. Org. Chem. 2007; 72:6599-601.

[91] Kantchev E A B, Peh G-R, Zhang C, and Ying J Y. Practical Heck-Mizoroki Coupling Protocol for Challenging Substrates Mediated by an N-Heterocyclic Carbene-Ligated Palladacycle. Org. Lett. 2008; 10:3949-52.

[92] Bechara G, Leygue N, Galaup C, Mestre-Voegtle B, and Picard C. Polyazamacrocycles based on a tetraaminoacetate moiety and a (poly)pyridine intracyclic unit: direct synthesis and application to the photosensitization of Eu(III) and Tb(III) ions in aqueous solutions. Tetrahedron 2010; 66:8594-604.

Abbreviations

SPECT, single photon emission computer tomography;
PET, positron emission tomography
HPLC, High performance liquid chromatography;
HRMS, High-resolution mass spectrometry;
PBS, phosphate buffered saline;
SPE, solid-phase extraction;
TFA, trifluoroacetic acid;
GMP: manufacturing good manufacturing;
NET: neuroendocrine tumor
FDG, 2-fluoro-2-dexoy-D-glucose
DOTA: 1,4,7,10-tetraazacyclododecane-1,4,7,10-tetraacetic acid [1]
DOTA-TOC, DOTA-D-Phe-c(Cys-Tyr-D-Trp-Lys-Thr-Cys)-Thr-ol
DOTA-TATE, DOTA-D-Phe-c(Cys-Tyr-D-Trp-Lys-Thr-Cys)-Thr
DOTA-NOC, DOTA-D-Phe-c(Cys-Nal-D-Trp-Lys-Thr-Cys)-Thr-ol
NOTA: 1,4,7-triazacyclononane-N,N',N"-triacetic acid [2, 3]
NODAGA: 1,4,7-triazacyclononane,1-glutaric acid-4,7-acetic acid [4, 5]
HBED-CC: N,N'-Bis[2-hydroxy-5-(carboxyethyl)-benzyl]ethylenediamine-N,N'-diacetic acid, [6, 7]
TRAP: 1,4,7-triazacyclononane-N,N',N"-tris(methylenephosphonic) acid [3]
DEDPA: 1,2-[[6-(carboxy)-pyridin-2-yl]-methylamino] ethane [8, 9]
AAZTA: 6-[bis(hydroxycarbonyl-methyl)amino]-1,4-bis(hydroxycarbonyl methyl)-6-methylperhydro-1,4-diazepine, [10, 11]
EDTMP (ethylene-diamino-N,N,N',N'-tetrakis-methylene-phosphoric acid)
bis-(Glu-NH—CO—NH-Lys-(Ahx)-HBED-CC)
[$^{11}$C]-MCG: [$^{11}$C](S)-2-[3-((R)-1-carboxy-2-methylsulfanyl-ethyl)-ureido]-pentanedioic acid, [12]
[$^{18}$F]DCFBC: N—[N—[(S)-1,3-dicarboxypropyl]carbamoyl]-4-[$^{18}$F]-fluorobenzyl-L-cysteine, [13, 14]
[$^{18}$F]DCFPyL: 2-(3-(1-carboxy-5-[(6-[$^{18}$F]fluoro-pyridine-3-carbonyl)-amino]-pentyl)-ureido)-pentanedioic acid, [15, 16]
PSMA-11 Glu-NH—CO—NH-Lys-(Ahx)-(HBED-CC) [17-19]
PSMA-617: 2-[3-(1-Carboxy-5-(3-naphthalen-2-yl-2-[(4-([2-(4,7,10-tris-carboxy methyl-1,4,7,10-tetraaza-cyclododec-1-yl)-acetylamino]-methyl)-cyclohexanecarbonyl)-amino]-Propionylamino)-pentyl)-ureido]-pentanedioic acid [20-22]
PSMA I&T: [23, 24]
GPI 2[(3-amino-3-carboxypropyl)(hydroxy)(phosphinyl)-methyl]pentane-1,5-dioic acid
2-PMPA 2-(3-mercaptopropyl)pentane-dioic acid

What is claimed is:

1. A compound according to Formula IV:

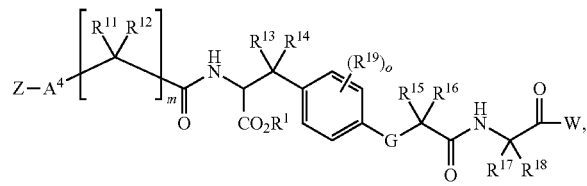

IV or a pharmaceutically acceptable salt thereof, wherein

Z is a chelating moiety, or a group having the structure:

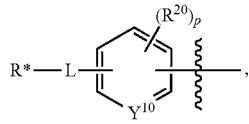

wherein $Y^{10}$ is CH or N;

L is a bond or a divalent linking moiety comprising 1 to 6 carbon atoms in a chain, a ring, or a combination thereof, wherein at least one carbon atom is optionally replaced with O, —$NR^3$—, or —C(O)—;

R* is a positron emitting radioactive isotope;

$R^{20}$ is selected from the group consisting of alkyl, alkoxyl, halide, haloalkyl, and CN;

p is an integer from 0 to 4, wherein when p is greater than 1, each $R^{20}$ is the same or different;

W is a PSMA-targeting ligand;

$A^4$ is a bond or a divalent linking moiety comprising 1 to 10 carbon atoms in a chain, a ring, or a combination thereof, wherein at least one carbon atom is optionally replaced with O, —$NR^3$—, or —C(O)—;

G is O, S, or $NR^3$;

$R^1$ is hydrogen or a carboxylic acid protecting group;

$R^3$ is selected from the group consisting of hydrogen, alkyl, cycloalkyl, heterocycloalkyl, aryl, alkylaryl, and heteroaryl;

$R^{11}$, $R^{12}$, $R^{13}$, $R^{14}$, $R^{15}$, and $R^{16}$ are each independently hydrogen, alkyl, alkoxyl, or halide;

$R^{17}$ and $R^{18}$ are each independently hydrogen, alkyl, aryl, or alkylaryl;

$R^{19}$ is selected from the group consisting of alkyl, alkoxyl, halide, haloalkyl, and CN;

m is an integer from 1 to 6; and o is an integer from 0 to 4, wherein when o is greater than 1, each $R^{19}$ is the same or different.

2. The compound of claim 1, or a pharmaceutically acceptable salt thereof, wherein Z is a chelating moiety selected from the group consisting of DOTA, HBED-CC, NOTA, NODAGA, TRAP, NOPO, PCTA, DFO, DTPA, CHX-DTPA, AAZTA, DEDPA, and oxo-Do3A.

3. The compound of claim 1, or a pharmaceutically acceptable salt thereof, wherein Z is

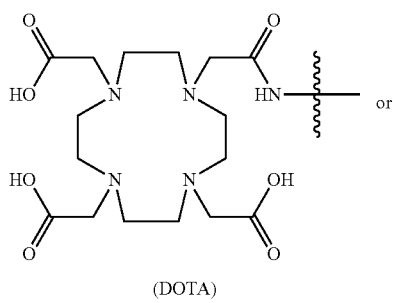

(DOTA)

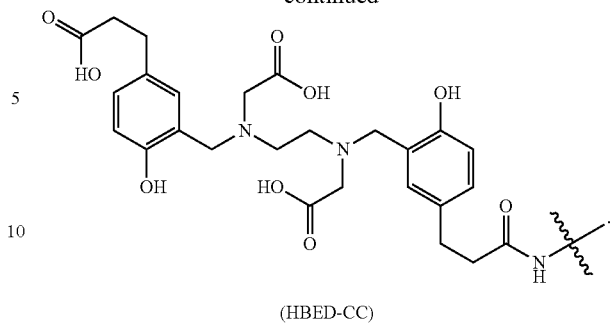

(HBED-CC)

4. The compound of claim 1, or a pharmaceutically acceptable salt thereof, wherein Z-$A^4$- is

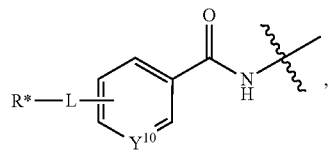

wherein R* is $^{123}$I, $^{125}$I, $^{131}$I, or $^{18}$F.

5. The compound of claim 1, or a pharmaceutically acceptable salt thereof, wherein $A^4$ is a bond, (CH$_2$), —NHC(O)—, —(OCH$_2$CH$_2$)$_n$—, —(NHCH$_2$CH$_2$)—, —NH(CO)CH$_2$—, —NHC(O)CH$_2$(OCH$_2$CH$_2$)$_n$—, or —NHC(O)CH$_2$(NHCH$_2$CH$_2$)$_n$—; and L is a bond, (CH$_2$)$_n$, —(OCH$_2$CH$_2$)$_n$—, —(NHCH$_2$CH$_2$)$_n$—, or —C(O)(CH$_2$)$_n$—;

wherein n is independently 1, 2, or 3.

6. The compound of claim 5, or a pharmaceutically acceptable salt thereof, wherein $A^4$ is a bond, —(OCH$_2$CH$_2$)$_n$—, or —NHC(O)CH$_2$(OCH$_2$CH$_2$)$_n$—; and L is a bond, or —(OCH$_2$CH$_2$)$_n$—;

wherein n is independently 1 or 2.

7. The compound of claim 1, or a pharmaceutically acceptable salt thereof, wherein W has the structure:

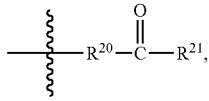

wherein $R^{20}$ and $R^{21}$ are each independently an amino acid residue linked via an amino group thereof to the adjacent —C(O)— group.

8. The compound of claim 1, or a pharmaceutically acceptable salt thereof, wherein W has the structure:

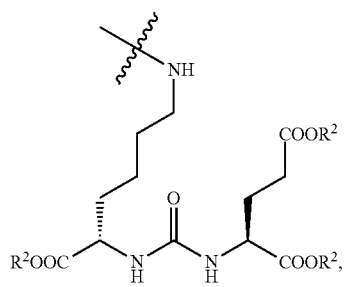

wherein $R^2$ is hydrogen or a carboxylic acid protecting group.

9. The compound of claim 1, having the structure:

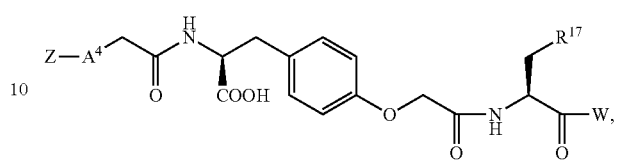

IV-a or a pharmaceutically acceptable salt thereof, wherein $R^{17}$ is aryl.

10. The compound of claim 1, having the structure:

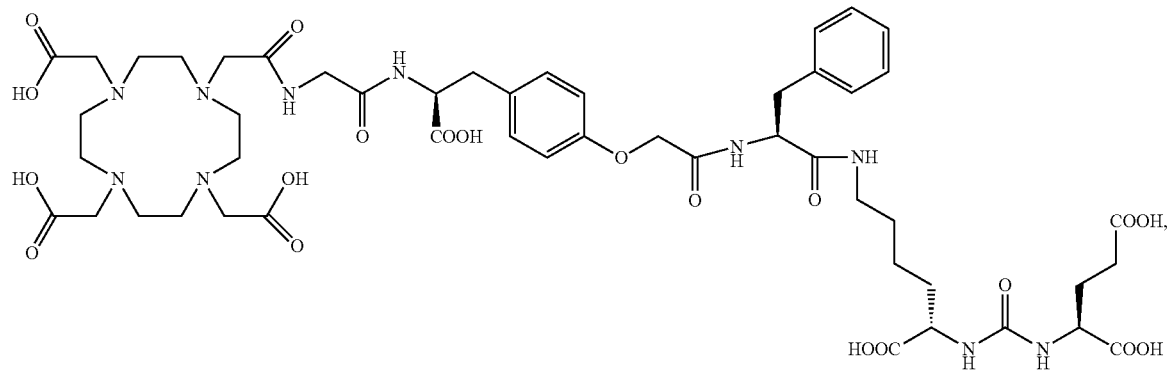

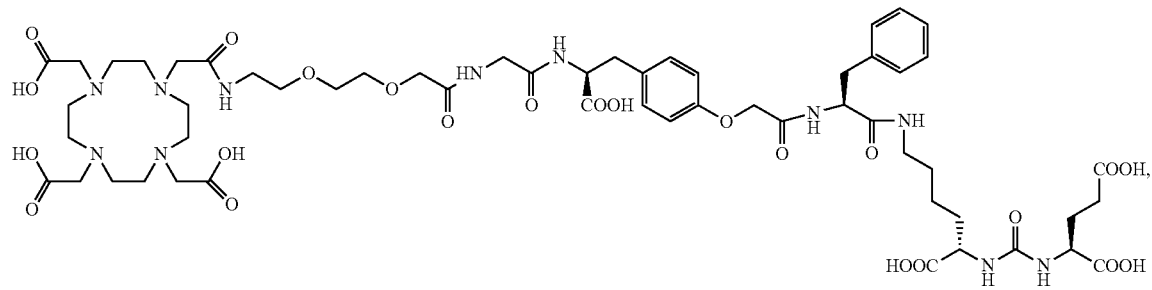

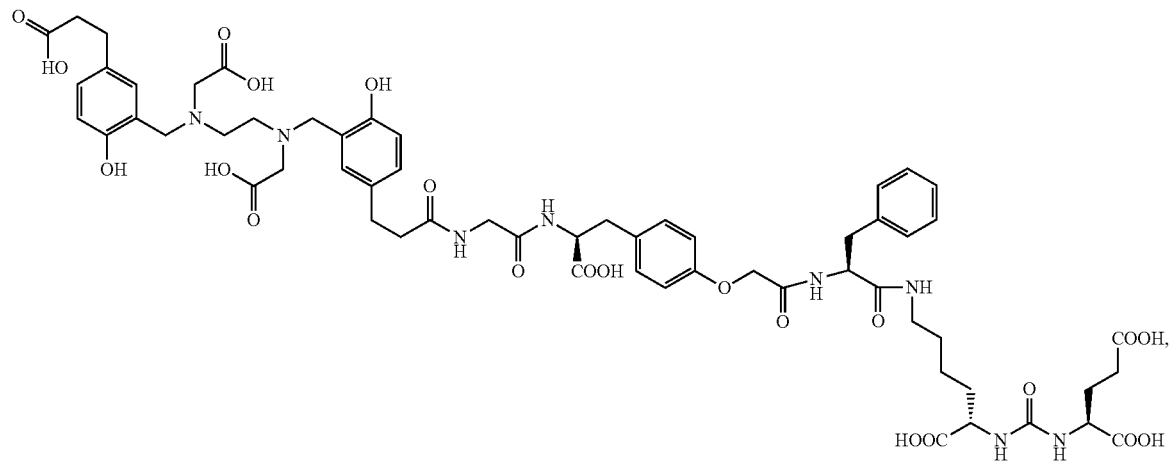

or a pharmaceutically acceptable salt thereof.

11. The compound of claim 1, having the structure:

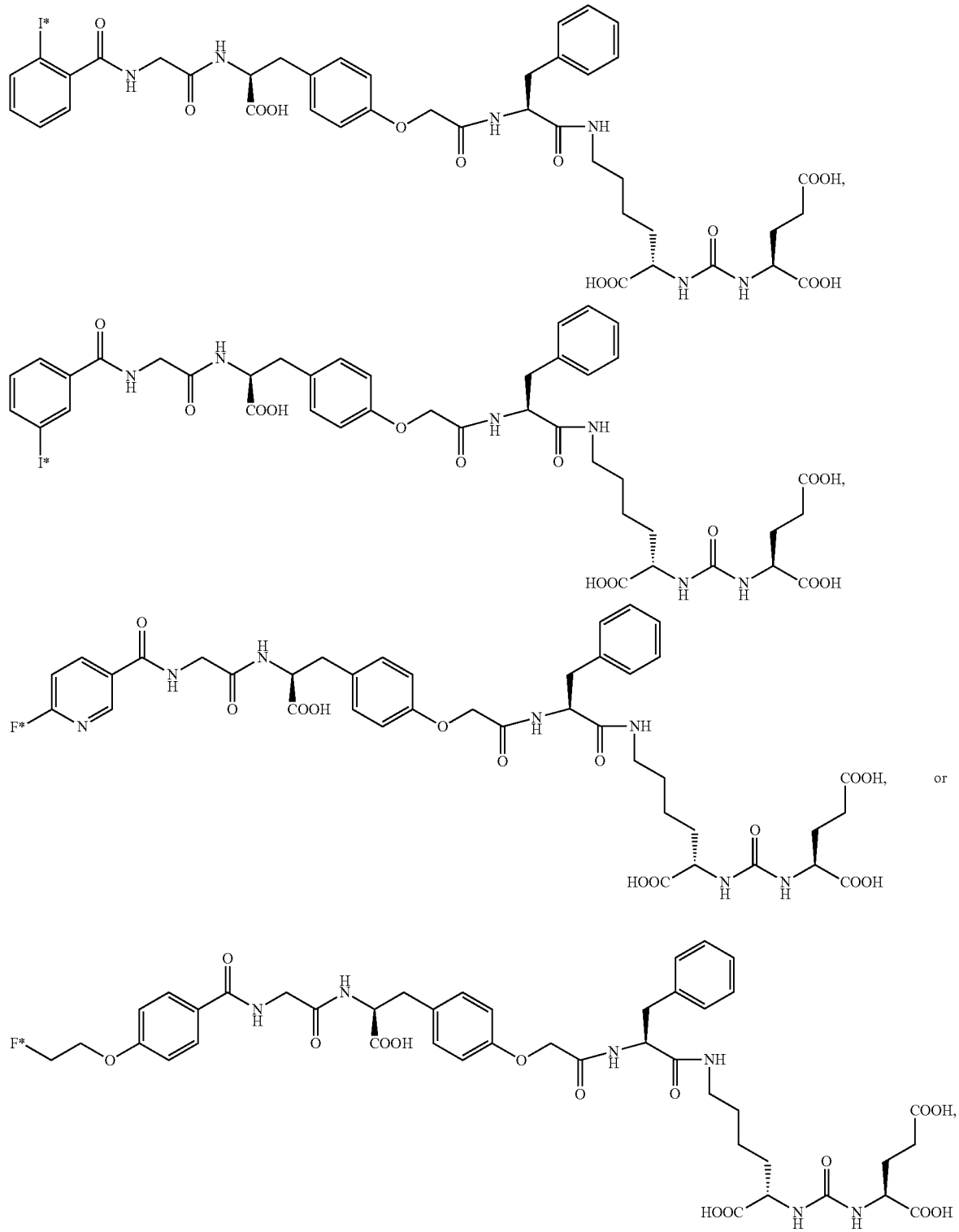

or a pharmaceutically acceptable salt thereof, wherein I* is $^{123}$I, $^{125}$I, or $^{131}$I, and F* is $^{18}$F.

12. A complex comprising the compound according to claim 1 chelated to a metal M, wherein Z is a chelating moiety, and wherein M is selected from the group consisting of $^{44}$Sc, $^{47}$Sc, $^{203}$Pb, $^{67}$Ga, $^{68}$Ga, $^{99m}$Tc, $^{72}$As, $^{111}$In, $^{90}$Y, $^{97}$Ru, $^{62}$Cu, $^{64}$Cu, $^{52}$Fe, $^{52m}$Mn, $^{140}$La, $^{175}$Yb, $^{153}$Sm, $^{166}$Ho, $^{149}$Pm, $^{177}$Lu, $^{142}$Pr, $^{159}$Gd, $^{243}$Bi, $^{67}$Cu, $^{111}$Ag, $^{199}$Au, $^{161}$Tb, and $^{51}$Cr, $^{99m}$Tc.

13. The complex of claim 12, having the structure:

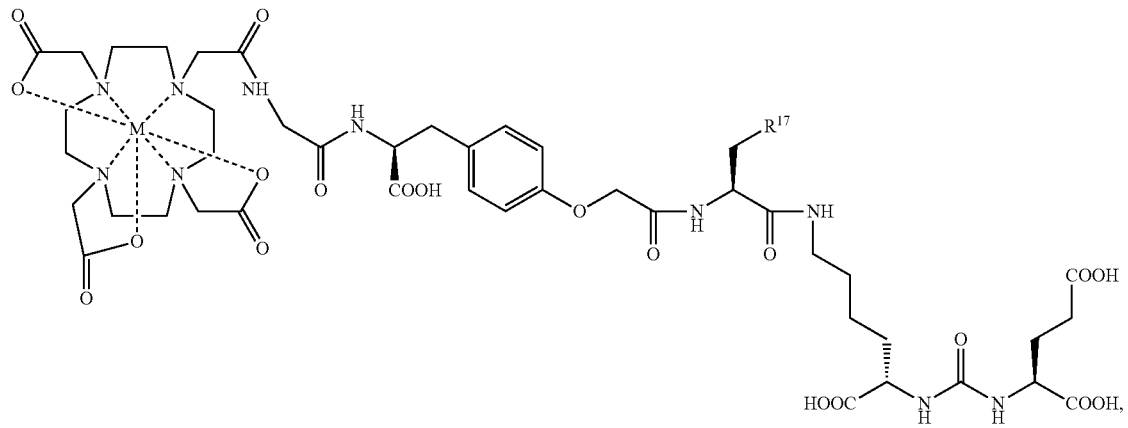

wherein $R^{17}$ is aryl.

14. The complex of claim 12, having the structure:

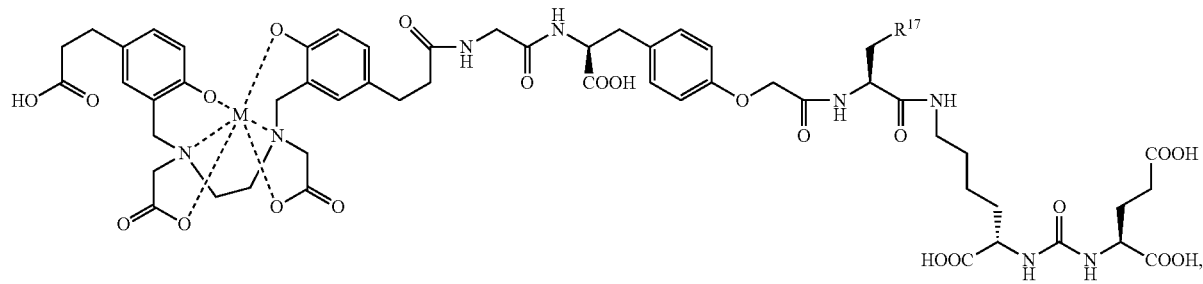

wherein $R^{17}$ is aryl.

15. The complex of claim 12, having the structure:

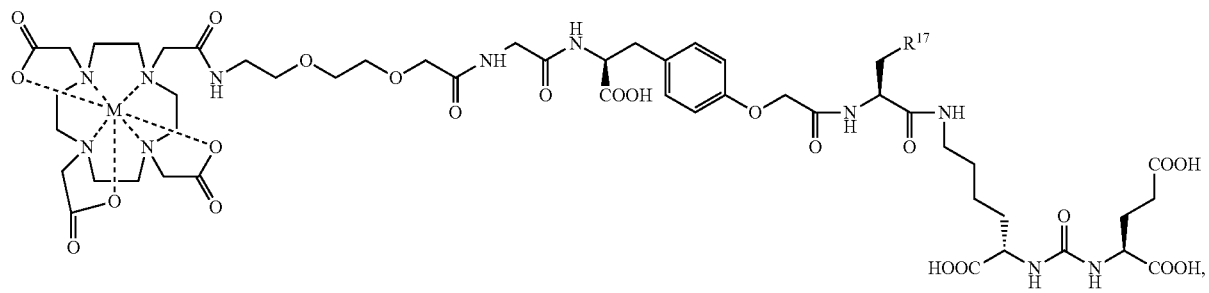

wherein $R^{17}$ is aryl.

16. The complex of claim 12, wherein $R^{17}$ is phenyl.

17. The complex of claim 12, wherein M is $^{68}$Ga.

18. A method for imaging in a subject, comprising administering the compound claim 1 to said subject; and obtaining an image of said subject or a portion of said subject.

19. The method of claim 18, comprising obtaining an image with a device that is capable of detecting positron emission.

20. A pharmaceutical composition comprising a pharmaceutically acceptable carrier and the compound according to claim 1 or a pharmaceutically acceptable salt thereof.

21. A method of in vivo imaging comprising administering an effective amount of the compound according to claim 1 to a subject, and detecting the pattern of radioactivity of the compound in said subject.

22. A kit comprising a sterile container containing an effective amount of the compound of claim 1 or a pharmaceutically acceptable salt thereof, and instructions for therapeutic use.

* * * * *

UNITED STATES PATENT AND TRADEMARK OFFICE
CERTIFICATE OF CORRECTION

PATENT NO. : 10,688,200 B2  
APPLICATION NO. : 15/385490  
DATED : June 23, 2020  
INVENTOR(S) : Kung et al.

Page 1 of 1

It is certified that error appears in the above-identified patent and that said Letters Patent is hereby corrected as shown below:

In the Claims

In Column 150, Claim 5, Line 38, delete "$(CH_2)$," and insert -- $(CH_2)_n$, --, therefor.

In Column 150, Claim 5, Line 39, delete "$-(NHCH_2CH_2)-$," and insert -- $-(NHCH_2CH_2)_n-$, --, therefor.

In Column 154, Claim 12, Line 66, delete "$^{243}Bi$," and insert -- $^{213}Bi$, --, therefor.

In Column 155, Claim 15, Line 55, delete "$R'^7$" and insert -- $R^{17}$ --, therefor.

Signed and Sealed this  
Nineteenth Day of January, 2021

Andrei Iancu  
*Director of the United States Patent and Trademark Office*